(12) United States Patent
Duggan et al.

(10) Patent No.: US 6,211,184 B1
(45) Date of Patent: Apr. 3, 2001

(54) INTEGRIN ANTAGONISTS

(75) Inventors: Mark E. Duggan, Schwenksville; George D. Hartman; William F. Hoffman, both of Lansdale; Robert S. Meissner, Schwenksville; James J. Perkins, Churchville; Ben C. Askew, Lansdale; Paul J. Coleman, Wallingford; John J. Hutchinson, Philadelphia; Adel M. Naylor-Olsen, Lansdale, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/242,885

(22) PCT Filed: Aug. 25, 1997

(86) PCT No.: PCT/US97/14912

§ 371 Date: Jun. 14, 1999

§ 102(e) Date: Jun. 14, 1999

(87) PCT Pub. No.: WO98/08840

PCT Pub. Date: Mar. 5, 1998

Related U.S. Application Data

(60) Provisional application No. 60/025,125, filed on Aug. 29, 1996, provisional application No. 60/033,579, filed on Dec. 19, 1996, and provisional application No. 60/047,177, filed on May 20, 1997.

(51) Int. Cl.[7] .................... C07D 401/02; A61K 31/495; A61K 31/435

(52) U.S. Cl. .................... 514/255.02; 514/256; 514/300; 544/315; 544/405; 544/406; 546/122

(58) Field of Search ...................... 544/315, 406, 544/405; 546/122; 514/300, 255.02, 256

(56) References Cited

U.S. PATENT DOCUMENTS

| 5,260,277 | 11/1993 | McKenzie | 544/18 |
|---|---|---|---|
| 5,281,585 | * 1/1994 | Duggan et al. | 514/79 |
| 5,455,243 | 10/1995 | Duggan et al. | 514/218 |
| 5,534,524 | 7/1996 | Bonewald et al. | 514/314 |
| 5,668,159 | 9/1997 | Jin et al. | 514/363 |

FOREIGN PATENT DOCUMENTS

| WO 95/32710 | 7/1995 | (WO) . |
|---|---|---|
| WO 97/26250 | 7/1997 | (WO) . |
| WO 98/08840 | 5/1998 | (WO) . |

* cited by examiner

*Primary Examiner*—Zinna Northington Davis
(74) *Attorney, Agent, or Firm*—Philippe L. Durette; Melvin Winokur

(57) ABSTRACT

This invention relates to certain novel compounds and derivatives thereof, their synthesis, and their use as vitronectin receptor antagonists. The vitronectin receptor antagonist compounds of the present invention are αvβ3 antagonists, αvβ5 antagonists or dual αvβ3/αvβ5 antagonists useful for inhibiting bone resorption, treating and preventing osteoporosis, and inhibiting restenosis, diabetic retinopathy, macular degeneration, angiogenesis, atherosclerosis, inflammation and tumor growth.

16 Claims, No Drawings

INTEGRIN ANTAGONISTS

RELATED APPLICATION DATA

This is a National Phase U.S. application of PCT/US97/14912, filed Aug. 25, 1997, which claims priority from U.S. provisional application Serial No. 60/047,177, filed May 20, 1997; U.S. provisional application Serial No. 60/033,579, filed Dec. 19, 1996; and U.S. provisional application Serial No. 60/025,123, filed Aug. 29, 1996.

FIELD OF THE INVENTION

The present invention is related to U.S. provisional applications Serial No. 60/047,177, filed May 20, 1997, U.S. provisional application Serial No. 60/033,579, filed Dec. 19, 1996, and U.S. provisional application Serial No. 60/025,123, filed Aug. 29, 1996, the contents of which are hereby incorporated by reference.

The present invention provides novel compounds and derivatives thereof, their synthesis, and their use as vitronectin receptor ligands. More particularly, the compounds of the present invention are $\alpha v \beta 3$ antagonists, $\alpha v \beta 5$ antagonists or dual $\alpha v \beta 3/\alpha v \beta 5$ antagonists useful for inhibiting bone resorption, treating and preventing osteoporosis, and inhibiting vascular restenosis, diabetic retinopathy, macular degeneration, angiogenesis, atherosclerosis, inflammation and tumor growth.

BACKGROUND OF THE INVENTION

This invention relates to compounds for inhibiting bone resorption that is mediated by the action of a class of cells known as osteoclasts.

Osteoclasts are multinucleated cells of up to 400 $\mu$m in diameter that resorb mineralized tissue, chiefly calcium carbonate and calcium phosphate, in vertebrates. They are actively motile cells that migrate along the surface of bone. They can bind to bone, secrete necessary acids and proteases and thereby cause the actual resorption of mineralized tissue from the bone.

More specifically, osteoclasts are believed to exist in at least two physiological states. In the secretory state, osteoclasts are flat, attach to the bone matrix via a tight attachment zone (sealing zone), become highly polarized, form a ruffled border, and secrete lysosomal enzymes and protons to resorb bone. The adhesion of osteoclasts to bone surfaces is an important initial step in bone resorption. In the migratory or motile state, the osteoclasts migrate across bone matrix and do not take part in resorption until they attach again to bone.

Integrins are transmembrane, heterodimeric, glycoproteins which interact with extracellular matrix and are involved in osteoclast attachment, activation and migration. The most abundant integrin in osteoclasts (rat, chicken, mouse and human) is the vitronectin receptor, or $\alpha v \beta 3$, thought to interact in bone with matrix proteins that contain the RGD sequence. Antibodies to $\alpha v \beta 3$ block bone resorption in vitro indicating that this integrin plays a key role in the resorptive process. There is increasing evidence to suggest that $\alpha v \beta 3$ ligands can be used effectively to inhibit osteoclast mediated bone resoption in vivo in mammals.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment.

All these conditions are characterized by bone loss, resulting from an imbalance between bone resorption (breakdown) and bone formation, which continues throughout life at the rate of about 14% per year on the average. However, the rate of bone turnover differs from site to site, for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

There are currently 20 million people with detectable fractures of the vertebrae due to osteoporosis in the United States. In addition, there are 250,000 hip fractures per year attributed to osteoporosis. This clinical situation is associated with a 12% mortality rate within the first two years, while 30% of the patients require nursing home care after the fracture.

Individuals suffering from all the conditions listed above would benefit from treatment with agents which inhibit bone resorption.

Additionally, $\alpha v \beta 3$ ligands have been found to be useful in treating and/or inhibiting restenosis (recurrence of stenosis after corrective surgery on the heart valve), atherosclerosis, diabetic retinopathy, macular degeneration and angiogenesis (formation of new blood vessels). Moreover, it has been postulated that the growth of tumors depends on an adequate blood supply, which in turn is dependent on the growth of new vessels into the tumor; thus, inhibition of angiogenesis can cause tumor regression in animal models. (See, *Harrison's Principles of Internal Medicine*, 12th ed., 1991). $\alpha v \beta 3$ antagonists, which inhibit angiogenesis, are therefore useful in the treatment of cancer for inhibiting tumor growth. (See e.g., Brooks et al., *Cell*, 79:1157–1164 (1994)).

Moreover, compounds of this invention can also inhibit neovascularization by acting as antagonists of the integrin receptor $\alpha v \beta 5$. A monoclonal antibody for $\alpha v \beta 5$ has been shown to inhibit VEGF-induced angiogenesis in rabbit cornea and the chick chorioallantoic membrane model; M. C. Friedlander, et.al., *Science* 270, 1500–1502, 1995. Thus, compounds that antagonize $\alpha v \beta 5$ are useful for treating and preventing macular degeneration, diabetic retinopathy, and tumor growth.

In addition, certain compounds of this invention antagonize both the $\alpha v \beta 3$ and $\alpha v \beta 5$ receptors. These compounds, referred to as "dual $\alpha v \beta 3/\alpha v \beta 5$ antagonists," are useful for inhibiting bone resorption, treating and preventing osteoporosis, and inhibiting vascular restenosis, diabetic retinopathy, macular degeneration, angiogenesis, atherosclerosis, inflammation and tumor growth.

It is an object of the present invention to identify compounds which bind to the $\alpha v \beta 3$ receptor, $\alpha v \beta 5$ receptor or both the $\alpha v \beta 3$ and $\alpha v \beta 5$ receptors.

It is a further object of the invention to identify compounds which act as antagonists of the $\alpha v \beta 3$ receptor. It is another object of the invention to identify $\alpha v \beta 3$ antagonist compounds which are useful agents for inhibiting: bone resorption mediated by osteoclast cells, restenosis, atherosclerosis, inflammation, diabetic retinopathy, macular degeneration and angiogenesis in animals, preferably mammals, especially humans. Still another object of the invention is to identify $\alpha v \beta 3$ antagonists which cause tumor regression and/or inhibit tumor growth in animals.

A further object of the invention is to identify $\alpha v \beta 3$ antagonists useful for preventing or treating osteoporosis. An additional object of the invention is to identify $\alpha v \beta 3$ antagonists useful for treating cancer.

It has now been found that the compounds of the present invention, αvβ3 ligands, are useful for inhibiting bone resorption in mammals. Thus, the compounds of the present invention are useful for preventing or reducing the incidence of osteoporosis. Additionally, the αvβ3 ligands of the present invention are also useful for treating and/or inhibiting restenosis, diabetic retinopathy, macular degeneration, atherosclerosis and/or angiogenesis in mammals.

SUMMARY OF THE INVENTION

The present invention provides a method of eliciting a vitronectin receptor antagonizing effect in a mammal in need thereof, comprising administering to the mammal a therapeutically effective amount of a compound of the formula

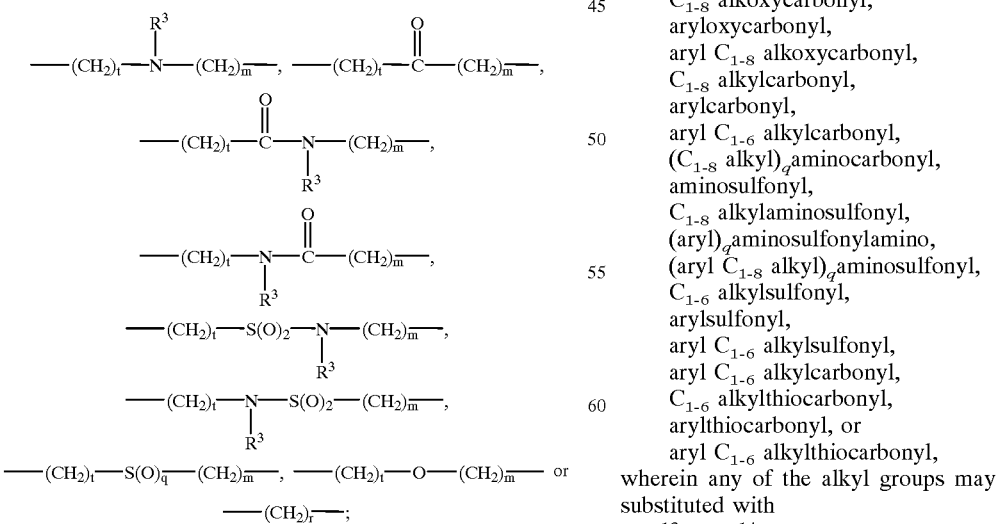

wherein X is selected from

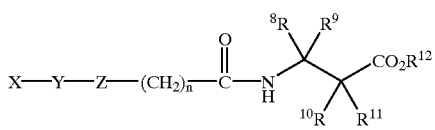

a 5- or 6-membered monocyclic aromatic or nonaromatic ring system containing 0, 1, 2, 3 or 4 heteroatoms selected from N, O or S wherein the 5- or 6-membered ring system is either unsubstituted or substituted on a carbon or nitrogen atom with one or more groups chosen from $R^1$, $R^2$, $R^{15}$ or $R^{16}$;

a 9- to 10-membered polycyclic ring system, wherein one or more of the rings is aromatic, and wherein the polycyclic ring system contains 0, 1, 2, 3 or 4 heteroatoms selected from N, O or S, and wherein the polycyclic ring system is either unsubstituted or substituted on a carbon or nitrogen atom with one or more groups chosen from $R^1$, $R^2$, $R^{15}$ or $R^{16}$;

Y is selected from

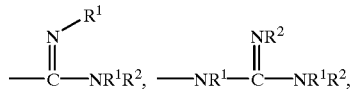

Z is a 5–11 membered aromatic or nonaromatic mono- or polycyclic ring system containing 0 to 6 double bonds, and containing 0 to 6 heteroatoms chosen from N, O and S, and wherein the ring system is either unsubstituted or substituted on a carbon or nitrogen atom with one or more groups independently selected from $R^4$, $R^5$, $R^6$ and $R^7$; provided that Z is not a 6-membered monocyclic aromatic ring system, an isoxazoline ring or an isoxazole ring;

$R^1$, $R^2$, $R^4$, $R^5$, $R^{13}$, $R^{14}$, $R^{15}$ and $R^{16}$ are each independently selected from hydrogen, halogen, $C_{1-10}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $(C_{1-6}$ alkyl$)_q$amino, $(C_{1-6}$ alkyl$)_q$ amino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl-$S(O)_q$, $(C_{1-8}$ alkyl$)_q$ aminocarbonyl, $C_{1-8}$ alkyloxycarbonylamino, $(C_{1-8}$ alkyl$)_q$aminocarbonyloxy, oxo, (aryl $C_{1-8}$ alkyl$)_q$ amino, (aryl$)_q$amino, aryl $C_{1-8}$ alkylsulfonylamino or $C_{1-8}$ alkylsulfonylamino;

$R^3$ is selected from
hydrogen,
aryl,
aryl-$(CH_2)_p$—,
hydroxyl,
$C_{1-5}$ alkoxy,
aminocarbonyl,
$C_{3-8}$ cycloalkyl,
amino $C_{1-6}$ alkyl,
(aryl)$_q$aminocarbonyl,
(aryl $C_{1-5}$ alkyl)$_q$aminocarbonyl,
hydroxycarbonyl $C_{1-6}$ alkyl,
$C_{1-8}$ alkyl,
aryl $C_{1-6}$ alkyl,
$(C_{1-6}$ alkyl$)_q$amino $C_{1-6}$ alkyl,
(aryl $C_{1-6}$ alkyl)$_q$amino $C_{1-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}$ alkyl$)_q$aminocarbonyl,
aminosulfonyl,
$C_{1-8}$ alkylaminosulfonyl,
(aryl)$_q$aminosulfonylamino,
(aryl $C_{1-8}$ alkyl)$_q$aminosulfonyl,
$C_{1-6}$ alkylsulfonyl,
arylsulfonyl,
aryl $C_{1-6}$ alkylsulfonyl,
aryl $C_{1-6}$ alkylcarbonyl,
$C_{1-6}$ alkylthiocarbonyl,
arylthiocarbonyl, or
aryl $C_{1-6}$ alkylthiocarbonyl,
wherein any of the alkyl groups may be unsubstituted or substituted with
$R^{13}$ and $R^{14}$;
$R^6$, $R^7$, $R^8$, $R^9$, $R^{10}$ and $R^{11}$ are each independently selected from hydrogen,
aryl,
aryl-$(CH_2)_p$—,
aryl-$(CH_2)_n$—O—$(CH_2)_m$—,
aryl-$(CH_2)_n$—S(O)$_q$—$(CH_2)_m$—,
aryl-$(CH_2)_n$—C(O)—$(CH_2)_m$—,
aryl-$(CH_2)_n$—C(O)—N(R$^3$)—$(CH_2)_m$—,
aryl-$(CH_2)_n$—N(R$^3$)—C(O)—$(CH_2)_m$—,
aryl-$(CH_2)_n$—N(R$^3$)—$(CH_2)_m$—,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_q$aminocarbonyl,
$C_{1-6}$ alkylcarbonyloxy,
$C_{3-8}$ cycloalkyl,
oxo,
$(C_{1-6}$ alkyl$)_q$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
$C_{1-8}$ alkyl, either unsubstituted or substituted, with one or more groups selected from: halogen, hydroxyl, $C_{1-5}$ alkylcarbonylamino, aryl $C_{1-5}$ alkoxy, $C_{1-5}$ alkoxycarbonyl, aminocarbonyl, $(C_{1-5}$ alkyl$)_q$ aminocarbonyl, $C_{1-5}$ alkylcarbonyloxy, $C_{3-8}$ cycloalkyl, oxo, $(C_{1-3}$ alkyl$)_q$amino, amino $C_{1-3}$ alkyl, (aryl$)_q$aminocarbonyl, (aryl $C_{1-5}$ alkyl$)_q$ aminocarbonyl, aminocarbonyl, aminocarbonyl $C_{1-4}$ alkyl, hydroxycarbonyl or hydroxycarbonyl $C_{1-5}$ alkyl,
CH≡C—$(CH_2)_s$—,
$C_{1-6}$ alkyl-C≡C—$(CH_2)_s$—,
$C_{3-7}$ cycloalkyl-C≡C—$(CH_2)_s$—,
aryl-C≡C—$(CH_2)_s$—,
$C_{1-6}$ alkylaryl-C≡C—$(CH_2)_s$—,
$CH_2$=CH—$(CH_2)_s$—,
$C_{1-6}$ alkyl-CH=CH—$(CH_2)_s$—,
$C_{3-7}$ cycloalkyl-CH=CH—$(CH_2)_s$—,
aryl-CH=CH—$(CH_2)_s$—,
$C_{1-6}$ alkylaryl-CH=CH—$(CH_2)_s$—,
$C_{1-6}$ alkyl-SO$_2$—$(CH_2)_s$—,
$C_{1-6}$ alkylaryl-SO$_2$—$(CH_2)_s$—,
$C_{1-6}$ alkoxy,
aryl $C_{1-6}$ alkoxy,
aryl $C_{1-6}$ alkyl,
$(C_{1-6}$ alkyl$)_q$amino $C_{1-6}$ alkyl,
(aryl$)_q$amino,
(aryl$)_q$amino $C_{1-6}$ alkyl,
(aryl $C_{1-6}$ alkyl$)_q$amino,
(aryl $C_{1-6}$ alkyl$)_q$amino $C_{1-6}$ alkyl,
arylcarbonyloxy,
aryl $C_{1-6}$ alkylcarbonyloxy,
$(C_{1-6}$ alkyl$)_q$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-6}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_q$aminocarbonylamino,
$(C_{1-8}$ alkyl$)_q$aminocarbonylamino $C_{1-6}$ alkyl,
(aryl$)_q$aminocarbonylamino $C_{1-6}$ alkyl,
(aryl $C_{1-8}$ alkyl$)_q$aminocarbonylamino,
(aryl $C_{1-8}$ alkyl$)_q$aminocarbonylamino $C_{1-6}$ alkyl,
aminosulfonylamino $C_{1-6}$ alkyl,
$(C_{1-8}$ alkyl$)_q$aminosulfonylamino,
$(C_{1-8}$ alkyl$)_q$aminosulfonylamino $C_{1-6}$ alkyl,
(aryl$)_q$aminosulfonylamino $C_{1-6}$ alkyl,
(aryl $C_{1-8}$ alkyl$)_q$aminosulfonylamino,
(aryl $C_{1-8}$ alkyl$)_q$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_q$aminocarbonyl $C_{1-6}$ alkyl,
(aryl$)_q$aminocarbonyl $C_{1-6}$ alkyl,
(aryl $C_{1-8}$ alkyl$)_q$aminocarbonyl, or
(aryl $C_{1-8}$ alkyl$)_q$aminocarbonyl $C_{1-6}$ alkyl,
wherein any of the alkyl groups may be unsubstituted or substituted with R$^{13}$ and R$^{14}$; and provided that the carbon atom to which R$^8$ and R$^9$ are attached is itself attached to no more than one heteroatom; and provided further that the carbon atom to which R$^{10}$ and R$^{11}$ are attached is itself attached to no more than one heteroatom;
R$^{12}$ is selected from
hydrogen,
$C_{1-8}$ alkyl,
aryl,
aryl $C_{1-8}$ alkyl,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, or
$C_{1-8}$ dialkylaminocarbonylmethylene;
m, s and t are each independently an integer from 0 to 3;
n is an integer from 1 to 3;
p is an integer from 1 to 4;
q is an integer from 0 to 2;
r is an integer from 0 to 6;
and the pharmaceutically acceptable salts thereof.

In one embodiment of the present invention is the method of eliciting a vitronectin antagonizing effect wherein
X is
a 9- to 10-membered polycyclic ring system, wherein one or more of the rings is aromatic, and wherein the polycyclic ring system contains 0, 1, 2, 3 or 4 heteroatoms selected from N, O or S, and wherein the polycyclic ring system is either unsubstituted or substituted on a carbon atom with $R^1$ and $R^2$; and
Z is selected from
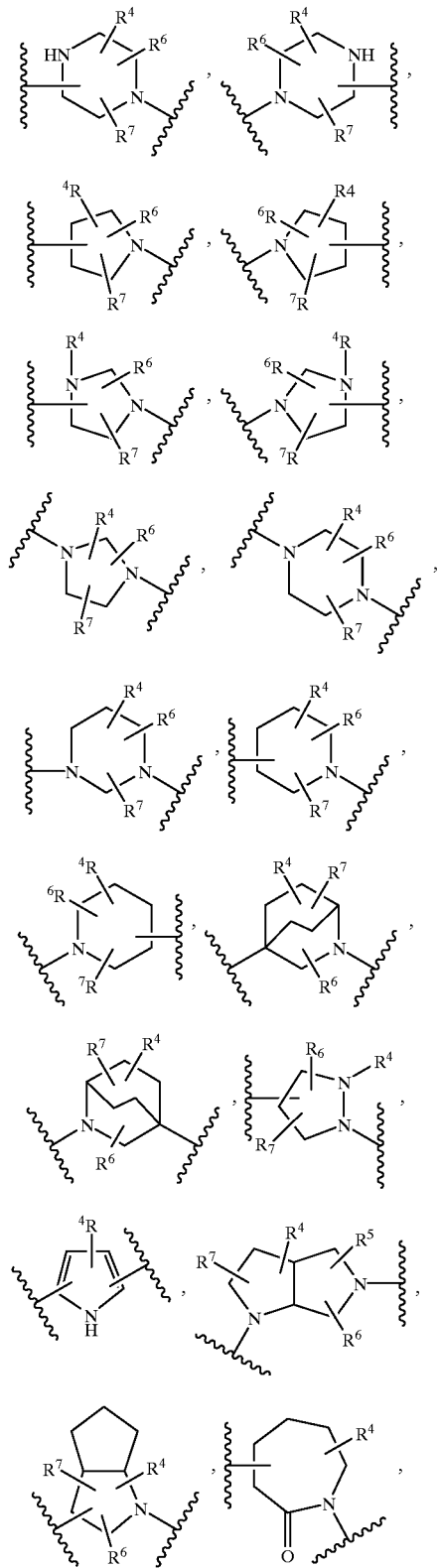
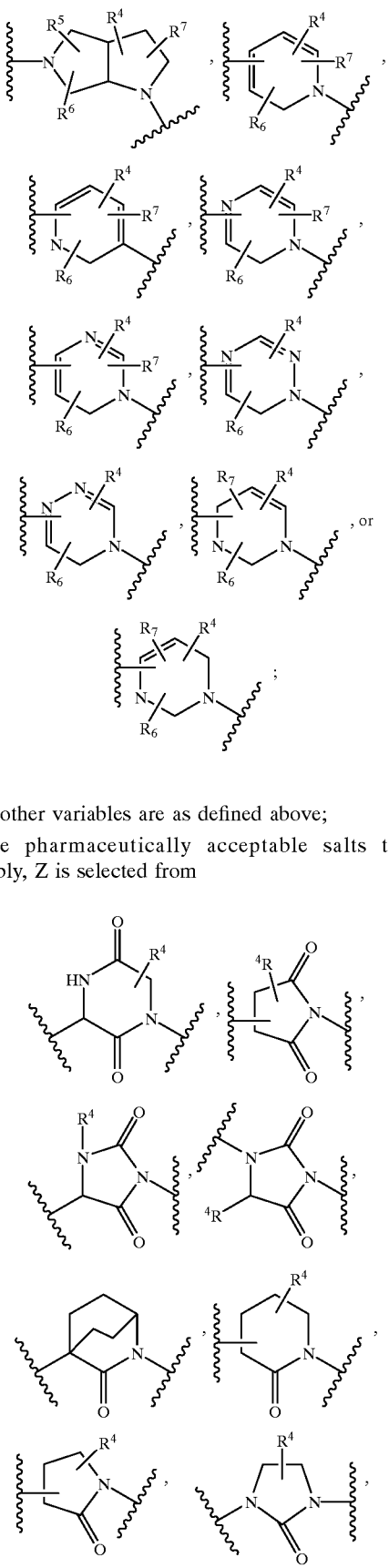
and all other variables are as defined above;
and the pharmaceutically acceptable salts thereof. Preferably, Z is selected from -continued wherein X is selected from

[chemical structures of tetrahydronaphthyridines and benzimidazole bearing R¹, R²]

Y is selected from —(CH$_2$)$_r$— or —(CH$_2$)$_m$—NR$^3$—(CH$_2$)$_t$—;

R$^3$ is selected from
  hydrogen,
  aryl-(CH$_2$)$_p$—,
  C$_{1-5}$ alkoxycarbonyl,
  C$_{3-8}$ cycloalkyl,
  (aryl)$_q$aminocarbonyl,
  (aryl C$_{1-5}$ alkyl)$_q$aminocarbonyl,
  C$_{1-8}$ alkyl,
  aryl C$_{1-6}$ alkyl,
  C$_{1-8}$ alkylsulfonyl,
  arylsulfonyl,
  aryl C$_{1-6}$ alkylsulfonyl,
  C$_{1-8}$ alkoxycarbonyl,
  aryloxycarbonyl,
  aryl C$_{1-8}$ alkoxycarbonyl,
  C$_{1-8}$ alkylcarbonyl,
  arylcarbonyl,
  aryl C$_{1-6}$ alkylcarbonyl,
  (C$_{1-8}$ alkyl)$_q$aminocarbonyl,
  C$_{1-6}$ alkylsulfonyl, or
  aryl C$_{1-6}$ alkylcarbonyl,
  wherein any of the alkyl groups may be unsubstituted or substituted with R$^3$ and R$^{14}$;

R$^4$ is selected from
  hydrogen, C$_{1-6}$ alkyl, C$_{3-8}$ cycloalkyl, C$_{3-8}$ cycloheteroalkyl,
  C$_{3-8}$ cycloalkyl C$_{1-6}$ alkyl, C$_{3-8}$ cycloheteroalkyl C$_{1-6}$ alkyl,
  aryl or aryl C$_{1-8}$ alkyl, R$^8$ is selected from
  hydrogen,
  aryl,
  aryl-(CH$_2$)$_p$—,
  CH≡C—(CH$_2$)$_s$—,
  C$_{1-6}$ alkyl-C≡C—(CH$_2$)$_s$—,
  C$_{3-7}$ cycloalkyl-C≡C—(CH$_2$)$_s$—,
  aryl-C≡C—(CH$_2$)$_s$—,
  C$_{1-6}$ alkylaryl-C≡C—(CH$_2$)$_s$—,
  CH$_2$=CH—(CH$_2$)$_s$—,
  C$_{1-6}$ alkyl-CH=CH—(CH$_2$)$_s$—,
  C$_{3-7}$ cycloalkyl-CH=CH—(CH$_2$)$_s$—,
  aryl-CH=CH—(CH$_2$)$_s$—,
  C$_{1-6}$ alkylaryl-CH=CH—(CH$_2$)$_s$—,
  C$_{1-6}$ alkyl-SO$_2$—(CH$_2$)$_s$—,
  C$_{1-6}$ alkylaryl-SO$_2$—(CH$_2$)$_s$—; and r is an integer from 0 to 3;

In a class of the invention is the method of eliciting a vitronectin antagonizing effect wherein the compound has the formula

X—Y—Z—CH$_2$NH—C(=O)—CH(R$^8$)—CO$_2$R$^{12}$ and all other variables are as defined above;
and the pharmaceutically acceptable salts thereof.

In a subclass of the invention is the method wherein the compound has the formula

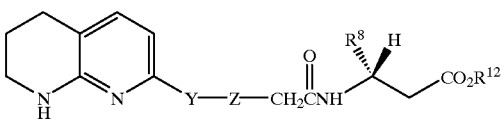

wherein Z is selected from

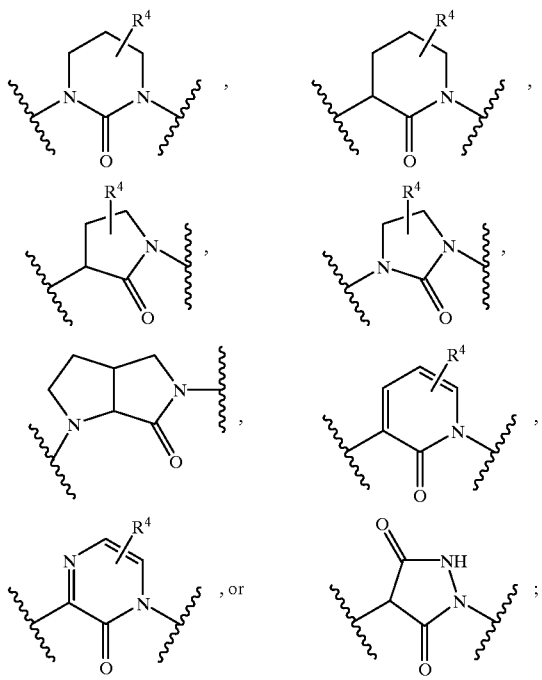

$R^8$ is selected from hydrogen,

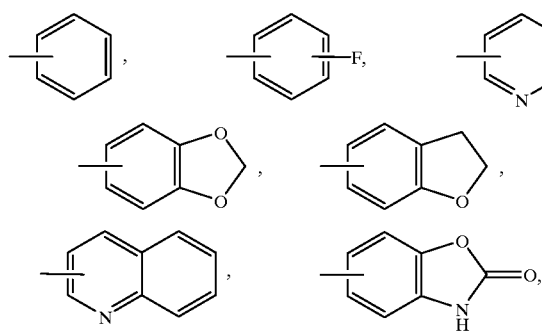

indolyl-$(CH_2)_p$—,
CH≡C—$(CH_2)_s$—,
$C_{1-6}$ alkyl-C≡C—$(CH_2)_s$—,
$C_{3-7}$ cycloalkyl-C≡C—$(CH_2)_s$—,
aryl-C≡C—$(CH_2)_s$—,
$C_{1-6}$ alkylaryl-C≡C—$(CH_2)_s$—,
$CH_2$=CH—$(CH_2)_s$—,
$C_{1-6}$ alkyl-CH=CH—$(CH_2)_s$—,
$C_{3-7}$ cycloalkyl-CH=CH—$(CH_2)_s$—,
aryl-CH=CH—$(CH_2)_s$—,
$C_{1-6}$ alkylaryl-CH=CH—$(C_{112})_s$—, $C_{1-6}$ alkyl-$SO_2$—$(CH_2)_s$—,
$C_{1-6}$ alkylaryl-$SO_2$—$(CH_2)_s$—; and
$R^{12}$ is selected from hydrogen or $C_{1-8}$ alkyl;
s is an integer from 0 to 3;
and all other variables are as defined above;
and the pharmaceutically acceptable salts thereof.

Illustrative of the invention is the method of eliciting a vitronectin antagonizing effect wherein the compound is selected from 2-Oxo-3-[2-(5,6,7,8-tetrahydro[1,8]-naphthyridin-2-yl) ethyl]piperidin-1-yl-acetyl-3(S)-pyridin-3-yl-β-alanine ethyl ester;

2-Oxo-3-[2-(5,6,7,8-tetrahydro[1,8]-naphthyridin-2-yl) ethyl]piperin-1-yl-acetyl-3(S)-pyridin-3-yl-β-alanine trifluoroacetate;

2-Oxo-3(S)-[2-(5,6,7,8-tetrahydro[1,8]-naphthyridin-2-yl)ethyl]pyrrolidin-1-yl)acetyl-3(S)-ethynyl-β-alanine ethyl ester;

2-Oxo-3(S)-[2-(5,6,7,8-tetrahydro[1,8]-naphthyridin-2-yl)ethyl]pyrrolidin-1-yl)acetyl-3(S)-ethynyl-β-alanine;

2-Oxo-3(S)-[2-(5,6,7,8-tetrahydro[1,8]-naphthyridin-2-yl)ethyl]-pyrrolidin-1-yl)acetyl-3(S)-pyridin-3-yl-β-alanine ethyl ester;

2-Oxo-3(S)-[2-(5,6,7,8-tetrahydro[1,8]-naphthyridin-2-yl)ethyl]pyrrolidin-1-yl)acetyl-3(S)-pyridin-3-yl-β-alanine;

2-Oxo-3(R)-[2-(5,6,7,8-tetrahydro[1,8]-naphthyridin-2-yl)ethyl]pyrrolidin-1-yl)acetyl-3(S)-ethynyl-β-alanine ethyl ester;

2-Oxo-3(R)-[2-(5,6,7,8-tetrahydro[1,8]-naphthyridin-2-yl)ethyl]pyrrolidin-1-yl)acetyl-3(S)-ethynyl-β-alanine;

2-Oxo-3(R)-[2-(5,6,7,8-tetrahydro[1,8]-naphthyridin-2-yl)ethyl]-pyrrolidin-1-yl)acetyl-3(S)-pyridin-3-yl-β-alanine ethyl ester;

2-Oxo-3(R)-[2-(5,6,7,8-tetrahydro[1,8]-naphthyridin-2-yl)ethyl]pyrrolidin-1-yl)acetyl-3(S)-pyridin-3-yl-β-alanine;

Ethyl 2-oxo-3-[2-(5,6,7,8-tetrahydro[1,8]naphthyridin-2-yl)ethyl]-tetrahydropyrimidin-1-yl -acetyl-3(S)-pyridin-3-yl-β-alanine;

2-Oxo-3-[2-(5,6,7,8-tetrahydro[1,8]naphthyridin-2-yl) ethyl]-tetrahydropyrimidin-1-yl-acetyl-3(S)-pyridin-3-yl-β-alanine;

Ethyl 2-oxo-3-[2-(5,6,7,8-tetrahydro[1,8]naphthyridin-2-yl)ethyl]imidazolidin-1-yl-acetyl-3(S)-pyridin-3-yl-β-alanine;

2-Oxo-3-[2-(5,6,7,8-tetrahydro[1,8]naphthyridin-2-yl}ethyl]-imidazolidin-1-yl-acetyl-3(S)-pyridin-3-yl-β-alanine;

Ethyl 2-oxo-3(R)-[2-(5,6,7,8-tetrahydro[1,8] naphthyridin-2-yl)ethyl]pyrrolidin-1-yl)acetyl-3(R)—(2-ethylindol-3-yl)-β-alanine;

2-Oxo-3(R)-[2-(5,6,7,8-tetrahydro[1,8]naphthyridin-2-yl)ethyl]pyrrolidin-1-yl)acetyl-3(R)—(2-ethylindol-3-yl)-β-alanine;

Ethyl 3-(2-{2-oxo-3(S)-[(5,6,7,8-tetrahydro-[1,8] naphthyridin-2-ylmethyl)-amino]-pyrrolidin-1-yl}-acetylamino)-3-(S)-pyridin-3-yl-propionic acid;

3-(2-{2-Oxo-3(S)-[(5,6,7,8-tetrahydro-[1,8]naphthyridin-2-ylmethyl)-amino]pyrrolidin-1-yl}-acetylamino)-3-(S)-pyridin-3-yl-propionic acid;

3-{2-[6-Oxo-1-(5,6,7,8-tetrahydro-[1,8]naphthyridin-2-ylmethyl)-hexahydro-(3aS, 6aS)pyrrolo[3,4-b]pyrrol-5-yl]-acetylamino}-3-(S)-pyridin-3-yl-propionic acid;

3-{2-[6-Oxo-1-(5,6,7,8-tetrahydro-[1,8]naphthyridin-2-ylmethyl)-hexahydro-(3aR, 6aR)pyrrolo[3,4-b]pyrrol-5-yl]-acetylamino}-3(S)-pyridin-3-yl-propionic acid;

2-Oxo-5(R)-methyl-3(S)-[2-(5,6,7,8-tetrahydro[1,8]-naphthyridin-2-yl)-ethyl]pyrrolidin-1-yl)acetyl-3(S)-ethynyl-β-alanine ethyl ester;

2-Oxo-5(R)-methyl-3(S)-[2-(5,6,7,8-tetrahydro[1,8]-naphthyridin-2-yl)ethyl]pyrrolidin-1-yl)acetyl-3(S)-ethynyl-β-alanine;

2-Oxo-5(S)-benzyl-3(S)-[2-(5,6,7,8-tetrahydro[1,8]-naphthyridin-2-yl)-ethyl]pyrrolidin-1-yl)acetyl-3(S)-pyridin-3-yl-β-alanine ethyl ester;

2-Oxo-5(S)-benzyl-3(S)-[2-(5,6,7,8-tetrahydro[1,8]-naphthyridin-2-yl)ethyl]pyrrolidin-1-yl)acetyl-3(S)-pyridin-3-yl-β-alanine;

5(R)-Methyl-2-oxo-3(S)-[2-(5,6,7,8-tetrahydro[1,8]-naphthyridin-2-ylmethyl)-amino]pyrrolidin-1-yl)acetyl-3(S)-ethynyl-β-alanine ethyl ester;

5(R)-Methyl-2-oxo-3(S)-[2-(5,6,7,8-tetrahydro[1,8]-naphthyridin-2-ylmethyl)-amino]pyrrolidin-1-yl)acetyl-3(S)-ethynyl-β-alanine;

3(S)—(2,3-Dihydro-benzofuran-6-yl)-3-(2-{2-oxo-3(S)-[2-(5,6,7,8-tetrahydro-[1,8]naphthyridin-2-yl)-ethyl]-pyrrolidin-1-yl}-acetylamino)-propionic acid ethyl ester; or 3(S)-(2,3-Dihydro-benzofuran-6-yl)-3-(2-{2-oxo-3(S)-[2-(5,6,7,8-tetrahydro-[1,8]naphthyridin-2-yl)-ethyl]-pyrrolidin-1-yl }-acetylamino)-propionic acid;

3-{2-(2-Oxo-3(S)-[2-(5,6,7,8-tetrahydro-[1,8] naphthyridin-2-yl)-ethyl]-pyrrolidin-1-yl)-acetylamino}-3(S)-quinolin-3-yl-propionic acid;

3-(2-(5(S)-Ethyl-2-oxo-3(S)-[2-(5,6,7,8-tetrahydro-[1,8] naphthyridin-2-yl)-ethyl]-pyrolidin-1-yl)-acetylamino)-3-(S)-quinolin-3-yl-propionic acid trifluoroacetate;

3-(2-{6-Methyl-2-oxo-3-[(5,6,7,8-tetrahydro-[1,8] naphthyridin-2-ylmethyl)-amino]-2H-pyridin-1-yl}-acetylamino)-3(S)-pyridin-3-yl-propionic acid bis trifluoroacetate; or 3-(2-{6-Methyl-2-oxo-3-[(5,6,7,8-tetrahydro-[1,8] napthyridin-2-ylmethyl)-amino]-2H-pyridin-1-yl}-acetylamino)-3(S)-pyridin-3-yl-propionic acid ethyl ester;

and the pharmaceutically acceptable salts thereof.

Preferably, the compound is selected from

2-Oxo-3-[2-(5,6,7,8-tetrahydro[1,8]-naphthyridin-2-yl)ethyl]piperin-1-yl-acetyl-3(S)-pyridin-3-yl-β-alanine trifluoroacetate;

2-Oxo-3(S)-[2-(5,6,7,8-tetrahydro[1,8]-naphthyridin-2-yl)ethyl]pyrrolidin-1-yl)acetyl-3(S)-ethynyl-β-alanine;

2-Oxo-3(S)-[2-(5,6,7,8-tetrahydro[1,8]-naphthyridin-2-yl)ethyl]pyrrolidin-1-yl)acetyl-3(S)-pyridin-3-yl-β-alanine;

2-Oxo-3(R)-[2-(5,6,7,8-tetrahydro[1,8]-naphthyridin-2-yl)ethyl]pyrrolidin-1-yl)acetyl-3(S)-ethynyl-β-alanine;

2-Oxo-3(R)-[2-(5,6,7,8-tetrahydro[1,8]-naphthyridin-2-yl)ethyl]pyrrolidin-1-yl)acetyl-3(S)-pyridin-3-yl-β-alanine;

2-Oxo-3-[2-(5,6,7,8-tetrahydro[1,8]naphthyridin-2-yl}ethyl]-imidazolidin-1-yl-acetyl-3-(S)-pyridin-3-yl-β-alanine;

2-Oxo-3-[2-(5,6,7,8-tetrahydro[1,8]naphthyridin-2-yl}ethyl]-tetrahydropyrimidin-1-yl-acetyl-3-(S)-pyridin-3-yl-β-alanine;

2-Oxo-3(R)-[2-(5,6,7,8-tetrahydro[1,8]naphthyridin-2-yl)ethyl]pyrrolidin-1-yl)acetyl-3(R)-(2-ethylindol-3-yl)-β-alanine;

3-(2-{-2-oxo-3(S)-[(5,6,7,8-tetrahydro-[1,8] naphthyridin-2-ylmethyl)-amino]pyrrolidin-1-yl}-acetylamino)-3-(S)-pyridin-3-yl-propionic acid;

3-{2-[6-Oxo-1-(5,6,7,8-tetrahydro-[1,8]naphthyridin-2-ylmethyl)-hexahydro-(3aS, 6aS)pyrrolo[3,4-b]pyrrol-5-yl]-acetylamino}-3-(S)-pyridin-3-yl-propionic acid;

3-{2-[6-Oxo-1-(5,6,7,8-tetrahydro-[1,8]naphthyridin-2-ylmethyl)-hexahydro-(3aR, 6aR)pyrrolo[3,4-b]pyrrol-5-yl]-acetylamino}-3-(S)-pyridin-3-yl-propionic acid;

2-Oxo-5(R)-methyl-3(S)-[2-(5,6,7,8-tetrahydro[1,8]-naphthyridin-2-yl)ethyl]pyrrolidin-1-yl)acetyl-3(S)-ethynyl-β-alanine;

2-Oxo-5(S)-benzyl-3(S)-[2-(5,6,7,8-tetrahydro[1,8]-naphthyridin-2-yl)ethyl]pyrrolidin-1-yl)acetyl-3(S)-pyridin-3-yl-β-alanine;

5(R)-Methyl-2-oxo-3(S)-[2-(5,6,7,9-tetrahydro[1,8]-naphthyridin-2-ylmethyl)-amino]pyrrolidin-1-yl)acetyl-3(S)-ethynyl-β-alanine; or 3(S)-(2,3-Dihydro-benzofuran-6-yl )-3-(2-{2-oxo-3(S)-[2-(5,6,7,8-tetrahydro-[1,8]naphthyridin-2-yl)-ethyl]-pyrrolidin-1-yl}-acetylamino)-propionic acid;

and the pharmaceutically acceptable salts thereof.

Exemplifying the invention is the method wherein the vitronectin receptor antagonizing effect is an αvβ3 antagonizing effect. An illustration of the invention is the method wherein the αvβ3 antagonizing effect is selected from inhibition of: bone resorption, restenosis, angiogenesis, diabetic retinopathy, macular degeneration, inflammation or tumor growth. Preferably, the αvβ3 antagonizing effect is the inhibition of bone resorption.

An example of the invention is the method wherein the vitronectin receptor antagonizing effect is an αvβ5 antagonizing effect. More specifically, the αvβ5 antagonizing effect is selected from inhibition of: restenosis, angiogenesis, diabetic retinopathy, macular degeneration, inflammation or tumor growth.

Illustrating the invention is the method wherein the vitronectin receptor antagonizing effect is a dual αvβ3/αvβ5 antagonizing effect. More particularly, the dual αvβ3/αvβ5 antagonizing effect is selected from inhibition of: bone resorption, restenosis, angiogenesis, diabetic retinopathy, macular degeneration, inflammation or tumor growth.

In a second embodiment of the present invention is a method of eliciting an αvβ3 antagonizing effect in a mammal in need thereof, comprising administering to the mammal a therapeutically effective amount of a compound of the formula

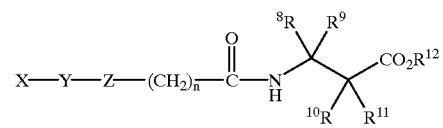

wherein X is selected from

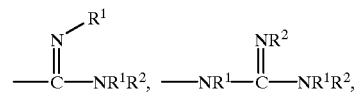

a 5- or 6-membered monocyclic aromatic or nonaromatic ring system containing 0, 1, 2, 3 or 4 heteroatoms selected from N, O or S wherein the 5- or 6-membered ring system is either unsubstituted or substituted on a carbon atom with $R^1$ and $R^2$, or a 9- to 10-membered polycyclic ring system, wherein one or more of the rings is aromatic, and wherein the polycyclic ring system contains 0, 1, 2, 3 or 4 heteroatoms selected from N, O or S, and wherein the polycyclic ring system is either unsubstituted or substituted on a carbon atom with $R^1$ and $R^2$;

Y is selected from

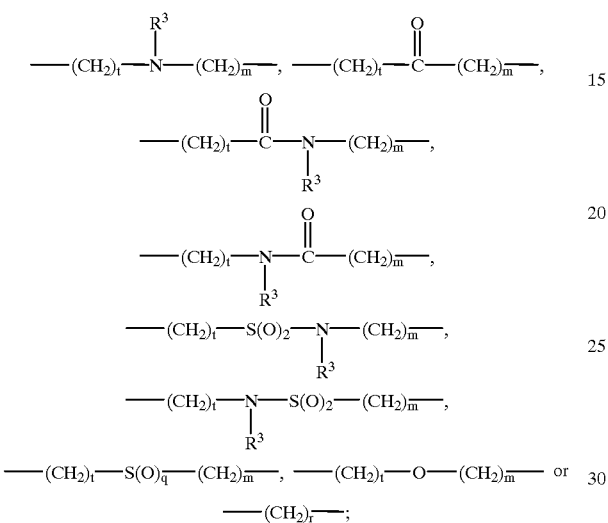

Z is a 5–11 membered aromatic or nonaromatic mono- or polycyclic ring system containing 0 to 6 double bonds, and containing 0 to 6 heteroatoms chosen from N, O and S, and wherein the ring system is either unsubstituted or substituted on a carbon or nitrogen atom with one or more groups independently selected from $R^4$, $R^5$, $R^6$ and $R^7$; provided that Z is not a 6-membered monocyclic aromatic ring system; preferably, Z is selected from

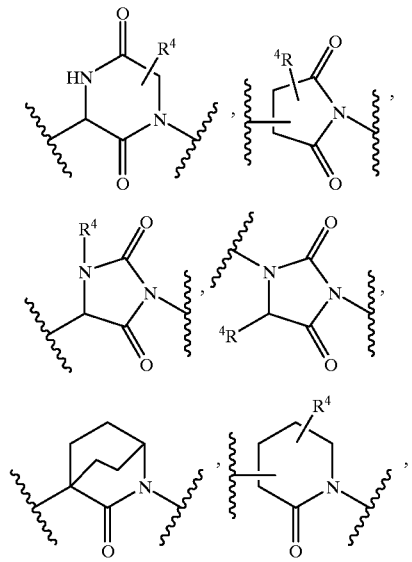

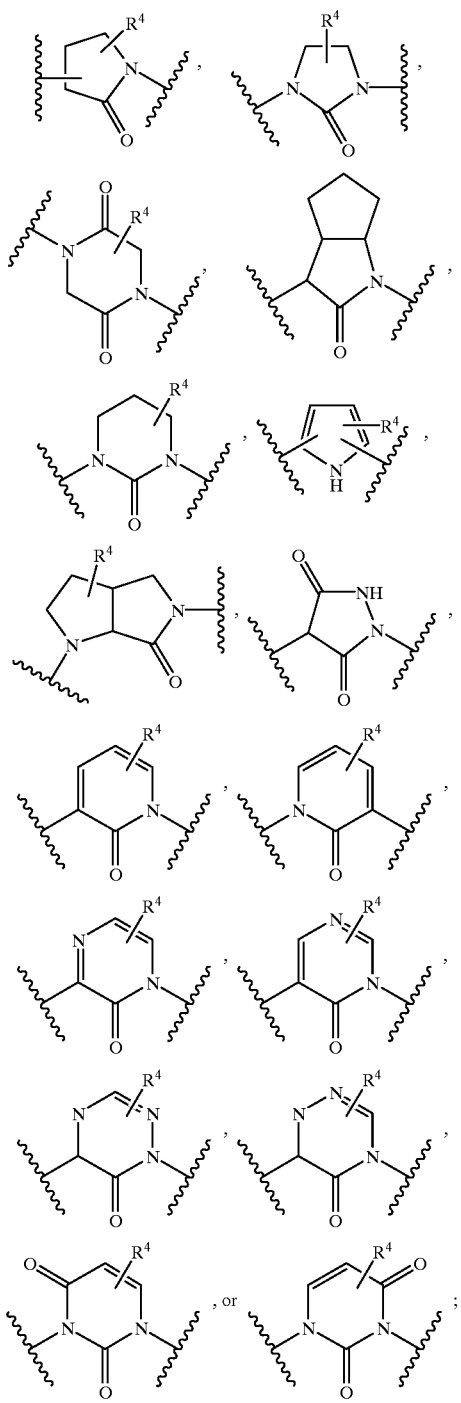

$R^1$, $R^2$, $R^3$, $R^4$, $R^5$, $R^{13}$ and $R^{14}$ are each independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino-$C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy or hydroxy $C_{1-6}$ alkyl;

$R^6$, $R^7$, $R^8$, $R^9$, $R^{10}$ and $R^{11}$ are each independently selected from hydrogen,
aryl,
—(CH$_2$)$_p$-aryl,
halogen,
hydroxyl,
C$_{1-8}$ alkylcarbonylamino,
aryl C$_{1-5}$ alkoxy,
C$_{1-5}$ alkoxycarbonyl,
aminocarbonyl,
C$_{1-8}$ alkylaminocarbonyl,
C$_{1-6}$ alkylcarbonyloxy,
C$_{3-8}$ cycloalkyl,
oxo,
amino,
C$_{1-6}$ alkylamino,
amino C$_{1-6}$ alkyl,
arylaminocarbonyl,
aryl C$_{1-5}$ alkylaminocarbonyl,
aminocarbonyl,
aminocarbonyl C$_{1-6}$ alkyl,
hydroxycarbonyl,
hydroxycarbonyl C$_{1-6}$ alkyl,
C$_{1-8}$ alkyl, either unsubstituted or substituted, with one or more groups selected from: halogen, hydroxyl, C$_{1-5}$ alkylcarbonylamino, aryl C$_{1-5}$ alkoxy, C$_{1-5}$ alkoxycarbonyl, aminocarbonyl, C$_{1-5}$ alkylaminocarbonyl, C$_{1-5}$ alkylcarbonyloxy, C$_{3-8}$ cycloalkyl, oxo, amino, C$_{1-3}$ alkylamino, amino C$_{1-3}$ alkyl, arylaminocarbonyl, aryl C$_{1-5}$ alkylaminocarbonyl, aminocarbonyl, aminocarbonyl C$_{1-4}$ alkyl, hydroxycarbonyl, or hydroxycarbonyl C$_{1-5}$ alkyl,
—(CH$_2$)$_s$ C≡CH,
—(CH$_2$)$_s$ C≡C-C$_{1-6}$ alkyl,
—(CH$_2$)$_s$ C≡C-C$_{3-7}$ cycloalkyl,
—(CH$_2$)$_s$ C≡C-aryl,
—(CH$_2$)$_s$ C≡C-C$_{1-6}$ alkylaryl,
—(CH$_2$)$_s$ CH=CH$_2$,
—(CH$_2$)$_s$ CH=CH C$_{1-6}$ alkyl,
—(CH$_2$)$_s$ CH=CH-C$_{3-7}$ cycloalkyl,
—(CH$_2$)$_s$ CH=CH aryl,
—(CH$_2$)$_s$ CH=CH C$_{1-6}$ alkylaryl,
—(CH$_2$)$_s$ SO$_2$C$_{1-6}$ alkyl,
—(CH$_2$)$_s$ SO$_2$C$_{1-6}$ alkylaryl,
C$_{1-6}$ alkoxy,
aryl C$_{1-6}$ alkoxy,
aryl C$_{1-6}$ alkyl,
C$_{1-6}$ alkylamino C$_{1-6}$ alkyl,
arylamino,
arylamino C$_{1-6}$ alkyl,
aryl C$_{1-6}$ alkylamino,
aryl C$_{1-6}$ alkylamino C$_{1-6}$ alkyl,
arylcarbonyloxy,
aryl C$_{1-6}$ alkylcarbonyloxy,
C$_{1-6}$ dialkylamino,
C$_{1-6}$ dialkylamino C$_{1-6}$ alkyl,
C$_{1-6}$ alkylaminocarbonyloxy,
C$_{1-8}$ alkylsulfonylamino,
C$_{1-8}$ alkylsulfonylamino C$_{1-6}$ alkyl,
arylsulfonylamino C$_{1-6}$ alkyl,
aryl C$_{1-6}$ alkylsulfonylamino,
aryl C$_{1-6}$ alkylsulfonylamino C$_{1-6}$ alkyl,
C$_{1-8}$ alkoxycarbonylamino,
C$_{1-8}$ alkoxycarbonylamino C$_{1-8}$ alkyl,
aryloxycarbonylamino C$_{1-8}$ alkyl,
aryl C$_{1-8}$ alkoxycarbonylamino,
aryl C$_{1-8}$ alkoxycarbonylamino C$_{1-8}$ alkyl,
C$_{1-8}$ alkylcarbonylamino,
C$_{1-8}$ alkylcarbonylamino C$_{1-6}$ alkyl,
arylcarbonylamino C$_{1-6}$ alkyl,
aryl C$_{1-6}$ alkylcarbonylamino,
aryl C$_{1-6}$ alkylcarbonylamino C$_{1-6}$ alkyl,
aminocarbonylamino C$_{1-6}$ alkyl,
C$_{1-8}$ alkylaminocarbonylamino,
C$_{1-8}$ alkylaminocarbonylamino C$_{1-6}$ alkyl,
arylaminocarbonylamino C$_{1-6}$ alkyl,
aryl C$_{1-8}$ alkylaminocarbonylamino,
aryl C$_{1-8}$ alkylaminocarbonylamino C$_{1-6}$ alkyl,
aminosulfonylamino C$_{1-6}$ alkyl,
C$_{1-8}$ alkylaminosulfonylamino,
C$_{1-8}$ alkylaminosulfonylamino C$_{1-6}$ alkyl,
arylaminosulfonylamino C$_{1-6}$ alkyl,
aryl C$_{1-8}$ alkylaminosulfonylamino,
aryl C$_{1-8}$ alkylaminosulfonylamino C$_{1-6}$ alkyl,
C$_{1-6}$ alkylsulfonyl,
C$_{1-6}$ alkylsulfonyl C$_{1-6}$ alkyl,
arylsulfonyl C$_{1-6}$ alkyl,
aryl C$_{1-6}$ alkylsulfonyl,
aryl C$_{1-6}$ alkylsulfonyl C$_{1-6}$ alkyl,
C$_{1-6}$ alkylcarbonyl,
C$_{1-6}$ alkylcarbonyl C$_{1-6}$ alkyl,
arylcarbonyl C$_{1-6}$ alkyl,
aryl C$_{1-6}$ alkylcarbonyl,
aryl C$_{1-6}$ alkylcarbonyl C$_{1-6}$ alkyl,
C$_{1-6}$ alkylthiocarbonylamino,
C$_{1-6}$ alkylthiocarbonylamino C$_{1-6}$ alkyl,
arylthiocarbonylamino C$_{1-6}$ alkyl,
aryl C$_{1-6}$ alkylthiocarbonylamino,
aryl C$_{1-6}$ alkylthiocarbonylamino C$_{1-6}$ alkyl,
C$_{1-8}$ alkylaminocarbonyl C$_{1-6}$ alkyl,
arylaminocarbonyl C$_{1-6}$ alkyl,
aryl C$_{1-8}$ alkylaminocarbonyl, or
aryl C$_{1-8}$ alkylaminocarbonyl C$_{1-6}$ alkyl,
wherein any of the alkyl groups may be unsubstituted or substituted with R$^{13}$ and R$^{14}$; and provided that the carbon atom to which R$^8$ and R$^9$ are attached is itself attached to no more than one heteroatom; and provided further that the carbon atom to which R$^{10}$ and R$^{11}$ are attached is itself attached to no more than one heteroatom;
R$^{12}$ is selected from
hydrogen,
C$_{1-8}$ alkyl,
aryl,
aryl C$_{1-8}$ alkyl,
hydroxy,
C$_{1-8}$ alkoxy,
aryloxy,
aryl C$_{1-6}$ alkoxy,
C$_{1-8}$ alkylcarbonyloxy C$_{1-4}$ alkoxy,
aryl C$_{1-8}$ alkylcarbonyloxy C$_{1-4}$ alkoxy,
C$_{1-8}$ alkylaminocarbonylmethyleneoxy, or
C$_{1-8}$ dialkylaminocarbonylmethyleneoxy;
m is an integer from 0 to 3;
n is an integer from 1 to 3;
p is an integer from 1 to 4;
q is an integer from 0 to 2;
r is an integer from 0 to 6;
s is an integer from 0 to 3; and
t is an integer from 0 to 3;
and the pharmaceutically acceptable salts thereof.

In a third embodiment of the invention is a method of eliciting an αvβ3 antagonizing effect in a mammal in need thereof, comprising administering to the mammal a therapeutically effective amount of a compound of the formula

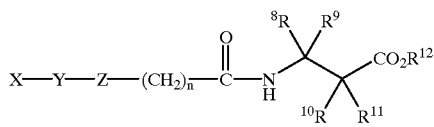

wherein X is selected from

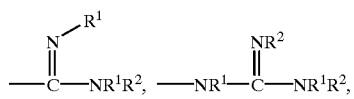

a 5- or 6-membered monocyclic aromatic or nonaromatic ring system containing 0, 1, 2, 3 or 4 heteroatoms selected from N, O or S wherein the 5- or 6-membered ring system is either unsubstituted or substituted on a carbon atom with $R^1$ and $R^2$, or a 9- to 10-membered polycyclic ring system, wherein one or more of the rings is aromatic, and wherein the polycyclic ring system contains 0, 1, 2, 3 or 4 heteroatoms selected from N, O or S, and wherein the polycyclic ring system is either unsubstituted or substituted on a carbon atom with $R^1$ and $R^2$;

Y is selected from

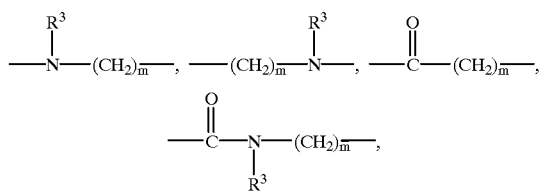

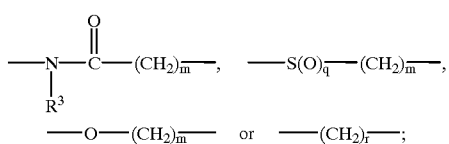

Z is
a 5–11 membered aromatic or nonaromatic mono- or polycyclic ring system containing 0 to 6 double bonds, and containing 0 to 6 heteroatoms chosen from N, O and S, and wherein the ring system is either unsubstituted or substituted on a carbon or nitrogen atom with one or more groups independently selected from $R^4$, $R^5$, $R^6$ and $R^7$; provided that Z is not a 6-membered monocyclic aromatic ring system; preferably Z is selected from

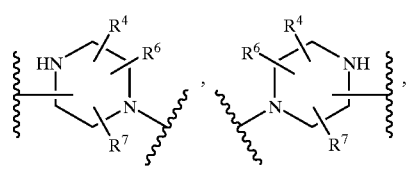

-continued

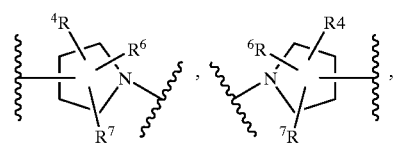

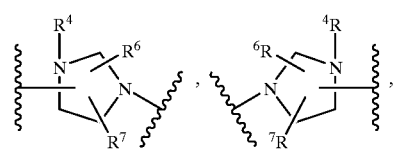

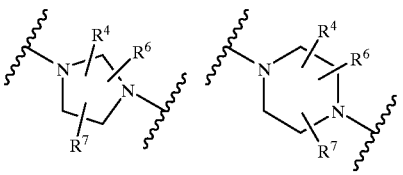

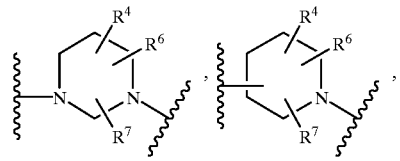

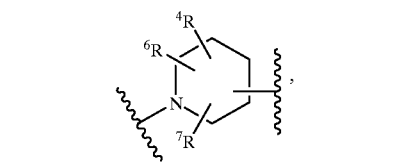

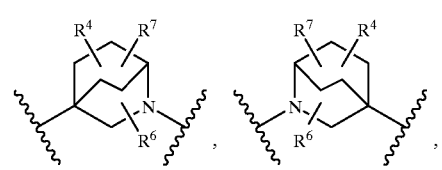

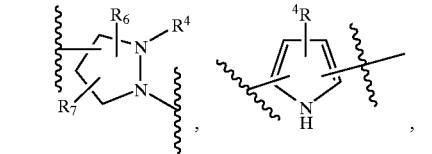

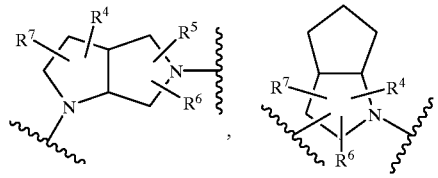

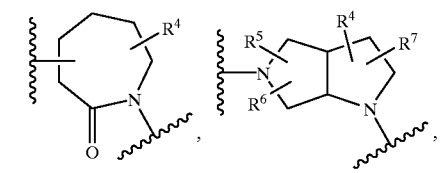

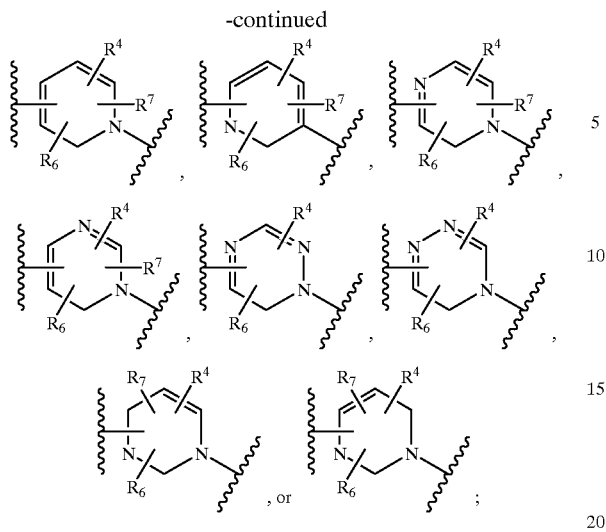

$R^1$, $R^2$, $R^4$, $R^5$, $R^{13}$ and $R^{14}$ are each independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino-$C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl-S(O)$_q$, $C_{1-8}$ aminocarbonyl, $C_{1-8}$ dialkylaminocarbonyl, $C_{1-8}$ alkyloxycarbonylamino, $C_{1-8}$ alkylaminocarbonyloxy or $C_{1-8}$ alkylsulfonylamino;

$R^3$ is selected from
hydrogen,
aryl,
—(CH$_2$)$_p$-aryl,
hydroxyl,
$C_{1-5}$ alkoxycarbonyl,
aminocarbonyl,
$C_{3-8}$ cycloalkyl,
amino $C_{1-6}$ alkyl,
arylaminocarbonyl,
aryl $C_{1-5}$ alkylaminocarbonyl,
hydroxycarbonyl $C_{1-6}$ alkyl,
$C_{1-8}$ alkyl,
aryl $C_{1-6}$ alkyl,
$C_{1-6}$ alkylamino $C_{1-6}$ alkyl,
aryl $C_{1-6}$ alkylamino $C_{1-6}$ alkyl,
$C_{1-6}$ dialkylamino $C_{1-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$C_{1-8}$ alkylaminocarbonyl,
aminosulfonyl,
$C_{1-8}$ alkylaminosulfonyl,
arylaminosulfonylamino,
aryl $C_{1-8}$ alkylaminosulfonyl,
$C_{1-6}$ alkylsulfonyl,
arylsulfonyl,
aryl $C_{1-6}$ alkylsulfonyl,
aryl $C_{1-6}$ alkylcarbonyl,
$C_{1-6}$ alkylthiocarbonyl,
arylthiocarbonyl, or
aryl $C_{1-6}$ alkylthiocarbonyl,
wherein any of the alkyl groups may be unsubstituted or substituted with $R^{13}$ and $R^{14}$;

$R^6$, $R^7$, $R^8$, $R^9$, $R^{10}$ and $R^{11}$ are each independently selected from
hydrogen,
aryl,
—(CH$_2$)$_p$-aryl,
halogen,
hydroxyl,
$C_{1-8}$ alkylcarbonylamino,
aryl $C_{1-5}$ alkoxy,
$C_{1-5}$ alkoxycarbonyl,
aminocarbonyl,
$C_{1-8}$ alkylaminocarbonyl,
$C_{16}$ alkylcarbonyloxy,
$C_{3-8}$ cycloalkyl,
oxo,
amino,
$C_{1-6}$ alkylamino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
$C_{1-8}$ alkyl, either unsubstituted or substituted, with one or more groups selected from: halogen, hydroxyl, $C_{1-5}$ alkylcarbonylamino, aryl $C_{1-5}$ alkoxy, $C_{1-5}$ alkoxycarbonyl, aminocarbonyl, $C_{1-5}$ alkylaminocarbonyl, $C_{1-5}$ alkylcarbonyloxy, $C_{3-8}$ cycloalkyl, oxo, amino, $C_{1-3}$ alkylamino, amino $C_{1-3}$ alkyl, arylaminocarbonyl, aryl $C_{1-5}$ alkylaminocarbonyl, aminocarbonyl, aminocarbonyl $C_{1-4}$ alkyl, hydroxycarbonyl, or hydroxycarbonyl $C_{1-5}$ alkyl,
—(CH$_2$)$_s$ C≡CH,
—(CH$_2$)$_s$ C≡C-$C_{1-6}$ alkyl,
—(CH$_2$)$_s$ C≡C-$C_{3-7}$ cycloalkyl,
—(CH$_2$)$_s$ C≡C-aryl,
—(CH$_2$)$_s$ C≡C-$C_{1-6}$ alkylaryl,
—(CH$_2$)$_s$ CH=CH$_2$,
—(CH$_2$)$_s$ CH=CH $C_{1-6}$ alkyl,
—(CH$_2$)$_s$ CH=CH-$C_{3-7}$ cycloalkyl,
—(CH$_2$)$_s$ CH=CH aryl,
—(CH$_2$)$_s$ CH=CH $C_{1-6}$ alkylaryl,
—(CH$_2$)$_s$ SO$_2$$C_{1-6}$ alkyl,
—(CH$_2$)$_s$ SO$_2$$C_{1-6}$ alkylaryl,
$C_{1-6}$ alkoxy,
aryl $C_{1-6}$ alkoxy,
aryl $C_{1-6}$ alkyl,
$C_{1-6}$ alkylamino $C_{1-6}$ alkyl,
arylamino,
arylamino $C_{1-6}$ alkyl,
aryl $C_{1-6}$ alkylamino,
aryl $C_{1-6}$ alkylamino $C_{1-6}$ alkyl,
arylcarbonyloxy,
aryl $C_{1-6}$ alkylcarbonyloxy,
$C_{1-6}$ dialkylamino,
$C_{1-6}$ dialkylamino $C_{1-6}$ alkyl,
$C_{1-6}$ alkylaminocarbonyloxy,
$C_{1-8}$ alkylsulfonylamino, $C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$C_{1-8}$ alkylaminocarbonylamino,
$C_{1-8}$ alkylaminocarbonylamino $C_{1-6}$ alkyl,
arylaminocarbonylamino $C_{1-6}$ alkyl,
aryl $C_{1-8}$ alkylaminocarbonylamino,
aryl $C_{1-8}$ alkylaminocarbonylamino $C_{1-6}$ alkyl,
aminosulfonylamino $C_{1-6}$ alkyl,
$C_{1-8}$ alkylaminosulfonylamino,
$C_{1-8}$ alkylaminosulfonylamino $C_{1-6}$ alkyl,
arylaminosulfonylamino $C_{1-6}$ alkyl,
aryl $C_{1-8}$ alkylaminosulfonylamino,
aryl $C_{1-8}$ alkylaminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$C_{1-8}$ alkylaminocarbonyl $C_{1-6}$ alkyl,
arylaminocarbonyl $C_{1-6}$ alkyl,
aryl $C_{1-8}$ alkylaminocarbonyl, or
aryl $C_{1-8}$ alkylaminocarbonyl $C_{1-6}$ alkyl,
wherein any of the alkyl groups may be unsubstituted or substituted with $R^{13}$ and $R^{14}$; and provided that the carbon atom to which $R^8$ and $R^9$ are attached is itself attached to no more than one heteroatom; and provided further that the carbon atom to which $R^{10}$ and $R^{11}$ are attached is itself attached to no more than one heteroatom;

$R^{12}$ is selected from
hydrogen,
$C_{1-8}$ alkyl,
aryl,
aryl $C_{1-8}$ alkyl,
hydroxy,
$C_{1-8}$ alkoxy,
aryloxy,
aryl $C_{1-6}$ alkoxy,
$C_{1-8}$ alkylcarbonyloxy $C_{1-4}$ alkoxy,
aryl $C_{1-8}$ alkylcarbonyloxy $C_{1-4}$ alkoxy,
$C_{1-8}$ alkylaminocarbonylmethyleneoxy, or
$C_{1-8}$ dialkylaminocarbonylmethyleneoxy;

m is an integer from 0 to 3;
n is an integer from 1 to 3;
p is an integer from 1 to 4;
q is an integer from 0 to 2;
r is an integer from 0 to 6; and
s is an integer from 0 to 3;
and the pharmaceutically acceptable salts thereof.

Illustrating the invention is the method wherein the αvβ3 antagonizing effect is selected from inhibition of bone resorption, inhibition of restenosis, inhibition of angiogenesis, inhibition of diabetic retinopathy, inhibition of macular degeneration, inhibition of atherosclerosis, inflammation or inhibition of tumor growth. Preferably, the αvβ3 antagonizing effect is the inhibition of bone resorption.

An illustration of the invention is a compound of the formula

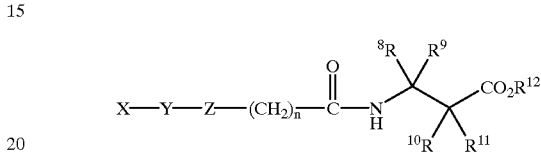

wherein X is
a 9- to 10-membered polycyclic ring system, wherein one or more of the rings is aromatic, and wherein the polycyclic ring system contains 0, 1, 2, 3 or 4 heteroatoms selected from N, O or S, and wherein the polycyclic ring system is either unsubstituted or substituted on a carbon or nitrogen atom with one or more groups chosen from $R^1$, $R^2$, $R^{15}$ or $R^{16}$;

Y is selected from

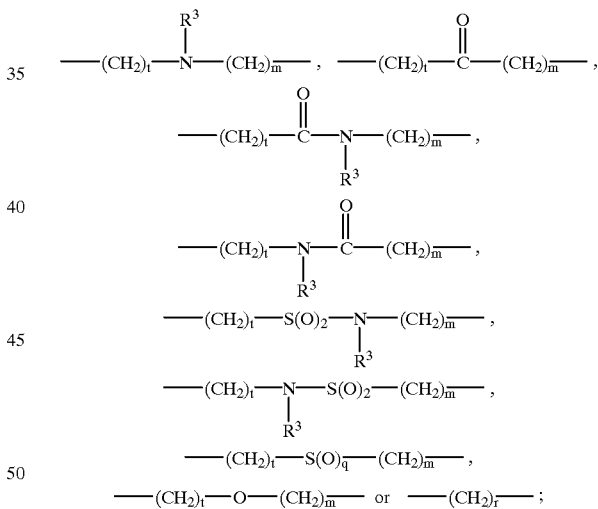

Z is
a 5–11 membered aromatic or nonaromatic mono- or polycyclic ring system containing 0 to 6 double bonds, and containing 0 to 6 heteroatoms chosen from N, O and S, and wherein the ring system is either unsubstituted or substituted on a carbon or nitrogen atom with one or more groups independently selected from $R^4$, $R^5$, $R^6$ and $R^7$; provided that Z is not a 6-membered monocyclic aromatic ring system, an isoxazoline ring or an isoxazole ring;

$R^1$, $R^2$, $R^4$, $R^5$, $R^{13}$, $R^{14}$, $R^{15}$ and $R^{16}$ are each independently selected from
hydrogen, halogen, $C_{1-10}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $(C_{1-6}$ alkyl$)_q$amino, $(C_{1-6}$ alkyl$)_q$ amino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl-$S(O)_q$, $(C_{1-8}$ alkyl$)_q$ aminocarbonyl, $C_{1-8}$ alkyloxycarbonylamino, $(C_{1-8}$ alkyl$)_q$aminocarbonyloxy, oxo, (aryl $C_{1-8}$ alkyl$)_q$ amino, (aryl$)_q$amino, aryl $C_{1-8}$ alkylslfonylamino or $C_{1-8}$ alkylsulfonylamino;

$R^3$ is selected from
hydrogen,
aryl,
aryl-$(CH_2)_p$—,
hydroxyl,
$C_{1-5}$ alkoxy,
aminocarbonyl,
$C_{3-8}$ cycloalkyl,
amino $C_{1-6}$ alkyl,
(aryl$)_q$aminocarbonyl,
(aryl $C_{1-5}$ alkyl$)_q$aminocarbonyl,
hydroxycarbonyl $C_{1-6}$ alkyl,
$C_{1-8}$ alkyl,
aryl $C_{1-6}$ alkyl,
$(C_{1-6}$ alkyl$)_q$amino $C_{1-6}$ alkyl,
(aryl $C_{1-6}$ alkyl$)_q$amino $C_{1-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}$ alkyl$)_q$aminocarbonyl,
aminosulfonyl,
$C_{1-8}$ alkylaminosulfonyl,
(aryl$)_q$aminosulfonylamino,
(aryl $C_{1-8}$ alkyl$)_q$aminosulfonyl,
$C_{1-6}$ alkylsulfonyl,
arylsulfonyl,
aryl $C_{1-6}$ alkylsulfonyl,
aryl $C_{1-6}$ alkylcarbonyl,
$C_{1-6}$ alkylthiocarbonyl,
arylthiocarbonyl, or
aryl $C_{1-6}$ alkylthiocarbonyl,
wherein any of the alkyl groups may be unsubstituted or substituted with $R^{13}$ and $R^{14}$;

$R^6$, $R^7$, $R^8$, $R^9$, $R^{10}$ and $R^{11}$ are each independently selected from
hydrogen,
aryl,
aryl-$(CH_2)_p$—,
aryl-$(CH_2)_n$—O—$(CH_2)_m$—,
aryl-$(CH_2)_n$—$S(O)_q$—$(CH_2)_m$—,
aryl-$(CH_2)_n$—C(O)—$(CH_2)_m$—,
aryl-$(CH_2)_n$—C(O)—N($R^3$)—$(CH_2)_m$—,
aryl-$(CH_2)_n$—N($R^3$)—C(O)—$(CH_2)_m$—,
aryl-$(CH_2)_n$—N($R^3$)—$(CH_2)_m$—,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_q$aminocarbonyl,
$C_{1-6}$ alkylcarbonyloxy,
$C_{3-8}$ cycloalkyl,
oxo,
$(C_{1-6}$ alkyl$)_q$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
$C_{1-8}$ alkyl, either unsubstituted or substituted, with one or more groups selected from: halogen, hydroxyl, $C_{1-5}$ alkylcarbonylamino, aryl $C_{1-5}$ alkoxy, $C_{1-5}$ alkoxycarbonyl, aminocarbonyl, $(C_{1-5}$ alkyl$)_q$ aminocarbonyl, $C_{1-5}$ alkylcarbonyloxy, $C_{3-8}$ cycloalkyl, oxo, $(C_{1-3}$ alkyl$)_q$amino, amino $C_{1-3}$ alkyl, (aryl$)_q$aminocarbonyl, (aryl $C_{1-5}$ alkyl$)_q$ aminocarbonyl, aminocarbonyl, aminocarbonyl $C_{1-4}$ alkyl, hydroxycarbonyl or hydroxycarbonyl $C_{1-5}$ alkyl,
$CH\equiv C$—$(CH_2)_s$—,
$C_{1-6}$ alkyl-$C\equiv C$—$(CH_2)_s$—,
$C_{3-7}$ cycloalkyl-$C\equiv C$—$(CH_2)_s$—,
aryl-$C\equiv C$—$(CH_2)_s$—,
$C_{1-6}$ alkylaryl-$C\equiv C$—$(CH_2)_s$—,
$CH_2$=$CH$—$(CH_2)_s$—,
$C_{1-6}$ alkyl-$CH$=$CH$—$(CH_2)_s$—,
$C_{3-7}$ cycloalkyl-$CH$=$CH$—$(CH_2)_s$—,
aryl-$CH$=$CH$—$(CH_2)_s$—,
$C_{1-6}$ alkylaryl-$CH$=$CH$—$(CH_2)_s$—,
$C_{1-6}$ alkyl-$SO_2$—$(CH_2)_s$—,
$C_{1-6}$ alkylaryl-$SO_2$—$(CH_2)_s$—,
$C_{1-6}$ alkoxy,
aryl $C_{1-6}$ alkoxy,
aryl $C_{1-6}$ alkyl,
$(C_{1-6}$ alkyl$)_q$amino $C_{1-6}$ alkyl,
(aryl$)_q$amino,
(aryl$)_q$amino $C_{1-6}$ alkyl,
(aryl $C_{1-6}$ alkyl$)_q$amino,
(aryl $C_{1-6}$ alkyl$)_q$amino $C_{1-6}$ alkyl,
arylcarbonyloxy,
aryl $C_{1-6}$ alkylcarbonyloxy,
$(C_{1-6}$ alkyl$)_q$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_q$aminocarbonylamino,
$(C_{1-8}$ alkyl$)_q$aminocarbonylamino $C_{1-6}$ alkyl,
(aryl$)_q$aminocarbonylamino $C_{1-6}$ alkyl,
(aryl $C_{1-8}$ alkyl$)_q$aminocarbonylamino,
(aryl $C_{1-8}$ alkyl$)_q$aminocarbonylamino $C_{1-6}$ alkyl, aminosulfonylamino $C_{1-6}$ alkyl,
$(C_{1-8}$ alkyl$)_q$aminosulfonylamino,
$(C_{1-8}$ alkyl$)_q$aminosulfonylamino $C_{1-6}$ alkyl,
(aryl$)_q$aminosulfonylamino $C_{1-6}$ alkyl,
(aryl $C_{1-8}$ alkyl$)_q$aminosulfonylamino,
(aryl $C_{1-8}$ alkyl$)_q$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_q$aminocarbonyl $C_{1-6}$ alkyl,
(aryl$)_q$aminocarbonyl $C_{1-6}$ alkyl,
(aryl $C_{1-8}$ alkyl$)_q$aminocarbonyl, or
(aryl $C_{1-8}$ alkyl$)_q$aminocarbonyl $C_{1-6}$ alkyl,
wherein any of the alkyl groups may be unsubstituted or substituted with $R^{13}$ and $R^{14}$; and provided that the carbon atom to which $R^8$ and $R^9$ are attached is itself attached to no more than one heteroatom; and provided further that the carbon atom to which $R^{10}$ and $R^{11}$ are attached is itself attached to no more than one heteroatom;

$R^{12}$ is selected from
hydrogen,
$C_{1-8}$ alkyl,
aryl,
aryl $C_{1-8}$ alkyl,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, or
$C_{1-8}$ dialkylaminocarbonylmethylene;

m, s and t are each independently an integer from 0 to 3;
n is an integer from 1 to 3;
p is an integer from 1 to 4;
q is an integer from 0 to 2;
r is an integer from 0 to 6;
and the pharmaceutically acceptable salts thereof.

Particularly illustrative of the invention is the compound wherein Z is a 5–11 membered nonaromatic mono- or polycyclic ring system containing 0 to 6 double bonds, and containing 0 to 6 heteroatoms chosen from N, O and S, and wherein the ring system is either unsubstituted or substituted on a carbon or nitrogen atom with one or more groups independently selected from $R^4$, $R^5$, $R^6$ and $R^7$; and all other variables are as defined above.

Exemplifying the invention is the compound wherein Z is selected from

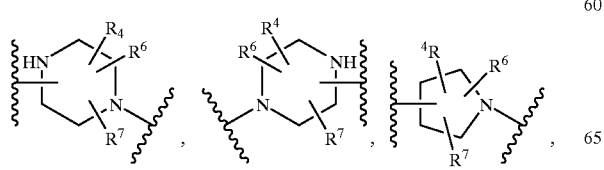

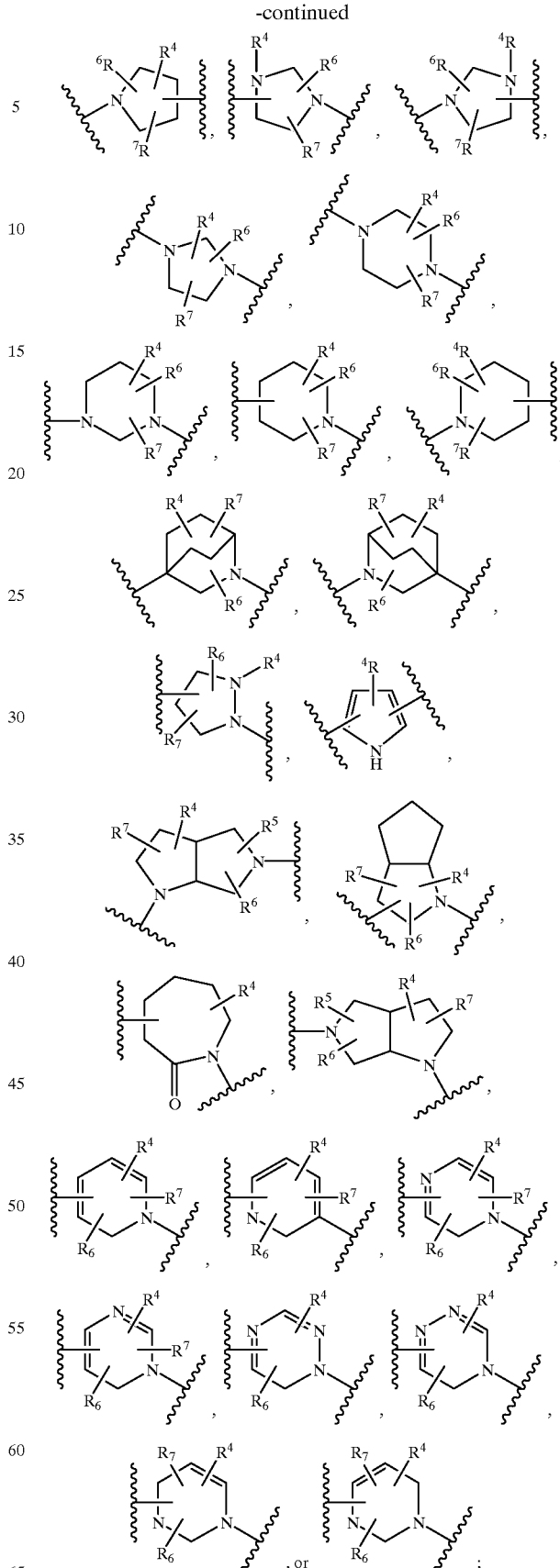

and the pharmaceutically acceptable salts thereof. Preferably Z is selected from

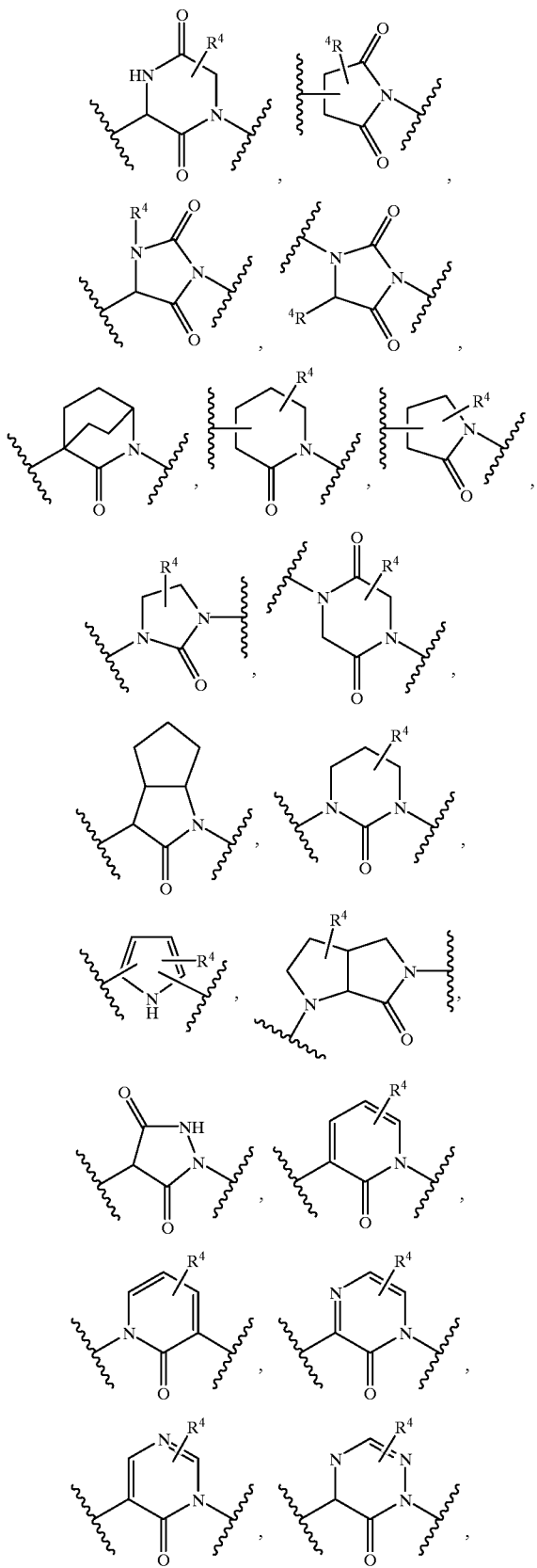

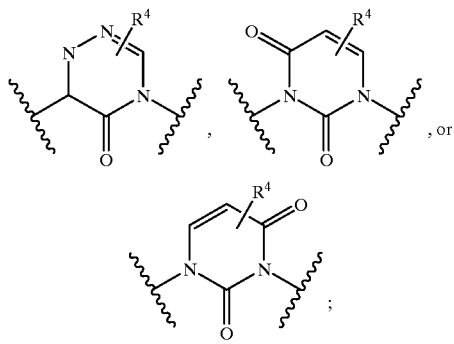

An example of the invention is the compound of the formula

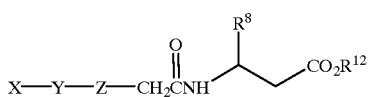

wherein X is selected from

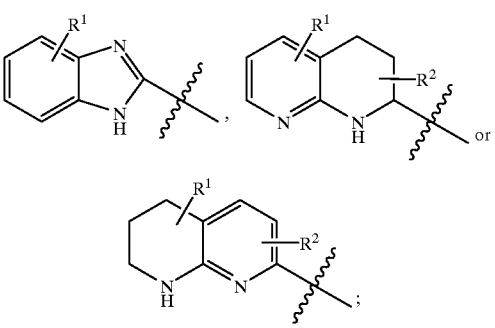

Y is selected from —(CH$_2$)$_r$— or —(CH$_2$)$_m$—NR$^3$—(CH$_2$)$_t$—;

R$^3$ is selected from
  hydrogen,
  aryl-(CH$_2$)$_p$—,
  C$_{1-5}$ alkoxycarbonyl,
  C$_{3-8}$ cycloalkyl,
  (aryl)$_q$aminocarbonyl,
  (aryl C$_{1-5}$ alkyl)$_q$aminocarbonyl,
  C$_{1-8}$ alkyl,
  aryl C$_{1-6}$ alkyl,
  C$_{1-8}$ alkylsulfonyl,
  arylsulfonyl,
  aryl C$_{1-6}$ alkylsulfonyl,
  C$_{1-8}$ alkoxycarbonyl,
  aryloxycarbonyl,
  aryl C$_{1-8}$ alkoxycarbonyl,
  C$_{1-8}$ alkylcarbonyl,
  arylcarbonyl,
  aryl C$_{1-6}$ alkylcarbonyl,
  (C$_{1-8}$ alkyl)$_q$aminocarbonyl,
  C$_{1-6}$ alkylsulfonyl, or
  aryl C$_{1-6}$ alkylcarbonyl,
  wherein any of the alkyl groups may be unsubstituted or substituted with R$^{13}$ and R$^{14}$;

R$^4$ is selected from
  hydrogen, C$_{1-6}$ alkyl, C$_{3-8}$ cycloalkyl, C$_{3-8}$ cycloheteroalkyl, C$_{3-8}$ cycloalkyl C$_{1-6}$ alkyl, C$_{3-8}$ cycloheteroalkyl C$_{1-6}$ alkyl, aryl or aryl C$_{1-8}$ alkyl, $R^8$ is selected from
hydrogen,
aryl,
aryl-$(CH_2)_p$—,
$CH\equiv C$—$(CH_2)_s$—,
$C_{1-6}$ alkyl-$C\equiv C$—$(CH_2)_s$—,
$C_{3-7}$ cycloalkyl-$C\equiv C$—$(CH_2)_s$—,
aryl-$C\equiv C$—$(CH_2)_s$—,
$C_{1-6}$ alkylaryl-$C\equiv C$—$(CH_2)_s$—,
$CH_2=CH$—$(CH_2)_s$—,
$C_{1-6}$ alkyl-$CH=CH$—$(CH_2)_s$—,
$C_{3-7}$ cycloalkyl-$CH=CH$—$(CH_2)_s$—,
aryl-$CH=CH$—$(CH_2)_s$—,
$C_{1-6}$ alkylaryl-$CH=CH$—$(CH_2)_s$—,
$C_{1-6}$ alkyl-$SO_2$—$(CH_2)_s$—,
$C_{1-6}$ alkylaryl-$SO_2$—$(CH_2)_s$—; and
r is an integer from 0 to 3;
wherein all other variables are as defined above; and the pharmaceutically acceptable salts thereof.

Further illustrating the invention is the compound of the formula

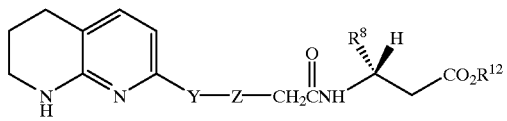

wherein Z is selected from

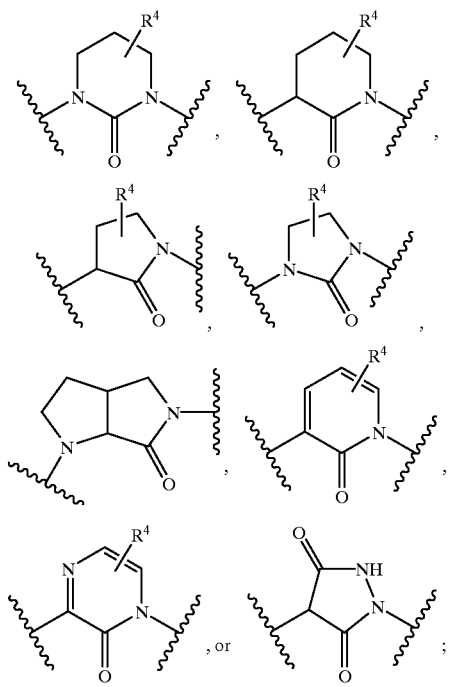

$R^8$ is selected from
hydrogen,

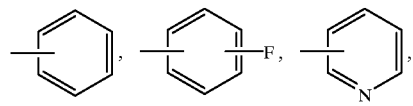

indolyl-$(CH_2)_p$—,
$CH\equiv C$—$(CH_2)_s$—,
$C_{1-6}$ alkyl-$C\equiv C$—$(CH_2)_s$—,
$C_{3-7}$ cycloalkyl-$C\equiv C$—$(CH_2)_s$—,
aryl-$C\equiv C$—$(CH_2)_s$—,
$C_{1-6}$ alkylaryl-$C\equiv C$—$(CH_2)_s$—,
$CH_2=CH$—$(CH_2)_s$—,
$C_{1-6}$ alkyl-$CH=CH$—$(CH_2)_s$—,
$C_{3-7}$ cycloalkyl-$CH=CH$—$(CH_2)_s$—,
aryl-$CH=CH$—$(CH_2)_s$—,
$C_{1-6}$ alkylaryl-$CH=CH$—$(CH_2)_s$—,
$C_{1-6}$ alkyl-$SO_2$—$(CH_2)_s$—,
$C_{1-6}$ alkylaryl-$SO_2$—$(CH_2)_s$—; and
$R^{12}$ is selected from hydrogen or $C_{1-8}$ alkyl; and
s is an integer from 0 to 3;
and all other variables are as defined above;
and the pharmaceutically acceptable salts thereof.

Further exemplifying the invention is the compound selected from

2-Oxo-3-[2-(5,6,7,8-tetrahydro[1,8]-naphthyridin-2-yl)ethyl]piperidin-1-yl-acetyl-3(S)-pyridin-3-yl-β-alanine ethyl ester;

2-Oxo-3-[2-(5,6,7,8-tetrahydro[1,8]-naphthyridin-2-yl)ethyl]piperin-1-yl-acetyl-3(S)-pyridin-3-yl-β-alanine trifluoroacetate;

2-Oxo-3(S)-[2-(5,6,7,8-tetrahydro[1,8]-naphthyridin-2-yl)ethyl]pyrrolidin-1-yl)acetyl-3(S)-alkynyl-β-alanine ethyl ester;

2-Oxo-3(S)-[2-(5,6,7,8-tetrahydro[1,8]-naphthyridin-2-yl)ethyl]pyrrolidin-1-yl)acetyl-3(S)-alkynyl-β-alanine;

2-Oxo-3(S)-[2-(5,6,7,8-tetrahydro[1,8]-naphthyridin-2-yl)ethyl]-pyrrolidin-1-yl)acetyl-3(S)-pyridin-3-yl-β-alanine ethyl ester;

2-Oxo-3(S)-[2-(5,6,7,8-tetrahydro[1,8]-naphthyridin-2-yl)ethyl]pyrrolidin-1-yl)acetyl-3(S)-pyridin-3-yl-β-alanine;

2-Oxo-3(R)-[2-(5,6,7,8-tetrahydro[1,8]-naphthyridin-2-yl)ethyl]pyrrolidin-1-yl)acetyl-3(S)-alkynyl-β-alanine ethyl ester;

2-Oxo-3(R)-[2-(5,6,7,8-tetrahydro[1,8]-naphthyridin-2-yl)ethyl]pyrrolidin-1-yl)acetyl-3(S)-alkynyl-β-alanine;

2-Oxo-3(R)-[2-(5,6,7,8-tetrahydro[1,8]-naphthyridin-2-yl)ethyl]-pyrrolidin-1-yl)acetyl-3(S)-pyridin-3-yl-β-alanine ethyl ester;

2-Oxo-3(R)-[2-(5,6,7,8-tetrahydro[1,8]-naphthyridin-2-yl)ethyl]pyrrolidin-1-yl)acetyl-3(S)-pyridin-3-yl-β-alanine;

Ethyl 2-oxo-3-[2-(5,6,7,8-tetrahydro[1,8]naphthyridin-2-yl)ethyl]-tetrahydropyrimidin-1-yl-acetyl-3(S)-pyridin-3-yl-β-alanine;

2-Oxo-3-[2-(5,6,7,8-tetrahydro[1,8]naphthyridin-2-yl}ethyl]-tetrahydropyrimidin-1-yl-acetyl-3(S)-pyridin-3-yl-β-alanine;

Ethyl 2-oxo-3-[2-(5,6,7,8-tetrahydro[1,8]naphthyridin-2-yl)ethyl]imidazolidin-1-yl-acetyl-3(S)-pyridin-3-yl-β-alanine;

2-Oxo-3-[2-(5,6,7,8-tetrahydro[1,8]naphthyridin-2-yl}ethyl]-imidazolidin-1-yl-acetyl-3(S)-pyridin-3-yl-β-alanine;

Ethyl 2-oxo-3(R)-[2-(5,6,7,8-tetrahydro[1,8]naphthyridin-2-yl)ethyl]pyrrolidin-1-yl)acetyl-3(R)-(2-ethylindol-3-yl)-β-alanine;

2-Oxo-3(R)-[2-(5,6,7,8-tetrahydro-[1,8]naphthyridin-2-yl)ethyl]pyrrolidin-1-yl)acetyl-3(R)-(2-ethylindol-3-yl)-β-alanine;

Ethyl 3-(2-{2-oxo-3(S)-[(5,6,7,8-tetrahydro-[1,8]naphthyridin-2-ylmethyl)-amino]-pyrrolidin-1-yl}-acetylamino)-3-(S)-pyridin-3-yl-propionic acid;

3-(2-{2-Oxo-3(S)-[(5,6,7,8-tetrahydro-[1,8]naphthyridin-2-ylmethyl)-amino]pyrrolidin-1-yl)-acetylamino)-3-(S)-pyridin-3-yl-propionic acid;

3-{2-[6-Oxo-1-(5,6,7,8-tetrahydro-[1,8]naphthyridin-2-ylmethyl)-hexahydro-(3aS, 6aS)pyrrolo[3,4-b]pyrrol-5-yl]-acetylamino}-3-(S)-pyridin-3-yl-propionic acid;

3-{2-[6-Oxo-1-(5,6,7,8-tetrahydro-[1,8]naphthyridin-2-ylmethyl)-hexahydro-(3aR, 6aR)pyrrolo[3,4-b]pyrrol-5-yl]-acetylamino}-3-(S)-pyridin-3-yl-propionic acid;

2-Oxo-5(R)-methyl-3(S)-[2-(5,6,7,8-tetrahydro[1,8]-naphthyridin-2-yl)-ethyl]pyrrolidin-1-yl)acetyl-3(S)-alkynyl-β-alanine ethyl ester;

2-Oxo-5(R)-methyl-3(S)-[2-(5,6,7,8-tetrahydro[1,8]-naphthyridin-2-yl)-ethyl]pyrrolidin-1-yl)acetyl-3(S)-alkynyl-β-alanine;

2-Oxo-5(S)-benzyl-3(S)-[2-(5,6,7,8-tetrahydro[1,8]-naphthyridin-2-yl)-ethyl]pyrrolidin-1-yl)acetyl-3(S)-pyridin-3-yl-β-alanine ethyl ester;

2-Oxo-5(S)-benzyl-3(S)-[2-(5 ,6,7 ,8-tetrahydro[1,8]-naphthyridin-2-yl)ethyl]pyrrolidin-1-yl)acetyl-3(S)-pyridin-3-yl-β-alanine;

5(R)-Methyl-2-oxo-3(S)-[2-(5,6,7,8-tetrahydro[1,8]-naphthyridin-2-ylmethyl)-amino]pyrrolidin-1-yl)acetyl-3(S)-alkynyl-β-alanine ethyl ester;

5(R)-Methyl-2-oxo-3(S)-[2-(5,6,7,8-tetrahydro[1,8]-naphthyridin-2-ylmethyl)-amino]pyrrolidin-1-yl)acetyl-3(S)-alkynyl-β-alanine;

3(S)-(2,3-Dihydro-benzofuran-6-yl)-3-(2-{2-oxo-3(S)-[2-(5,6,7,8-tetrahydro-[1,8]naphthyridin-2-yl)-ethyl]-pyrrolidin-1-yl}-acetylamino)-propionic acid ethyl ester; or 3(S)-(2,3-Dihydro-benzofuran-6-yl)-3-(2-{2-oxo-3(S)-[2-(5,6,7,8-tetrahydro-[1,8]naphthyridin-2-yl)-ethyl]-pyrrolidin-1-yl}-acetylamino)-propionic acid;

and the pharmaceutically acceptable salts thereof.

Preferably, the compound is selected from

2-Oxo-3-[2-(5,6,7,8-tetrahydro[1,8]-naphthyridin-2-yl)ethyl]piperin-1-yl-acetyl-3(S)-pyridin-3-yl-β-alanine trifluoroacetate;

2-Oxo-3(S)-[2-(5,6,7,8-tetrahydro[1,8]-naphthyridin-2-yl)ethyl]pyrrolidin-1-yl)acetyl-3(S)-alkynyl-β-alanine;

2-Oxo-3(S)-[2-(5,6,7,8-tetrahydro[1,8]-naphthyridin-2-yl)ethyl]pyrrolidin-1-yl)acetyl-3(S)-pyridin-3-yl-β-alanine;

2-Oxo-3(R)-[2-(5,6,7,8-tetrahydro[1,8]naphthyridin-2-yl)ethyl]pyrrolidin-1-yl)acetyl-3(S)-alkynyl-β-alanine;

2-Oxo-3(R)-[2-(5,6,7,8-tetrahydro[1,8]naphthyridin-2-yl)ethyl]pyrrolidin-1-yl)acetyl-3(S)-pyridin-3-yl-β-alanine;

2-Oxo-3-[2-(5,6,7,8-tetrahydro[1,8]naphthyridin-2-yl}ethyl]-imidazolidin-1-yl-acetyl-3-(S)-pyridin-3-yl-β-alanine;

2-Oxo-3-[2-(5,6,7,8-tetrahydro[1,8]naphthyridin-2-yl}ethyl]-tetrahydropyrimidin-1-yl-acetyl-3-(S)-pyridin-3-yl-β-alanine;

2-Oxo-3(R)-[2-(5,6,7,8-tetrahydro[1,8]naphthyridin-2-yl)ethyl]pyrrolidin-1-yl)acetyl-3(R)-(2-ethylindol-3-yl)-β-alanine;

3-(2-{2-Oxo-3(S)-[(5,6,7,8-tetrahydro-[1,8]naphthyridin-2-ylmethyl)-amino]pyrrolidin-1-yl}-acetylamino)-3-(S)-pyridin-3-yl-propionic acid;

3-{2-[6-Oxo-1-(5,6,7,8-tetrahydro-[1,8]naphthyridin-2-ylmethyl)-hexahydro-(3aS, 6aS)pyrrolo[3,4-b]pyrrol-5-yl]-acetylamino}-3-(S)-pyridin-3-yl-propionic acid; or 3-{2-[6-Oxo-1-(5,6,7,8-tetrahydro-[1,8]naphthyridin-2-ylmethyl)-hexahydro-(3aR, 6aR)pyrrolo[3,4-b]pyrrol-5-yl]-acetylamino}-3-(S)-pyridin-3-yl-propionic acid;

2-Oxo-5(R)-methyl-3(S)-[2-(5,6,7,8-tetrahydro[1,8]-naphthyridin-2-yl)ethyl]pyrrolidin-1-yl)acetyl-3(S)-alkynyl-β-alanine;

2-Oxo-5(S)-benzyl-3(S)-[2-(5,6,7,8-tetrahydro[1,8]-naphthyridin-2-yl)ethyl]pyrrolidin-1-yl)acetyl-3(S)-pyridin-3-yl-β-alanine;

5(R)-Methyl-2-oxo-3(S)-[2-(5,6,7,8-tetrahydro[1,8]-naphthyridin-2-ylmethyl)-amino]pyrrolidin-1-yl)acetyl-3(S)-alkynyl-β-alanine; or 3(S)-(2,3-Dihydro-benzofuran-6-yl)-3-(2-{2-oxo-3(S)-[2-(5,6,7,8-tetrahydro-[1,8]naphthyridin-2-yl)-ethyl]-pyrrolidin-1-yl}-acetylamino)-propionic acid;

and the pharmaceutically acceptable salts thereof.

An additional example of the invention is a compound of the formula $$X-Y-Z-(CH_2)_n-\underset{H}{\overset{O}{\underset{\|}{C}}}-N-\underset{{}^{10}R\ R^{11}}{\overset{{}^{8}R\ R^{9}}{C}}-CO_2R^{12}$$

wherein X is a 9- to 10-membered polycyclic ring system, wherein one or more of the rings is aromatic, and wherein the polycyclic ring system contains 0, 1, 2, 3 or 4 heteroatoms selected from N, O or S, and wherein the polycyclic ring system is either unsubstituted or substituted on a carbon atom with $R^1$ and $R^2$;

Y is selected from $$-\underset{R^3}{N}-(CH_2)_{\overline{m}}-,\ -(CH_2)_{\overline{m}}-\underset{R^3}{N}-,\ -\overset{O}{\underset{\|}{C}}-(CH_2)_{\overline{m}}-,$$

$$-\overset{O}{\underset{\|}{C}}-\underset{R^3}{N}-(CH_2)_{\overline{m}}-,$$

$$-\underset{R^3}{N}-\overset{O}{\underset{\|}{C}}-(CH_2)_{\overline{m}}-,$$

$-S(O)_q-(CH_2)_m-$, $-O-(CH_2)_m-$ or $-(CH_2)_r-$;

Z is a 5–11 membered aromatic or nonaromatic mono- or polycyclic ring system containing 0 to 6 double bonds, and containing 0 to 6 heteroatoms chosen from N, O and S, and wherein the ring system is either unsubstituted or substituted on a carbon or nitrogen atom with one or more groups independently selected from $R^4$, $R^5$, $R^6$ and $R^7$; provided that Z is not a 6-membered monocyclic aromatic ring system; preferably, Z is selected from $R^1$, $R^2$, $R^3$, $R^4$, $R^5$, $R^{13}$ and $R^{14}$ are each independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino-$C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy or hydroxy $C_{1-6}$ alkyl;

$R^6$, $R^7$, $R^8$, $R^9$, $R^{10}$ and $R^{11}$ are each independently selected from
hydrogen,
aryl,
—$(CH_2)_p$-aryl,
halogen,
hydroxyl,
$C_{1-8}$ alkylcarbonylamino,
aryl $C_{1-5}$ alkoxy,
$C_{1-5}$ alkoxycarbonyl,
aminocarbonyl,
$C_{1-8}$ alkylaminocarbonyl,
$C_{1-6}$ alkylcarbonyloxy,
$C_{3-8}$ cycloalkyl,
oxo,
amino,
$C_{1-6}$ alkylamino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
$C_{1-8}$ alkyl, either unsubstituted or substituted, with one or more groups selected from: halogen, hydroxyl, $C_{1-5}$ alkylcarbonylamino, aryl $C_{1-5}$ alkoxy, $C_{1-5}$ alkoxycarbonyl, aminocarbonyl, $C_{1-5}$ alkylaminocarbonyl, $C_{1-5}$ alkylcarbonyloxy, $C_{3-8}$ cycloalkyl, oxo, amino, $C_{1-3}$ alkylamino, amino $C_{1-3}$ alkyl, arylaminocarbonyl, aryl $C_{1-5}$ alkylaminocarbonyl, aminocarbonyl, aminocarbonyl $C_{1-4}$ alkyl, hydroxycarbonyl, or hydroxycarbonyl $C_{1-5}$ alkyl,
—$(CH_2)_s$ C≡CH, —$(CH_2)_s$ C≡C-$C_{1-6}$ alkyl,
—$(CH_2)_s$ C≡C-$C_{3-7}$ cycloalkyl,
—$(CH_2)_s$ C≡C-aryl,
—$(CH_2)_s$ C≡C-$C_{1-6}$ alkylaryl,
—$(CH_2)_s$ CH=$CH_2$,
—$(CH_2)_s$ CH=CH $C_{1-6}$ alkyl,
—$(CH_2)_s$ CH=CH-$C_{3-7}$ cycloalkyl,
—$(CH_2)_s$ CH=CH aryl,
—$(CH_2)_s$ CH=CH $C_{1-6}$ alkylaryl,
—$(CH_2)_s$ $SO_2C_{1-6}$ alkyl, or
—$(CH_2)_s$ $SO_2C_{1-6}$ alkylaryl;
$C_{1-6}$ alkoxy,
aryl $C_{1-6}$ alkoxy,
aryl $C_{1-6}$ alkyl,
$C_{1-6}$ alkylamino $C_{1-6}$ alkyl,
arylamino,
arylamino $C_{1-6}$ alkyl,
aryl $C_{1-6}$ alkylamino,
aryl $C_{1-6}$ alkylamino $C_{1-6}$ alkyl,
arylcarbonyloxy,
aryl $C_{1-6}$ alkylcarbonyloxy,
$C_{1-6}$ dialkylamino,
$C_{1-6}$ dialkylamino $C_{1-6}$ alkyl,
$C_{1-6}$ alkylaminocarbonyloxy,
$C_{1-8}$ alkylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$C_{1-8}$ alkylaminocarbonylamino,
$C_{1-8}$ alkylaminocarbonylamino $C_{1-6}$ alkyl,
arylaminocarbonylamino $C_{1-6}$ alkyl,
aryl $C_{1-8}$ alkylaminocarbonylamino,
aryl $C_{1-8}$ alkylaminocarbonylamino $C_{1-6}$ alkyl,
aminosulfonylamino $C_{1-6}$ alkyl,
$C_{1-8}$ alkylaminosulfonylamino,
$C_{1-8}$ alkylaminosulfonylamino $C_{1-6}$ alkyl,
arylaminosulfonylamino $C_{1-6}$ alkyl,
aryl $C_{1-8}$ alkylaminosulfonylamino,
aryl $C_{1-8}$ alkylaminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$C_{1-8}$ alkylaminocarbonyl $C_{1-6}$ alkyl,
arylaminocarbonyl $C_{1-6}$ alkyl,
aryl $C_{1-8}$ alkylaminocarbonyl, or
aryl $C_{1-8}$ alkylaminocarbonyl $C_{1-6}$ alkyl, wherein any of the alkyl groups may be unsubstituted or substituted with $R^{13}$ and $R^{14}$; and provided that the carbon atom to which $R^8$ and $R^9$ are attached is itself attached to no more than one heteroatom; and provided further that the carbon atom to which $R^{10}$ and $R^{11}$ are attached is itself attached to no more than one heteroatom;

$R^{12}$ is selected from
hydrogen,
$C_{1-8}$ alkyl,
aryl,
aryl $C_{1-8}$ alkyl,
hydroxy,
$C_{1-8}$ alkoxy,
aryloxy,
aryl $C_{1-6}$ alkoxy,
$C_{1-8}$ alkylcarbonyloxy $C_{1-4}$ alkoxy,
aryl $C_{1-8}$ alkylcarbonyloxy $C_{1-4}$ alkoxy,
$C_{1-8}$ alkylaminocarbonylmethyleneoxy, or
$C_{1-8}$ dialkylaminocarbonylmethyleneoxy;

m is an integer from 0 to 3;
n is an integer from 1 to 3;
p is an integer from 1 to 4;
q is an integer from 0 to 2;
r is an integer from 0 to 6; and
s is an integer from 0 to 3;

and the pharmaceutically acceptable salts thereof.

An additional illustration of the invention is a compound of the formula

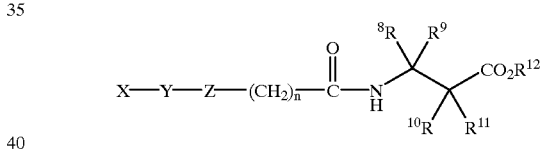

wherein X is
a 9- to 10-membered polycyclic ring system, wherein one or more of the rings is aromatic, and wherein the polycyclic ring system contains 0, 1, 2, 3 or 4 heteroatoms selected from N, O or S, and wherein the polycyclic ring system is either unsubstituted or substituted on a carbon atom with $R^1$ and $R^2$;

Y is selected from

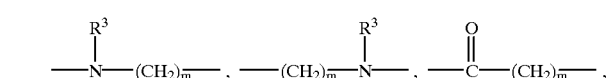

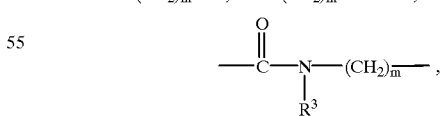

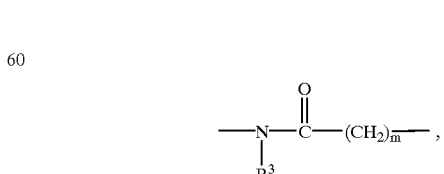

—$S(O)_q$—$(CH_2)_m$—, —O—$(CH_2)_m$— or —$(CH_2)_r$—;

Z is
a 5–11 membered aromatic or nonaromatic mono- or polycyclic ring system containing 0 to 6 double bonds, and containing 0 to 6 heteroatoms chosen from N, O and S, and wherein the ring system is either unsubstituted or substituted on a carbon or nitrogen atom with one or more groups independently selected from $R^4$, $R^5$, $R^6$ and $R^7$; provided that Z is not a 6-membered monocyclic aromatic ring system; preferably, Z is selected from

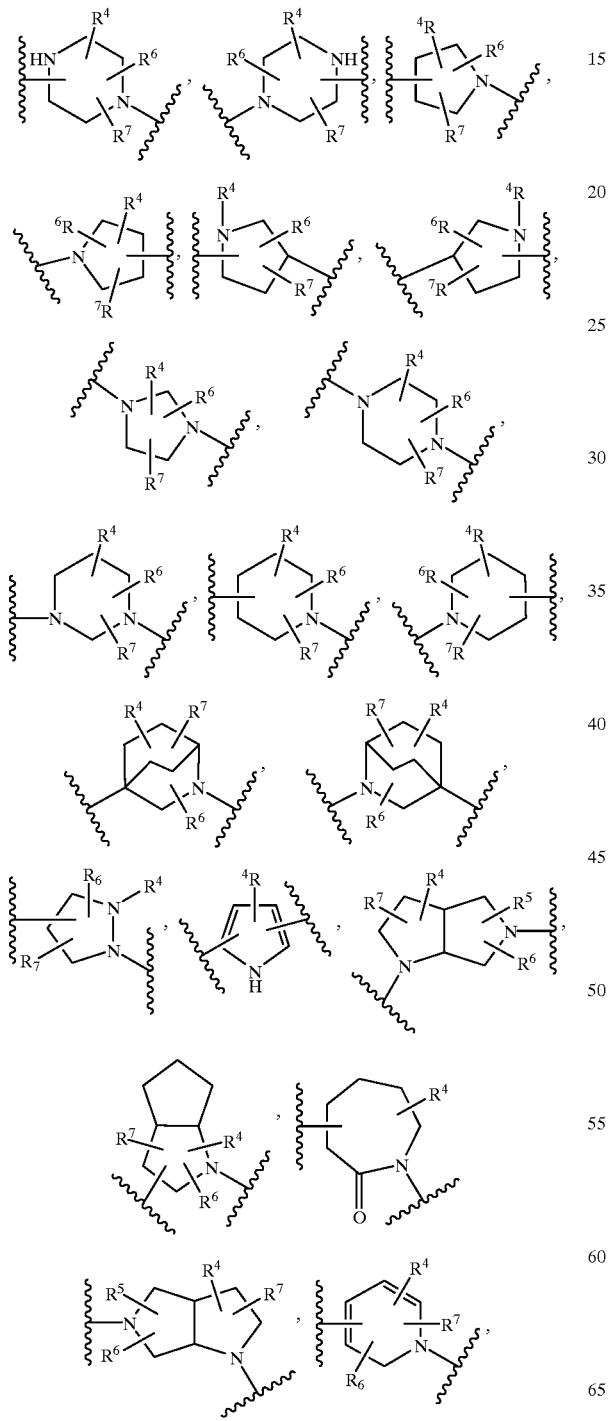

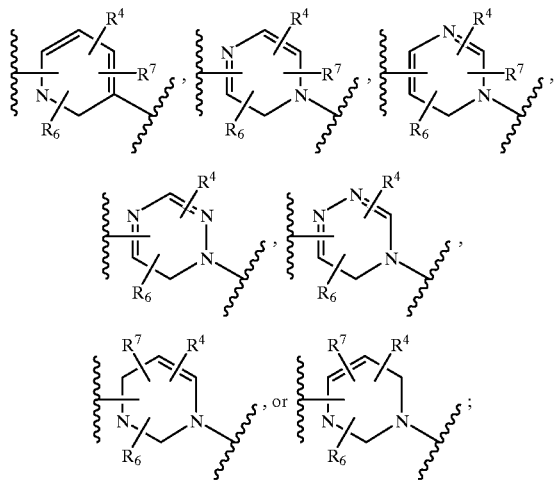

$R^1$, $R^2$, $R^4$, $R^5$, $R^{13}$ and $R^{14}$ are each independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino-$C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl-$S(O)_q$, $C_{1-8}$ aminocarbonyl, $C_{1-8}$ dialkylaminocarbonyl, $C_{1-8}$ alkyloxycarbonylamino, $C_{1-8}$ alkylaminocarbonyloxy or $C_{1-8}$ alkylsulfonylamino;

$R^3$ is selected from
hydrogen,
aryl,
—$(CH_2)_p$-aryl,
hydroxyl,
$C_{1-5}$ alkoxycarbonyl,
aminocarbonyl,
$C_{3-8}$ cycloalkyl,
amino $C_{1-6}$ alkyl,
arylaminocarbonyl,
aryl $C_{1-5}$ alkylaminocarbonyl,
hydroxycarbonyl $C_{1-6}$ alkyl,
$C_{1-8}$ alkyl,
aryl $C_{1-6}$ alkyl,
$C_{1-6}$ alkylamino $C_{1-6}$ alkyl,
aryl $C_{1-6}$ alkylamino $C_{1-6}$ alkyl,
$C_{1-6}$ dialkylamino $C_{1-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$C_{1-8}$ alkylaminocarbonyl,
aminosulfonyl,
$C_{1-8}$ alkylaminosulfonyl,
arylaminosulfonylamino,
aryl $C_{1-8}$ alkylaminosulfonyl,
$C_{1-6}$ alkylsulfonyl,
arylsulfonyl, aryl $C_{1-6}$ alkylsulfonyl,
aryl $C_{1-6}$ alkylcarbonyl,
$C_{1-6}$ alkylthiocarbonyl,
arylthiocarbonyl, or
aryl $C_{1-6}$ alkylthiocarbonyl,
wherein any of the alkyl groups may be unsubstituted or substituted with $R^{13}$ and $R^{14}$;
$R^6$, $R^7$, $R^8$, $R^9$, $R^{10}$ and $R^{11}$ are each independently selected from
hydrogen,
aryl,
—$(CH_2)_p$-aryl,
halogen,
hydroxyl,
$C_{1-8}$ alkylcarbonylamino,
aryl $C_{1-5}$ alkoxy,
$C_{1-5}$ alkoxycarbonyl,
aminocarbonyl,
$C_{1-8}$ alkylaminocarbonyl,
$C_{1-6}$ alkylcarbonyloxy,
$C_{3-8}$ cycloalkyl,
oxo,
amino,
$C_{1-6}$ alkylamino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
$C_{1-8}$ alkyl, either unsubstituted or substituted, with one or more groups selected from: halogen, hydroxyl, $C_{1-5}$ alkylcarbonylamino, aryl $C_{1-5}$ alkoxy, $C_{1-5}$ alkoxycarbonyl, aminocarbonyl, $C_{1-5}$ alkylaminocarbonyl, $C_{1-5}$ alkylcarbonyloxy, $C_{3-8}$ cycloalkyl, oxo, amino, $C_{1-3}$ alkylamino, amino $C_{1-3}$ alkyl, arylaminocarbonyl, aryl $C_{1-5}$ alkylaminocarbonyl, aminocarbonyl, aminocarbonyl $C_{1-4}$ alkyl, hydroxycarbonyl, or hydroxycarbonyl $C_{1-5}$ alkyl,
—$(CH_2)_s$ C≡CH,
—$(CH_2)_s$ C≡C-$C_{1-6}$ alkyl,
—$(CH_2)_s$ C≡C-$C_{3-7}$ cycloalkyl,
—$(CH_2)_s$ C≡C-aryl,
—$(CH_2)_s$ C≡C-$C_{1-6}$ alkylaryl,
—$(CH_2)_s$ CH=$CH_2$,
—$(CH_2)_s$ CH=CH $C_{1-6}$ alkyl,
—$(CH_2)_s$ CH=CH-$C_{3-7}$ cycloalkyl,
—$(CH_2)_s$ CH=CH aryl,
—$(CH_2)_s$ CH=CH $C_{1-6}$ alkylaryl,
—$(CH_2)_s$ $SO_2C_{1-6}$ alkyl, or
—$(CH_2)_s$ $SO_2C_{1-6}$ alkylaryl;
$C_{1-6}$ alkoxy,
aryl $C_{1-6}$ alkoxy,
aryl $C_{1-6}$ alkyl,
$C_{1-6}$ alkylamino $C_{1-6}$ alkyl,
arylamino,
arylamino $C_{1-6}$ alkyl,
aryl $C_{1-6}$ alkylamino,
aryl $C_{1-6}$ alkylamino $C_{1-6}$ alkyl,
arylcarbonyloxy,
aryl $C_{1-6}$ alkylcarbonyloxy,
$C_{1-6}$ dialkylamino,
$C_{1-6}$ dialkylamino $C_{1-6}$ alkyl,
$C_{1-6}$ alkylaminocarbonyloxy,
$C_{1-8}$ alkylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$C_{1-8}$ alkylaminocarbonylamino,
$C_{1-8}$ alkylaminocarbonylamino $C_{1-6}$ alkyl,
arylaminocarbonylamino $C_{1-6}$ alkyl,
aryl $C_{1-8}$ alkylaminocarbonylamino,
aryl $C_{1-8}$ alkylaminocarbonylamino $C_{1-6}$ alkyl,
aminosulfonylamino $C_{1-6}$ alkyl,
$C_{1-8}$ alkylaminosulfonylamino,
$C_{1-8}$ alkylaminosulfonylamino $C_{1-6}$ alkyl,
arylaminosulfonylamino $C_{1-6}$ alkyl,
aryl $C_{1-8}$ alkylaminosulfonylamino,
aryl $C_{1-8}$ alkylaminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$C_{1-8}$ alkylaminocarbonyl $C_{1-6}$ alkyl,
arylaminocarbonyl $C_{1-6}$ alkyl,
aryl $C_{1-8}$ alkylaminocarbonyl, or
aryl $C_{1-8}$ alkylaminocarbonyl $C_{1-6}$ alkyl,
wherein any of the alkyl groups may be unsubstituted or substituted with $R^{13}$ and $R^{14}$; and provided that the carbon atom to which $R^8$ and $R^9$ are attached is itself attached to no more than one heteroatom; and provided further that the carbon atom to which $R^{10}$ and $R^{11}$ are attached is itself attached to no more than one heteroatom;
$R^{12}$ is selected from
hydrogen,
$C_{1-8}$ alkyl,
aryl,
aryl $C_{1-8}$ alkyl,
hydroxy,
$C_{1-8}$ alkoxy,
aryloxy,
aryl $C_{1-6}$ alkoxy,
$C_{1-8}$ alkylcarbonyloxy $C_{1-4}$ alkoxy,
aryl $C_{1-8}$ alkylcarbonyloxy $C_{1-4}$ alkoxy,
$C_{1-8}$ alkylaminocarbonylmethyleneoxy, or
$C_{1-8}$ dialkylaminocarbonylmethyleneoxy;
m is an integer from 0 to 3;
n is an integer from 1 to 3;

p is an integer from 1 to 4;
q is an integer from 0 to 2;
r is an integer from 0 to 6; and
s is an integer from 0 to 3;
and the pharmaceutically acceptable salts thereof.

More particularly illustrating the invention is a pharmaceutical composition comprising any of the compounds described above and a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Further illustrating the invention is a method of treating and/or preventing a condition mediated by antagonism of a vitronectin receptor in a mammal in need thereof, comprising administering to the mammal a therapeutically effective amount of any of the compounds described above. Preferably, the condition is selected from bone resorption, osteoporosis, restenosis, diabetic retinopathy, macular degeneration, angiogenesis, atherosclerosis, inflammation, cancer and tumor growth. More preferably, the condition is selected from osteoporosis and cancer. Most preferably, the condition is osteoporosis.

More specifically exemplifying the invention is a method of eliciting a vitronectin antagonizing effect in a mammal in need thereof, comprising administering to the mammal a therapeutically effective amount of any of the compounds or any of the pharmaceutical compositions described above. Preferably, the vitronectin antagonizing effect is an $\alpha v\beta 3$ antagonizing effect; more specifically the $\alpha v\beta 3$ antagonizing effect is selected from inhibition of bone resorption, inhibition of restenosis, inhibition of atherosclerosis, inhibition of angiogenesis, inhibition of diabetic retinopathy, inhibition of macular degeneration, inhibition of inflammation or inhibition of tumor growth. Most preferably, the $\alpha v\beta 3$ antagonizing effect is inhibition of bone resorption. Alternatively, the vitronectin antagonizing effect is an $\alpha v\beta 5$ antagonizing effect or a dual $\alpha v\beta 3/\alpha v\beta 5$ antagonizing effect. Examples of $\alpha v\beta 5$ antagonizing effects are inhibition of: restenosis, atherosclerosis, angiogenesis, diabetic retinopathy, macular degeneration, inflammation or tumor growth. Examples of dual $\alpha v\beta 3/\alpha v\beta 5$ antagonizing effects are inhibition of: bone resorption, restenosis, atherosclerosis, angiogenesis, diabetic retinopathy, macular degeneration, inflammation or tumor growth.

Additional examples of the invention are methods of inhibiting bone resorption and of treating and/or preventing osteoporosis in a mammal in need thereof, comprising administering to the mammal a therapeutically effective amount of any of the compounds or any of the pharmaceutical compositions decribed above.

Further exemplifying the invention is any of the compositions described above, further comprising a therapeutically effective amount of a second bone resorption inhibitor; preferably, the second bone resorption inhibitor is alendronate.

More particularly illustrating the invention is any of the methods of treating and/or preventing osteoporosis and/or of inhibiting bone resoption described above, wherein the compound is administered in combination with a second bone resorption inhibitor; preferably, the second bone resorption inhibitor is alendronate.

Additional illustrations of the invention are methods of treating hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment in a mammal in need thereof, comprising administering to the mammal a therapeutically effective amount of any of the compounds or any of the pharmaceutical compositions described above.

More particularly exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone resorption, tumor growth, cancer, restenosis, atherosclerosis, diabetic retinopathy, macular degeneration, inflammation and/or angiogenesis.

Additional illustrations of the invention are methods of treating tumor growth in a mammal in need thereof, comprising administering to the mammal a therapeutically effective amount of a compound described above and one or more agents known to be cytotoxic or antiproliferative, e.g., taxol and doxorubicin.

DETAILED DESCRIPTION OF THE INVENTION

Representative compounds of the present invention are integrin antagonists which display submicromolar affinity for the human $\alpha v\beta 3$ receptor. Compounds of this invention are therefore useful for treating mammals suffering from a bone condition caused or mediated by increased bone resorption, who are in need of such therapy. Pharmacologically effective amounts of the compounds, including pharmaceutically acceptable salts thereof, are administered to the mammal, to inhibit the activity of mammalian osteoclasts.

The compounds of the present invention are administered in dosages effective to antagonize the $\alpha v\beta 3$ receptor where such treatment is needed, as, for example, in the prevention or treatment of osteoporosis. For use in medicine, the salts of the compounds of this invention refer to non-toxic "pharmaceutically acceptable salts." Other salts may, however, be useful in the preparation of the compounds according to the invention or of their pharmaceutically acceptable salts. Salts encompassed within the term "pharmaceutically acceptable salts" refer to non-toxic salts of the compounds of this invention which are generally prepared by reacting the free base with a suitable organic or inorganic acid. Representative salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The compounds of the present invention, may have chiral centers and occur as racemates, racemic mixtures, diastereomeric mixtures, and as individual diastereomers, or enantiomers with all isomeric forms being included in the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodmgs," ed. H. Bundgaard, Elsevier, 1985. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "vitronectin receptor antagonist," as used herein, refers to a compound which binds to and antagonizes either the $\alpha v \beta 3$ receptor or the $\alpha v \beta 5$ receptor, or a compound which binds to and antagonizes both the $\alpha v \beta 3$ and $\alpha v \beta 5$ receptors (i.e., a dual $\alpha v \beta 3 / \alpha v \beta 5$ receptor antagonist).

The term "bone resorption," as used herein, refers to the process by which osteoclasts degrade bone.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "alkynyl" shall mean straight or branched chain alkynes of two to ten total carbon atoms, or any number within this range.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

The term "cycloheteroalkyl," as used herein, shall mean a 3- to 8-membered fully saturated heterocyclic ring containing one or two heteroatoms chosen from N, O or S. Examples of cycloheteroalkyl groups include, but are not limited to piperidinyl, pyrrolidinyl, azetidinyl, morpholinyl, piperazinyl.

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "aryl," as used herein, refers to a monocyclic or polycyclic system composed of 5- and 6-membered fully unsaturated or partially unsaturated rings, such that the system comprises at least one fully unsaturated ring, wherein the rings contain 0, 1, 2, 3 or 4 heteroatoms chosen from N, O or S, and either unsubstituted or substituted with one or more groups independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino $C_{1-8}$ alkyl, $C_{1-6}$ dialkylamino, $C_{1-6}$ dialkylamino-$C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Examples of aryl include, but are not limited to, phenyl, naphthyl, pyridyl, pyrazinyl, pyrimidinyl, imidazolyl, benzimidazolyl, indolyl, thienyl, furyl, dihydrobenzofuryl, benzo(1,3) dioxolane, oxazolyl, isoxazolyl and thiazolyl, which are either unsubstituted or substituted with one or more groups independently selected from hydrogen, halogen, $C_{1-10}$ alkyl, $C_{3-9}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino-$C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Preferably, the aryl group is unsubstituted, mono-, di-, tri- or tetra-substituted with one to four of the above-named substituents; more preferably, the aryl group is unsubstituted, mono-, di- or tri-substituted with one to three of the above-named substituents; most preferably, the aryl group is unsubstituted, mono- or di-substituted with one to two of the above-named substituents.

Whenever the term "alkyl" or "aryl" or either of their prefix roots appear in a name of a substituent (e.g., aryl $C_{0-8}$ alkyl) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. The $C_{0-m}$ or $C_{1-m}$ designation where m may be an integer from 1–10 or 2–10 respectively refers to the alkyl component of the arylalkyl or alkylaryl unit. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluene, ethylbenzene, propylbenzene, methylpyridine, ethylpyridine, propylpyridine and butylpyridine.

When substituent $R^1$, $R^2$, $R^3$, $R^4$, $R^5$, $R^6$, $R^7$, $R^8$, $R^9$, $R^{10}$, $R^{11}$, $R^{12}$, $R^{13}$ or $R^{14}$ includes the definition $C_0$ (e.g., aryl $C_{0-8}$ alkyl), the group modified by $C_0$ is not present in the substituent. Similarly, when any of the variables m, q, r or s is zero, then the group modified by the variable is not present; for example, when s is zero, the group "—$(CH_2)_s$ C≡CH" is "—C≡CH". In addition, the substituent "$(C_{1-6}$ alkyl$)_q$amino" where q is zero, one or two, refers to an amino, $C_{1-6}$ alkylamino and $C_{1-6}$ dialkylamino group, respectively. When a $C_{1-6}$ dialkylamino substituent is intended, the $C_{1-6}$ alkyl groups can be the same (e.g., dimethylamino) or different (e.g., $N(CH_3)(CH_2CH_3)$). Similarly, the substituent "(aryl)$_q$amino" or["(aryl $C_{1-6}$ alkyl)$_q$amino"], where q is zero, one or two, refers to an amino, arylamino and diarylamino group, [or an amino, aryl $C_{1-6}$ alkylamino or di-(aryl $C_{1-6}$ alkyl)amino] respectively, where the aryl[or aryl $C_{1-6}$ alkyl] groups in a diarylamino[or di-(aryl $C_{1-6}$ alkyl)amino] substituent can be the same or different.

The term "halogen" shall include iodine, bromine, chlorine and fluorine.

The term "oxy" means an oxygen (O) atom. The term "thio" means a sulfur (S) atom. The term "oxo" shall mean =O.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Under standard nonmenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

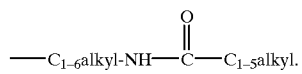

The present invention is also directed to combinations of the compounds of the present invention with one or more agents useful in the prevention or treatment of osteoporosis. For example, the compounds of the instant invention may be effectively administered in combination with effective amounts of other agents used in the treatment of osteoporosis such as bisphosphonate bone resorption inhibitors; preferably, the bone resorption inhibitor is the bisphosphonate alendronate, now sold as FOSAMAX®. Preferred combinations are simultaneous or alternating treatments of an αvβ3 receptor antagonist of the present invention and FOSAMAX®.

In addition, the integrin (αvβ3) antagonist compounds of the present invention may be effectively administered in combination with a growth hormone secretagogue in the therapeutic or prophylactic treatment of disorders in calcium or phosphate metabolism and associated diseases. These diseases include conditions which can benefit from a reduction in bone resorption. A reduction in bone resorption should improve the balance between resorption and formation, reduce bone loss or result in bone augmentation. A reduction in bone resorption can alleviate the pain associated with osteolytic lesions and reduce the incidence and/or growth of those lesions. These diseases include: osteoporosis (including estrogen deficiency, immobilization, glucocorticoid induced and senile), osteodystrophy, Paget's disease, myositis ossificans, Bechterew's disease, malignant hypercalcemia, metastatic bone disease, periodontal disease, cholelithiasis, nephrolithiasis, urolithiasis, urinary calculus, hardening of the arteries (sclerosis), arthritis, bursitis, neuritis and tetany. Increased bone resorption can be accompanied by pathologically high calcium and phosphate concentrations in the plasma, which would be alleviated by this treatment. Similarly, the present invention would be useful in increasing bone mass in patients with growth hormone deficiency. Thus, preferred combinations are simultaneous or alternating treatments of an αvβ3 receptor antagonist of the present invention and a growth hormone secretagogue, optionally including a third component comprising FOSAMAX®.

In addition, the vitronectin receptor antagonist compounds of the present invention may be effectively administered in combination with one or more agents known to be cytoxic or antiproliferative, e.g. taxol and doxorubicin.

In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating αvβ3 related conditions includes in principle any combination with any pharmaceutical composition useful for treating osteoporosis.

As used herein, the term "composition" is intended to encompass a product comprising the specified ingredients in the specified amounts, as well as any product which results, directly or indirectly, from combination of the specified ingredients in the specified amounts.

The compounds of the present invention can be administered in such oral dosage forms as tablets, capsules (each of which includes sustained release or timed release formulations), pills, powders, granules, elixers, tinctures, suspensions, syrups and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts. An effective but non-toxic amount of the compound desired can be employed as an αvβ3 inhibitor.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about I mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In the schemes and examples below, various reagent symbols and abbreviations have the following meanings:

AcOH: Acetic acid.
$BH_3 \cdot DMS$: Borane·dimethylsulfide.
BOC(Boc): t-Butyloxycarbonyl.
BOP: Benzotriazol-1-yloxytris(dimethylamino)-phosphonium hexafluorophosphate.
CBZ(Cbz): Carbobenzyloxy or benzyloxycarbonyl.
CDI: Carbonyldiimidazole.
$CH_2Cl_2$: Methylene chloride.
$CHCl_3$: Chloroform.
DEAD: Diethyl azodicarboxylate.
DIAD: Diisopropyl azodicarboxylate.
DIBAH or
DIBAL-H: Diisobutylaluminum hydride.
DIPEA: Diisopropylethylamine.
DMAP: 4-Dimethylaminopyridine.
DME: 1,2-Dimethoxyethane.
DMF: Dimethylformamide.
DMSO: Dimethylsulfoxide.
DPFN: 3,5-Dimethyl-1-pyrazolylformamidine nitrate.
EDC: 1-(3-Dimethylaminopropyl)-3-ethylcarbodiimide.
EtOAc: Ethyl acetate.
EtOH: Ethanol.
HOAc: Acetic acid.
HOAT: 1-Hydroxy-7-azabenzotriazole
HOBT: 1-Hydroxybenzotriazole.
LDA: Lithium diisopropylamide.
MeOH: Methanol.
$NEt^3$: Triethylamine.
NMM: N-methylmorpholine.
PCA•HCl: Pyrazole carboxamidine hydrochloride.
Pd/C: Palladium on activated carbon catalyst.
Ph: Phenyl.
pTSA p-Toluene sulfonic acid.
TEA: Triethylamine.
TFA: Trifluoroacetic acid.
THF: Tetrahydrofuran.
TLC: Thin Layer Chromatography.
TMEDA: N,N,N',N'-Tetramethylethylenediamine.
TMS: Trimethylsilyl.

The novel compounds of the present invention were prepared according to the procedure of the following schemes and examples, using appropriate materials and are further exemplified by the following specific examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

The following Schemes and Examples describe procedures for making representative compounds of the present invention. Moreover, by utilizing the procedures described in detail in PCT International Application Publication Nos. WO95/32710, published Dec. 7, 1995, and WO95/17397, published Jun. 29, 1995, in conjunction with the disclosure contained herein, one of ordinary skill in the art can readily prepare additional compounds of the present invention claimed herein.

More specifically, procedures for preparing the N-terminus of the compounds of the present invention are described in WO 95/32710. Additionally, for a general review describing the synthesis of β-alanines which can be utilized as the C-terminus of the compounds of the present invention, see Cole, D. C., *Recent Stereoselective Synthetic Approaches to β-Amino Acids, Tetrahedron,* 1994, 50, 9517–9582; Juaristi, E, et al., *Enantioselective Synthesis of β-Amino Acids, Aldrichemica Acta,* 1994, 27, 3. In particular, synthesis of the 3-methyl β-alanine is taught in Duggan, M. F. et al., *J. Med. Chem.,* 1995, 38, 3332–3341; the 3-ethynyl β-alanine is taught in Zablocki, J. A., et al., *J. Med. Chem.,* 1995, 38, 2378–2394; the 3-pyrid-3-yl β-alanine is taught in Rico, J. G. et al., *J. Org. Chem.,* 1993, 58, 7948–7951; and the 2-amino and 2-toslylamino β-alanines are taught in Xue, C-B, et al., *Biorg. Med. Chem. Letts.,* 1996, 6, 339–344.

SCHEME 1

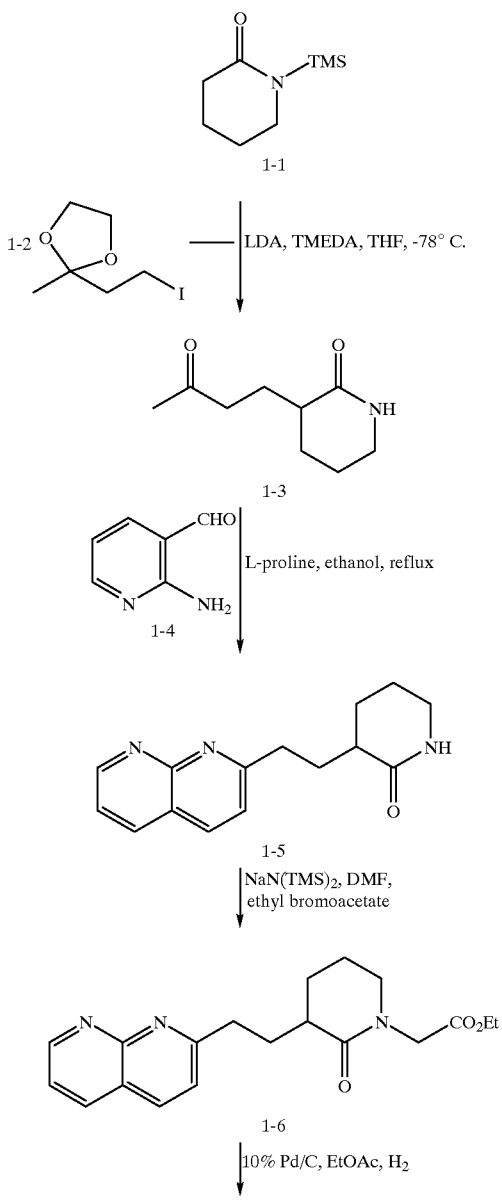

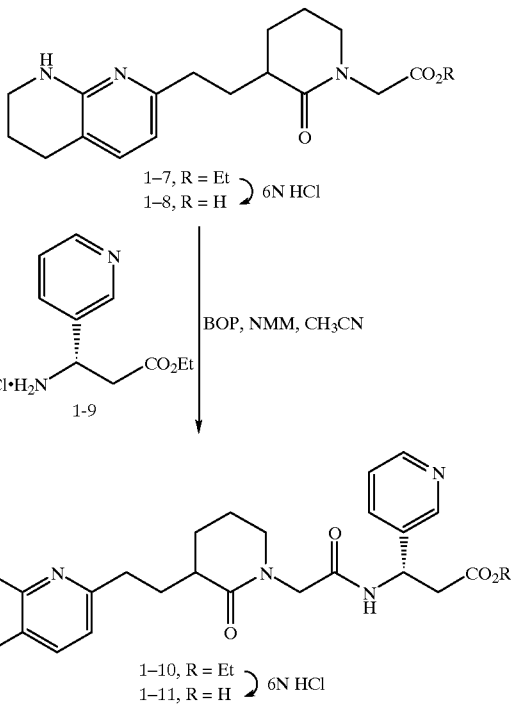

2-Oxo-3-(3-oxobutyl)piperidine (1-3)

A stirred solution of TMEDA (3.0 g, 20 mmol), 0.5 M LDA (6 mL, in THF), and THF (10 mL) at −78° C. was treated with 1-1 (1.7 g, 10 mmol) (for preparation, see: JOC, 1990, 55, 3682) to effect an orange solution.

After 1 h, the iodide 1-2 (2.4 g, 10 mmol) (*J. Org. Chem.,* 1983, 48, 5381) was added to the orange solution and the resulting solution stirred for 2 h at −78° C., 3 h at −15° C. and then 16 h at ambient temperature. The reaction mixture was concentrated and then treated with 1N HCl (30 mL). The mixture was then basified with 1N NaOH/brine followed by extraction with EtOAc (3×). The combined extracts were dried (MgSO$_4$) and concentrated to give a yellow oil. Flash chromatography (silica, EtOAc→10% CH$_3$OH/EtOAc) gave 1-3 as a colorless solid.

TLC R$_f$ 0.42 (silica, 10% CH$_3$OH/EtOAc); $^1$H NMR (300 MHz, CDCl$_3$) δ 5.75 (bs, 1H), 3.28 (m, 2H), 2.64 (t, 7 Hz, 2H), 2.30–1.50 (m, 7H), 2.16 (s, 3H).

2-Oxo-3-[2-([1,8]-naphthyridin-2-yl)ethyl-]piperidine (1-5)

A solution of 1-3 (0.25 g, 1.5 mmol), L-proline (85 mg, 0.75 mmol), 1-4 (0.18 g, 1.5 mmol) (for preparation see: *Synth. Commun.* 1987, 17, 1695), and ethanol (10 mL) was refluxed for 24 hr. The cooled solution was concentrated and the residue purified by flash chromatography (silica, EtOAc→20% CH$_3$OH/EtOAc) to give 1-5 as a solid.

TLC R$_f$=0.32 (silica, 20% CH$_3$OH/EtOAc); $^1$H NMR (300 MHz, CDCl$_3$) δ 9.08 (m, 1H), 8.16 (m, 1H), 8.10 (d, J=8 Hz, 1H), 7.50 (d, J=8 Hz, 1H), 7.45 (m, 1H), 5.64 (bs, 1H), 3.31 (m, 2H), 3.18 (m, 2H), 2.50–1.60 (m, 7H).

Ethyl 2-Oxo-3-[2-([1,8]-naphthyridin-2-yl)ethyl]piperidin-1-yl-acetate (1-6)

A solution of 1-5 (0.28 g, 1.1 mmol) and DMF (10 mL) at −15° C. was treated with NaN(TMS)$_2$ (1.2 mL, 1.2 mmol, 1M in hexanes) to give a red solution. After 30 min, the red solution was treated with ethyl bromoacetate (128 μL, 1.2 mmol), followed by continued stirring for 1 h. The reaction mixture was then quenched with sat. NH₄Cl and then extracted with EtOAc (3×). The combined extracts were washed with brine, dried (MgSO₄), and concentrated. Flash chromatography (silica, 10% CH₃OH/EtOAc) gave 1-6 as a yellow gum.

TLC R$_f$=0.50 (silica, 10% CH₃OH/EtOAc); ¹H NMR (300 MHz, CDCl₃) δ 9.07 (m, 1H), 8.16 (m, 1H), 8.10 (d, J=8 Hz, 1H), 7.50 (d, J=8 Hz, 1H), 7.44 (m, 1H), 4.30–3.90 (m, 4H), 3.50–3.30 (m, 2H), 3.17 (m, 2H), 2.46 (m, 2H), 2.20–1.70 (m, 5H), 1.28 (t, J=7 Hz, 3H).

Ethyl 2-Oxo-3-[2-(5,6,7,8-tetrahydro-[1,8]-naphthyridin-2-yl)ethyl]piperidin-1-yl-acetate (1-7)

A mixture of 1-6 (102 mg, 0.3 mmol), 10% Pd/C (50 mg), and EtOAc (25 mL) was stirred under a hydrogen atmosphere (1 atm) for 24 h. The catalyst was then removed by filtration through celite and the filtrate concentrated. Flash chromatography (silica, 20% CH₃OH/EtOAc) gave 1-7 as a yellow gum.

TLC R$_f$=0.45 (silica, 30% CH₃OH/EtOAc); ¹H NMR (300 MHz, CDCl₃) δ 7.05 (d, J=6 Hz, 1H), 6.41 (d, J=6 Hz, 1H), 4.80 (bs, 1H), 4.18 (q, J=7 Hz, 2H), 4.08 (m, 2H), 3.37 (m, 4H), 2.80–1.60 (m, 13H), 1.26 (t, 7 Hz, 3H).

2-Oxo-3-[2-(5,6,7,8-tetrahydro[1,8]-naphthyridin-2-yl)ethyl]piperidin-1-yl-acetic acid (1-8)

A solution of 17 (71 mg, 0.21 mmol) and 6N HCl (15 mL) was stirred at 55° C. for 2 h, followed by concentration to give 1-8 as a pale yellow gum.

TLC R$_f$=0.09 (silica, 20% CH₃OH/EtOAc);

2-Oxo-3-[2-(5,6,7,8-tetrahydro-[1,8]-naphthyridin-2-yl)ethyl]piper-idin-1-yl-acetyl-3(S)-pyridin-3-yl-1-alanine ethyl ester (1-10)

A stirred mixture of 1-8 (71 mg, 0.20 mmol), 1-9 (59 mg, 0.22 mmol) (Rico et al., *J. Org. Chem.*, 1993, 58, 7948), NMM (88 μL, 0.8 mmol), and CH₃CN (25 mL) was treated with BOP (97 mg, 0.22 mmol). After 24 h, the reaction mixture was concentrated to dryness, dissolved in EtOAc, and then washed with H₂O, dried (MgSO₄), and concentrated. Flash chromatography (silica, 10% (NH₃/EtOH/EtOAc) gave 1-10 as a colorless gum.

TLC R$_f$=0.9 (silica, 10% (NH₃/EtOH)/EtOAc); ¹H NMR (300 MHz, CD₃OD) δ 8.55 (m, 1H), 8.43 (m, 1H), 7.83 (m, 1H), 7.40 (m, 1H), 7.11 (m, 1H), 6.37 (m, 1H), 5.38 (m, 1H), 4.08 (q, J=7 Hz, 2H), 4.00 (m, 2H), 3.37 (m, 4H), 2.90 (m, 1H), 2.70–1.60 (m, 14H), 1.14 (t, J=7 Hz, 3H).

2-Oxo-3-[2-(5,6,7,8-tetrahydro-[1,8]-naphthyridin-2-yl)ethyl]piperin-1-yl-acetyl-3(S)-pyridin-3-yl-β-alanine trifluoroacetate (1-11)

A stirred solution of 1-11 (52 mg, 0.10 mmol) and 6N HCl (10 mL) was heated at 55° C. for 2 h, followed by concentration.

Preparative HPLC (VYDAC C₁₈ semiprep column, gradient elution: [95:5 (0.1% TFA/H₂0/0.1% TFA/CH₃CN) to 50:50 (0.1% TFA/H₂0/0. 1% TFA/CH₃CN) 80 min] gave 1-11 as a colorless solid.

¹H NMR (300 MHz, CD₃OD) δ 8.90 (s, 1H), 8.74 (d, J=5 Hz, 1H), 8.61 (d, J=8 Hz, 1H), 8.03 (m, 1H), 7.56 (d, J=7 Hz, 1H), 6.59 (d, J=7 Hz, 1H) 5.43 (m, 1H), 4.03 (m, 2H), 3.40 (m, 5H), 3.00 (m, 2H), 2.78 (m, 4H), 2.40–1.60 (m, 12H).

SCHEME 2

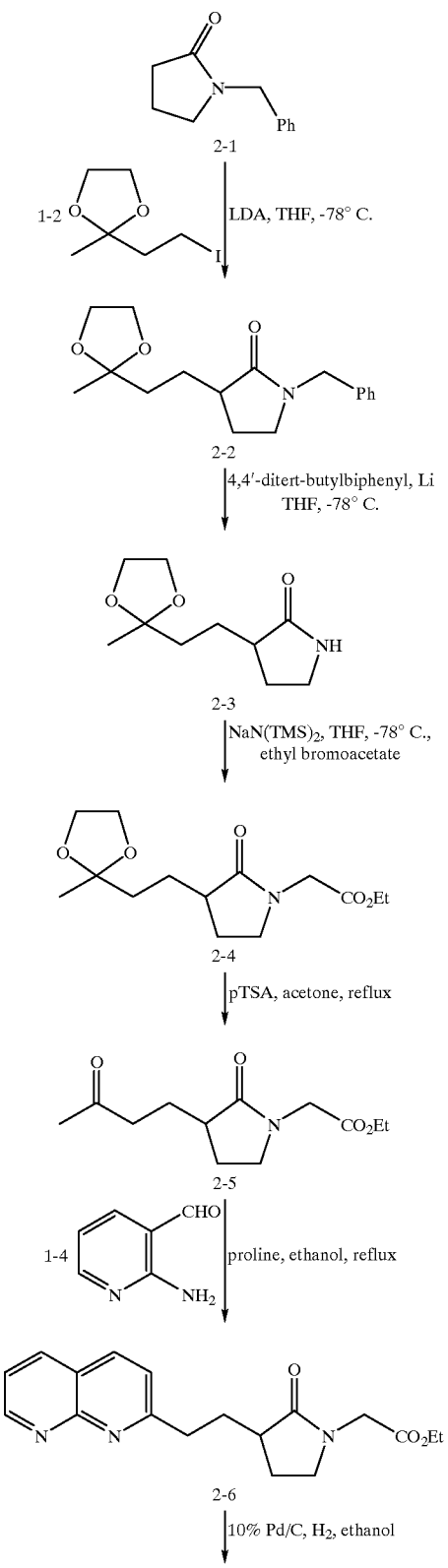

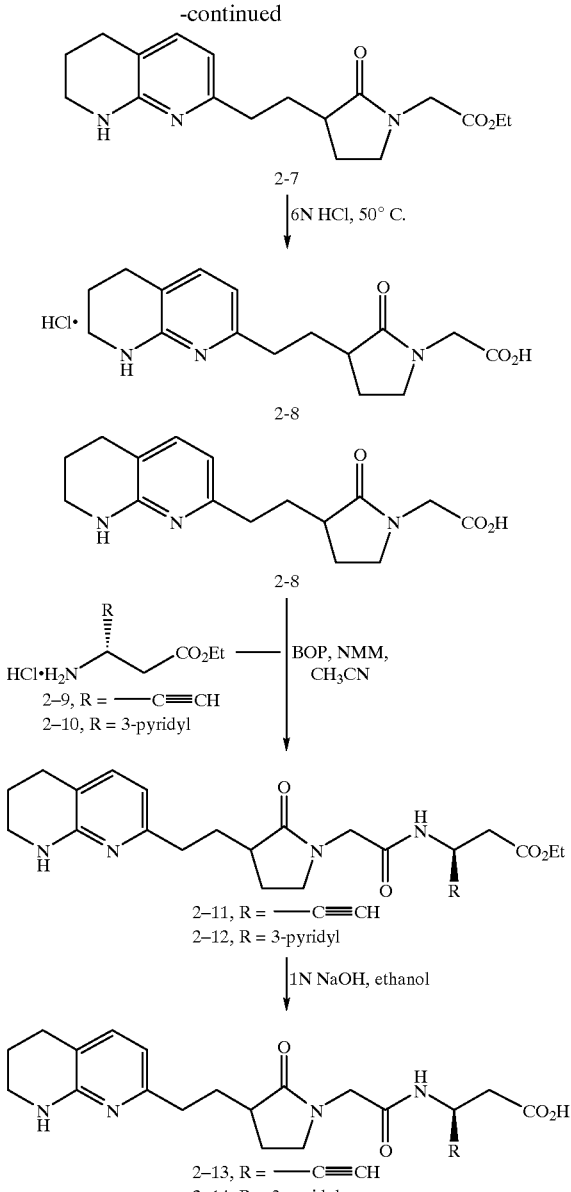

(2-Oxo-3-(3-(ethylendioxy)butyl)pyrrolidin-1-yl) benzyl (2-2)

To a stirred solution of 2-1 (5.3 g, 30 mmol) and THF (100 mL) at −78° C. was added LDA (17.5 mL, 35 mmol, 2.0 M in hexanes) dropwise over a 10 minute period. After 30 min, 1-2 (5.0 g, 21 mmol) was added followed by removal of the cooling bath. After 1 h, the reaction was quenched with AcOH (10 mL) and then diluted with EtOAc, washed with sat. NaHCO$_3$ and brine, dried (MgSO$_4$) and concentrated. Flash chromatography (silica, 25%→75% EtOAc/hexanes) gave 2-2 as an oil.

TLC R$_f$=0.38 (silica, EtOAc); $^1$H NMR (300 MHz, CDCl$_3$) δ 7.25 (m, 5H), 4.48 (d, J=15 Hz,1H), 4.40 (d, J=15 Hz, 1H), 3.94 (s, 4H), 3.18 (m, 2H), 2.44 (m, 1H), 2.30–1.30 (m, 9H).

2-Oxo-3-(3-(ethylendioxy)butyl)pyrrolidine (2-3)

To a stirred solution of 2-2 (4.1 g, 14.2 mmol) in THF (100 mL) at −78° C. was added a solution of Li 4,4'-di-tert-butylbiphenyl (188 mL, 0.5 M in THF) in 4 portions. After 1 h, the reaction was quenched with AcOH (25 mnL). The resulting mixture was diluted with EtOAc and then washed with H$_2$O, sat. NaHCO$_3$, and brine, dried (MgSO$_4$) and concentrated. Flash chromatography (silica, EtOAc→10% CH$_3$OH/EtOAc) gave 2-3 as a yellow oil.

TLC R$_f$=0.1 (silica, EtOAc); $^1$H NMR (300 MHz, CDCl$_3$) δ 6.23 (bs, 1H), 3.94 (s, 4H), 3.30 (m, 2H), 2.70 (m, 2H), 2.10–1.30 (m, 9H).

Ethyl (2-Oxo-3-(3-ethylendioxy)butyl)pyrrolidin-1-yl)acetate (2-4)

To a rapidly stirred solution of 2-3 (0.86 g, 4.3 mmol) and THF (25 mL) at −78° C. was added NaN(TMS)$_2$ (5.2 mL, 5.2 mmol, 1.0 M in THF). After 20 min, ethyl bromoacetate (0.58 mL, 5.2 mmol) was added followed by removal of the cooling bath. After 1 h, the reaction mixture was diluted with EtOAc and then washed with H$_2$O, sat. NaHCO$_3$ and brine, dried (MgSO$_4$), and concentrated to give 2-4 as a yellow oil.

TLC R$_f$=0.53 (silica, EtOAc); $^1$H NMR (300 MHz, CDCl$_3$) δ 4.18 (q, J=7 Hz, 2H), 4.04 (m, 2H), 3.93 (s, 4H), 3.39 (m, 2H), 2.44 (m, 1H), 2.23 (m, 1H), 2.00–1.30 (m, 9H), 1.25 (t, J=7H, 3H).

Ethyl (2-Oxo-3-(3-oxobutyl)pyrrolidin-1-yl)acetate (2-5)

A solution of 2-4 (1.1 g, 3.9 mmol), p-TSA (5 mg) and acetone (50 mL) was heated at reflux for 1 hr. The cooled reaction mixture was diluted with EtOAc and then washed with sat. NaHCO$_3$ and brine, dried (MgSO$_4$), and concentration to afford 2-5 as a yellow oil.

TLC R$_f$=0.48 (silica, EtOAc); $^1$H NMR (300 MHz, CDCl$_3$) δ 4.18 (q, J=7 Hz, 2H), 4.01 (s, 2H), 3.40 (m, 2H), 2.67 (t, J=7 Hz, 2H), 2.48 (m, 1H), 2.30–1.60 (m, 4H), 2.15 (s, 3H), 1.25 (t, J=7 Hz, 3H).

Ethyl (2-Oxo-3-(2-([1,8]naphthyridin-2-yl)ethyl) pyrrolidin-1-yl)-acetate (2-6)

A mixture of 2-5 (0.77 g, 3.0 mmol), 1-4 (0.55 g, 4.5 mmol, for preparation see Het, 1993, 36, 2513), L-proline (0.17 g, 1.5 mmol) and ethanol (25 mL) was heated at reflux for 20 hr. The cooled reaction mixture was concentrated and the residue purified by flash chromatography (silica, EtOAc→5% CH$_3$OH/EtOAc) to give 2-6 as a yellow oil.

TLC R$_f$=0.13 (silica, 10% CH$_3$OH/EtOAc); $^1$H NMR (300 MHz, CDCl$_3$) δ 9.08 (m, 1H), 8.17 (m, 1H), 8.12 (d, J=8 Hz, 1H), 7.49 (d, J=8 Hz, 1H), 7.46 (m, 1H), 4.15 (q, J=7 Hz, 2H), 4.04 (m, 2H), 3.42 (m, 2H), 3.21 (t, J=8 Hz, 2H), 2.60–1.80 (m, 5H), 1.25 (t, J=7 Hz, 3H).

Ethyl (2-Oxo-3-(2-(5,6,7,8-tetrahydro-[1,8]-naphthyridin-2-yl)ethyl)pyrrolidin-1-yl)acetate (2-7)

A mixture of 2-6 (0.87 g, 2.6 mmol), 10% Pd/C (0.5 g), and CH$_3$OH (25 mL) was stirred under a hydrogen atmosphere (1 atm) for 2 hr. The catalyst was then removed by filtration through a celite pad followed by concentration of the filtrate. Flash chromatogrphy (silica, EtOAc→5% CH$_3$OH/EtOAc) gave 2-7 as a yellow oil.

TLC R$_f$=0.18 (silica, 5% CH$_3$OH/EtOAc); $^1$H NMR (300 MHz, CDCl$_3$) δ 7.05 (d, J=7 Hz, 1H), 6.40 (d, J=7 Hz, 1H), 4.83 (bs, 1H), 4.17 (q, J=7 Hz, 2H), 4.03 (m, 2H), 3.40 (m, 4H), 2.80–1.60 (m, 1H), 1.27 (t, J=7 Hz, 3H).

(2-Oxo-3-(2-(5,6,7,8-tetrahydro[1,8]-naphthyridin-2-yl)ethyl)pyrrolidin-1-yl)acetic acid hydrochloride (2-8)

A stirred mixture of 2-7 (0.45 g, 1.4 mmol) and 6N HCl (10 mL) was heated at 50° C. for 1 h, followed by concentration to give 2-8 as a yellow oil.

$^1$H NMR (300 MHz, CD$_3$OD) δ 7.60 (d, J=7 Hz, 1H), 6.66 (d, J=7 Hz, 1H), 4.05 (s, 2H), 3.50 (m, 4H), 2.83 (m, 4H), 2.54 (m, 1H), 2.32 (m, 1H), 2.10 (m, 1H), 2.00–1.75 (m, 4H).

(2-Oxo-3-(2-(5,6,7,8-tetrahydro[1,8]-naphthyridin-2-yl)ethyl)pyrrolidin-1-yl)acetyl-3(S)-ethynyl-β-alanine ethyl ester (2-11)

To a stirred solution of 2-8 (50 mg, 0.15 mmol), 2-9 (29 mg, 0.17 mmol) (Zablocki et al., *J. Med Chem.*, 1995, 38, 2378), NMM (83 µL, 0.75 mmol), and CH$_3$CN (1 mL) was added BOP (74 mg, 0.17 mmol). After 20 h, the reaction mixture was diluted with EtOAc and then washed with sat. NaHCO$_3$, H$_2$O and brine, dried (MgSO$_4$), and concentrated to give 2-11 as a yellow oil.

TLC R$_f$=0.24 (silica, 10% CH$_3$OH/EtOAc).

(2-Oxo-3-(2-(5,6,7,8-tetrahydro[1,8]-naphthyridin-2-yl)ethyl)pyrrolidin-1-yl)acetyl-3(S)-pyridin-3-yl-β-alanine ethyl ester (2-12)

To a stirred solution of 2-8 (50 mg, 0.15 mmol), 2-10 (44 mg, 0.17 mmol) (Rico et al., *J. Org. Chem.*, 1993, 58, 7948), NMM (83 µL, 0.75 mmol), and CH$_3$CN (1 mL) was added BOP (74 mg, 0.17 mmol). After 20 h, the reaction mixture was diluted with EtOAc and then washed with sat. NaHCO$_3$, H$_2$O and brine, dried (MgSO$_4$), and concentrated to give 2-12 as a brown oil.

TLC R$_f$=0.24 (silica, 20% CH$_3$OH/EtOAc).

(2-Oxo-3-(2-(5,6,7,8-tetrahydro[1,8]-naphthyridin-2-yl)ethyl)pyrrolidin-1-yl)acetyl-3(S)-ethynyl-β-alanine (2-13)

A mixture of 2-11 (0.1 g, 0.15 mmol), 1N NaOH (300 µL, and ethanol (1 mL) was stirred at ambient temperature for 1 hr. Concentration and then flash chromagraphy (silica, 25:10:1:1→15:10:1:1 EtOAc/EtOH/NH$_4$OH/H$_2$O) gave 2-13 as a white solid.

TLC R$_f$=0.18 (silica, 10:10:1:1 EtOAc/EtOH/NH$_4$OH/H$_2$O) $^1$H NMR (300 MHz, CD$_3$OD) δ 7.45 (m, 1H), 6.50 (m, 1H), 4.53 (m, 1H), 3.80–3.30 (m, 5H), 3.05 (m, 1H), 2.80–2.15 (m, 9H), 2.00–1.75 (m, 4H).

(2-Oxo-3-(2-(5,6,7,8-tetrahydro[1,8]-naphthyridin-2-yl)ethyl)pyrrolidin-1-yl)acetyl-3(S)-pyridin-3-yl-β-alanine (2-14)

A mixture of 2-12 (0.1 g, 0.15 mmol), 1N NaOH (300 µL) and ethanol (1 mL) was stirred at ambient temperature for 1 hr. Concentration and the flash chromatography (silica, 25:10:1:1→15:10:1:1 EtOAc/EtOH/NH$_4$OH/H$_2$O) gave 2-14 as a white solid.

TLC R$_f$=0.10 (silica, 10:10:1:1 EtOAc/EtOH/NH$_4$OH/H$_2$O); $^1$H NMR (300 MHz, CD$_3$OD) δ 8.57 (m, 1H), 8.40 (m, 1H), 7.86 (m, 1H), 7.40 (m, 2H), 6.50 (m, 1H), 5.28 (m, 1H), 4.65–4.40 (m, 1H), 3.90–1.80 (M, 19H).

SCHEME 3

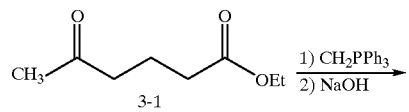

-continued

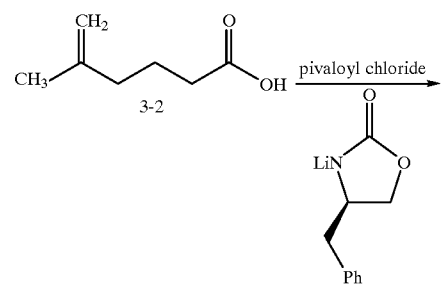

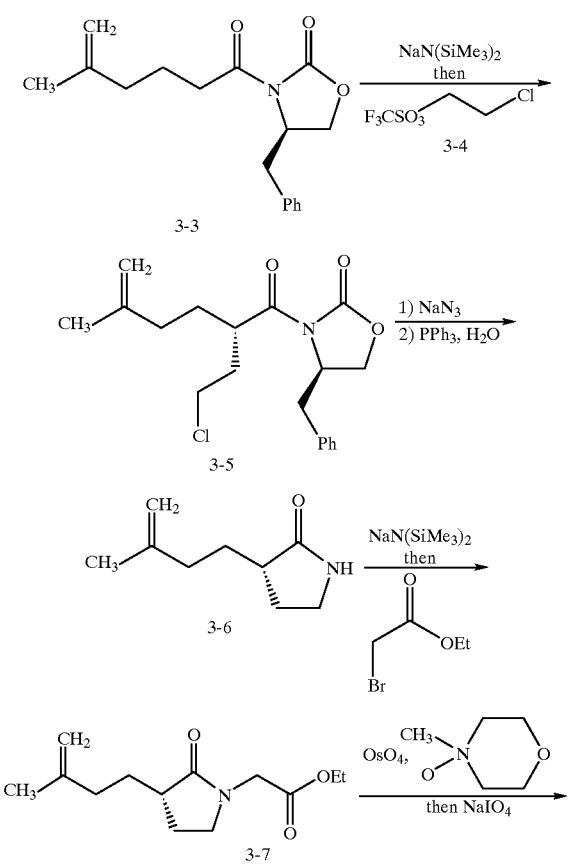

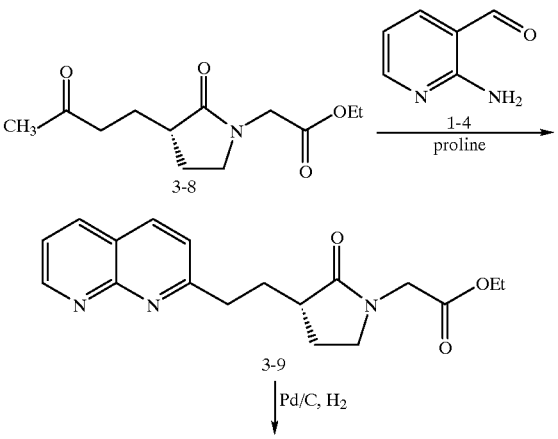

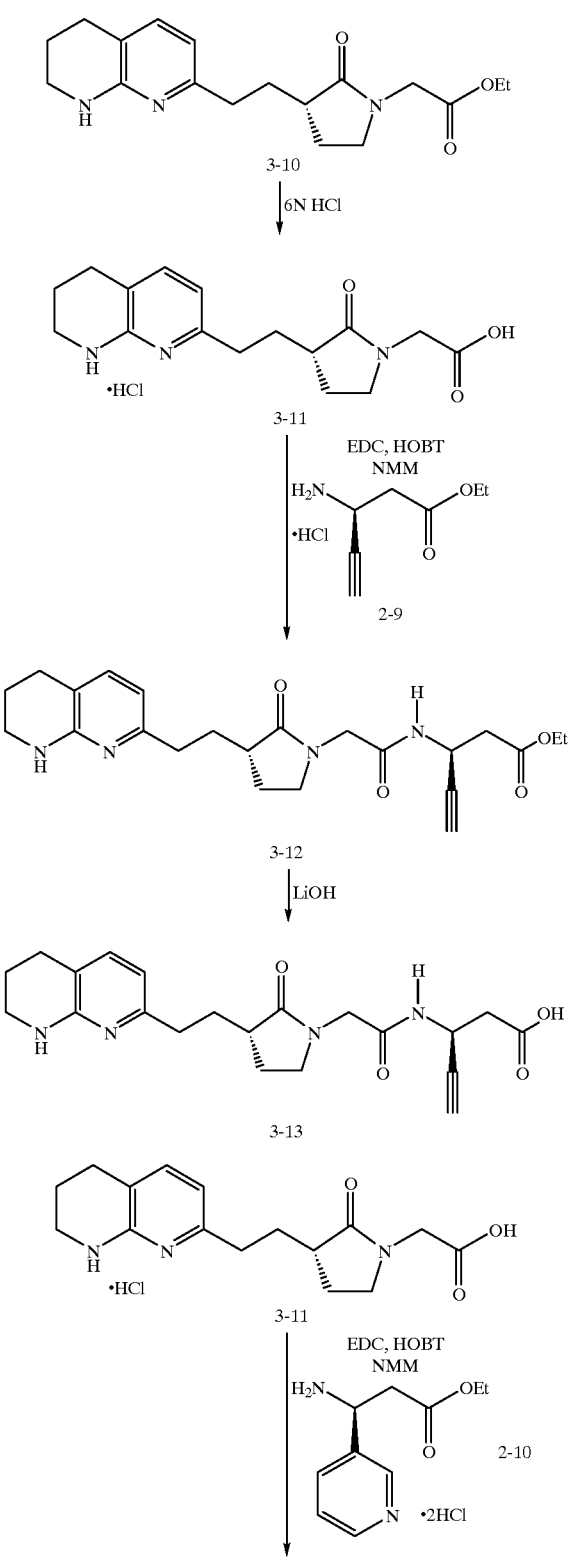

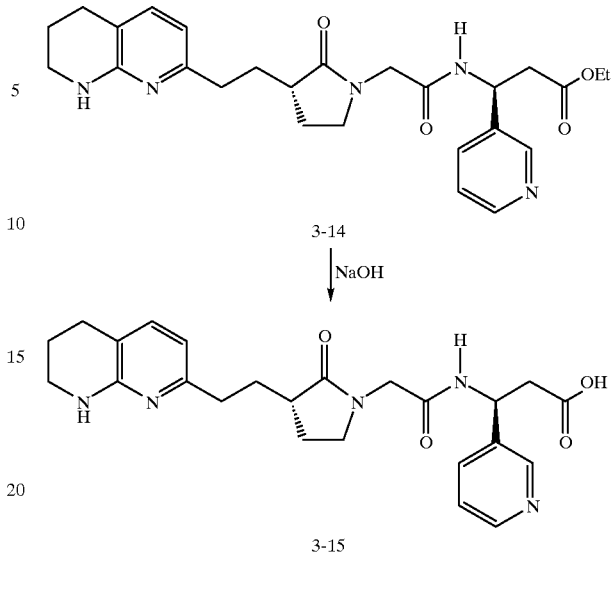

4-(Propyl-2-ene)butyric acid (3-2)

To a stirred suspension of of methyltriphenylphosphonium bromide (67.7 g, 190 mmol) in 1 L THF at 0° C. was added a solution of sodium bis(trimethylsilyl)amide (190 mL, 190 mmol, 1M THF). After an additional 30 minutes, 3-1 ethyl 4-acetylbutyrate (Aldrich Chemical Co.)(25.0 g, 158 mmol) was added, and the mixture stirred for 18 h. The mixture was filtered, and the filtrate concentrated. The residue was triturated with hexanes, and then filtered. Following evaporative removal of the solvent, the residue was chromatographed on silica gel, eluting with 10% ethyl acetate/hexanes to give the olefin as a colorless oil. TLC Rf=0.52 (10% ethyl acetate/hexanes).

$^1$H NMR (300 MHz, CHCl$_3$) δ 4.71 (d, 2H, J=13 Hz), 4.13 (q, 2H, J=7 Hz), 2.29 (t, 2H, J=7 Hz), 2.05 (t, 2H, J=8 Hz), 1.77 (m, 2H), 1.72 (s, 3H), 1.26 (t, 3H, J=7 Hz).

A solution of the above olefin (15.4 g, 98.6 mmol), 1 N NaOH (150 mL), and EtOH (300 mL) was stirred at ambient temperature for 2 h. Following acidification with 1 N HCl, the mixture was extracted with ether. The ether layer was washed with brine, dried over magnesium sulfate, and concentrated to give 3-2 as a colorless oil.

$^1$H NMR (300 MHz, CHCl$_3$) δ 4.70 (d, 2H, J=13 Hz), 2.27 (t, 2H, J=7 Hz), 2.06 (t, 2H, J=7 Hz), 1.72 (m, 5H).

(4-(Propyl-2-ene)butanoyl)-4(R)-benzyl-2-oxazolidinone (3-3)

To a solution of 3-2 (6.0 g, 46.8 mmol) in THF (200 ml) at −78° C. was added triethylamine (7.19 mL, 51.5 mmol) followed by pivaloyl chloride (6.35 mL, 51.5 mmol). The mixture was warmed to 0° C. for 1 h, then recooled to −78° C. In a separate flask, of (R)-(+)-4-benzyl-2-oxazolidinone (9.15 g, 51.5 mmol) was dissolved in THF (100 mL), cooled to −78° C., and n-BuLi (32.3 mL, 51.5 mmol; 1.6 M hexanes) was added dropwise. After 10 minutes, the lithium oxazolidinone was added to the pivalic anhydride. After 10 minutes, the mixture was warmed to 0° C. for 1.5 h. The mixture was then poured into ethyl acetate, washed with aqueous sodium bicarbonate, and dried over magnesium sulfate. Following evaporative removal of the solvent, the residue was chromatographed (silica gel, dichloromethane) to give 3-3 as a slightly yellow oil.

TLC Rf=0.8 (CH$_2$Cl$_2$). $^1$H NMR (300 MHz, CHCl$_3$) δ 7.40–7.18 (m, 5H), 4.80–4.60 (m, 3H), 4.18 (m, 2H), 3.30 (dd, 1H, J=3.2, 13.2 Hz), 2.95 (m, 2H), 2.76 (dd, 1H, J=9.5, 13.1 Hz), 2.11 (t, 2H, J=7.5 Hz), 1.87 (m, 2H), 1.74 (s, 3H).

2-Chloroethyltriflate (3-4)

To a solution of 1.67 mL (24.8 mmol) of 2-chloroethanol and 3.47 mL (29.8 mmol) of 2,6-lutidine in 20 mL of dichloromethane at 0° C. was added 4.59 mL (27.3 mmol) of triflic anhydride. After 1 h, the mixture was diluted with hexanes, washed with ice-cold 1N HCl, and dried over sodium sulfate. The solvents were evaporated to give 3-4 as a pink oil.

$^1$H NMR (300 MHz, CHCl$_3$) δ 4.69 (t, 2H, J=5.3 Hz), 3.78 (t, 2H, J=5.6 Hz).

2(S)-Chloroethyl-4-(propyl-2-ene)butanoyl-(4(R)-benzyl-2-oxazolidinone) (3-5)

To a solution of 3-3 (11.0 g, 38.3 mmol) in THF (60 mL) at −78° C. was added a solution of sodium bis(trimethylsilyl) amide (42.1 mL, 42.1 mmol; 1M/THF). After 20 min, 3-4 (16.2 ml, 115 mmol) was added over 5 min, and the resulting mixture stirred for 1.5 h at −78° C., then 2 h at −15° C. The mixture was diluted with hexanes, washed with sat. ammonium chloride, and dried over sodium sulfate. Following evaporative removal of the solvent, the residue was chromatographed (silica gel, 14% ethyl acetate/hexanes) to give 3-5 as a colorless oil. TLC Rf=0.5 (20% ethyl acetate/hexanes).

$^1$H NMR (300 MHz, CHCl$_3$) δ 7.30–7.18 (m, 5H), 4.67 (m, 3H), 4.19 (m, 2H), 3.99 (m, 1H), 3.58 (m, 2H), 3.33 (dd, 1H, J=3.2, 12.0 Hz), 2.75 (dd, 1H, J=9.7, 13.5 Hz), 2.23 (m, 1H), 2.18–1.82 (m, 4H), 1.77–1.60 (m, 1H), 1.71 (s, 3H).

Ethyl 2-oxo-3(S)-(3-methylenebutyl)pyrrolidine (3-6)

A mixture of 3-5 (8.15 g, 23.3 mmol) and NaN3 (4.54 g, 69.8 mmol) in DMSO (120 mL) was heated at 75° C. for 2 h. After cooling, the mixture was diluted with ether and hexanes, washed with water, and dried over sodium sulfate. Evaporative removal of the solvent gave the azide as a colorless oil.

TLC Rf=0.5 (20% ethyl acetate/hexanes). $^1$H NMR (300 MHz, CHCl$_3$) δ 7.30–7.22 (m, 5H), 4.69 (m, 3H), 4.17 (d, 2H, J=5.1 Hz), 3.89 (m, 1H), 3.38 (m, 3H), 2.74 (m, 1H), 2.13–1.63 (m, 6H), 1.71 (s, 3H).

To a solution of of this azide (8.0 g, 22.4 mmol) in THF (250 mL) and water (40 mL) was added triphenylphosphine (8.24 g, 31.4 mmol) in 4 portions over 5 minutes. This mixture was heated at reflux for 2 h, cooled, and evaporated. The residue was chromatographed (silica gel, 10% chloroform/ethyl acetate) to give 3-6 as a colorless oil.

TLC Rf=0.40 (20% chloroform/ethyl acetate). $^1$H NMR (300 MHz, CHCl$_3$) δ 6.47 (br s, 1H), 4.73 (m, 2H), 3.31 (m, 2H), 2.33 (m, 2H), 2.08 (m, 3H), 1.81 (m, 1H), 1.74 (s, 3H), 1.44 (s, 1H).

Ethyl 2-oxo-3(S)-(3-methylenebutyl)pyrrolidin-1-yl) acetate (3-7)

To a solution of 3-6 (2.50 g, 16.3 mmol) in THF (40 mL) at −78° C. was added sodium bis(trimethylsilyl)amide (17.1 mL, 17.1 mmol; 1M/ THF) dropwise. After an additional 20 min, ethyl bromoacetate (2.17 mL, 19.6 mmol) was added dropwise over 3 min. After an additional 20 min, 20 mL sat. aqueous NH$_4$Cl was added, and the cooling bath removed. The layers were separated, the aqueous layer washed with ether, and the combined organic extracts were dried over sodium sulfate. Following evaporative removal of the solvent, the residue was chromatographed (silica gel, 40% ethyl acetate/hexanes) to give 3-7 as a colorless oil.

TLC Rf=0.85 (50% chloroform/ethyl acetate). $^1$H NMR (300 MHz, CHCl$_3$) δ 4.73 (m, 2H), 4.18 (q, 2H, J=7.1 Hz), 4.06 (dd, 2H, J=17.6, 20.8 Hz), 3.42 (m, 2H), 2.44 (m, 1H), 2.27 (m, 1H), 2.12 (m, 3H), 1.75 (m, 1H), 1.74 (s, 3H), 1.50 (m, 1H), 1.28 (t, 3H, J=7.3 Hz).

Ethyl 2-oxo-3(S)-(3-oxo-butyl)pyrrolidin-1-yl) acetate (3-8)

To a solution of 3-7 (3.35 g, 14.0 mmol) and N-methylmorpholine-N-oxide (3.27 g, 28.0 mmol) in THF (10 mL) and water (1 mL) was added OsO$_4$ (5.7 mL, 0.56 mmol; 2.5% t-butanol). After 1 h, NaIO$_4$ (5.99 g , 28 mmol) in warm water (30 mL) was added over 2 min, and the resulting mixture stirred for 1 h. Water was then added, and the aqueous layer washed with ether and ethyl acetate, and the combined organic extracts were dried over sodium sulfate. Evaporative removal of the solvent gave 3-8 as a dark oil containing residual OsO$_4$.

TLC Rf=0.78 (70:20:10 chloroform/ethyl acetate/MeOH). $^1$H NMR (300 MHz, CHCl$_3$) δ 4.19 (m, 2H, J=7.2 Hz), 4.03 (s, 2H), 3.41 (m, 2H), 2.68 (t, 2H, J=9.4 Hz) 2.45 (m, 1H), 2.27 (m, 1H), 2.17 (s, 3H), 1.97 (m, 1H), 1.78 (m, 2H), 1.28 (t, 3H, J=7.2 Hz).

Ethyl 2-oxo-3(S)-[2-([1,8]-naphthyridin-2-yl)ethyl]pyrrolidin-1-yl)acetate (3-9)

A mixture of 3-8 (3.25 g, 13.5 mmol), 1-4, 2-amino-3-formylpyridine (2.2 g, 18.2 mmol; for preparation see *Synth. Commun.* 1987, 17, 1695) and proline (0.62 g, 5.39 mmol) in absolute ethanol (45 mL) was heated at reflux for 15 h. Following evaporative removal of the solvent, the residue was chromatographed (silica gel, 70:25:5 chloroform/ethyl acetate/MeOH to give 3-9 as a colorless oil.

TLC Rf=0.24 (70:25:5 chloroform/ethyl acetate/MeOH). $^1$H NMR (300 MHz, CHCl$_3$) δ 9.08 (m, 1H), 8.16 (m, 2H), 7.47 (m, 2H), 4.17 (m, 4H), 3.42 (m, 2H), 3.21 (t, 2H, J=6.0 Hz), 2.56 (m, 1H), 2.39 (m, 2H), 2.08 (m, 1H), 1.87 (m, 1H), 1.27 (t, 3H, J=7.1 Hz).

Ethyl 2-oxo-3(S)-[2-(5,6,7,8-tetrahydro[1,8]-naphthyridin-2-yl)ethyl]pyrrolidin-1-yl)acetate (3-10)

A mixture of 3-9 (3.33 g, 10.2 mmol) and 10% Pd/carbon (1.5 g) in EtOH (50 mL) was stirred under a balloon of hydrogen for 13 h. Following filtration and evaporative removal of the solvent, the residue was chromatographed (silica gel, 70:20:10 chloroform/ethyl acetate/MeOH to give 3-10 as a colorless oil.

TLC Rf=0.20 (70:20:10 chloroform/ethyl acetate/MeOH). $^1$H NMR (300 MHz, CHCl$_3$) δ 7.05 (d, 1H, J=7.3 Hz), 6.38 (d, 1H, J=7.3 Hz), 4.88 (br s, 1H), 4.17 (dd, 2H, J=7.0, 14.4 Hz), 4.04 (dd, 2H, J=17.6, 27.3 Hz), 3.40 (m, 4H), 2.69 (m, 4H), 2.51 (m, 1H), 2.28 (m, 2H), 1.90 (m, 2H), 1.78 (m, 2H), 1.27 (t, 3H, J=6.9 Hz).

2-Oxo-3(S)-[2-(5,6,7,8-tetrahydro[1,8]-naphthyridin-2-yl)ethyl]pyrrolidin-1-yl)acetic acid (3-11)

A mixture of 3-10 (0.60 g, 1.81 mmol) and 6N HCl (25 mL) was heated at 60° C. for 1 h. Evaporative removal of the solvent gave 3-11 as a yellow oil.

¹H NMR (300 MHz, DMSO-d₆) δ 8.4 (br s, 1H), 7.60 (d, 1H, J=7.3 Hz), 6.63 (d, 1H, J=7.3 Hz), 3.92 (dd, 2H, J=17.6, 25.9 Hz), 3.43 (m, 2H), 3.35 (m, 2H), 2.74 (m, 4H), 2.28 (m, 2H), 2.03 (m, 1H), 1.82 (m, 2H), 1.67 (m, 2H).

2-Oxo-3(S)-[2-(5,6,7,8-tetrahydro[1,8]-naphthyridin-2-yl)ethyl]pyrrolidin-1-yl)acetyl-3(S)-ethynyl-β-alanine ethyl ester (3-12)

A mixture of 3-11 (0.20 g, 0.588 mmol), 2-9 (0.157 g, 0.882 mmol), EDC (0.147 g, 0.765 mmol), HOBT (0.095 g, 0.706 mmol) and NMM (0.453 mL, 4.12 mmol) in CH₃CN (3 mL) and DMF (2 mL) was stirred for 20 h. The mixture was diluted with ethyl acetate, washed with water, brine, and dried over sodium sulfate. Following evaporative removal of the solvent, the residue was chromatographed (silica gel, 70:20:10 chloroform/ethyl acetate/MeOH to give 3-12 as a colorless foam.

TLC Rf=0.44 (70:20:10 chloroform/ethyl acetate/MeOH). ¹H NMR (300 MHz, CHCl₃) δ 7.06 (d, 1H, J=7.3 Hz), 6.39 (d, 1H, J=7.3 Hz), 5.07 (m, 1H), 4.94 (br s, 1H), 4.18 (q, 2H, J=6.1 Hz), 3.95 (q, 2H, J=16.1 Hz), 3.39 (m, 4H), 2.90 (s, 1H), 2.68 (m, 6H), 2.50 (m, 1H), 2.27 (m, 3H), 1.82 (m, 4H), 1.27 (t, 3H, J=7.1 Hz).

2-Oxo-3(S)-[2-(5,6,7,8-tetrahydro[1,8]-naphthyridin-2-yl)ethyl]-pyrrolidin-1-yl)acetyl-3(S)-ethynyl-β-alanine (3-13)

To a solution of 3-12 (0.050 g, 0.117 mmol) in ETOH (1 mL) was added 1N NaOH (0.164 ml, 0.164 mmol). After stirring for 2 h, the solvents were evaporated and the residue was chromatographed (silica gel, 25:10:1:1 ethyl acetate/EtOH/water/NH₄OH to give 3-13 as a colorless foam.

TLC Rf=0.26 (25:10:1:1 ethyl acetate/EtOH/water/NH₄OH). ¹H NMR (300 MHz, DMSO-d₆) δ 7.75 (br s, 1H), 7.14 (d, 1H, J=7.3 Hz), 6.31 (d, 1H, J=7.3 Hz), 4.74 (m, 1H), 3.90 (d, 1H, J=16.6 Hz), 3.67 (d, 1H, J=16.6 Hz), 3.23 (m, 4H), 2.57 (m, 7H), 2.30 (m, 1H), 2.11 (m, 2H), 1.73 (m, 2H), 1.59 (m, 2H).

2-Oxo-3(S)-[2-(5,6,7,8-tetrahydro[1,8]-naphthyridin-2-yl)ethyl]-pyrrolidin-1-yl)acetyl-3(S)-pyridin-3-yl-β-alanine ethyl ester (3-14)

A mixture of 3-11 (0.30 g, 0.882 mmol), 2-10 (0.354 g, 1.32 mmol), EDC (0.220 g (1.15 mmol), HOBT (0.143 g, 1.05 mmol) and NMM (0.680 mL (6.18 mmol) in CH₃CN (5 mL) and DMF (3 mL) at 0° C. was stirred for 10 min, then allowed to warm and stir for 20 h. The mixture was diluted with ethyl acetate, washed with water, brine, and dried over sodium sulfate. Following evaporative removal of the solvent, the residue was chromatographed (silica gel, 70:20:10 chloroform/ethyl acetate/MeOH to give 3-14 as a colorless foam .

TLC Rf=0.31(70:20:10 chloroform/ethyl acetate/MeOH). ¹H NMR (300 MHz, CHCl₃δ 8.55 (d, 1H, J=2.2 Hz), 8.50 (dd, 1H, J=1.5, 4.6 Hz), 7.64 (m, 2H), 7.23 (m, 1H), 7.05 (d, 1H, J=7.3 Hz), 6.38 (d, 1H, J=7.3 Hz), 5.40 (m, 1H), 4.98 (br s, 1H), 4.01 (m, 4H), 3.39 (m, 4H), 2.85 (m, 2H), 2.68 (m, 4H), 2.49 (m, at), 2.25 (m, 2H), 1.83 (m, 4H), 1.16 (t, 3H, J=7.2 Hz).

2-Oxo-3(S)-[2-(5,6,7,8-tetrahydro[1,8]-naphthyridin-2-yl)ethl]pyrrolidin-1-yl)acetyl-3(S)-pyridin-3-yl-β-alanine (3-15)

To a solution of 3-14 (0.049 g, 0.102 mmol) in THF (1 mL) and water (0.3 mL) at 0° C. was added 1M LiOH (0.112 ml, 0.112 mmol). After warming to ambient temperature and stirring for 2 h, the solvents were evaporated and the residue was chromatographed (silica gel, 25:10:1:1 ethyl acetate/EtOH/water/NH₄OH to give 3-15 as a colorless foam.

TLC Rf=0.15 (25:10:1:1 ethyl acetate/EtOH/water/NH₄OH). ¹H NMR (300 MHz, DMSO-d₆) δ 8.74 (d, 1H, J=8.3 Hz), 8.51 (m, 1H), 8.42 (m, 2H), 7.70 (d, 1H, J=8.1 Hz), 7.33 (m, 1H), 7.21 (d, 1H, J=7.3 Hz), 6.36 (d, 1H, J=7.3 Hz), 5.14 (m, 1H), 4.00 (d, 1H, J=16.8 Hz), 3.70 (d, 1H, J=16.6 Hz), 3.30 (m, 4H), 2.68 (m, 7H), 2.20 (m, 3H), 1.71 (m, 4H).

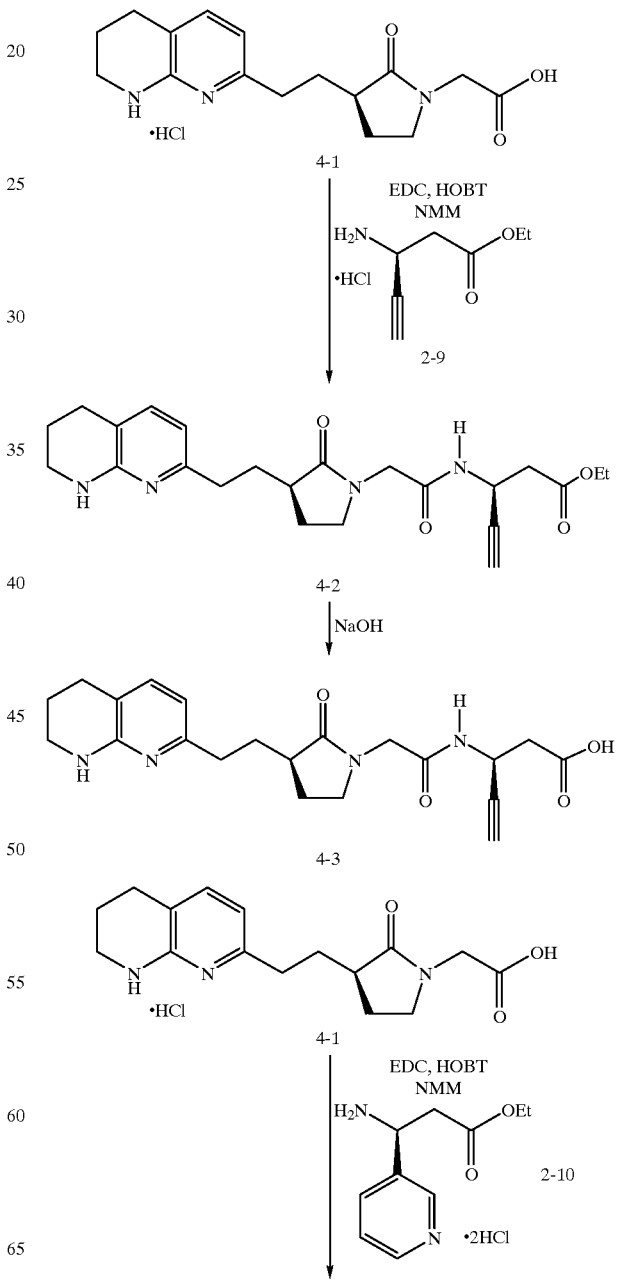

SCHEME 4

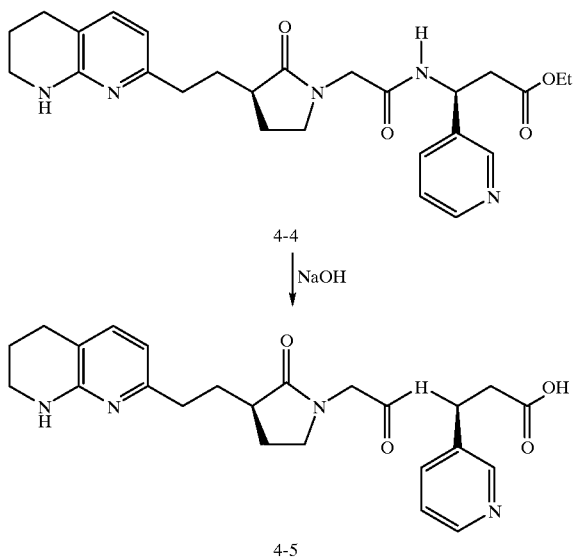

2-Oxo-3(R)-[2-(5,6,7,8-tetrahydro[1,8]-naphthyridin-2-yl)ethyl]pyrrolidin-1-yl)acetyl-3(S)-ethynyl-β-alanine ethyl ester (4-2)

Prepared from 4-1 (prepared by the method used to prepare 3-11, utilizing (S)-(—)-4-benzyl-2-oxazolidinone) and 2-9, by the method used to prepare 3-12.

$^1$H NMR (300 MHz, CHCl$_3$) δ 7.06 (d, 1H, J=7 Hz), 6.39 (d, 1H), J=7 Hz), 5.06 (m, 1H), 4.84 (br s, 1H), 4.16 (q, 2H, J=6 Hz), 3.93 (m, 2H), 3.38 (m, 4H), 2.68 (m, 6H), 2.52 (m, 1H), 2.25 (m, 2H), 1.90 (m, 2H), 1.78 (m, 2H), 1.26 (t, 3H, J=7 Hz).

2-Oxo-3(R)-[2-(5,6,7,8-tetrahydro[1,8]-naphthyridin-2-yl)ethyl]pyrrolidin-1-yl)acetyl-3(S)-ethynyl-β-alanine (4-3)

Prepared from 4-2 (0.05 g, 0.11 mmol) by the method used to prepare 3-13.

$^1$H NMR (300 MHz, CD$_3$OD, 1 drop 1N NaOD) δ 7.11 (d, 1H, J=7 Hz), 6.40 (d, 1H, J=7 Hz), 4.90 (m, 1H), 3.94 (q, 2H, J=17 Hz), 3.39 (m, 4H), 2.69 (d, 2H, J=6 Hz), 2.60 (m, 2H), 2.52 (d, J=7 Hz), 2.49 (m, 1H), 2.27 (m, 1H), 2.13 (m, 1H), 1.85 (m, 4H), 1.68 (m, 1H).

2-Oxo-3(R)-[2-(5,6,7,8-tetrahydro[1,8]-naphthyridin-2-yl)ethyl]-pyrrolidin-1-yl)acetyl-3(S)-pyridin-3-yl-β-alanine ethyl ester (4-4)

Prepared from 4-1 (0.35 g, 1.0 mmol) and 2-10 (0.33 g, 1.2 mmol) by the method used to prepare 3-14.

$^1$H NMR (300 MHz, CHCl$_3$) δ 8.55 (d, 1H, J=2 Hz), 8.55 (dd, 1H, J=2, 5 Hz), 7.61 (m, 1H), 7.54 (m, 1H), 7.06 (d, 1H), 6.38 (d, 1H, J=7 Hz), 5.40 (m, 1H), 4.90 (br s, 1H), 4.05 (q, 2H, J=7 Hz), 3.95 (m, 2H), 3.42 (m, 4H), 2.85 (dd, 2H, J=2, 6 Hz), 2.67 (m, 4H), 2.53 (m, 1H), 2.27 (m, 2H), 1.90 (m, 2H), 1.78 (m, 2H), 1.16 (m, 3H, J=7 Hz).

2-Oxo-3(R)-[2-(5,6,7,8-tetrahydro-[1,8]-naphthyridin-2-yl)ethyl]pyrrolidin-1-yl)acetyl-3(S)-pyridin-3-yl-β-alanine (4-5)

Prepared from 4-4 (0.16 g, 0.33 mmol) by the method used to prepare 3-15.

$^1$H NMR (300 MHz, CD$_3$OD) δ 8.57 (s, 1H), 8.42 (m, 1H), 7.86 (d, 1H, J=6 Hz), 7.43 (m, 2H), 6.51 (d, 1H, J=7 Hz), 5.28 (m, 1H), 4.63 (d, 1H, J=17 Hz), 3.60 (m, 2H), 3.47 (d, 1H, J=17 Hz), 3.35 (m, 3H), 3.14 (td, 1H, J=5, 13 Hz), 2.75 (m, 5H), 2.42 (m, 1H), 2.23 (m, 1H), 1.90 (m, 4H).

SCHEME 5

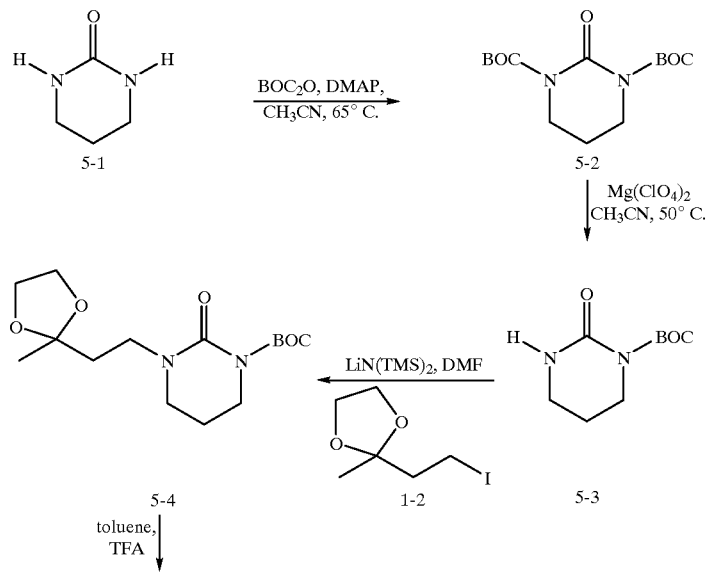

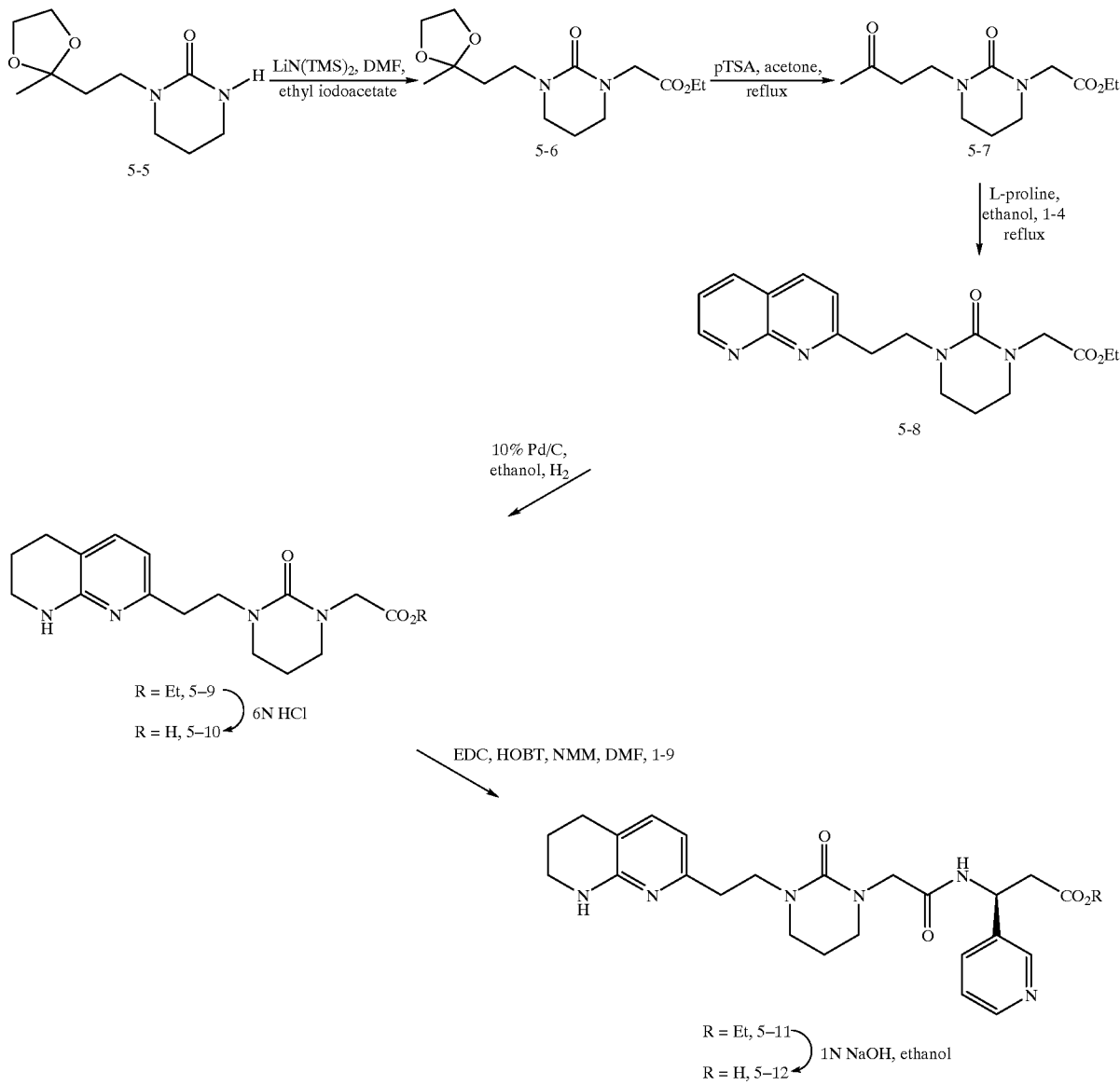

1,3-Di-tert-buyloxycarbonyl-tetrahydropyrimidine (5-2)

A heterogeneous mixture of 5-1 (10.0 g, 100 mmol), $BOC_2O$ (48 g, 220 mmol), DMAP (20 mg), and $CH_3CN$ (500 mL) was heated for 40 hr at 65° C. followed by addition of DMF (100 mL) and then continued heating for 24 hr. The cooled reaction mixture was diluted with EtOAc and then washed with $H_2O$, sat. $NaHCO_3$, 1N HCl, and brine, dried ($MgSO_4$), and concentrated. The residue was triturated with hexanes to give 5-2 as a yellow solid.

TLC RF=0.93 (EtOAc); $^1$HNMR (300 MHz, $CDCl_3$) δ 3.68 (t, J=7 Hz, 4H), 2.00 (m, 2H), 1.48 (s, 18 H).

Tert-Butyloxycarbonyl-tetrahydropyrimidine (5-3)

A solution of 5-2 (19.0 g, 63 mmol), $Mg(ClO_4)_2$ (2.8 g, 12.7 mmol), and $CH_3CN$ was heated at 50° C. for 2 hr. The cooled solution was diluted with $CHCl_3$ and then washed with 1N HCl, sat. $NaHCO_3$, and brine, dried ($MgSO_4$), and concentrated. Flash chromatography (silica, 75% EtOAc/hexanes→EtOAc) gave 5-3 as a brown solid.

TLC RF=0.26 (silica, EtOAc); $^1$HNMR (300 MHz, $CDCl_3$) δ 5.50 (bs, 1H), 3.70 (m, 2H), 3.29 (m, 2H), 1.97 (m, 2H), 1.48 (s, 9H).

Tert-Butyloxycarbonyl-2-oxo-3-(3-ethylene glycolbutyl)-tetrahydropyrimidine (5-4)

To a stirred solution of 5-3 (3.2g, 16.1 mmol) and DMF (50 mL) was added $LiN(TMS)_2$ (21 mL, 1M/hexanes). After 20 minutes, the iodide 1-2 (8.6 g, 35.2 mmol) in DMF (10 mL) was added and the reaction mixture heated at 50° C. for 2 hours. The cooled solution was diluted with $CHCl_3$ and then washed with $H_2O$ and brine, dried ($MgSO_4$), and concentrated. Flash chromatography (silica, 60% to 75% EtOAc/hexanes) gave 5-4 as an orange oil.

TLC RF=0.74 (silica, 70:15:15 $CHCl_3$/EtOAc/$CH_3OH$); $^1$H NMR (300 MHz, $CDCl_3$) δ 3.93 (s, 4H), 3.66 (t, J=6 Hz, 2H), 3.,44 (m, 2H), 3.30 (m, 2H), 1.96 (m, 2H), 1.48 (s, 9H), 1.32 (s, 3H).

1-Oxo-2-(3-ethylene glycol-butyl) tetrahydro-pyrimidine (5-5)

A mixture of 5-4 (3.0 g, 9.5 mmol), TFA (1.5 mL, and toluene (30 mL) was stirred at ambient temperature for 20 minutes, concentrated and the residue azeotroped with toluene to remove excess TFA. The residue was then dissolved in toluene (30 mL) and treated with NaHCO$_3$ (3 g), filtered, and the filtrate concentrated to give a yellow oil. Flash chromatography (silica, 70:15:15 CHCl$_3$/EtOAc/CH$_3$OH) gave 5-5 as a yellow oil.

TLC RF=0.63 (silica, 70:15:15 CHCl$_3$/EtOAc/CH$_3$OH); $^1$H NMR (300 MHz, CDCl$_3$) δ 5.16 (bs, 1H), 3.94 (s, 4H), 3.40 (m, 2H), 3.24 (m, 4H), 1.90 (m, 2H), 1.34 (s, 3H).

Ethyl 2-oxo-3-[3-ethylene glycol-butyl] tetrahydropyrimidin-1-yl-acetate (5-6)

To a stirred solution of 5-5 (2.0 g, 9.3 mmol) and DMF (50 mL) was added LiN(TMS)$_2$ (12.1 mL, 1.0 M/THF). After 20 min, ethyl iodoacetate (1.66 mL, 14.0 mmol) was added followed by heating at 60° C. for 1 hr. The cooled solution was diluted with EtOAc and then washed with H$_2$O, sat. NaHCO$_3$, and brine, dried (MgSO$_4$), and concentrated. Flash chromatography (silica, 50% to 75% EtOAc/hexanes) gave 5-6 as a colorless oil.

TLC RF=0.72 (silica, 70:15:15 CHCl$_3$/EtOAc/CH$_3$OH); $^1$H NMR (300 MHz, CDCl$_3$) δ 4.18 (q, J=7 Hz, 2H), 3.93 (s, 4H), 3.42 (m, 2H), 3.34 (m, 4H), 1.98 (m, 2H), 1.92 (m, 2H), 1.34 (s, 3H), 1.25 (t, J=7 Hz, 3H).

Ethyl 2-oxo-3-[3-oxo-butyl]tetrahydro-pyrimidin-1-yl-acetate (5-7)

A solution of 5-6 (750 mg, 2.5 mmol), p-TSA (10 mg), and acetone (30 mL) was refluxed for 1 hr. The cooled solution was diluted with CHCl$_3$ and then washed with sat. NaHCO$_3$ and brine, dried (MgSO$_4$), and concentrated to give 5-7 as a yellow oil.

TLC RF=0.36 (silica, 10% CH$_3$OH/EtOAc); $^1$H NMR (300 MHz, CDCl$_3$) δ 4.17 (q, J=7 Hz, 2H), 3.56 (m, 2H), 3.34 (m, 4H), 2.76 (t, J=7 Hz, 2H), 2.17 (s, 3H), 2.00 (m, 2H), 1.27 (t, J=7 Hz, 3H).

Ethyl 2-oxo-3-[2-naphthyridin-2-yl)ethyl]-tetrahydropyrimidin-1-yl-acetate (5-8)

A mixture of 5-7 (600 mg, 2.3 mmol), 1-4 (343 mg, 2.8 mmol), L-proline (175 mg), and ethanol (25 mL) was heated at reflux for 18 hr. The cooled reaction mixture was concentrated and the residue purified by flash chromatography (silica, 10% CH$_3$OH/EtOAc) gave 5-8 as a yellow solid.

TLC RF=0.21 (silica, 10% CH$_3$OH/EtOAc); $^1$H NMR (300 MHz, CDCl$_3$) δ 9.10 (m, 1H), 8.19 (m, 1H), 8.14 (d, J=8 Hz, 1H), 7.52 (d, J=8 Hz, 1H), 7.44 (m, 1H), 4.18 (q, J=7 Hz, 2H), 3.83 (m, 2H), 3.32 (m, 6H), 1.93 (m, 2H), 1.24 (t, J=7 Hz, 3H).

Ethyl 2-oxo-3-[2-(5,6,7,8-tetrahydro-[1,8]-naphthyridine-2-yl)ethyl]tetrahydropyrimidine-1-yl-acetate (5-9)

A mixture of 5-8 (600 mg, 1.75 mmol), 10% Pd/C (300 mg), and ethanol (10 mL) was stirred at ambient temperature under a hydrogen atmosphere (1 atm) for 20 hr. The catalyst was removed by filtration through a celite pad and the filtrate concentrated to give 5-9 as a yellow oil.

$^1$H NMR (300 MHz, CDCl$_3$) δ 7.04 (d, J=8 Hz, 1H), 6.42 (d, J=8 Hz, 1H), 4.80 (bs, 1H), 4.22-4.03 (m, 4H), 3.60 (m, 2H), 2.78 (m, 2H), 2.66 (m, 2H), 1.96 (m, 4H), 1.24 (t, J=7 Hz, 3H).

2-Oxo-3-[2-(5,6,7,8-tetrahydro-[1,8]naphthridin-2-yl)tetrahydro-pyrimidin-1-yl-acetic acid (5-10)

A solution of 5-9 (600 mg, 1.73 mmol) and 6N HCl (20 mL) was heated at 50° C. for 2 hr. The solution was concentrated followed by azeotropic removal of H$_2$O with CH$_3$CN to give 5-10 as a yellow solid. $^1$H NMR (300 MHz, CD$_3$OD) δ 7.58 (d, J=8 Hz, 1H), 6.63 (d, J=8 Hz, 1H), 3.98 (s, 2H), 3.62 (t, J=7 Hz, 2H), 3.50 (m, 2H), 3.36 (m, 4H), 2.93 (m, 2H), 2.80 (m, 2H), 2.00 (m, 4H).

Ethyl 2-oxo-3-[2-(5,6,7,8-tetrahydro-[1,8] naphthyridin-2-yl)ethyl]-tetrahydropyrimidin-1-yl-acetyl-3(S)-pyridin-3-yl-β-alanine (5-11)

To a stirred solution of 5-10 (250 mg, 0.70 mmol), 1-9 (210 mg, 0.77 mmol), EDC (148 mg, 0.77 mmol), HOBT (95 mg, 0.70 mmol), CH$_3$CN (2 mL), and DMF (2 mL) was added NMM (542 μL, 4.9 mmol). After stirring at ambient temperature for 20 hr, the reaction mixture was diluted with EtOAc and then washed with H$_2$O, sat. NaHCO$_3$, brine, dried (MgSO$_4$), and concentrated. Flash chromatography (silica, 70:15:15 CHCl$_3$/EtOAc/CH$_3$OH) gave 5-11 as a colorless oil.

TLC RF=0.31 (silica, 70:15:15 CHCl$_3$/EtOAc/CH$_3$OH); $^1$H NMR (300 MHz, CDCl$_3$) δ 8.58 (m, 1H), 8.50 (m, 1H), 7.94 (m, 1H), 7.66 (m, 1H), 7.22 (m, 1H), 7.05 (d, J=8 Hz, 1H), 6.40 (d, J=8 Hz, 1H), 5.43 (m, 1H), 4.06 (q, J=7 Hz, 2H), 4.02 (m, 1H), 3.90 (m, 1H), 3.60 (m, 2H), 3.39 (m, 2H), 3.29 (m, 2H), 3.19 (m, 2H), 2.88 (m, 2H), 2.77 (m, 2H), 2.70 (m, 2H), 1.90 (m, 4H), 1.16 (t, J=7 Hz, 3H).

2-Oxo-3-[2-(5,6,7,8-tetrahydro-[1,8]naphthyridin-2-yl}ethyl]-tetrahydropyrimidin-1-yl-acetyl-3-(S)-pyridin-3-yl-β-alanine (5-12)

A mixture of 5-11 (100 mg, 0.22 mmol), 1N NaOH (300 μL), and ethanol (1 mL) was stirred at ambient temperature for 1 hr, followed by concentration. Flash chromatography (silica, 25:10:1:1 to 15:10:1:1 EtOAc/EtOH/NH$_4$OH/H$_2$O) gave 5-12 as a white solid. TLC RF=0.22 (silica, 10:10:1:1 EtOAc/ethanol/NH$_4$OH, H$_2$O); $^1$H NMR (300 MHz, CD$_3$OD) δ 8.66 (m, 1H), 8.39 (m, 1H), 7.95 (m, 1H), 7.53 (d, J=8 Hz, 1H), 7.40 (m, 1H), 6.66 (d, J=8 Hz,1H), 5.1 8 (m, 1H), 4.27 (d, J=7 Hz, 1H), 4.16 (m, 1H), 3.64 (d, J=7 Hz, 1H), 3.50–3.10 (m, 8H), 3.00–2.65 (m, 6H), 1.95 (m, 4H).

SCHEME 6
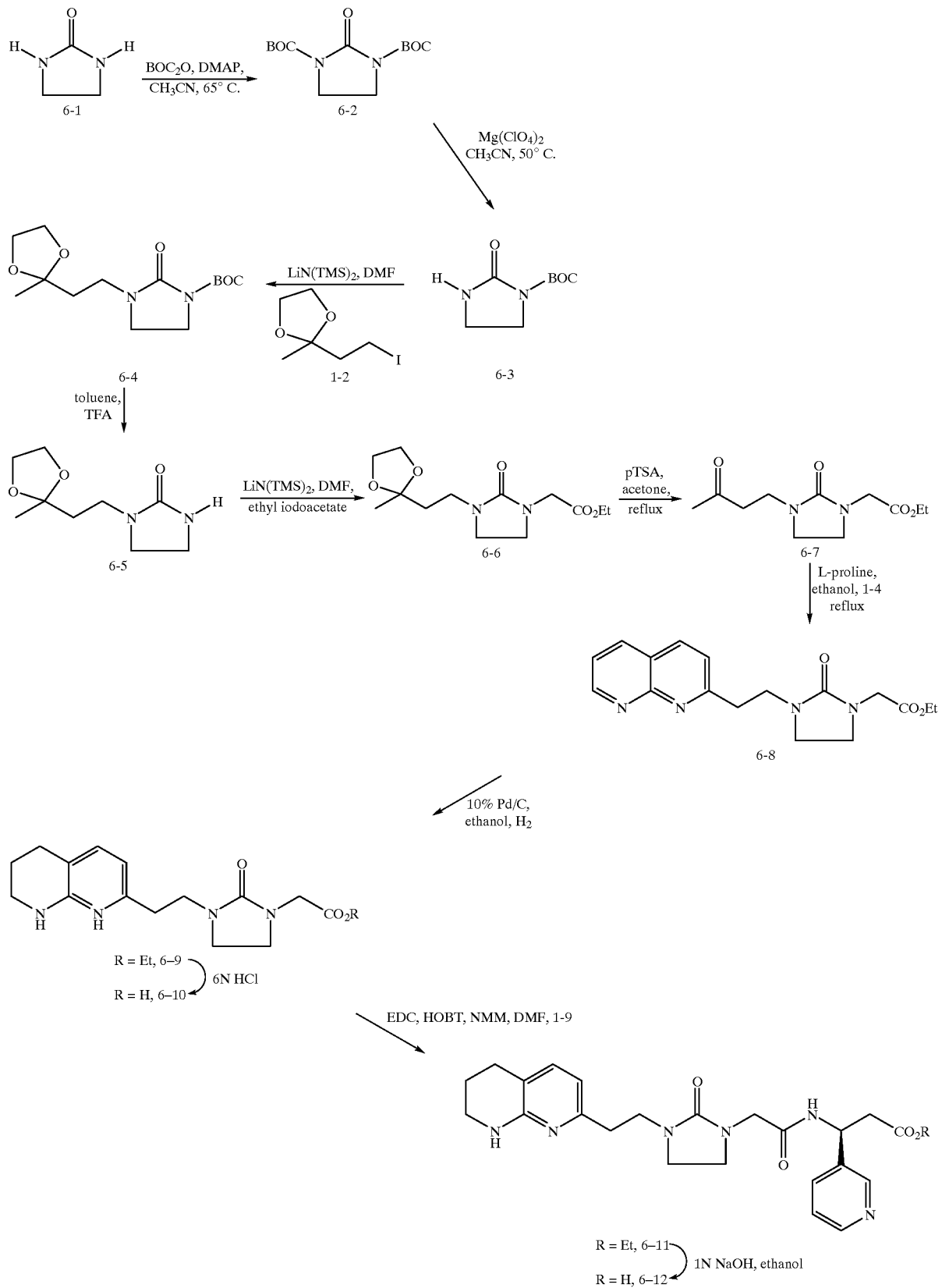

1,3-Di-tert-buyloxycarbonyl-imidazolidin-2-one (6-2)

A heterogeneous mixture of 6-1 (10.0 g, 116 mmol), $BOC_2O$ (56 g, 255 mmol), DMAP (20 mg), and $CH_3CN$ (400 mL) was heated for 18 hr at 60° C. The cooled reaction mixture was diluted with EtOAc and then washed with $H_2O$, sat. $NaHCO_3$, 1N HCl, and brine, dried ($MgSO_4$), and concentrated. The residue was triturated with hexanes to give 6-2 as a white solid.

TLC RF=0.91 (EtOAc); $^1H$ NMR (300 MHz, $CDCl_3$) δ 3.73 (s, 4H), 1.53 (s, 18 H).

Tert-Butyloxycarbonyl-imidazolidin-2-one (6-3)

A solution of 6-2 (28.0 g, 98 mmol), $Mg(ClO_4)_2$ (4.3 g, 20 mmol), and $CH_3CN$ (400 mL) was heated at 50° C. for 3 hr. The cooled solution was diluted with $CHCl_3$ and then washed with 1N HCl, sat. $naHCO_3$, and brine, dried ($MgSO_4$), and concentrated. Flash chromatography (silica, 50% EtOAc/hexanes→EtOAc) gave 6-3 as a yellow solid.

TLC RF=0.31 (silica, EtOAc); $^1H$ NMR (300 MHz, $CDCl_3$) δ 6.27 (bs, 1H), 3.86 (m, 2H), 3.47 (m, 2H), 1.50 (s, 9H).

1-Tert-Butyloxycarbonyl-3-(3-ethylene glycol-butyl)imidazolidin-2-one (6-4)

To a stirred solution of 6-3 (4.5 g, 24 mmol) and DMF (50 mL) was added $LiN(TMS)_2$ (26.6 mL, 1M/hexanes). After 20 minutes, the iodide 1-2 (8.6 g, 35.2 mmol) in DMF (10 mL) was added and the reaction mixture heated at 60° C. for 4 hours. The cooled solution was diluted with $CHCl_3$ and then washed with $H_2O$ and brine, dried ($MgSO_4$), and concentrated. Flash chromatography (silica, 75% EtOAc/hexanes) gave 6-4 as an yellow solid.

TLC RF=0.71 (silica, 70:15:15 $CHCl_3/EtOAc/CH_3OH$); $^1H$ NMR (300 MHz, $CDCl_3$) δ 3.93 (s, 4H), 3.75 (m, 2H), 3.36 (m, 4H), 1.90 (m, 2H), 1.53 (s, 9H), 1.34 (s, 3H).

1-(3-Ethylene glycol-butyl)imidazolidin-2-one (6-5)

A mixture of 6-4 (4.0 g, 13.3 mmol), TFA (3 mL, and toluene (60 mL) was stirred at 50° C. for 60 minutes, concentrated and the residue azeotroped with toluene to remove excess TFA. The residue was then dissolved in toluene (30 mL) and treated with $NaHCO_3$ (3 g), filtered, and the filtrate concentrated to give a yellow oil. Flash chromatography (silica, 70:25:5 $CHCl_3/EtOAc/CH_3OH$) gave 6-5 as a white solid.

TLC RF=0.58 (silica, 70:15:15 $CHCl_3/EtOAc/CH_3OH$); $^1H$ NMR (300 MHz, $CDCl_3$) δ 4.25 (bs, 1H), 3.94 (s, 4H), 3.44 (m, 4H), 3.32 (m, 2H), 1.90 (m, 2H), 1.35 (s, 3H).

Ethyl 2-oxo-3-[3-ethylene glycol-butyl]imidazolidin-1-yl-acetate (6-6)

To a stirred solution of 6-5 (2.0 g, 10 mmol) and DMF (50 mL) was added $LiN(TMS)_2$ (11 mL, 1.0 M/THF). After 20 min, ethyl iodoacetate (3.5 mL, 30 mmol) was added at ambient temperature. After 3 hr the solution was diluted with EtOAc and then washed with $H_2O$, sat. $NaHCO_3$, and brine, dried ($MgSO_4$), and concentrated. Flash chromatography (silica, 50% to 75% EtOAc/hexanes) gave 6-6 as a colorless oil.

TLC RF=0.71 (silica, 70:15:15 $CHCl_3/EtOAc/CH_3OH$); $^1H$ NMR (300 MHz, $CDCl_3$) δ 4.18 (q, J=7 Hz, 2H), 3.93 (s, 4H), 3.91 (m, 2H), 3.50–3.30 (m, 6H), 1.90 (m, 2H), 1.92 (m, 2H), 1.35 (s, 3H), 1.25 (t, J=7 Hz, 3H).

Ethyl 2-oxo-3-[3-oxo-butyl]imidazolidin-1-yl-acetate (6-7)

A solution of 6-6 (1.4 g, 4.9 mmol), p-TSA (10 mg), and acetone (30 mL) was refluxed for 1 hr. The cooled solution was diluted with $CHCl_3$ and then washed with sat. $NaHCO_3$ and brine, dried ($MgSO_4$), and concentrated to give 6-7 as a yellow oil.

TLC RF=0.34 (silica, EtOAc); $^1H$ NMR (300 MHz, $CDCl_3$) δ 4.17 (q, J=7 Hz, 2H), 3.94 (s, 2H), 3.48 (m, 2H), 3.42 (m, 4H), 2.72 (t, J=7 Hz, 2H), 2.17 (s, 3H), 1.27 (t, J=7 Hz, 3H).

Ethyl 2-oxo-3-[2-naphthyridin-2-yl)ethylimidazolidin-1-yl-acetate (6-8)

A mixture of 6-7 (1.0 g, 4.1 mmol), 1-4 (604 mg, 4.9 mmol), L-proline (238 mg), and ethanol (50 mL) was heated at reflux for 20 hr. The cooled reaction mixture was concentrated and the residue purified by flash chromatography (silica, 70:25:5 $CHCl_3/EtOAc/CH_3OH$) gave 6-8 as a yellow oil.

TLC RF=0.42 (silica, 70:15:15 $CHCl_3/EtOAc/CH_3OH$); $^1H$ NMR (300 MHz, $CDCl_3$) δ 9.10 (m, 1H), 8.19 (m, 1H), 8.14 (d, J=8 Hz, 1H), 7.52 (d, J=8 Hz, 1H), 7.44 (in, 1H), 4.17 (q, J=7 Hz, 2H), 3.81 (m, 2H), 3.42 (m, 4H), 3.32 (m, 4H), 1.24 (t, J=7 Hz, 3H).

Ethyl 2-oxo-3-[2-(5,6,7,8-tetrahydro-[1,8]-naphthyridine-2-yl)ethylimidazolidin-1-yl-acetate (6-9)

A mixture of 6-8 (1.1 g, 3.35 mmol), 10% Pd/C (500 mg), and ethanol (30 mL) was stirred at ambient temperature under a hydrogen atmosphere (1 atm) for 20 hr. The catalyst was removed by filtration through a celite pad and the filtrate concentrated to give 6-9 as a colorless oil.

TLC RF=0.11 (silica, 70:25:5 $CHCl_3/EtOAc/CH_3OH$); $^1H$ NMR (300 MHz, $CDCl_3$) δ 7.04 (d, J=8 Hz, 1H), 6.42 (d, J=8 Hz, 1H), 4.80 (bs, 1H), 4.22–4.03 (in, 4H), 3.96 (s, 2H), 3.55 (m, 2H), 3.40 (m, 2H), 2.78 (m, 2H), 2.68 (m, 2H), 1.90 (m, 2H), 1.24 (t, J=7 Hz, 3H).

2-Oxo-3-[2-(5,6,7,8-tetrahydro-[1,8]naphthridin-2-yl)imidazolidin-1-yl-acetic acid (6-10)

A solution of 6-9 (1.0 g, 3.0 mmol) and 6N HCl (40 mL) was heated at 60° C. for 1 hr. The solution was concentrated followed by azeotropic removal of $H_2O$ with $CH_3CN$ to give 6-10 as a yellow solid.

$^1H$ NMR (300 MHz, $CD_3OD$) δ 7.58 (d, J=8 Hz, 1H), 6.63 (d, J=8 Hz, 1H), 3.98 (s, 2H), 3.50 (m, 4H), 3.36 (m, 4H), 2.93 (m, 2H), 2.82 (m, 2H), 1.97 (m, 4H).

Ethyl 2-oxo-3-[2-(5,6,7,8-tetrahydro-[1,8]naphthyridin-2-yl)ethyl]imidazolidin-1-yl-acety1-3 (S)-pyridin-3-yl-β-alanine (6-11)

To a stirred solution of 6-10 (240 mg, 0.70 mmol), 1-9 (207 mg, 0.77 mmol), EDC (269 mg, 1.4 mmol), HOBT (95 mg, 0.70 mmol), and $CH_3CN$ (3 mL) was added NMM (619 μL, 5.6 mmol). After stirring at ambient temperature for 20 hr, the reaction mixture was diluted with EtOAc and then washed with $H_2O$, sat. $NaHCO_3$, brine, dried ($MgSO_4$), and concentrated. Flash chromatography (silica, 70:15:15 $CHCl_3/EtOAc/CH_3OH$) gave 6-11 as a colorless oil.

TLC RF=0.41 (silica, 70:15:15 $CHCl_3/EtOAc/CH_3OH$); $^1H$ NMR (300 MHz, $CDCl_3$) δ 8.58 (m, 1H), 8.50 (m, 1H), 7.94 (m, 1H), 7.66 (m, 1H), 7.22 (m, 1H), 7.05 (d, J=8 Hz, 1H), 6.40 (d, J=8 Hz, 1H), 5.43 (m, 1H), 4.06 (q, J=7 Hz, 2H), 3.85 (m, 1H), 3.55 (m, 2H), 3.40 (m, 2H), 3.33 (m, 4H), 2.90 (m, 2H), 2.77 (m, 2H), 2.70 (m, 2H), 1.90 (m, 2H), 1.77 (m, 2H), 1.18s (t, J=7 Hz, 3H).

2-Oxo-3-[2-(5,6,7,8-tetrahydro-[1,8]naphthyridin-2-yl}ethyl]-imidazolidin-1-yl-acetyl-3-(S)-pyridin-3-yl-β-alanine (6-12)

A mixture of 6-11 (160 mg, 0.33 mmol), 1N NaOH (500 μL), and ethanol (1 mL) was stirred at ambient temperature for 1 hr, followed by concentration. Flash chromatography (silica, 25:10:1:1 to 15:10:1:1 EtOAc/EtOH/NH$_4$OH/H$_2$O) gave 6-12 as a white solid.

TLC RF=0.21 (silica, 10:10:1:1 EtOAc/ethanol/NH$_4$OH, H$_2$O); $^1$H NMR (300 MHz, CD$_3$OD) δ 8.66 (m, 1H), 8.39 (m, 1H), 7.95 (m, 1H), 7.53 (d, J=8 Hz, 1H), 7.40 (m, 1H), 6.66 (d, J=8 Hz, 1H), 5.22 (m, 1H), 3.93 (d, J=17 Hz, 1H), 3.74 (d, J=17 Hz, 1H), 4.00–3.20 (m, 9H), 3.00–2.65 (m, 6H), 1.89 (m, 4H).

034), EDC (197 mg, 1.0 mmol), HOBT (70 mg, 0.52 mmol), and CH$_3$CN (3 mL) was added NMM (498 μL, 4.1 mmol). After stirring at ambient temperature for 20 hr, the reaction mixture was diluted with EtOAc and then washed with H$_2$O, sat. NaHCO$_3$, brine, dried (MgSO$_4$), and concentrated. Flash chromatography (silica, 70:25:5 CHCl$_3$/EtOAc/CH$_3$OH) gave 7-2 as a white solid.

TLC RF=0.11 (silica, 70:25:5 CHCl$_3$/EtOAc/CH$_3$OH); $^1$H NMR (300 MHz, CDCl$_3$) δ 8.29 (bs, 1H), 7.55 (d, J=7 Hz, 1H), 7.36 (d, J=7 Hz, 1H), 7.20–7.00 (m, 3H), 6.63 (d, J=7 Hz, 1H), 6.39 (d, J=7 Hz, 1H), 4.30 (m, 1H), 4.10 (q, J=7 Hz, 2H), 3.94 (d, J=17 Hz, 1H), 3.83 (d, J=17 Hz, 1H), 3.36 (m, 4H), 2.80 (m, 2H), 2.69 (m, 3H), 2.53 (d, J=6 Hz, 2H), 2.50 (m, 1H), 2.24 (m, 2H), 1.93 (m, 4H), 1.75 (m, 2H), 1.18 (t, J=7 Hz, 3H).

2-Oxo-3(R)-[2-(5,6,7,8-tetrahydro-[1,8]naphthyridin-2-yl)ethyl]pyrrolidin-1-yl)acetyl-3(R)-(2-ethylindol-3-yl)-β-alanine (7-3)

A mixture of 7-2 (60 mg, 0.11 mmol), 1N NaOH (132 μL), and ethanol (1 mL) was stirred at ambient temperature for 1 hr, followed by concentration. Flash chromatography (silica, 25:10:1:1 to 15:10:1:1 EtOAc/EtOH/NH$_4$OH/H$_2$O) gave 7-3 as a white solid.

TLC RF=0.12 (silica, 10:10:1:1 EtOAc/ethanol/NH$_4$OH/H$_2$O); $^1$H NMR (300 MHz, CD$_3$OD) δ 7.52 (d, J=7 Hz, 1H), 7.43 (d, J=7 Hz, 1H), 7.30 (d, J=8 Hz, 1H), 7.05 (m, 2H), 6.92 (m, 1H), 6.48 (d, J=7 Hz, 1H), 4.54 (d, J=17 Hz, 1H), 4.27 (m, 1H), 3.50–1.70 (m, 22H).

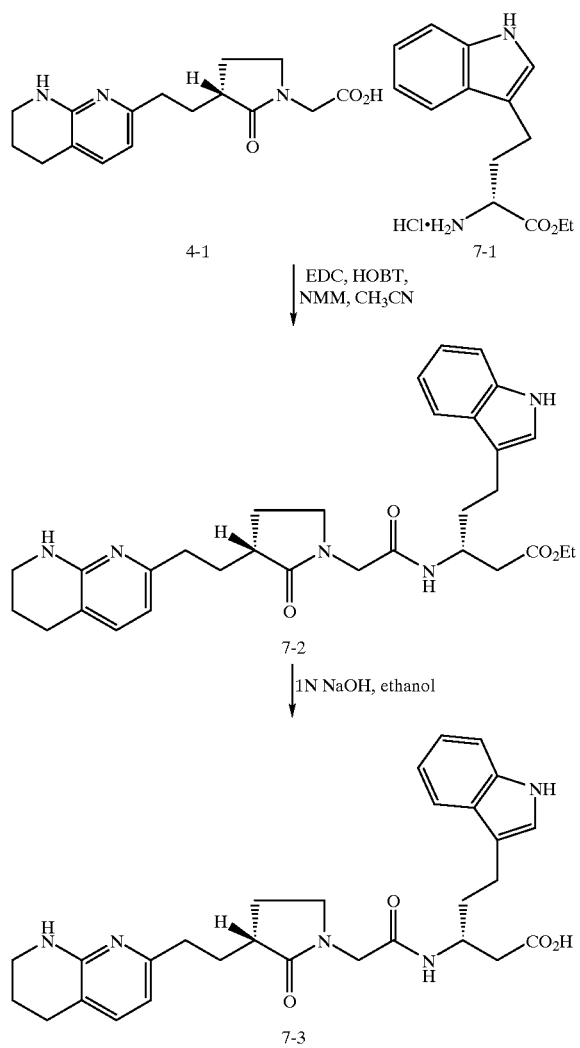

SCHEME 7

Ethyl 2-oxo-3(R)-[2-(5,6,7,8-tetrahydro-[1,8]naphthyridin-2-yl)ethyl]pyrrolidin-1-yl)acetyl-3(R)-(2-ethylindol-3-yl)-β-alanine (7-2)

To a stirred solution of 4-1 (175 mg, 0.52 mmol), 7-1 (214 mg, 0.72 mmol; for preparation see U.S. Pat. No. 5,321,

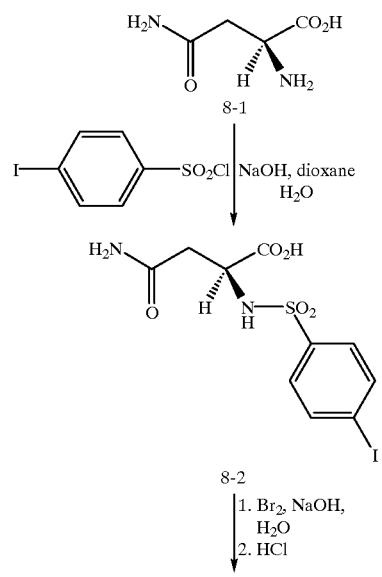

SCHEME 8
Synthesis of Radioligand for SPA Assay

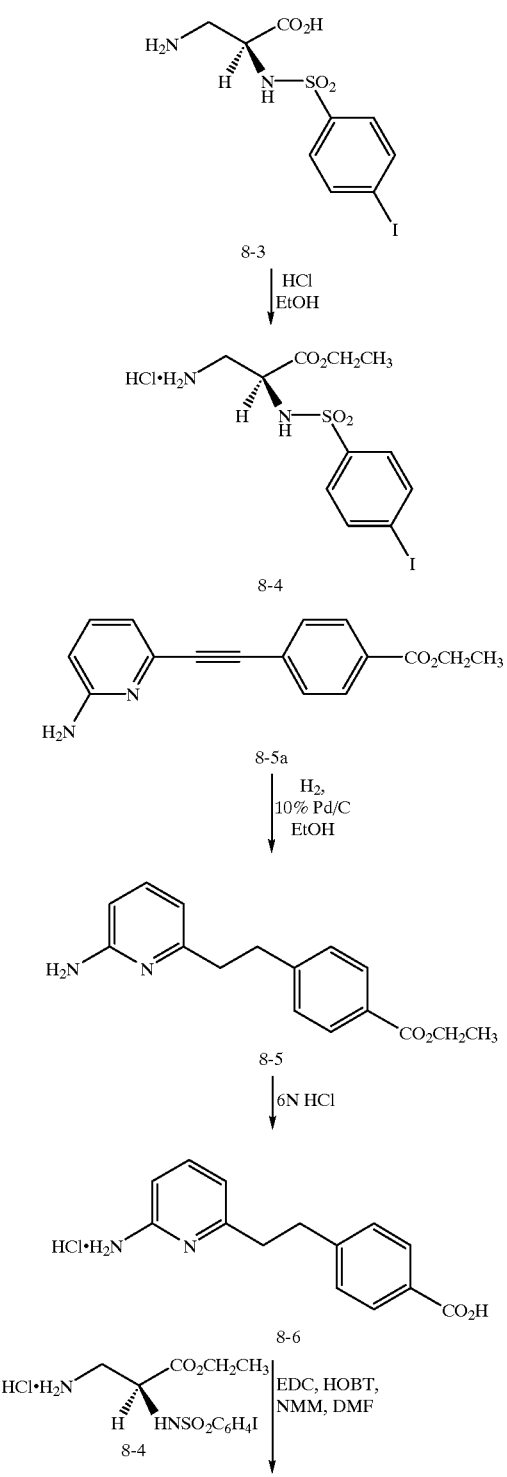

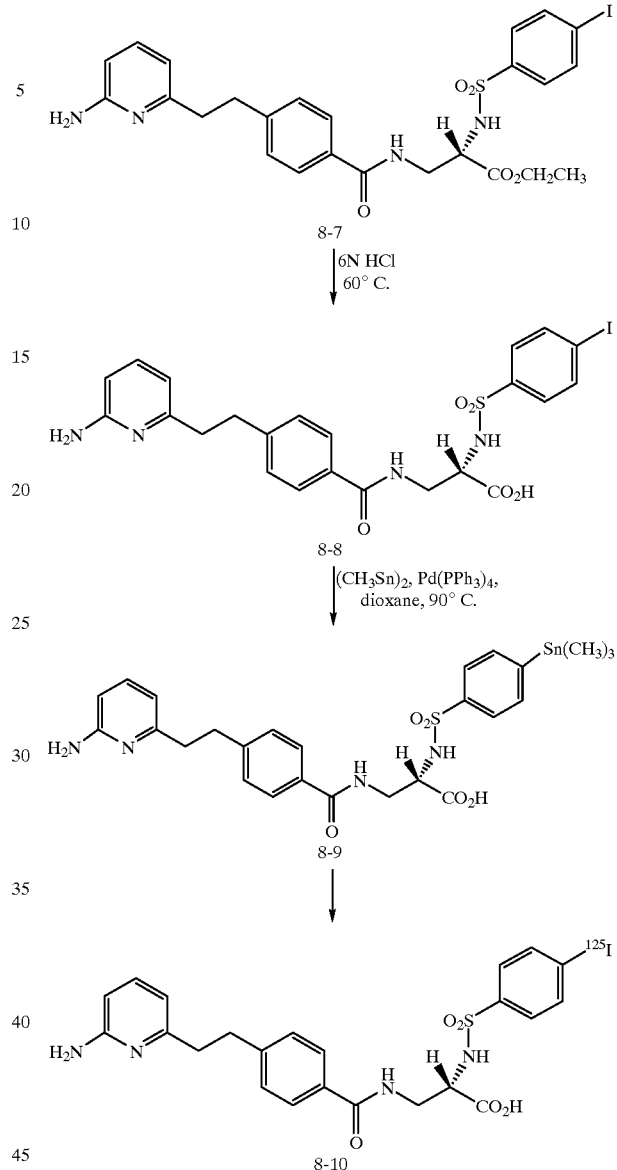

N-(4-Iodo-phenylsulfonylamino)-L-asparagine (8-2)

To a stirred solution of acid 8-1 (4.39 g, 33.2 mmol), NaOH (1.49 g, 37.2 mmol), dioxane (30 ml) and H$_2$O (30 ml) at 0° C. was added pipsyl chloride (10.34 g, 34.2 mmol). After ~5 minutes, NaOH (1.49, 37.2 mmol) dissolved in 15 ml H$_2$O, was added followed by the removal of the cooling bath. After 2.0 h, the reaction mixture was concentrated. The residue was dissolved in H$_2$O (300 ml) and then washed with EtOAc. The aqueous portion was cooled to 0° C. and then acidified with concentrated HCl. The solid was collected and then washed with Et$^2$O to provide acid 8-2 as a white solid.

$^1$H NMR (300 MHz, D$_2$O) δ 7.86 (d, 2H, J=8 Hz), 7.48 (d, 2H, J=8 Hz) 3.70 (m, 1H), 2.39 (m, 2H).

2(S)-(4-Iodo-phenylsulfonylamino)-β-alanine (8-3)

To a stirred solution of NaOH (7.14 g, 181.8 mmol) and H$_2$O (40 ml) at 0° C. was added Br$^2$ (1.30 ml, 24.9 mmol) dropwise over a ten minute period. After ~5 minutes, acid 8-2 (9.9 g, 24.9 mmol), NaOH (2.00 g, 49.8 mmol) and H$_2$O (35 ml) were combined, cooled to 0° C. and then added in a single portion to the reaction. After stirring for 20 minutes at 0° C., the reaction was heated to 90° C. for 30 minutes and then recooled to 0° C. The pH was adjusted to ~7 by dropwise addition of concentrated HCl. The solid was collected, washed with EtOAc, and then dried in vacuo to provide acid 8-3 as a white solid.

$^1$H NMR (300 MHz, D2O) δ 8.02 (d, 2H, J=8 Hz), 7.63 (d, 2H, J=8 Hz), 4.36 (m, 1H), 3.51 (dd, 1H, J=5 Hz, 13 Hz) 3.21 (m, 1H).

Ethyl 2(S)-(4-iodo-phenylsulfonylamino)-β-alanine-hydrochloride (8-4)

HCl gas was rapidly bubbled through a suspension of acid 8-3 (4.0 g, 10.81 mmol) in EtOH (50 ml) at 0° C. for 10 minutes. The cooling bath was removed and the reaction was heated to 60° C. After 18 h, the reaction was concentrated to provide ester 8-4 as a white solid. 1H NMR (300 MHz, CD$_3$OD) δ 7.98 (d, 2H, J=8 Hz), 7.63 (d, 2H, J=8 Hz), 4.25 (q, 1H, J=5 Hz), 3.92 (m, 2H), 3.33 (m, 1H), 3.06 (m, 1H), 1.01 (t, 3H, J=7 Hz).

Ethyl 4-[2-(2-Aminopyridin-6-yl)ethyl]benzoate (8-5)

A mixture of ester 8-5a (700 mg, 2.63 mmol), (for preparation, see: Scheme 29 of PCT International Application Publication No. WO 95/32710, published Dec. 7, 1995) 10% Pd/C (350 mg) and EtOH were stirred under 1 atm H$^2$. After 20 h, the reaction was filtered through a celite pad and then concentrated to provide ester 8-5 as a brown oil.

TLC R$_f$=0.23 (silica, 40% EtOAc/hexanes) $^1$H NMR (300 MHz, CDCl$_3$) δ 7.95 (d, 2H, J=8 Hz), 7.26 (m, 3H), 6.43 (d, 1H, J=7 Hz), 6.35 (d, 1H, J=8 Hz), 4.37 (m, 4H), 3.05 (m, 2H), 2.91 (m, 2H), 1.39 (t, 3H, J=7 Hz).

4-[2-(2-Aminopyridin-6-yl)ethyl]benzoic acid hydrochloride (8-6)

A suspension of ester 8-5 (625 mg, 2.31 mmol) in 6N HCl (12 ml) was heated to 60° C. After ~20 h, the reaction was concentrated to give acid 8-6 as a tan solid.

$^1$H NMR (300 MHz, CD$^3$OD) δ 7.96 (d, 2H, J=8 Hz), 7.80 (m, 1H), 7.33 (d, 2H, J=8 Hz), 6.84 (d, 1H, J=9 Hz), 6.69 (d, 1H, J=7 Hz), 3.09 (m, 4H).

Ethyl 4-[2-(2-Aminopyridin-6-yl)ethyl]benzoyl-2(S)-(4-iodophenylsulfonylamino)-β-alanine (8-7)

A solution of acid 8-6 (400 mg, 1.43 mmol), amine 8-4 (686 mg, 1.57 mmol), EDC (358 mg, 1.86 mmol), HOBT (252 mg, 1.86 mmol), NMM (632 μl, 5.72 mmol) and DMF (10 ml) was stirred for ~20 h. The reaction was diluted with EtOAc and then washed with sat NaHCO$_3$, brine, dried (MgSO$_4$) and concentrated. Flash chromatography (silica, EtOAC→5% isopropanol/EtOAc) provided amide 8-7 as a white solid.

TLC R$_f$=0.4 (silica, 10% isopropanol/EtOAc) $^1$H NMR (300 MHz, CD$^3$OD) δ 7.79 (d, 2H, J=9 Hz) 7.61 (d, 2H, J=8 Hz), 7.52 (d, 2H, J=9 Hz), 7.29 (m, 1H), 7.27 (d, 2H, J=8 Hz), 4.20 (m, 1H), 3.95 (q, 2H, J=7 Hz), 3.66 (dd, 1H, J=6 Hz, 14 Hz), 3.49 (dd, 1H, J=8 Hz, 13 Hz), 3.01 (m, 2H), 2.86 (m, 2H), 1.08 (t, 3H, J=7 Hz).

4-[2-(2-Aminopyridin-6-yl)ethyl]benzoyl-2(S)-(4-iodophenylsulfonylamino)-β-alanine (8-8)

A solution of ester 8-7 (200 mg, 0.3213 mmol) and 6N HCl (30 ml) was heated to 60° C. After ~20 h, the reaction mixture was concentrated. Flash chromatography (silica, 20:20:1:1 EtOAc/EtOH/NH$_4$OH/H$_2$O) provided acid 8-8 as a white solid.

TLC R$_f$=0.45 (silica, 20:20:1:1 EtOAc/EtOH/NH$_4$OH/H$_2$O) $^1$H NMR (400 MHz, DMSO) δ 8.40 (m, 1H), 8.14 (Bs, 1H), 7.81 (d, 2H, J=8 Hz), 7.62 (d, 2H, J=8 Hz), 7.48 (d, 2H, J=8 Hz), 7.27 (m, 3H), 6.34 (d, 1H, J=7 Hz), 6.25 (d, 1H, J=8 Hz), 5.85 (bs, 2H), 3.89 (bs, 1H), 3.35 (m, 2H), 2.97 (m, 2H), 2.79 (m, 2H).

4-[2-(2-Aminopyridin-6-yl)ethyl)benzoyl-2(S)-(4-trimethylstannylphenylsulfonylamino-β-alanine (8-9)

A solution of iodide 8-8 (70 mg, 0.1178 mmol), (CH$_3$Sn)$_2$ (49 μl, 0.2356 mmol), Pd(PPh$_3$)$_4$ (5 mg) and dioxane (7 ml) was heated to 90° C. After 2 h, the reaction was concentrated and then purified by prep HPLC (Delta-Pak C$_{18}$15 μM 100A°, 40×100 mm; 95:5→5:95 H$_2$O/CH$_3$CN) provided the trifluoroacetate salt. The salt was suspended in H$_2$O (10 ml), treated with NH$_4$OH (5 drops) and then lyophilized to provide amide 8-9 as a white solid.

$^1$H NMR (400 MHz, DMSO) δ 8.40 (m, 1H), 8.18 (d, 1H, J=8 Hz), 7.67 (m, 5H), 7.56 (d, 2H, J=8 Hz), 7.29 (d, 2H, J=8 Hz), 6.95–7.52 (m, 2H), 6.45 (bs, 2H), 4.00 (m, 1H), 3.50 (m, 1H), 3.33 (m, 1H), 2.97 (m, 2H), 2.86 (m, 2H).

4-[2-(2-Aminopyridin-6-yl)ethyl]benzoyl-2(S)-4-$^{125}$iodophenylsulfonylamino-β-alanine (8-10)

An iodobead (Pierce) was added to a shipping vial of 5 mCi of Na$^{125}$I (Amersham, IMS30) and stirred for five minutes at room temperature. A solution of 0.1 mg of 8-9 in 0.05 mL of 10% H$_2$SO$_4$/MeOH was made and immediately added to the Na$^{125}$I/iodobead vial. After stirring for three minutes at room temperature, approximately 0.04–0.05 mL of NH$_4$OH was added so the reaction mixture was at pH 6-7. The entire reaction mixture was injected onto the HPLC for purification[Vydac peptide-protein C-18 column, 4.6×250 mm, linear gradient of 10% acetonitrile (0.1% (TFA):H$_2$O (0.1% TFA) to 90% acetonitrile (0.1% TFA):H$_2$O (0.1% TFA) over 30 minutes, 1 mL/min]. The retention time of 8-10 is 17 minutes under these conditions. Fractions containing the majority of the radioactivity were pooled, lyophilized and diluted with ethanol to give approximately 1 mCi of 8-10, which coeluted on HPLC analysis with an authentic sample of 8-8.

Instrumentation: Analytical and preparative HPLC was carried out using a Waters 600E Powerline Multi Solvent Delivery System with 0.1 mL heads with a Rheodyne 7125 injector and a Waters 990 Photodiode Array Detector with a Gilson FC$_{203}$ Microfraction collector. For analytical and preparative HPLC a Vydac peptide-protein C-18 column, 4.6×250 mm was used with a C-18 Brownlee modular guard column. The acetonitrile used for the HPLC analyses was Fisher Optima grade. The HPLC radiodetector used was a Beckman 170 Radioisotope detector. A Vydac C-18 protein and peptide column, 3.9×250 mm was used for analytical and preparative HPLC. Solutions of radioactivity were concentrated using a Speedvac vacuum centrifuge. Calibration curves and chemical concentrations were determined using a Hewlett Packard Model 8452A UV/Vis Diode Array Spectrophotometer. Sample radioactivities were determined in a Packard A5530 gamma counter.

SCHEME 9

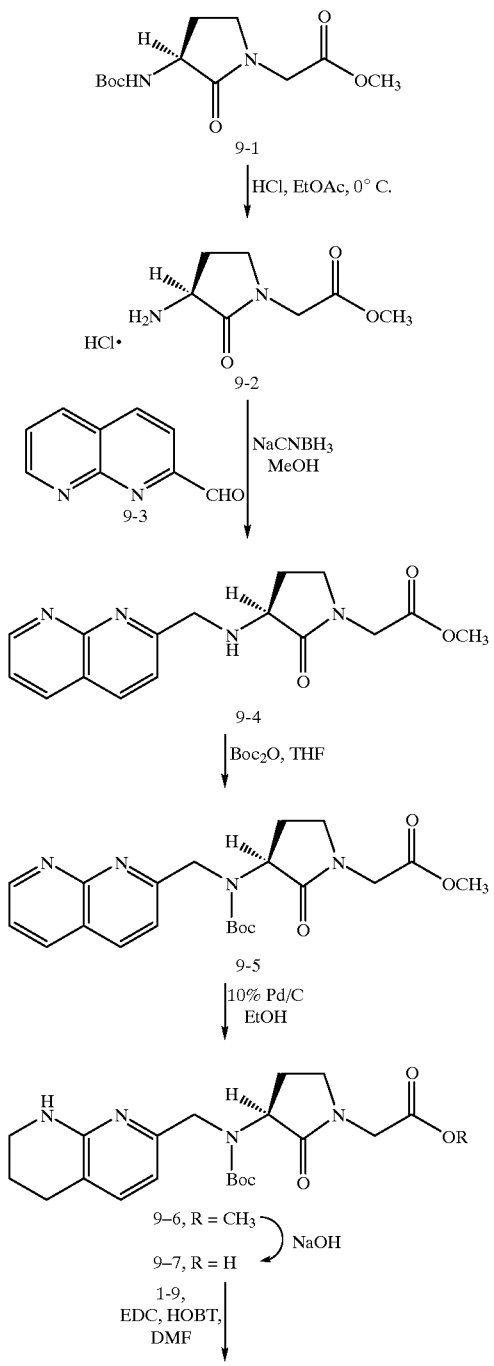

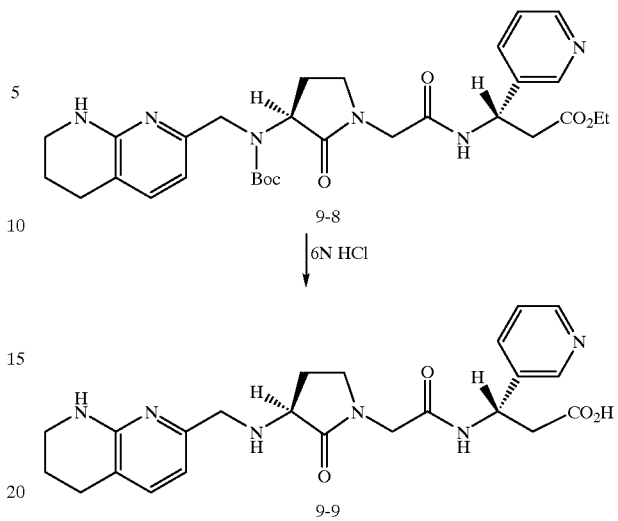

Methyl (S)-(3-amino-2-oxo-pyrrolidin-1-yl)-acetic acid hydrochloride(9-2)

A solution of 9-1 (0.50 g, 1.84 mmol) (prepared as described by Freidinger, R. M.; Perlow, D. S.; Veber, D. F.; *J. Org. Chem.*, 1982, 26, 104) in anhydrous ethyl acetate (50 mL) was cooled to 0° C. and saturated with HCl gas, then stirred at 0° C. for 2 h. The resulting colorless solution was concentrated at reduced pressure and the residue triturated with anhydrous diethyl ether giving 9-2 as a hygroscopic white solid.

$^1$H NMR (300 MHz, CD$_3$OD) δ 4.16 (d, 2H); 4.2 (m, 1H); 3.68 (s, 3H); 3.53 (m, 2H); 2.58 (m, 1H); 2.09 (m, 1H).

Methyl 2-oxo-3(S)-[1,8]naphthyridin-2-ylmethyl)-amino]-pyrrolidin-1-yl]-acetic acid (9-4)

A solution of 9-2 (232 mg, 1.11 mmol) and 9-3 (176 mg, 1.11 mmol) (prepared as reported by Weissenfels, M.; Ulrici, B.; *Z. Chem.* 1978, 18, 20. ) in anhydrous methanol (10 mL) was treated with NaOAc (91 mg, 1.11 mmol), NaBH$_3$CN (70 mg, 1.11 mmol) and powdered 4 Å molecular sieves (450 mg). The resulting mixture was stirred at 0° for 3.5 h, then concentrated and the residue subjected to flash chromatography on silica gel (95:4.5:0.5 CH$_2$Cl$_2$/MeOH/NH$_4$OH) to afford 9-4 as a colorless glass.

FAB MS (315, M$^{+1}$); $^1$H NMR (300 MHz, CD$_3$OD) δ 9.04 (d, 1H); 8.41 (dd, 1H); 8.38(d, 1H); 7.72 (d, 1H); 7.62 (dd, 1H); 4.31 (d, 2H); 4.21 (m, 2H); 3.68 (s, 3H); 3.63 (m, 1H); 3.53 (m, 2H); 2.52 (m, 1H); 1.95 (m, 1H).

Methyl[3(S)-[tert-butoxycarbonyl-[1,8]naphthyridin-2-ylmethyl)-amino]-2-oxo-pyrrolidin-1-yl]-acetic acid (9-5)

A solution of amine 9-4 (69 mg, 0.22 mmol) in THF (5 mL) was treated with Boc$_2$O (83 mg, 0.24 mmol) and stirred at room temperature for 18 h. The solvent was removed in vacuo and the resulting residue isolated by chromatography on silica gel (5% MeOH/CH$_2$Cl$_2$) to afford 9-5 as a yellow glass.

FAB MS (415, M$^{+1}$); $^1$H NMR (300 MHz, CD$_3$OD) δ 9.04 (d, 1H); 8.20 (m, 2H); 7.88 (d, 0.5H (rotamer a)); 7.82 (d, 0.5H (rotamer b)); 7.46(m, 1H); 5.1–4.3 (m, 5H); 3.81 (m, 2H); 3.72 (s, 3H); 3.41 (m, 2H); 2.36 (m, 2H); 1.47 (s, 4.5 H (rotamer a)); 1.30 (s, 4.5 H , (rotamer b)).

Methyl 3(S)-[tert-butoxycarbonyl-(5,6,7,8-tetrahydro-[1,8]naphthyridin-2-ylmethyl)-amino]-2-oxo-pyrrolidin-1-yl]-acetic acid (9-6)

A solution of 9-5 (40 mg, 0.097 mmol) in EtOH (5 mL) was treated with 10% Pd on C (8 mg) and then stirred under a H$_2$ filled balloon for 16 h. The catalyst was removed by filtration through celite and the filtrate concentrated to afford 9-6 as a colorless glass.

$^1$H NMR (300 MHz, CD$_3$OD) δ 7.10 (d, 1H) 6.78 (d, 0.5H (rotamer a)); 6.62 (d, 0.5H (rotamer b)); 4.8–3.9 (m, 5H); 3.81 (m, 2H); 3.72 (s, 3H); 3.38 (m, 2H); 2.36 (m, 2H); 1.21(s, 4.5 H (rotamer a)); 1.15 (s, 4.5 H, (rotamer b)).

3(S)-[tert-butoxycarbonyl-(5,6,7,8-tetrahydro-[1,8]naphthyridin-2-ylmethyl)-amino]-2-oxo-pyrrolidin-1-yl]-acetic acid (9-7)

A solution of 9-6 (38 mg, 0.091 mmol) in 50% aqueous THF (2 mL) was treated with 1.0 N NaOH (95 mL, 0.095 mmol) and stirred at room temperature for 2 h. The reaction was nuetralized with 1N CHl, evaporated, and the residue dissolved in MeOH (2.5 mL), filtered and evaporated to afford 9-7 as a colorless glass.

$^1$H NMR (300 MHz, CD$_3$OD) δ 7.31 (d, 1H) 6.78 (br, d, 1H); 4.8–3.9 (m, 5H); 3.81 (m, 2H); 3.38 (m, 2H); 2.36 (m, 2H); 1.21(s, 4.5 H (rotamer a)); 1.15 (s, 4.5 H , (rotamer b)).

Ethyl 3-(2-{2-oxo-3(S)-[(5,6,7,8-tetrahydro-[1,8]naphthyridin-2-ylmethyl)-amino]-pyrrolidin-1-yl}-acetylamino)-3-(S)-pyridin-3-yl-propionic acid (9-8)

9-7 (43 mg, 0.093 mmol), 1-9 (25 mg, 0093 mmol), EDC (18 mg, 0.093 mmol), HOBT (13 mg, 0.093 mmol), and N-methyl morpholine (31 mL, 0.28 mmol) in anhydrous DMF (5 mL) was stirred at room temperature for 18 h, then concentrated in vacuuo and the residue chromatographed on silica gel using 5% MeOH/CH$_2$Cl$_2$ as eluent affording 9-8 as a colorless glass.

$^1$H NMR (300 MHz, CDCl$_3$) δ 8.61 (s, 1H); 8.45 (d, 1H); 8.00 (m, 1H); 7.68, (d, 1H); 7.21 (m, 1H); 7.17 (d, 1H); 5.56 (m, 1H); 4.75 (s, 2H); 4.45 (m, 2H); 4.05 (q, 2H); 3.95 (m, 1H); 3.5–3.3 (m, 4H); 2.92 (m, 1H); 2.87 (m, 1H); 2.74 (m, 2H); 2.35 (m, 2H); 1.92 (m, 2H); 1.36 (s, 9H); 1.21 (t, 3H).

3-(2-{2-oxo-3(S)-[(5,6,7,8-tetrahydro-[1,8]naphthyridin-2-ylmethyl)-amino]-pyrrolidin-1-yl}-acetylamino)-3-(S)-pyridin-3-yl-propionic acid (9-9)

9-8 (25 mg, 0.043 mmol) was dissolved in 6N HCl (2 mL) and stirred at room temperature for 16 h, then evaporated to afford 9-9 as a pale yellow solid.

FAB MS (453, M$^{+1}$);

$^1$H NMR (300 MHz, CD$_3$OD) δ 9.00 (s, 1H); 8.81 (d, 1H); 8.79(m, 1H); 8.10 (m, 1H); 7.71 (d, 1H); 7.01 (m, 1H); 5.56 (m, 1H); 4.75 (s, 2H); 4.61 (m, 1H); 4.50 (m, 1H); 4.35 (m, 1H); 4.10 (s, 2H); 3.62 (m, 4H); 3.4–3.0 (m, 2H); 2.8 (m, 2H); 2.70 (m, 1H); 2.45 (m 1H); 1.98 (m, 2H).

Following the procedure described in Scheme 10, bicyclic compounds such as 10-6 are readily prepared by one of ordinary skill in the art.

SCHEME 10

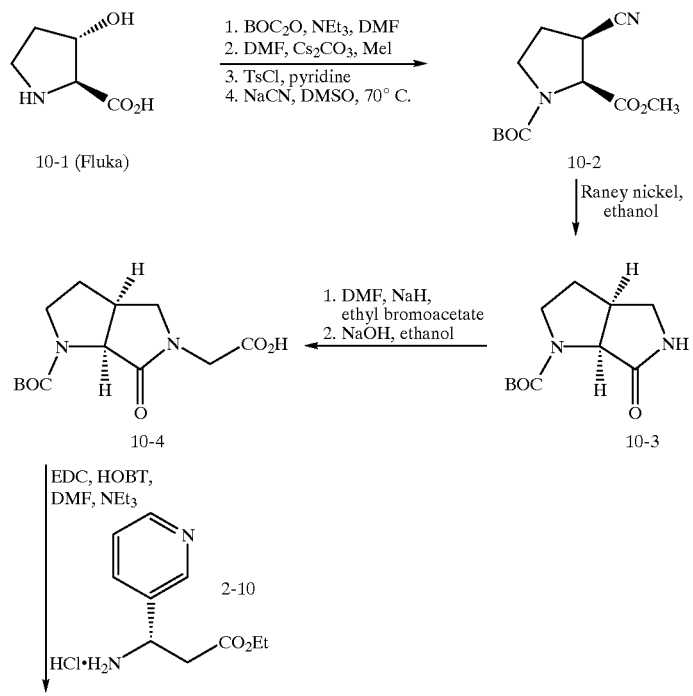

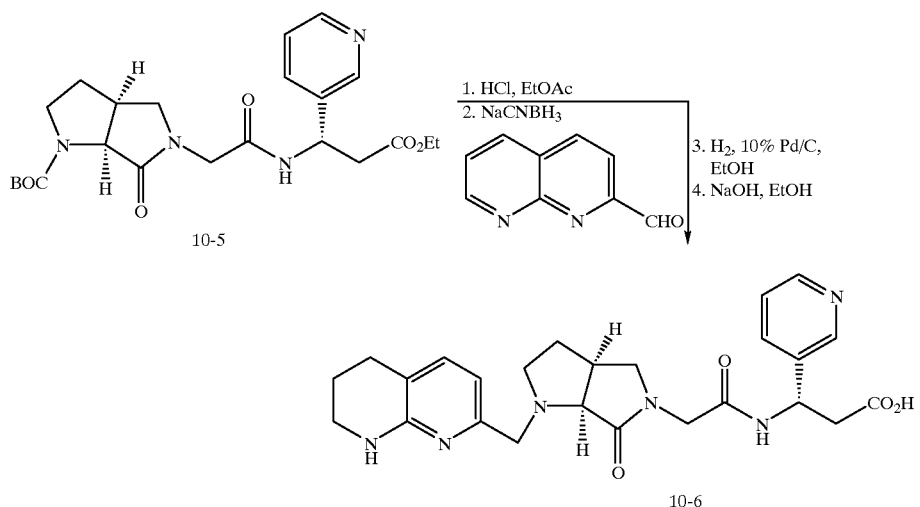
SCHEME 11
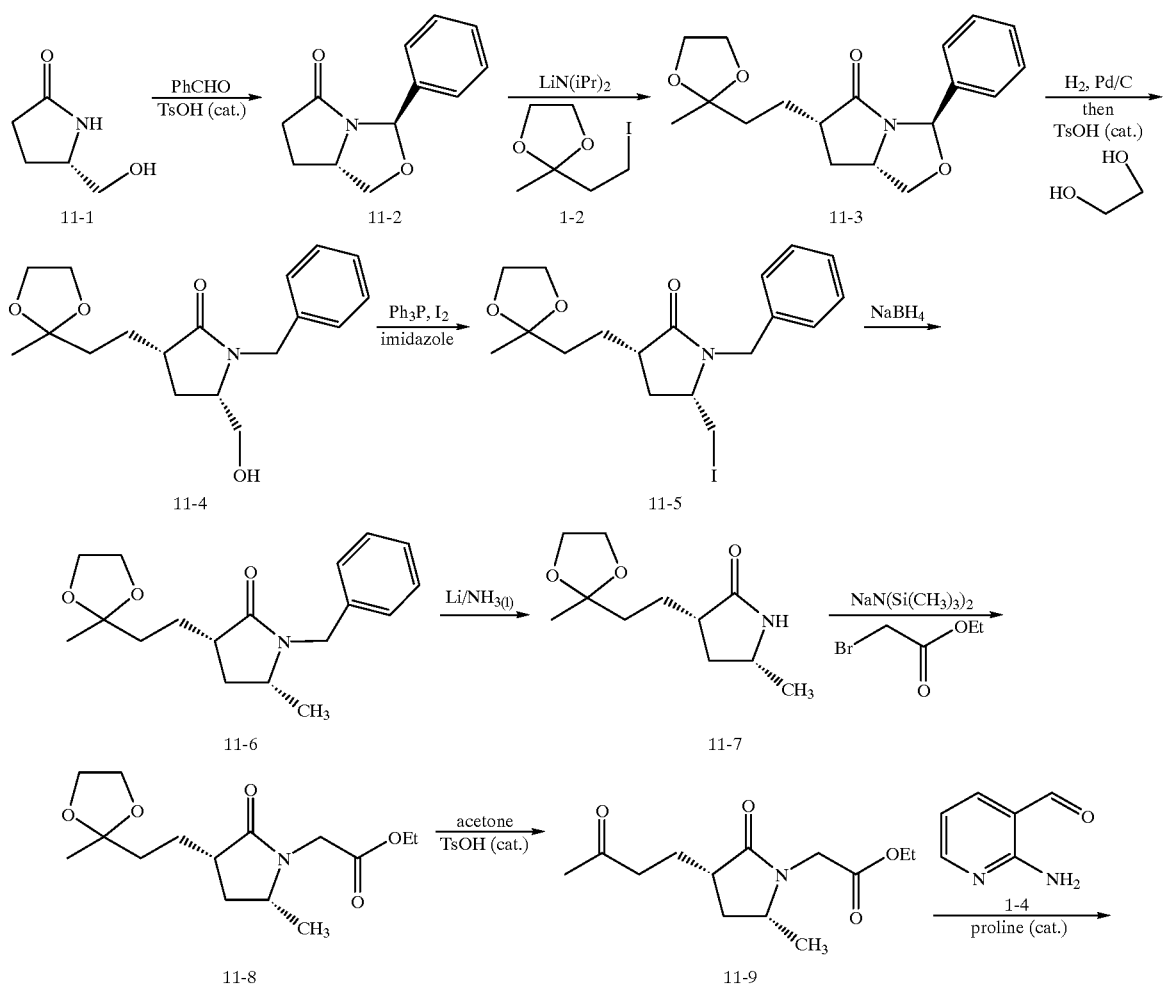

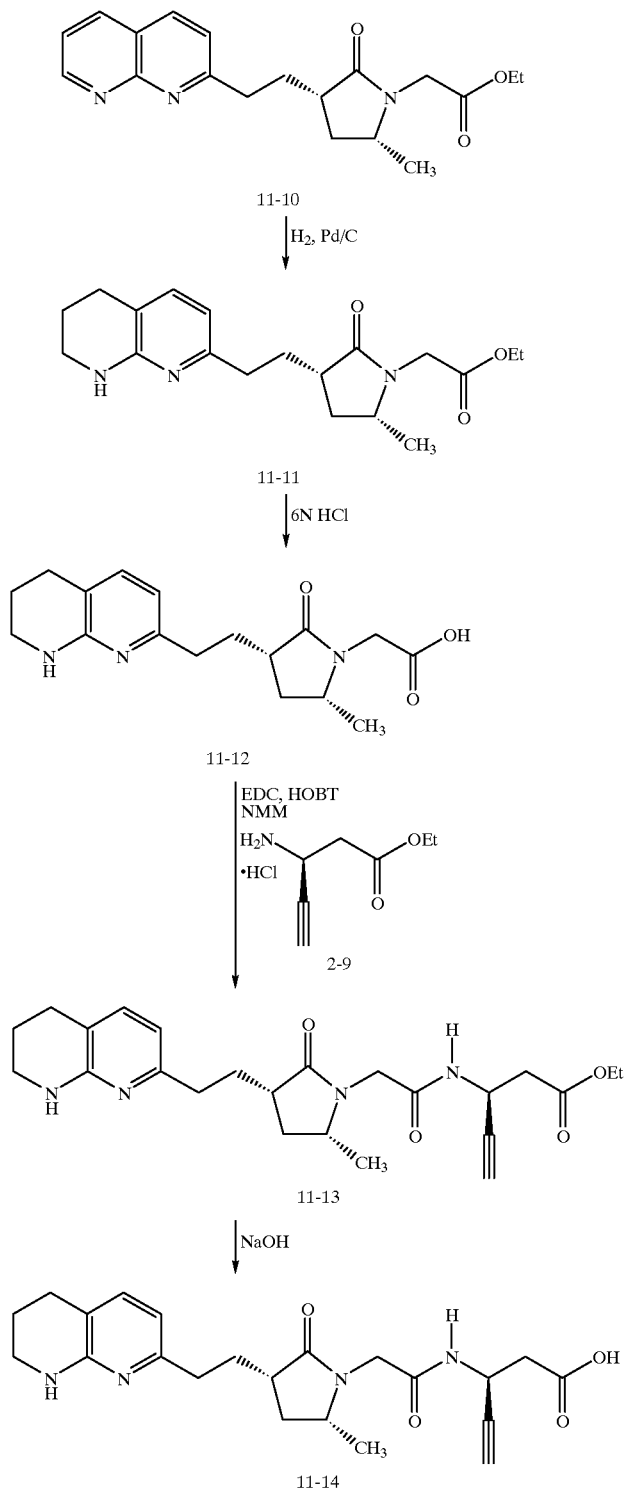

3(R)-phenyl-tetrahydro-pyrrolo[1,2(S)-c]oxazol-5-one (11-2)

A mixture of alcohol (S)-5-(hydroxymethyl)-2-pyrrolidinone (11-1, Fluka) (5.0 g, 43.4 mmol), benzaldehyde (5.7 mL, 56.4 mmol), p-TSA (80 mg, 0.4340 mmol) and toluene (125 mL) was heated to reflux with azeotropic removal of water for 18 hours. The solution was concentrated. Flash chromatography (silica, 50% EtOAc/hexanes) gave 11-2 as a yellow oil.

TLC $R_f$=0.21 (silica, 50% EtOAc/hexanes); $^1$H NMR (300 MHz, CDCl$_3$) δ 7.29→7.46 (m, 5H), 6.34 (s, 1H), 4.24 (m, 1H), 4.16 (t, J=5.8 Hz, 1H), 3.49 ((t, J=7.8 Hz, 1H), 2.82 (m, 1H), 2.55 (m, 1H), 2.39 (m, 1H), 1.97 (m, 1H).

6(S)-[2-(2-methyl-[1,3]dioxolan-2-yl)-ethyl]-3(R)-phenyl-tetrahydropyrrolo[1,2(S)-c]oxazol-5-one (11-3)

To a stirred solution of 11-2 (7.0 g, 34.4 mmol), HMPA (30.0 mL, 172 mmol) and THF (150 mL) at −78° C. was added LDA (18.9 mL, 37.8 mmol, 2.0 M in heptane/THF). After 10 minutes, the reaction was warmed to −15° C. After 20 min, 1-2 (8.3 g, 34.4 mmol), dissolved in 10 mL of THF, was added. After 2 h, the reaction was warmed to ambient temperature for 3.0 hours and then recooled to −15° C. for 18 hours. The reaction was warmed to ambient temperature for 2 hours and then diluted with $Et_2O$, washed with $H_2O$, dried ($MgSO_4$) and concentrated. Flash chromatography (silica, 40%→60% EtOAc/hexanes) gave 11-3 as an oil.

TLC $R_f$=0.28 (silica, 50% EtOAc/hexanes); $^1H$ NMR (300 MHz, $CDCl_3$) δ 7.25→7.46 (m, 5H), 6.33 (s, 1H), 4.24 (m, 1H), 4.11 (m, 1H), 3.95 (s, 4H), 3.52 (t, J=7.3 Hz, 1H), 2.87 (m, 1H), 2.57 (m, 1H), 2.10 (m, 1H) 1.40→1.86 (m, 4H), 1.34 (s, 3H).

1-benzyl-5(S)-hydroxymethyl-3(S)-[2-(2-methyl-[1,3]dioxolan-2-yl)-ethyl]-pyrrolidin-2-one (11-4)

A mixture of 11-3 (2.0 g, 6.30 mmol) and 10% Pd/carbon (2.0 g) in EtOH (30 mL) was stirred under a balloon of hydrogen for 1.0 h. Following filtration and evaporative removal of the solvent, the residue dissolved in benzene (30 mL), treated with TsOH (10 mg) and ethylene glycol (1.05 mL, 18.9 mmol) and then heated to reflux with azeotropic removal of water for 1 hour. The reaction was concentrated. Flash chromatography (silica, 70:23:7 $CHCl_3$/EtOAc/MeOH) gave 11-4 as an oil.

$^1H$ NMR (300 MHz, $CDCl_3$) δ 7.30 (m, 5H), 4.64 (d, J=15 Hz, 1H), 4.25 (d, J=15 Hz, 1H ), 3.95 (s, 4H), 3.72 (m, 1H), 3.49 (m, 2H), 2.46 (m, 1H), 2.15 (m, 2H), 1.74 (m, 2H), 1.53 (m, 2H) 1.35 (s, 3H).

1-benzyl-5(S)-iodomethyl-3(S)-[2-(2-methyl-[1,3]dioxolan-2-yl)-ethyl]-pyrrolidin-2-one (11-5)

To a stirred solution of 11-4 (2.0 g, 6.26 mmol), $PPh_3$ (2.63 g, 10.0 mmol), imidazole (725 mg, 10.6 mmol) and $CH_3CN$ (30 mL) at 0° C. was added $I^{12}$ (2.39 g, 9.39 mmol) in five portions over 15 minutes. After 20 minutes, the reaction was warmed to 50° C. for 30 minutes and then poured into 200 mL 1:1 EtOAc/hexanes. The solution was washed with 10% sodium bisulfite, sat $NaHCO_3$, brine, dried ($MgSO_4$) and concentrated. Flash chromatography (silica, 40% EtOAc/hexanes) gave 11-5 as an oil.

TLC $R_f$=0.27 (silica, 50% EtOAc/hexanes); $^1H$ NMR (300 MHz, $CDCl_3$) δ 7.19→7.35 (m, 5H), 5.04 (d, J=15.1 Hz, 1H), 3.96 (m, 5H), 3.30 (m 1H), 3.19 (m, 2H), 2.50 (m, 1H), 2.32 (m, 1H), 2.12 (m, 1H), 1.79 (m, 2H), 1.58 (m, 1H), 1.36 (m, 4H).

1-benzyl-5(R)-methyl-3(S)-[2-(2-methyl-[1,3]dioxolan-2-yl)-ethyl]-pyrrolidin-2-one (11-6)

To a stirred solution of 11-5 (900 mg, 6.26 mmol) and HMPA (30 mL) was added $NaBH_4$ (156 mg, 4.20 mmol). After 45 minutes, the reaction was poured into 50 mL 1:1 $Et_2O$/hexanes and then washed with $H_2O$, brine, dried ($MgSO_4$) and concentrated to provide 11-6 as an oil.

TLC $R_f$=0.34 (silica, 50% EtOAc/hexanes); $^1H$ NMR (300 MHz, $CDCl_3$) δ 7.20→7.33 (m, 5H), 4.95 (d, J=15.1 Hz, 1H),4.03 (d, J=14.9 Hz, 1H), 3.95 (s 4H), 3.41 (m, 1H), 2.38 (m, 2H), 2.10 (m, 1H), 1.75 (m, 2H), 1.48 (m, 1H), 1.35 (s, 3H), 1.16 (m, 4H).

5(R)-methyl-3(S)-[2-(2-methyl-[1,3]dioxolan-2-yl)-ethyl]-pyrrolidin-2-one (11-7)

Into a 3-necked 500 mL flask at −78° C. was condensed 200 mL of ammonia. Lithium (64 mg, 9.25 mmol) was washed with MeOH, then THF and then added to the ammonia. After 20 minutes, 11-6 (560 mg, 1.85 mmol), dissolved in 25 mL of THF, was added. After 30 minutes, the reaction was quenched with $NH_4Cl$; 200 mL of THF was added, the cooling bath was removed and the solution purged with argon for 30 minutes to remove the ammonia. The solution was dried ($MgSO_4$) and concentrated. Flash chromatography (silica, EtOAc→5%.

MeOH/EtOAc) gave 11-7 as an oil. TLC $R_f$=0.33 (silica, 10% MeOH/EtOAc) $^1H$ NMR (300 MHz, $CDCl_3$) δ 5.98 (br s, 1H), 3.94 (s, 4H), 3.67 (m 1H), 2.40 (m, 2H), 2.02 (m, 1H), 1.70 (m, 2H), 1.40 (m, 1H), 1.33 (s, 3H), 1.22 (m, 4H).

{5(R)-methyl-3(S)-[2-(2-methyl-[1,3]dioxolan-2-yl)-ethyl]-2-oxo-pyrrolidin-1-yl}-acetic acid ethyl ester (11-8)

To a stirred solution of 11-7 (355 mg, 1.67 mmol) and THF (10 mL) at −78° C. was added $NaN(TMS)_2$ (1.83 mL, 1.83 mmol, 1.0 M in THF). After 20 min, ethyl bromoacetate (0.203 mL, 1.84 mmol) was added and the reaction was warmed to 0° C. After 30 minutes, the reaction mixture was diluted with EtOAc and then washed with $H_2O$, brine, dried ($MgSO_4$), and concentrated to give 11-8 as a yellow oil.

TLC $R_f$=0.90 (silica, 10% MeOH/EtOAc) $^1H$ NMR (300 MHz, $CDCl_3$) δ 4.35 (d, J=17.6 Hz, 1H), 4.18 (q, J=7.1 Hz, 2H), 3.94 (s, 4H), 3.74 (m, 3H), 2.44 (m, 2H), 2.05 (m, 1H), 1.73 (m, 2H), 1.43 (m, 1H), 1.33 (s, 3H), 1.27 (t, J=7.1 Hz, 3H), 1.20 (d, J=6.4 Hz, 3H).

[5(R)-methyl-2-oxo-3(S)-(3-oxo-butyl)-pyrrolidin-1-yl]-acetic acid ethyl ester (11-9)

A solution of 11-10 (360 mg, 1.20 mmol), p-TSA (10 mg) and acetone (20 mL) was heated at reflux for 1 hr. The cooled reaction mixture was diluted with EtOAc and then washed with sat. $NaHCO_3$ and brine, dried ($MgSO_4$), and concentrated to afford 11-9 as an oil.

TLC $R_f$=0.54 (silica, 75%EtOAc/hexanes); $^1H$ NMR (300 MHz, $CDCl_3$) δ 4.32 (d, J=17.6 Hz,1H), 4.18 (q, J=7.1 Hz, 2H), 3.73 (m, 3H), 2.72 (m, 2H), 2.42 (m, 1H), 2.16 (s, 3H), 1.99 (m, 1H), 1.78 (m, 1H), 1.27 (t, J=7.1 Hz, 3H), 1.20 (d, J=6.1 Hz, 3H).

[5(R)-methyl-3(S)-(2-[1,8]naphthyridin-2-yl-ethyl)-2-oxo-pyrrolidin-1-yl]-acetic acid ethyl ester (11-10)

A mixture of 11-9 (220 mg, 0.8619 mmol), 1-4, 2-amino-3-formylpyridine (137 mg, 1.12 mmol) and proline (99 mg, 0.8619 mmol) in absolute ethanol (5 mL) was heated at reflux for 12 h. Following evaporative removal of the solvent, the residue was chromatographed (silica gel, 70:25:5 chloroform/ethyl acetate/MeOH) to give 11-10 as a yellow oil.

TLC Rf=0.37 (70:25:5 chloroform/ethyl acetate/MeOH). $^1H$ NMR (300 MHz, $CDCl_3$) δ 9.08 (m, 1H), 8.16 (dd, J=2

Hz, 6 Hz 1H), 8.12 (d,J=8 Hz, 1H), 7.46 (m, 2H), 4.33 (d, J=17.5 Hz, 1H), 4.17 (m, 2H), 3.71 (m, 3H), 3.21 (t, J=8.0 Hz, 2H), 2.54 (m, 2H), 2.39 (m, 1H), 2.02 (m, 1H), 1.35 (m, 1H), 1.26 (t, J=7.1 Hz, 3H), 1.21 (d, J=6.3 Hz, 3H).

{5(R)-methyl-2-oxo-3(S)-[2-(5,6,7,8-tetrahydro-[1,8]naphthyridin-2-yl)-ethyl]-pyrrolidin-1-yl}-acetic acid ethyl ester (11-11)

A mixture of 1-10 (250 mg, 0.7323 mmol) and 10% Pd/carbon (250 mg) in EtOH (5 mL) was stirred under a balloon of hydrogen for 20 h. Following filtration and evaporative removal of the solvent, the residue was chromatographed (silica gel, 70:25:5 chloroform/ethyl acetate/MeOH to give 11-11 as a colorless oil.

TLC Rf=0.25 (70:25:5 chloroform/ethyl acetate/MeOH). $^1$H NMR (300 MHz, CDCl$_3$) δ 7.05 (d, 1H, J=7.3 Hz), 6.39 (d, 1H, J=7.3 Hz), 4.77 (br s, 1H), 4.17 (d, 1H, J=17.5 Hz), 4.15 (m, 2H), 3.71 (m, 2H), 3.39 (m, 2H), 2.64 (m, 4H), 2.46 (m, 2H), 2.30 (m, 1H), 1.91 (m, 2H), 1.88 (m, 1H), 1.26(t, 3H, J=6.1 Hz) 1.23 (m, 1H), 1.19 (d, J=6.4 Hz, 3H).

{5(R)-methyl-2-oxo-3(S)-[2-(5,6,7,8-tetrahydro-[1,8]naphthyridin-2-yl)-ethyl]-pyrrolidin-1-yl}-acetic acid hydrochloride (11-12)

A mixture of 11-11 (185 mg, 0.5356 mmol) and 6N HCl (10 mL) was heated at 60° C. for 1 h. Evaporative removal of the solvent gave 11-12 as a yellow solid.

$^1$H NMR (300 MHz, CD$_3$OD) δ 7.59 (d, 1H, J=7.3 Hz), 6.66 (d, 1H, J=7.3 Hz), 4.17 (d, 12H, J=17.8, Hz), 3.90 (d, 1H, J=17.8, Hz), 3.77 (m, 1H), 3.50 (t, J=5.4 Hz, 2H), 3.31 (m, 4H), 2.52 (m, 2H), 2.25 (m, 1H), 1.95 (t, 2H, J=6.6 Hz), 1.80 (m, 1H), 1.34 (m, 1H), 1.25 (d, J=6.3 Hz, 3H).

2-Oxo-5(R)-methyl-3(S)-[2-(5,6,7,8-tetrahydro[1,8]-naphthyridin-2-yl)-ethyl]pyrrolidin-1-yl)acetyl-3(S)-ethynyl-β-alanine ethyl ester (11-13)

A mixture of 11-12 (350 mg, 0.9892 mmol), 2-9 (193 mg, 1.09 mmol), EDC (378 mg, 1.98 mmol), HOBT (134 mg, 0.9892 mmol) and NMM (1.10 mL, 7.91 mmol) in CH$_3$CN (5 mL) was stirred for 20 h. The mixture was diluted with ethyl acetate, washed with sat. NaHCO$_3$, brine, and dried over MgSO$_4$. Following evaporative removal of the solvent, the residue was chromatographed (silica gel, 70:25:5 chloroform/ethyl acetate/MeOH to give 11-13 as a colorless foam.

TLC Rf=0.15 (70:25:5 chloroform/ethyl acetate/MeOH). $^1$H NMR (300 MHz, CDCl$_3$) δ 7.05 (m, 2H), 6.39 (d, 1H, J=7.3 Hz), 5.04 (m, 1H), 4.16 (q, 2H, J=7.1 Hz), 3.90 (s, 2H), 3.64 (m, 1H),3.39 (m, 2H), 2.69 (m, 6H), 2.47 (m, 2H), 2.30 (m, 1H), 1.90 (m, 2H), 1.64 (m, 2H), 1.20 (m, 7H).

2-Oxo-5(R)-methyl-3(S)-[2-(5,6,7,8-tetrahydro[1,8]-naphthyridin-2-yl)ethyl]pyrrolidin-1-yl)acetyl-3(S)-ethynyl-β-alanine (11-14)

To a solution of 11-13 (70 mg, 0.1589 mmol) in EtOH (1 mL) was added 1N NaOH (0.175 ml, 0.164 mmol). After stirring for 1 h, the solvents were evaporated and the residue was chromatographed (silica gel, 25:10:1:1 to 15:10:1:1 ethyl acetate/EtOH/water/NH$_4$OH to give 11-14 as a colorless foam.

TLC Rf=0.21 (10:10:1:1 ethyl acetate/EtOH/water/NH$_4$OH). $^1$H NMR (300 MHz, CD$_3$OD) δ 7.42 (d, 1H, J=7.3 Hz), 6.49 (d, 1H, J=7.3 Hz), 4.35 (d,J=17.1 Hz,1H), 3.64 (m, 1H,), 3.50 (m, 3H,), 3.18 (m, 2H), 2.77 (t, J=5.6 Hz, 2H), 2.55 (m, 5H), 2.23 (m, 1H), 1.91 (m, 4H), 1.41 (m, 1H) 1.28 (d, J=6.3 Hz, 3H).

SCHEME 12

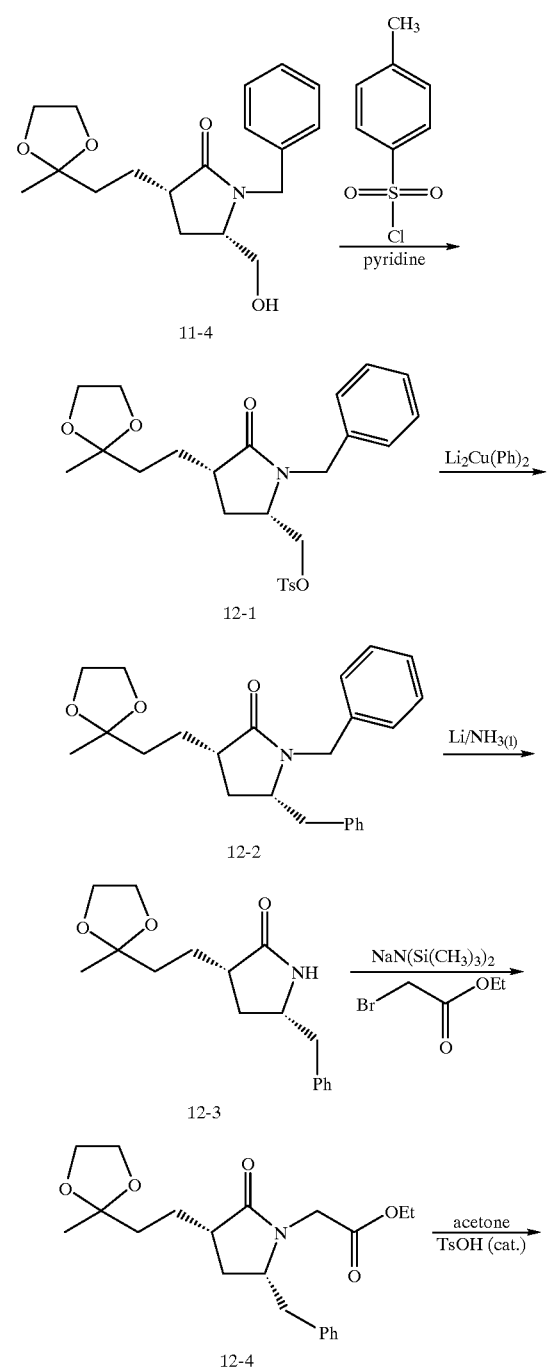

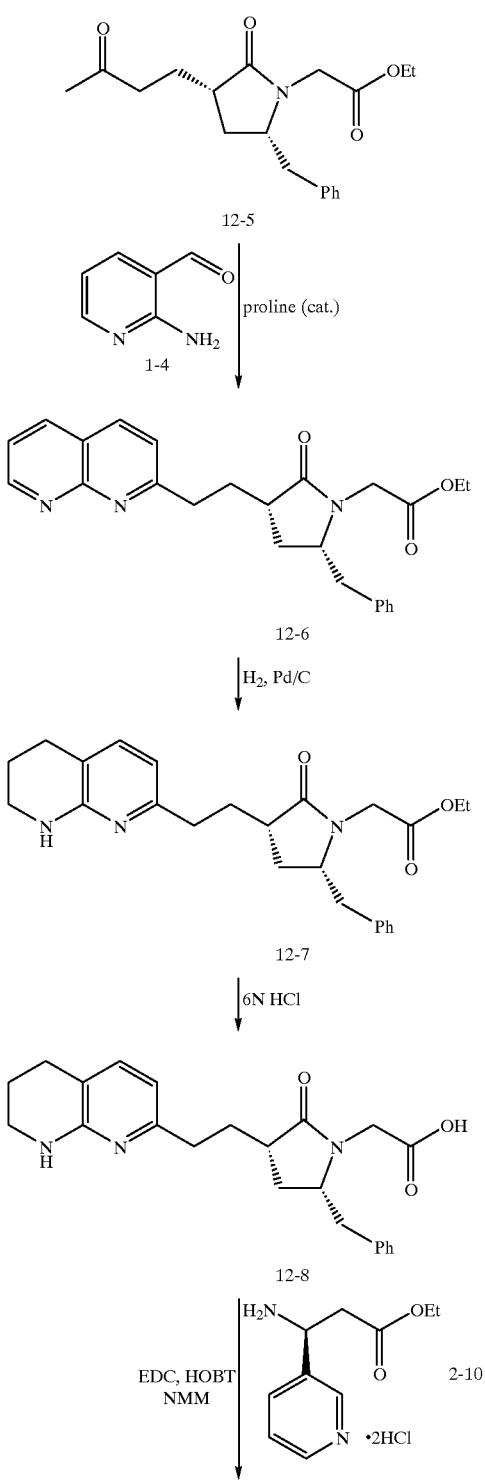

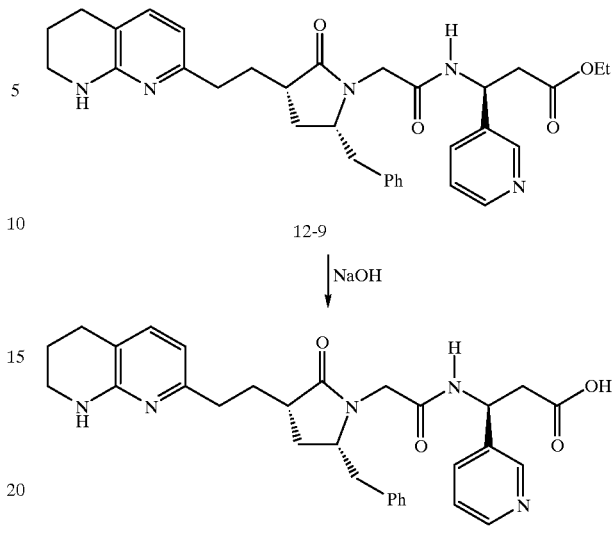

1-benzyl-5(S)-methyl-p-toluenesulfonate-3(S)-[2-(2-methyl-[1,31dioxolan-2-yl)-ethyl]-pyrrolidin-2-one (12-1)

To a stirred solution of 11-4 (1.8 g, 5.63 mmol) and THF (30 mL) at 0° C. was added NaH (248 mg, 6.19 mmol). After 30 minutes, TosCl was added followed by the removal of the cooling bath. After 1.0 hour, the reaction was diluted with EtOAc and then washed with $H_2O$, sat $NaHCO_3$, brine, dried ($MgSO_4$) and concentrated. Flash chromatography (silica, 40→60% EtOAc/hexanes) gave 12-1 as an oil.

TLC $R_f$=0.75 (silica, EtOAc) $^1$H NMR (300 MHz, $CDCl_3$) δ 7.72 (d, J=8.30 Hz, 2H), 7.35 (d, J=7.3 Hz, 2H), 7.25 (m, 3H), 7.09 (m 2H), 4.94 (d, J=14.9 Hz, 1H), 4.01 (m, 1H), 3.94 (m, 5H), 3.83 (d, J=15.1 Hz, 1H), 3.54 (m, 1H), 2.46 (s, 3H), 2.42 (m, 1H), 2.21 (m, 1H), 2.01 (m, 1H), 1.72 (M, 2H), 1.43 (m, 2H), 1.32 (s, 3H).

1-benzyl-5(S)-benzyl-3(S)-[2-(2-methyl-[1,3]dioxolan-2-yl)-ethyl]-pyrrolidin-2-one (12-2)

To a stirred suspension of CuI (2.57 g, 13.5 mmol) and $Et_2O$ (10 mL) at 0° C. was added PhLi (14.2 mL, 25.6 mmol, 1.8 M cyclohexane-ether) dropwise over a 1.0 hour period. After an additional hour, 12-1 (1.4 g, 2.96 mmol), dissolved in 10 mL $Et_2O$, was added. The reaction was stirred at −15° C. for 96 hours. The reaction was diluted with EtOAc and then washed with sat $NH_4Cl$, sat $NaHCO_3$, brine, dried ($MgSO_4$) and concentrated. Flash chromatography (silica, 30→60% EtOAc/hexanes) gave 12-2 as an oil.

TLC $R_f$=0.29 (silica, 50% EtOAc/hexanes); $^1$H NMR (300 MHz, $CDCl_3$) δ 7.13→7.36 (m, 8H), 7.02 (d, J=7.6 Hz, 2H), 5.06 (d, J=14.9 Hz, 1H), 4.14 (d, J=15.1 Hz, 1H), 3.95 (m, 4H), 3.55 (m, 1H), 3.18 (dd, J=4.2, 17.0 Hz, 1H), 2.35 (m, 2H), 2.04 (m, 2H), 1.66 (m, 2H), 1.32 (m, 5H).

5(S)-benzyl-3(S)-[2-(2-methyl-[1,3]dioxolan-2-yl)-ethyl]-pyrrolidin-2-one (12-3)

Into a 3-necked 500 mL flask at −78° C. was condensed 100 mL of ammonia. Next, 12-2 (470 mg, 1.24 mmol), dissolved in 20 mL of THF, was added. Lithium (19 mg, 2.48 mmol) was washed with MeOH, then THF and then added to the ammonia. After 20 minutes, the reaction was quenched with NH$_4$Cl; 200 mL of THF was added, the cooling bath was removed and the solution purged with argon for 30 minutes to remove the ammonia. The solution was dried (MgSO$_4$) and concentrated. Flash chromatography (silica, EtOAc) gave 12-3 as an oil.

TLC R$_f$=0.22 (silica, EtOAc); $^1$H NMR (300 MHz, CDCl$_3$) δ 7.18→7.35 (m, 5H), 5.43 (br s, 1H), 3.95 (s, 4H), 3.92 (m 1H), 2.88 (dd, J=5.3, 18.6 Hz, 1H), 2.41 (m, 2H), 2.03 (m, 1H), 1.71 (m, 2H), 1.43 (m, 2H), 1.33 (s, 3H).

{5(S)-benzyl-3(S)-[2-(2-methyl-[1,3]dioxolan-2-yl)-ethyl]-2-oxo-pyrrolidin-1-yl}-acetic acid ethyl ester (12-4)

To a stirred solution of 12-3 (210 mg, 0.7257 mmol) and THF (5 mL) at −78° C. was added NaN(TMS)$_2$ (0.943 mL, 0.943 mmol, 1.0 M in THF). After 30 min, ethyl bromoacetate (0.104 mL, 0.9434 mmol) was added and the reaction was warmed to 0° C. After 1.0 hour, the reaction mixture was diluted with EtOAc and then washed with sat NaHCO$_3$, brine, dried (MgSO$_4$), and concentrated to give 12-4 as a yellow oil.

TLC R$_f$=0.64 (silica, EtOAc); $^1$H NMR (300 MHz, CDCl$_3$) δ 7.15→7.33 (m, 5H), 4.40 (d, J=17.8 Hz, 1H), 4.15 (m, 2H), 3.93(m, 5H), 3.77 (d, J=17.8 Hz, 1H), 3.07 (dd, J=5.0, 18.6 Hz, 1H), 2.56 (m, 1H), 2.39 (m, 1H), 2.20 (m, 1H), 2.05 (m, 1H), 1.69 (m, 2H), 1.23→1.46 (m, 8H).

5(S)-benzyl-2-oxo-3(S)-(3-oxo-butyl)-pyrrolidin-1-yl]-acetic acid ethyl ester (12-5)

A solution of 12-4 (260 mg, 0.6925 mmol), p-TSA (10 mg) and acetone (20 mL) was heated at reflux for 1 hr. NaHCO$_3$ was added to the cooled reaction mixture and then the mixture was concentrated. The residue was diluted with CHCl$_3$ and then washed with brine, dried (MgSO$_4$), and concentrated to afford 12-5 as an oil.

TLC R$_f$=0.66 (silica, 75% EtOAc/hexanes); $^1$H NMR (300 MHz, CDCl$_3$) δ 7.22→7.36 (m, 3H), 7.15 (d, J=6.5 Hz, 2H), 4.37 (d, J=17.6 Hz, 1H), 4.18 (m, 2H), 3.97 (m, 1H), 3.77 (d, J=17.8 Hz, 1H), 3.06 (dd, J=5, 18 Hz, 1H), 2.60 (m, 3H), 2.42 (m, 1H), 2.17 (m, 1H), 2.14 (s, 3H), 1.96 (m, 1H), 1.74 (m, 1H) 1.27 (m, 4H).

[5(S)-benzyl-3(S)-(2-[1,8]naphthyridin-2-yl-ethyl)-2-oxo-pyrrolidin-1-yl]-acetic acid ethyl ester (12-6)

A mixture of 12-5 (230 mg, 0.6940 mmol), 1-4, (2-amino-3-formylpyridine, 110 mg, 0.9022 mmol) and proline (80 mg, 0.6940 mmol) in absolute ethanol (10 mL) was heated at reflux for 18 h. Following evaporative removal of the solvent, the residue was chromatographed (silica gel, 70:28:2 chloroform/ethyl acetate/MeOH) to give 12-6 as a yellow oil.

TLC Rf=0.38 (70:25:5 chloroform/ethyl acetate/MeOH). $^1$H NMR (300 MHz, CDCl$_3$) δ 9.08 (m, 1H), 8.16 (dd, J=2 Hz, 10 Hz 1H), 8.09 (d,J=8.3 Hz, 1H), 7.44 (m, 2H), 7.28 (m, 2H), 7.16 (d, J=8 Hz, 2H), 4.37 (d, J=17.6 Hz, 1H), 4.16 (m, 2H), 3.96 (m, 1H), 3.80 (d, J=17.6 Hz, 1H), 3.15 (m, 2H), 3.06 (dd, J=5.3, 18.5, 1H), 2.26→2.63 (m, 4H), 1.97 (m, 1H), 1.47 (m, 1H), 1.25 (t, J=7.1 Hz, 3H).

{5(S)-benzyl-2-oxo-3(S)-[2-(5,6,7,8-tetrahydro-[1,8]naphthyridin-2-yl)-ethyl]-pyrrolidin-1-yl}-acetic acid ethyl ester (12-7)

A mixture of 12-6 (220 mg, 0.5270 mmol) and 10% Pd/carbon (100 mg) in EtOH (4 mL) was stirred under a balloon of hydrogen for 2 h. Following filtration and evaporative removal of the solvent, the residue was chromatographed (silica gel, 70:25:5 chloroform/ethyl acetate/MeOH to give 12-7 as a colorless oil.

TLC Rf=0.25 (70:25:5 chloroform/ethyl acetate/MeOH). $^1$H NMR (300 MHz, CDCl$_3$) δ 7.26 (m, 3H), 7.16 (d, J=8.1 Hz, 2H), 7.04 (d, J=7.3 Hz, 1H), 6.36 (d, J=7.3 Hz, 1H), 4.74 (br s, 1H), 4.39 (d, J=17.8 Hz, 1H), 4.15 (m, 2H), 3.90 (m, 1H), 3.77 (d, J=17.5 Hz, 1H), 3.38 (m, 2H), 3.06 (dd, J=2.4, 18.8 Hz, 1H), 2.65 (m, 5H), 2.43 (m, 1H), 2.22 (m, 3H), 1.89 (m, 1H) 1.36 (m, 1H), 1.26 (t, J=7.1 Hz, 3H).

{5(s)-benzyl-2-oxo-3(S)-[2-(5,6,7,8-tetrahydro-[1,8]naphthyridin-2-yl)-ethyl]-pyrrolidin-1-yl}-acetic acid hydrochloride (12-8)

A mixture of 12-7 (150 mg, 0.3559 mmol) and 6N HCl (10 mL) was heated at 60° C. for 1 h. Evaporative removal of the solvent gave 12-8 as a yellow solid.

$^1$H NMR (300 MHz, CD$_3$OD) δ 7.57 (d, J=7.3 Hz, 1H), 7.24 (m, 5H), 6.60 (d, J=7.3 Hz, 1H), 4.24 (d, J=17.8, Hz, 1H), 4.03 (m, 2H), 3.49 (t, J=5.6 Hz, 2H), 3.15 (dd, J=4.4, 17.6 Hz, 1H), 2.71 (m, 5H), 2.46 (m, 1H), 2.21 (m, 1H), 1.97 (m, 3H), 1.64 (m, 1H), 1.45 (m, 1H).

2-Oxo-5(S)-benzyl-3(S)-[2-(5,6,7,8-tetrahydro [1,8]-naphthyridin-2-yl)-ethyl]pyrrolidin-1-yl)acetyl-3(S)-pyridin-3-yl-β-alanine ethyl ester (12-9)

A mixture of 12-8 (150 mg, 0.3559 mmol), 2-10 (60 mg, 0.2135 mmol), EDC (132 mg, 0.7118 mmol), HOBT (48 mg, 0.3559 mmol) and NMM (0.4 mL, 2.85 mmol) in DMF (4 mL) was stirred for 20 h. The mixture was diluted with ethyl acetate, washed with sat. NaHCO$_3$, brine, and dried over MgSO$_4$. Following evaporative removal of the solvent, the residue was chromatographed (silica gel, 70:20:10 chloroform/ethyl acetate/MeOH to give 12-9 as a colorless foam.

TLC Rf=0.15 (70:25:5 chloroform/ethyl acetate/MeOH). $^1$H NMR (300 MHz, CD$_3$OD) δ 8.55 (s, 1H), 8.44 (m, 1H), 7.82 (m, 1H), 7.6–7.1 (m, 7H), 6.33 (d, J=7.5 Hz, 1H), 5.40 (t, J=8 Hz, 1H), 4.2–3.8 (m, 6H), 3.38 (m, 1H), 3.17 (m, 2H), 2.90 (m, 2H), 2.67 (m, 2H), 2.54 (m, 2H), 2.12 (m, 2H),1.84 (m, 2H), 1.43 (m, 2H) 1.18 (m, 3H).

2-Oxo-5(S)-benzyl-3(S)-[2-(5,6,7,8-tetrahydro[1,8]-naphthyridin-2-yl)ethylpyrrolidin-1-yl)acetyl-3(S)-pyridin-3-yl-β-alanine (12-13)

To a solution of 12-9 (70 mg, 0.1229 mmol) in EtOH (1 mL) was added 1N NaOH (0.150 ml, 0.150 mmol). After stirring for 1.5 h, the solvents were evaporated and the residue was chromatographed (silica gel, 25:10:1:1 to 15:10:1:1 ethyl acetate/EtOH/water/NH$_4$OH to give 12-10 as a colorless foam.

TLC Rf=0.21 (10:10:1:1 ethyl acetate/EtOH/water/NH$_4$OH). $^1$H NMR (300 MHz, CD$_3$OD) δ 8.62 (s, 1H), 8.36 (m, 1H), 7.92 (m, 1H), 7.45–7.2 (m, 7H), 6.49 (d, J=7.1 Hz, 1H), 5.27 (m, 1H), 4.31 (d, J=17.3 Hz, 1H), 3.93 (m, 1H), 3.72 (d, J=17.5 Hz, 1H), 3.30 (m, 3H), 2.92–2.52 (m, 8H), 2.36 (m, 2H), 1.90 (m, 3H), 1.57 (m, 1H).

SCHEME 13
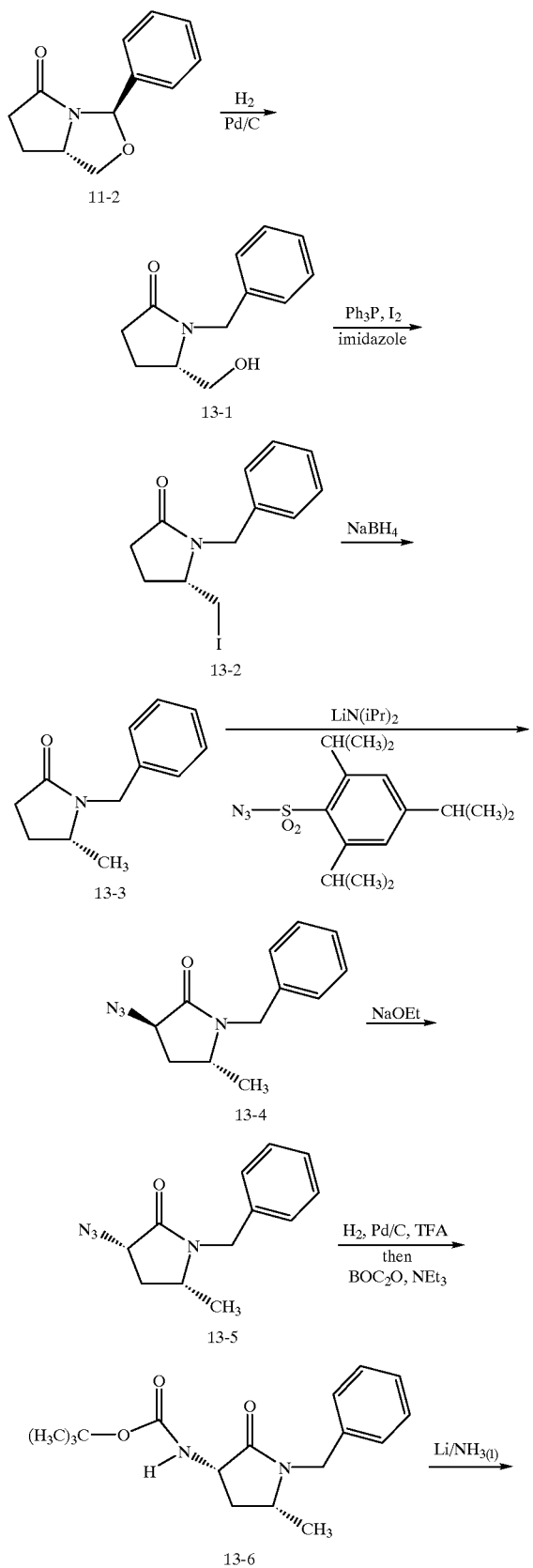
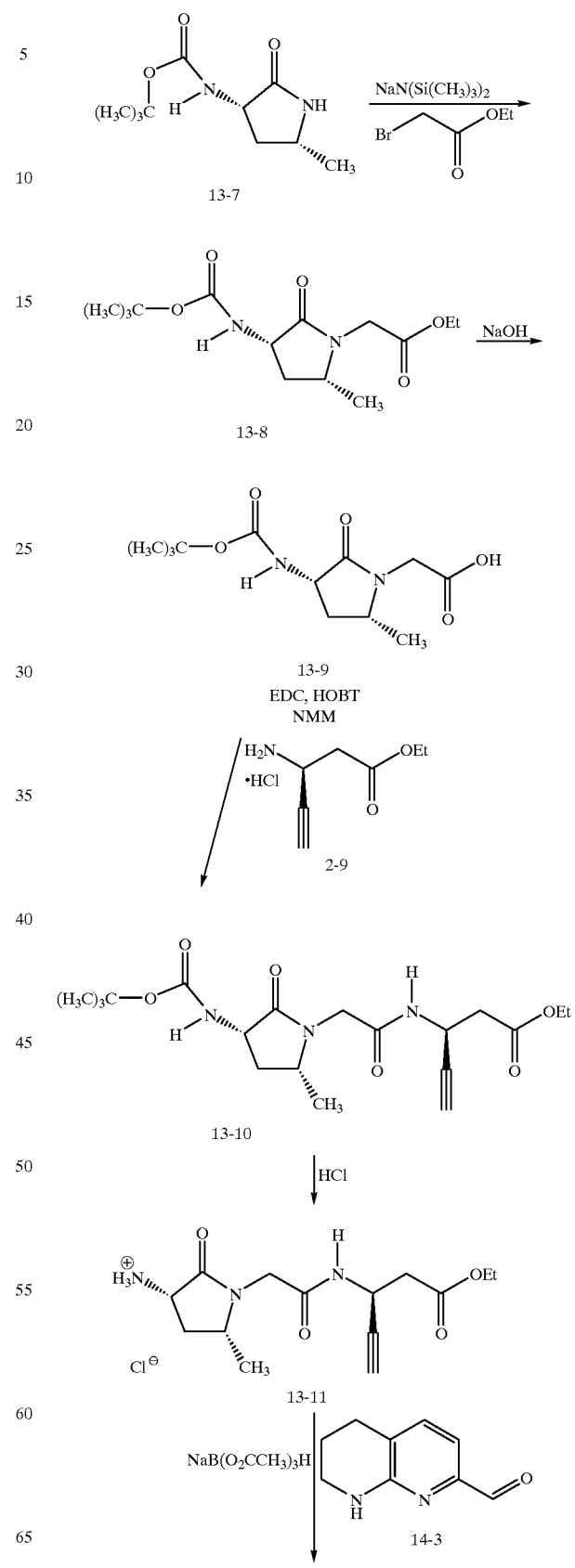

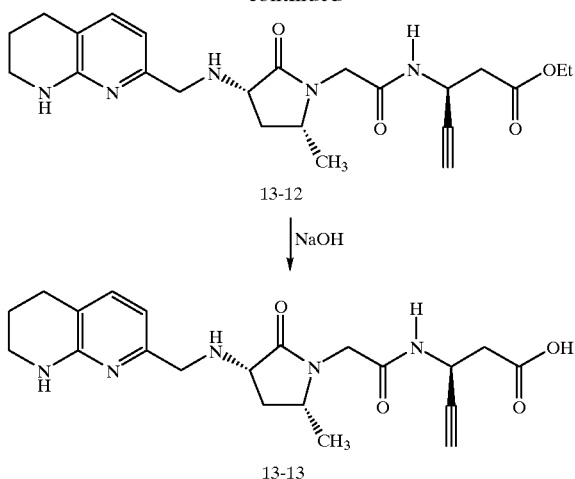

13-12

|NaOH 13-13

1-benzyl-5(S)-hydroxymethyl-pyrrolidin-2-one (13-1)

A mixture of 11-2 (5.0 g, 24.6 mmol), 10% Pd/C (2.5 g), and ethanol (80 mL) was stirred at ambient temperature under a hydrogen atmosphere (1 atm) for 5 hr. The catalyst was removed by filtration through a celite pad and the filtrate concentrated to give 13-1 as a colorless oil.

TLC RF=0.55 (silica, 70:20:10 CHCl$_3$/EtOAc/CH$_3$OH); $^1$H NMR (300 MHz, CDCl$_3$) δ 7.29 (m, 5H), 4.83 (d, 2H, J=15H), 4.25 (d, 1H, J=15 Hz), 3.77 (m, 1H), 3.51 (m, 2H), 2.54 (m, 1H), 2.40 (m, 1H), 1.92 (m, 2H).

1-benzyl-5(S)-iodomethyl-pyrrolidin-2-one (13-2)

To a solution of 13-1 (18.5 g, 90.1 mmol), triphenylphosphine (40.1 g, 153 mmol), and imidazole (11.03 g, 162 mmol) in 225 mL of acetonitrile and 150 mL of ether at 0° C. was added iodine (34.3 g, 135 mmol) in 5 portions over 5 minutes. After 10 minutes, the reaction was heated to 50° C., and a stream of argon passed over the reaction to purge the evaporating ether. After an additional 30 minutes, the mixture was diluted with ether, the organic layer washed with NaHCO$_3$ (sat.) and brine, dried over K$_2$CO$_3$, and the solvent evaporated. Flash chromatography of the residue (silica, 7–15% EtOAc/CHCl$_3$) gave 13-2 as a yellow oil.

TLC R$_f$=0.53 (silica, 30% EtOAc/CHCl$_3$); $^1$H NMR (300 MHz, CDCl$_3$) δ 7.31 (m, 5H), 5.05 (d, 1H, J=15 Hz), 3.92 (d, 1H, J=15 Hz), 3.41 (m, 1H), 3.26 (m, 2H), 2.62 (m, 1H), 2.43 (m, 1H), 2.16 (m, 1H), 1.81 (m, 1H).

1-benzyl-5(R)-methyl-pyrrolidin-2-one (13-3)

To a solution of 13-2 (22.1 g, 70 mmol) in 200 mL of hexamethylphosphorous triamide at 0° C. was added NaBH$_4$ (5.25 g, 140 mmol) in 5 portions over 5 minutes. After 10 minutes, the reaction was allowed to warm to ambient temperature and stirred for 2 h. The mixture was diluted with 1:1 ether/hexanes, quenched by the careful addition of 300 mL 10% KHSO$_4$ (aq), separated, the organics dried over K$_2$CO$_3$, and the solvent evaporated to give 13-2 as a yellow oil TLC R$_f$=0.45 (silica, 30% EtOAc/CHCl$_3$); $^1$H NMR (300 MHz, CDCl$_3$) δ 7.32 (mn, 5H), 4.95 (d, 1H, J=15 Hz), 4.00 (d, 1H, J=15 Hz), 3.52 (m, 1H), 2.46 (n, 2H), 2.15 (m, 1H), 1.60 (m, 1H), 1.16 (d, 3H, J=6.0 Hz)).

3(R)-azido-1-benzyl-5(R)-methyl-pyrrolidin-2-one (13-4)

To a solution of 13-3 (2.2 g, 11.6 mmol) in THF (45 mL) at −78° C. was added a solution of LDA (6.39 mL, 12.8 mmol; 2M/THF,ethylbenzene). The mixture was warmed to −15° C. for 20 minutes, then recooled to −78° C., and 2,4,6-triisopropylbenzenesulfonyl azide (4.31 g, 13.9 mmol, prepared as described in Harmon, et al, *J. Org. Chem.* 1973, 38, 11–16. ) was added rapidly as a solution in 40 mL THF at −78° C. After 10 minutes, glacial acetic acid (2.67 mL, 47 mmol) was added, and the resultant viscous liquid mixture allowed to warm to ambient temperature and stir for 1 hour. The solvent was then evaporated, the residue dissolved in CHCl$_3$, washed with NaHCO$_3$ (sat.), and dried over magnesium sulfate. Following evaporative removal of the solvent, the residue was chromatographed (silica gel, 25% ethyl acetate/hexanes) to give 13-4 as a colorless oil.

TLC Rf=0.38 (25% ethyl acetate/hexanes). $^1$H NMR (300 MHz, CHCl$_3$) δ 7.32 (m, 5H), 5.00 (d, 1H, J=15 Hz), 4.27 (t, 1H, J=7.5 Hz), 3.98 (d, 1H, J=15 Hz), 3.54 (m, 1H), 1.97 (m, 2H), 1.16 (d, 3H, J=6.0 Hz).

3(S)-azido-1-benzyl-5(R)-methyl-pyrrolidin-2-one

To a solution of 13-4 (2.17 g, 9.42 mmol) in EtOH (50 mL) was added a solution of NaOEt (3.52 mL, 9.42 mmol; 2.68 M/EtOH). The mixture was stirred for 90 minutes, then quenched by the addition of glacial acetic acid (3 mL). The solvent was then evaporated, the residue slurried in EtOAc, washed with NaHCO$_3$ (sat.), and dried over K$_2$CO$_3$. Following evaporative removal of the solvent, the residue was chromatographed (silica gel, 17% ethyl acetate/hexanes) to give 13-5 as a colorless oil and 13-4 as a colorless oil.

TLC Rf=0.44 (25% ethyl acetate/hexanes). $^1$H NMR (300 MHz, CHCl$_3$) δ 7.32 (m, 5H), 4.97 (d, 1H, J=15 Hz), 4.17 (t, 1H, J=7.5 Hz), 4.05 (d, 1H, J=15 Hz), 3.44 (m, 1H), 2.48 (m, 2H), 1.50 (m, 1H), 1.22 (d, 3H, J=6.6 Hz).

(1-benzyl-5(R)-methyl-2-oxo-pyrrolidin-3(S)-yl)-carbamic acid tert-butyl ester (13-6)

A mixture of 13-5 (2.38 g, 10.3 mmol), 10% Pd/C (1.0 g), TFA (10 mL), THF (80 mL) and methanol (100 mL) was stirred at ambient temperature under a hydrogen atmosphere (1 atm) for 3 hr. The catalyst was removed by filtration through a celite pad and the filtrate concentrated to give the intermediate amine salt as a colorless oil. To a solution of the crude amine salt in THF (50 mL) at 0° C. was added NEt$_3$ (2.88 mL, 20.7 mmol) and di-tert-butyl dicarbonate (2.59 g, 11.9 mmol). The mixture was allowed to warm to ambient temperature and stir for 4 hours. Following evaporative removal of the solvent, the residue was chromatographed (silica gel, 40% ethyl acetate/hexanes) to give 13-6 as a colorless oil.

TLC RF=0.44 (silica, 40% ethyl acetate/hexanes); $^1$H NMR (300 MHz, CHCl$_3$) δ 7.31 (m, 5H), 5.17 (br s, 1H), 4.94 (d, 1H, J=15 Hz), 4.20 (m, 1H), 4.07 (d, 1H, J=15 Hz), 3.44 (m, 1H), 2.77 (m, 1H), 1.45 (s, 9H), 1.20 (d, 3H, J=7 Hz).

(5(R)-methyl-2-oxo-pyrrolidin-3(S)-yl)-carbamic acid tert-butyl ester (13-7)

To a blue solution of lithium metal (0.237 g, 34.2 mmol) in NH$_3$ (1) (200 mL) at −78° C. was added a solution of 13-6 (2.60 g, 8.54 mmol) in THF (15 mL). The mixture was stirred for 15 minutes, then quenched by the addition of ammonium chloride until the blue color dispersed. An additional 30 mL of THF was added, and the mixture warmed to 35° C. to evaporate the ammonia. MgSO4 was added,the mixture was filtered through a celite pad. Following evaporative removal of the solvent, the residue was chromatographed (silica gel, 70:20:10 chloroform/ethyl acetate/MeOH) to give 13-7 as a colorless oil.

TLC Rf=0.45 (70:20:10 chloroform/ethyl acetate/MeOH). $^1$H NMR (300 MHz, CHCl$_3$) δ 6.97 (br s, 1H), 5.24 (d, 1H, J=7.6 Hz), 4.32 (br s, 1H), 3.66 (m, 1H), 2.79 (m, 1H), 1.45 (s, 9H), 1.25 (d, 3H, J=6.0 Hz).

(3(S)-tert-butoxycarbonylamino-5(R)-methyl-2-oxo-pyrrolidin-1-yl)-acetic acid ethyl ester (13-8)

To a solution of 13-7 (1.83 g, 8.4 mmol) in THF (22 mL) at −78° C. was added sodium bis(trimethylsilyl)amide (9.4 mL, 9.4 mmol; 1M/THF) dropwise. After an additional 20 min, ethyl bromoacetate (1.13 mL, 10.3 mmol) was added dropwise. After an additional 20 minutes, the mixture was allowed to warm to 0° C., and 20 mL sat. aqueous NH$_4$Cl was added. The layers were separated, the aqueous layer washed with EtOAc, and the combined organic extracts were dried over K$_2$CO$_3$. Following evaporative removal of the solvent, the residue was chromatographed (silica gel, 40% ethyl acetate/hexanes) to give 13-8 as a colorless oil.

TLC Rf=0.39 (40% ethyl acetate/hexanes). $^1$H NMR (300 MHz, CHCl$_3$) δ 5.20 (br s, 1H), 4.38 (d, 1H, J=18 Hz), 4.21 (m, 3H), 3.77 (m, 2H), 2.83 (m, 1H), 1.44 (s, 9H), 1.23 (m, 6H).

(3(S)-tert-butoxycarbonylamino-5(R)-methyl-2-oxo-pyrrolidin-1-yl)-acetic acid (13-9)

To a solution 13-8 (527 mg, 1.75 mmol) in EtOH was added 1N NaOH (1.93 mL, 1.925 mmol). After stirring for 1 h, the solvents were evaporated, the mixture was diluted with EtOAc, acidified with 10% KHSO$_4$, washed with brine, dried over MgSO$_4$, and evaporated to give 13-9 as a white solid.

TLC R$_f$=0.48 (silica, 9.5/0.5/0.5 CH$_2$Cl$_2$/MeOH/AcOH); $^1$H NMR (300 MHz, CD$_3$OD) δ 4.21 (m, 2H), 3.85 (d, 1H, J=18 Hz), 3.74 (m, 1H), 2.58 (m, 1H), 1.52 (m, 1H), 1.44 (s, 9H), 1.25 (d, J=6.3 Hz, 3H).

(3(S)-tert-butoxycarbonylamino-5(R)-methyl-2-oxo-pyrrolidin-1-yl)-acetyl-3(S)-ethynyl-β-alanine ethyl ester (13-10)

A mixture of 13-9 (440 mg, 1.62 mmol), 2-9 (290 mg, 1.62 mmol), EDC (373 mg, 1.94 mmol), HOBT (262 mg, 1.94 mmol) and NMM (1.20 mL, 11.34 mmol) in CH$_3$CN (5 mL) was stirred for 20 h. The mixture was diluted with EtOAc, washed with sat. NaHCO$_3$, brine, and dried over MgSO$_4$. Following evaporative removal of the solvent, the residue was chromatographed (silica gel, EtOAc) to give 13-10 as a colorless foam.

TLC Rf=0.20 (silica, EtOAc). $^1$H NMR (300 MHz, CDCl$_3$) δ 7.31 (bd, 1H), 5.33 (bd, 1H), 5.21 (m, 1H), 4.16 (m, 5H), 3.64 (m, 2H), 2.72 (m, 2H), 2.45 (d, J=2.2 Hz, 1H), 1.52 (m, 1H), 1.46 (s, 9H), 1.27 (m, 6H).

(3(S)-amino-5(R)-methyl-2-oxo-pyrrolidin-1-yl)-acetyl-3(S)-ethynyl-β-alanine ethyl ester hydrochloride (13-11)

To a solution of 13-10 (550 mg, 1.39 mmol) in EtOAc at 0° C. was bubbled HCl gas for 5 minutes. The reaction was stirred an additional 5 minutes, followed by removal of the cooling bath and then purged with Argon for 20 minutes. Evaporative removal of the solvent gave 13-11 as a white solid.

$^1$H NMR (300 MHz, CD$_3$OD) δ 5.02 (m, 1H), 4.12 (m, 4H), 3.93 (m, 2H), 2.77 (m, 2H), 1.59 (m, 1H), 1.25 (m, 6H).

5(R)-methyl-2-oxo-3(S)-[2-(5,6,7,8-tetrahydro[1,8]-naphthyridin-2-ylmethyl)-amino]pyrrolidin-1-yl) acetyl-3(S)-ethynyl-β-alanine ethyl ester (13-12)

To a solution of 13-11 (450 mg, 1.39 mmol) and 5,6,7,8-tetrahydro-[1,8]naphthyridine-2-carbaldehyde (225 mg, 1.39 mmol) in dichloroethane at 0° C. was added Na(OAc)$_3$BH. After 1.5 h the reaction was quenched with sat. NaHCO$_3$, diluted with EtOAc, washed with sat. NaHCO$_3$, brine and dried over MgSO$_4$. Following evaporative removal of the solvent, the residue was chromatographed (silica gel, 70:20:10 chloroform/ethyl acetate/MeOH to give 13-12 as a colorless foam.

TLC Rf=0.17 (70:15:15 chloroform/ethyl acetate/MeOH). $^1$H NMR (300 MHz, CDCl$_3$) δ 7.09 (d, J=6.8 Hz, 1H), 7.03 (d, J=8.5 Hz, 1H), 6.48 (d, J=7.3 Hz, 1H), 5.05 (m, 1H), 4.83 (bs, 1H), 4.17 (q, J=6.4, 1H), 3.92 (m, 2H), 3.74 (m, 2H), 3.58 (m, 4H), 3.40 (m, 2H), 2.70 (m, 4H), 2.54 (m, 1H), 2.26 (s, 1H), 1.90 (m, 2H), 1.55 (m, 2H), 1.25 (m, 6H).

5(R)-methyl-2-oxo-3(S)-[2-(5,6,7,8-tetrahydro[1,8]-naphthyridin-2-ylmethyl)-amino]pyrrolidin-1-yl) acetyl-3(S)-ethynyl-β-alanine (13-13)

To a solution of 13-12 (108 mg, 0.24 mmol) in EtOH (2 mL) was added 1N NaOH (0.270 ml, 0.264 mmol). After stirring for 1 h, the solvents were evaporated and the residue was chromatographed (silica gel, 25:10:1:1 to 15:10:1:1 ethyl acetate/EtOH/water/NH$_4$OH) to give 13-13 as a colorless foam.

TLC Rf=0.23 (12:10:1:1 ethyl acetate/EtOH/water/NH$_4$OH). $^1$H NMR (300 MHz, D$_2$O) δ 7.53 (d, 1H, J=7.3 Hz), 6.69 (d, 1H, J=7.3 Hz), 4.41 (m, 2H), 3.71 (m, 2H), 3.45 (t, J=5.8 Hz, 2H), 2.79 (t, J=5.8 Hz, 2H), 2.6 (m, 4H), 1.92 (m, 3H), 1.50 (m, 1H), 1.19 (m, 3H).

SCHEME 14

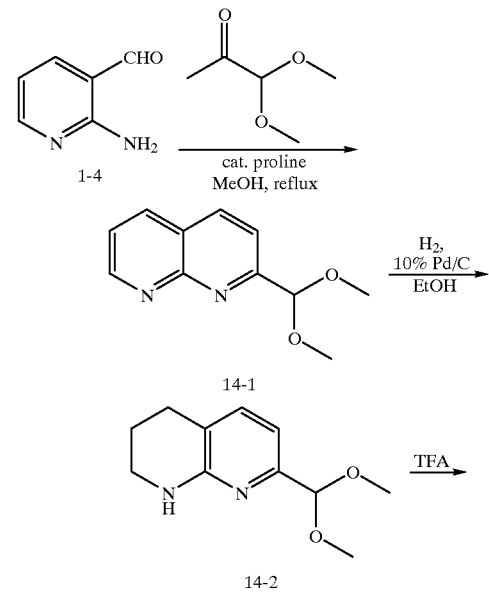

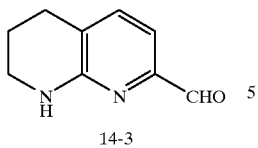

2-Dimethoxymethyl-[1,8]naphthyridine (14-1)

A mixture containing 1-4 (30 g, 0.245 mol), pyruvaldehyde dimethylacetal (87 g, 0.737 mol), and L-proline (7.0 g, 0.062 mol) in MeOH (300 mL) was refluxed under argon for 16 h. The cooled solution was filtered, evaporated and the residue dissolved in $CH_2Cl_2$ (500 mL) and washed with water and brine then dried and concentrated to a volumn of ca. 100 mL. Hexane (300 mL) was added and the mixture was kept at 0° C. for 3 h, then filtered affording 14-1 as an off-white crystalline solid.

$^1$H NMR (300 MHz, $CDCl_3$) δ 9.14 (d, J=2.2 Hz, 1H); 8.26 (d, J=8.7 Hz, 1H); 8.21 (dd, J=8.7, 2.2 Hz, 1H); 7.8 (d, J=8.3 Hz, 1H); 7.5 (m, 1H); 5.48 (s, 1H); 3.53 (s, 6H).

2-Dimethoxymethyl-5,6,7,8-tetrahydro-[1,8]naphthyridine (14-2)

A solution 14-1 (10 g, 0.049 mol) in MeOH, (100 ml) was treated with 10% Pd on C (1.5 g) and the resulting mixture stirred under a $H_2$ filled balloon for 12.5 h. The catalyst was removed by filtration through celite and the solution concentrated to afford 14-2 as a yellow crystalline solid.

$^1$H NMR (300 MHz, $CDCl_3$) δ 7.18 (d, J=7.12 Hz, 1H); 6.71 (d, J=7.12 Hz, 1H); 5.18 (s, 1H); 4.96 (br, s, 1H); 3.43 (s, 6H); 3.4 (m, 2H); 2.65 (m, 2H); 1.91 (m, 2H).

5,6,7,8-tetrahydro-[1,8]naphthyridine-2-carboxaldehyde (14-3)

14-2 (10 g, 0.048 mol) was trifluoroacetic acid (50 mL) and the resulting solution stirred under argon for 12.5 h. The TFA was removed at reduced pressure and the residue partitioned between sat. $NaHCO_3$ and $CH_2Cl_2$. The organic layer was dried, concentrated and passed through a 3 in. pad of silica gel (10% acetone/$CH_2Cl_2$) and concentrated to afford 14-3 as a yellow crystalline solid.

$^1$H NMR (300 MHz, $CDCl_3$) δ 9.80 (s, 1H); 7.31 (d, J=7.32 Hz, 1H); 7.16 (d, J=7.32 Hz, 1H); 5.31 (br, s, 1H); 3.48 (m, 2H); 2.81 (m, 2H); 1.94 (m, 2H).

SCHEME 15

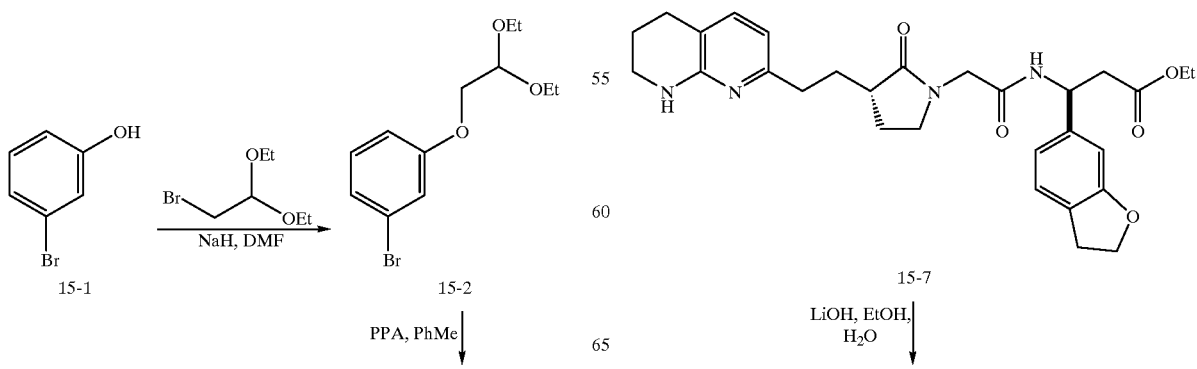

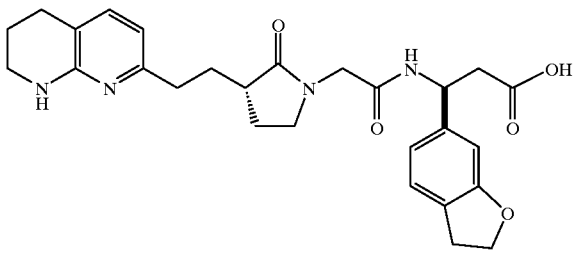

15-8

1-Bromo-3-(2,2-diethoxy-ethoxy)-benzene (15-2)

To a suspension of NaH (2.77 g, 115.6 mmol) in DMF (100 mL) at 0° C. was added a solution of 3-bromophenol 15-1 in DMF (40 mL) over 40 min. After the addition was complete, the solution was stirred for an additional 30 min. The solution was then treated with neat bromoacetaldehyde diethyl acetal (17.36 g, 115.6 mmol). The solution was heated at 100° C. for 8 h, cooled to room temperature, and extracted with $Et_2O$ (3×200 mL). The combined organic extracts were washed with 10% aq NaOH (100 mL) and brine (100 mL), dried over $MgSO_4$, filtered and concentrated to give 15-2 as a yellow oil.

TLC Rf=0.4 (10% ethyl acetate/hexanes). $^1$H NMR (300 MHz, $CHCl_3$) δ 7.19–7.05 (m, 3H), 6.85 (d, 1H), 4.81 (t, 1H, J=6.8 Hz), 3.99 (d, 2H, J=6.8 Hz), 3.71 (m, 4H), 1.22 (t, 6H, J=7.1 Hz) ppm.

6-Bromo-benzofuran (15-3)

To a solution of the acetal 15-2 in toluene (200 mL) was added polyphosphoric acid (20 g). The biphasic mixture was heated to 100° C. and stirred at this temperature for 4 h. The mixture was cooled to room temperature, poured onto ice, and extracted with Et2O (2×200 mL). The combined organic extracts were washed with saturated aq $NaHCO_3$ and brine. The solution was dried over $MgSO_4$, filtered, and concentrated. The residue was purified by flash chromatography (100% hexanes) to give the product 15-3 as a yellow oil.

TLC Rf=0.3 (100% hexanes). $^1$H NMR (300 MHz, $CHCl_3$) δ 7.68 (s, 1H), 7.60 (d, 1H, J=2.1 Hz), 7.46 (d, 1H, J=8.4 Hz), 7.36 (dd, 1H, J=8.1, 1.5 Hz), 6.75 (dd, 1H, J=7.1, 0.9 Hz) ppm.

3-Benzofuran-6-yl-acrylic acid ethyl ester (15-4)

A mixture of the 6-bromobenzofuran 15-3 (1.74 g, 8.79 mmol), ethyl acrylate (1.09 g, 10.98 mmol), $Pd(OAc)_2$ (0.099 g, 0.44 mmol), tri-o-tolylphosphine (0.268 g, 0.880 mmol), and sodium acetate (3.60 g, 43.9 mmol) in DMF (10 mL) was heated to 100° C. in a sealed tube for 4 h. The mixture was cooled to room temperature, diluted with water, and extracted with $Et^2O$ (2×40 mL). The combined organic extracts were washed with brine (30 mL), dried over $MgSO_4$, filtered, and concentrated. The residue was purified by flash chromatography (10% ethyl acetate/hexanes) to give the ester 15-4 as an off-white solid.

TLC Rf=0.3 (10% ethyl acetate/hexanes). $^1$H NMR (300 MHz, $CHCl_3$) δ 7.78 (d, 1H, J=15.9 Hz), 7.68 (d, 1H, J=2.4 Hz), 7.66 (s, 1H), 7.59 (d, 1H, J=8.4 Hz), 7.43 (dd, 1H, J=9.0, 1.5 Hz), 6.78 (m, 1H), 6.47 (d, 1H, J=15.9 Hz), 4.27 (q, 2H, J=7.2 Hz), 1.34 (t, 3H, J=7.2 Hz) ppm.

3-(S)-Benzofuran-6-yl-3-[benzyl-(1(R)-phenyl-ethyl)-amino]-propionic acid ethyl ester (15-5)

A solution of benzyl-α-(R)-methylbenzylamine (1.32 g, 6.30 mmol) in THF (25 mL) at 0° C. was treated with n-BuLi (2.52 mL of a 2.5 M soln in hexanes). The resulting solution was stirred at 0° C. for 30 min and then cooled to −78° C. A solution of acrylate 15-4 (0.681 g, 3.15 mmol) in THF (5 mL) was added. After stirring for 15 min at −78° C., satd aq $NH_4Cl$ soln (5 mL) was added and the cold bath removed. The mixture was warmed to room temperature, and extracted with $Et_2O$ (2×40 mL). The combined organic extracts were washed with brine (30 mL), dried over $MgSO_4$, filtered, and concentrated. The residue was purified by flash chromatography (10% ethyl acetate/hexanes) to give the β-aminoester 15-5 as a yellow oil.

TLC Rf=0.8 (10% ethanol/dichloromethane). $^1$H NMR (300 MHz, $CHCl_3$) δ 7.58 (m, 3H), 7.41 (m, 2H), 7.22 (m, 9H), 7.59 (s, 1H), 4.58 (m, 1H), 4.05 (m, 1H), 3.91 (q, 2H, J=7.1 Hz), 3.72 (m, 2H), 2.62 (m, 2H), 1.21 (d, 3H, J=7.2 Hz), 1.03 (t, 3H, J=7.1 Hz) ppm.

3(S)-Amino-3-(2,3-dihydro-benzofuran-6-yl)-propionic acid ethyl ester (15-6)

A mixture of the dibenzylamine 15-5 (1.19 g, 2.78 mmol) in $EtOH/H_2O/AcOH$ (26 mL/3 mL/1.0 mL) was degassed with argon and treated with $Pd(OH)_2$ (1.19 g). The mixture was placed under 1 atm of $H_2$. After stirring for 18 h, the mixture was diluted with EtOAc, and filtered through celite. The filtrate was concentrated and the residue purified by flash chromatography (10% ethyl acetate/dichloromethane) to give the ester 15-6 as a white solid.

TLC Rf=0.25 (10% ethanol/dichloromethane). $^1$H NMR (300 MHz, $CD_3OD$) as the trifluoroacetate salt: δ 7.25 (d, 1H, J=8.1 Hz), 6.88 (m, 1H), 7.66 (s, 1H), 6.82 (s, 1H), 4.58 (m, 3H), 4.12 (m, 2H), 3.30 (m, 1H), 3.19 (m, 2H), 2.98 (m, 2H), 1.11 (t, 3H, J=7.2 Hz) ppm.

3(S)-(2,3-Dihydro-benzofuran-6-yl)-3-(2-{2-oxo-3(S)-[2-(5,6,7,8-tetrahydro-[1,8]naphthyridin-2-yl)-ethyl]-pyrrolidin-1-yl}-acetylamino)-propionic acid ethyl ester (15-7)

A solution of the amine 15-6 (0.100 g, 0.425 mmol), acid 3-11 (0.155 g, 0.511 mmol), EDC (0.098 g, 0.511 mmol), NMM (0.103 g, 1.02 mmol), and HOAT (0.069 g, 0.511 mmol) in DMF (6 mL) was stirred at room temperature for 48 h. The solution was diluted with satd aq $NaHCO_3$ (3 mL) and extracted with EtOAc (2×10 mL). The combined organic extracts were washed with brine (10 mL), dried over $MgSO_4$, filtered, and concentrated. The residue was purified by flash chromatography (8% ethanol/dichloromethane) to give the ester 15-7 as an yellow oil.

TLC Rf=0.3 (10% ethanol/dichloromethane). $^1$H NMR (300 MHz, $CHCl_3$) δ 7.12 (m, 2H), 6.78 (m, 1H), 6.65 (s, 1H), 6.39 (m, 1H), 5.36 (m, 1H), 4.99 (br s, 1H), 4.55 (t, J=7.2 Hz, 2H), 4.11 (m, 2H), 3.91 (m, 2H), 3.39 (m, 2H), 3.19 (m, 2H), 2.79 (m, 2H), 2.70 (m, 2H), 2.51 (m, 1H), 2.28 (m, 2H), 1.85 (m, 3H), 1.18 (m, 3H) ppm.

3(S)-(2,3-Dihydro-benzofuran-6-yl)-3-(2-{2-oxo-3(S)-2-(5,6,7,8-tetrahydro-[1,8]naphthyridin-2-yl)-ethyl]-pyrrolidin-1-yl}-acetylamino)-propionic acid (15-9)

A solution of the ester 15-7 (0.038 g, 0.073 mmol) in $EtOH/H_2O$ (4.5 mL/0.5 mL) was treated with LiOH (0.009 g, 0.365 mmol) and the homogeneous solution stirred at room temperature for 4 h. The solution was concentrated to a solid residue which was dissolved in $H_2O$ and purified by preparative HPLC (gradient conditions: 95:05 to 50:50 $H_2O/MeCN$ with 0.1% TFA) to give the acid 15-8 as a white solid (as the bis-trifluoroacetate salt).

MS (LR, FAB) M+1 calcd 493, found 493.39. $^1$H NMR (300 MHz, CHCl$_3$) δ 7.91 (m, 1H), 7.35 (m, 1H), 7.09 (m, 1H), 6.76 (m, 1H), 6.68 (s, 1H), 6.43 (m, 2H), 5.28 (m, 1H), 4.53 (m, 2H), 4.41 (m, 1H), 3.38 (m, 7H), 3.14 (m, 3H), 2.81 (m, 5H), 2.60 (m, 1H), 2.28 (m, 1H), 2.05 (m, 3H) ppm.

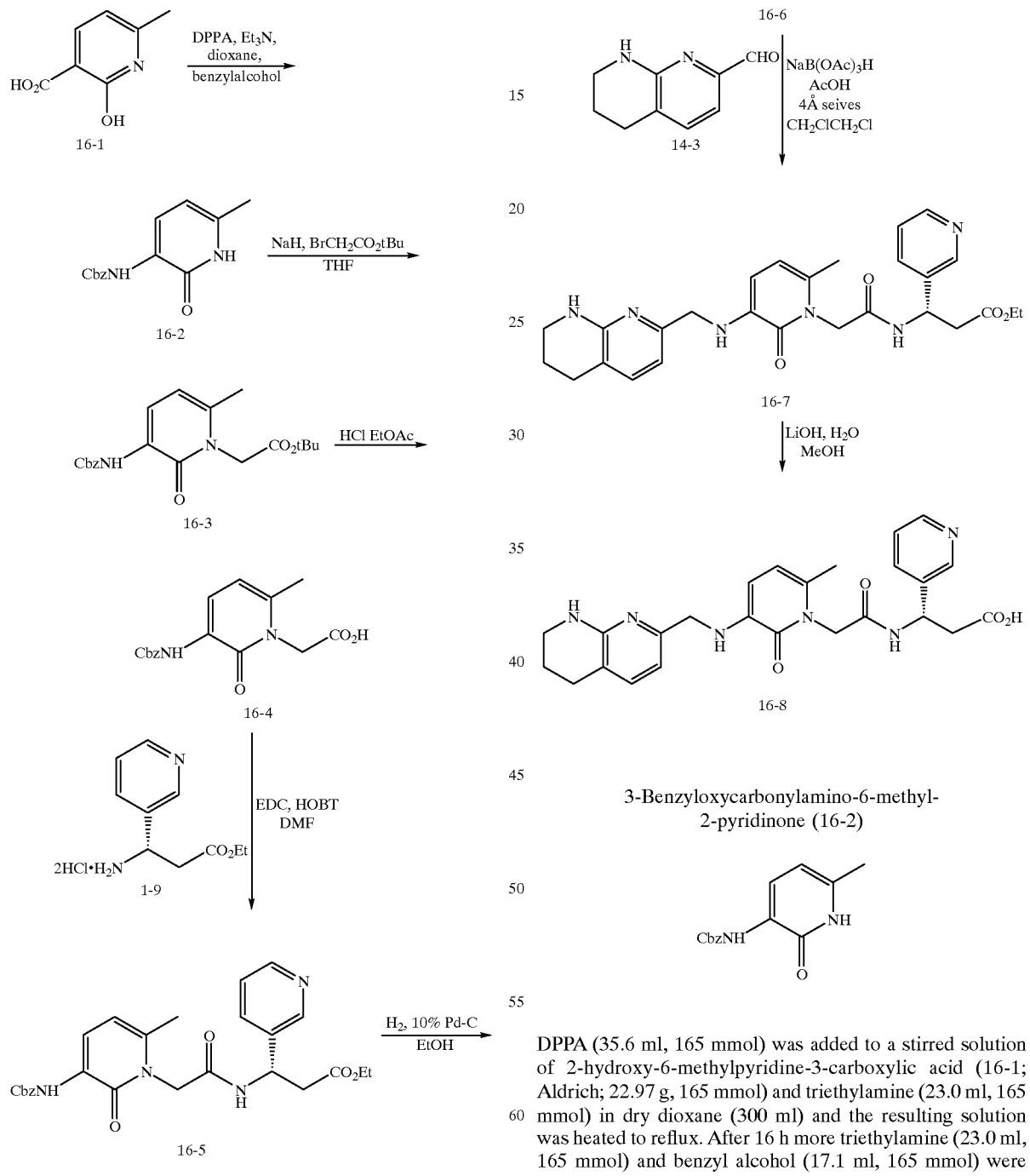

3-Benzyloxycarbonylamino-6-methyl-2-pyridinone (16-2)

DPPA (35.6 ml, 165 mmol) was added to a stirred solution of 2-hydroxy-6-methylpyridine-3-carboxylic acid (16-1; Aldrich; 22.97 g, 165 mmol) and triethylamine (23.0 ml, 165 mmol) in dry dioxane (300 ml) and the resulting solution was heated to reflux. After 16 h more triethylamine (23.0 ml, 165 mmol) and benzyl alcohol (17.1 ml, 165 mmol) were added and the solution was refluxed for a further 24 h. The reaction was concentrated in vacuo to remove most of the volatiles. The residue was partitioned between methylene chloride (500 ml) and brine (500 ml), acidified to pH 1 with 1 M HCl (165 ml). The aqueous layer was extracted methylene chloride (two times) and the combined organic layers were washed with sodium hydrogen carbonate solution and brine, dried (Na$_2$SO$_4$) and evaporated in vacuo to a brown solid. This was recrystallized from methanol, to give the title compound 16-2 as a tan solid: $^1$H NMR (300 MHz, CDCl$_3$) δ 2.29 (s, 3H, CH$_3$), 5.20 (s, 2H, PhCH$_2$), 6.06 (d, J=7.6 Hz, pyridinone-5-H), 7.32–7.43 (m, 5H, Ph), 7.67 (br s, 1H, CbzNH), 8.03 (br d, pyridinone-4-H).

2-[6-methyl-2-oxo-3-(benzyloxycarbonylamino)-2H-pyridin-1-yl]acetic acid t-butyl ester (16-3)

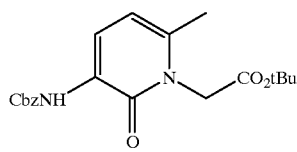

Sodium hydride (5.3 g, 0.22 mol) was added to a stirred slurry of 3-benzyloxycarbonylamino-6-methyl-2-pyridinone (16-2; 53.2 g, 0.20 mol) in THF at 0° C. t-Butylbromoacetate (45 ml, 0.27 mol) was added to the resulting solution and a precipitate rapidly forms. The reaction was warmed to rt over 1 h and after 2 h the solvent was evaporated in vacuo and the residue was partitioned between 1:1 water/brine (200 ml) and 6:1 THF/methylene chloride (700 ml). The organic layer was dried (Na$_2$SO$_4$) and evaporated in vacuo to a solid which was triturated with hexane to give the title compound 16-3 as a crystalline solid:

$^1$H NMR (400 Mz, CDCl$_3$) δ 1.47 (s, 9H), 2.25 (s, 3H), 4.75 (s, 2H), 5.19 (s, 2H), 6.09 (d, J=7.8 Hz), 7.30–7.40 (m, 5H), 7.75 (br s, 1H), 7.94 (br d, 1H).

2-[6-methyl-2-oxo-3-(benzyloxycarbonylamino)-2H-pyridin-1-yl]acetic acid (16-4)

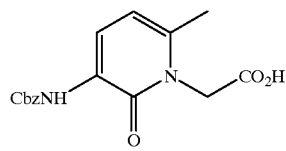

HCl gas was bubbled through a stirred suspension of 2-[6-methyl-2-oxo-3-(benzyloxycarbonylamino)-2H-pyridin-1-yl]acetic acid t-butyl ester (16-3; 12.3 g, 33 mmol) in ethyl acetate (250 ml) at −15° C. for 20 min. The resulting solution was allowed to warm to room temperature and was then stirred there for 3 h. After purging with argon, the bulk of the solvent was rotavapped off and ether added to the residue. The solid which precipitated was filtered off and washed with ether. The title compound 16-4 was thus obtained as a white fluffy powder: $^1$H NMR (CD$_3$OD) δ 2.32 (s, 3H), 4.86 (s, 2H), 5.18 (s, 2H), 6.24 (d, J=7.9 Hz, 1H), 7.31–7.41 (m, 6H), 7.94 (br s, 1H).

3-(2-{6-methyl-2-oxo-3-(benzyloxycarbonylamino)-2H-pyridin-1-yl}-acetylamino)-3(S)-pyridin-3-yl-propionic acid ethyl ester (16-5)

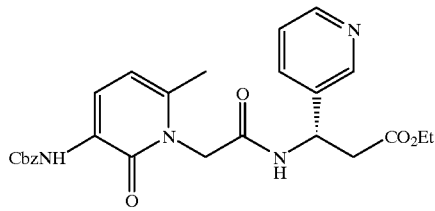

To a solution of the acid 2-4 (150 mg, 0.47 mmol) and the amine 1-9 (Rico et al; J. Org. Chem., 1993, 58, 7948; 139 mg, 0.52 mmol) in DMF (3 mL) was added HOBT (77 mg, 0.57 mmol) then Et$_3$N (200 μL, 1.42 mmol). After 15 minutes, EDC (136 mg, 0.71 mmol) was added and the mixture was stirred for 16 hours. The solution was poured into EtOAc, washed with saturated NaHCO$_3$ then brine, dried (MgSO$_4$), and evaporated to give the title compound 16-5 as a white solid which was used as such in the next step. $^1$H NMR (CDCl$_3$) δ 1.14 (3H, t), 2.40 (3H, s), 2.8–2.9 (2H, m), 4.05 (2H, q), 4.78 (2H, m), 5.22 (2H, s), 5.4 (1H, q), 6.17 (1H, d), 7.22 (1H, m), 7.3–7.45 (4H, m), 7.59 (1H, m), 7.7–7.8 (2H, m), 8.0 (1H, m), 8.52 (2H, m).

3-(2-{6-methyl-2-oxo-3-amino-2H-pyridin-1-yl}-acetylamino)-3(S)-pyridin-3-yl-propionic acid ethyl ester (16-6)

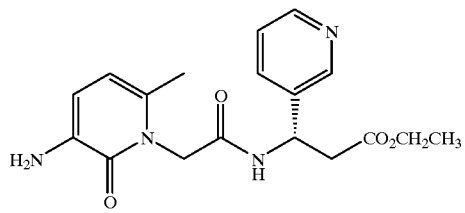

To a degassed solution of the pyridone 16-5 (243 mg; 0.49 mmol) in EtOH (20 mL) was added 10% Pd on carbon (25 mg) and this was then stirred under an atmosphere of hydrogen gas (balloon) for 3 hours. The mixture was filtered through a pad of celite and the solvent removed to give the title compound (16-6) as a viscous oil which was used as such in the next step.

3-(2-{6-methyl-2-oxo-3-[(5,6,7,8-tetrahydro-[1,8] naphthyridin-2-ylmethyl)-amino]-2H-pyridin-1-yl}-acetylamino)-3(S)-pyridin-3-yl-propionic acid ethyl ester (16-7)

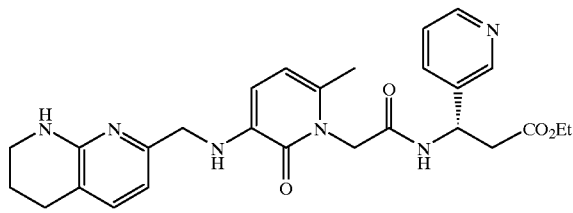

To a solution of the amine 16-6 (155 mg, 0.433 mmol), the aldehyde 14-3 (70 mg, 0.433 mmol) in CH$_2$ClCH$_2$Cl was added crushed 4 Å seives, AcOH (20 µL) and then NaB(OAc)$_3$H (184 mg, 0.866 mmol). After stirring for 48 hours, the mixture was filtered through celite, poured into EtOAc and washed with saturated NaHCO$_3$ then brine. The dried (MgSO$_4$) solution was concentrated in vacuo to give a foam type solid. Column chromatography (5% MeOH in CHCl$_3$) afforded the title compound 16-7 as a foam type solid.

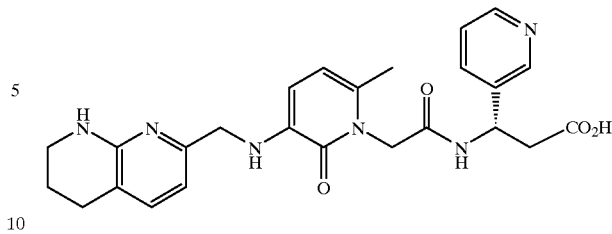

Analysis calculated for C$_{27}$H$_{32}$N$_6$O$_4$·0.25CHCl$_3$; C, 61.24; H, 6.08; N, 15.73; found C, 61.33; H, 6.09; N, 15.85. FAB mass spectrum. m/z=505.34 (M+H).

3-(2-{6-methyl-2-oxo-3-[(5,6,7,8-tetrahydro-1,8]naphthyridin-2-ylmethyl)-amino]-2H-pyridin-1-yl}-acetylamino)-3(S)-pyridin-3-yl-propionic acid bis trifluoroacetate (16-8)

The ester 16-7 (120 mg, 0.238 mmol) was dissloved in H$_2$O (1 mL) and THF (1 mL) and then 1N LiOH (1 mL, 1 mmol) was added. After 2 hours, the mixture was purified by reverse phase HPLC (Waters PrepPak C18 column eluting with H$_2$O/acetonitrile gradient) to give, after lyophilization, the title compound 16-8 as a powder Analysis calculated for C$_{25}$H$_{28}$N$_6$O$_4$·2.5TFA·0.55H$_2$O; C, 46.70; H, 4.13; N, 10.89; found C, 46.70; H, 4.14; N, 11.04. FAB mass spectrum. m/z=477.2 (M+H).

SCHEME 17

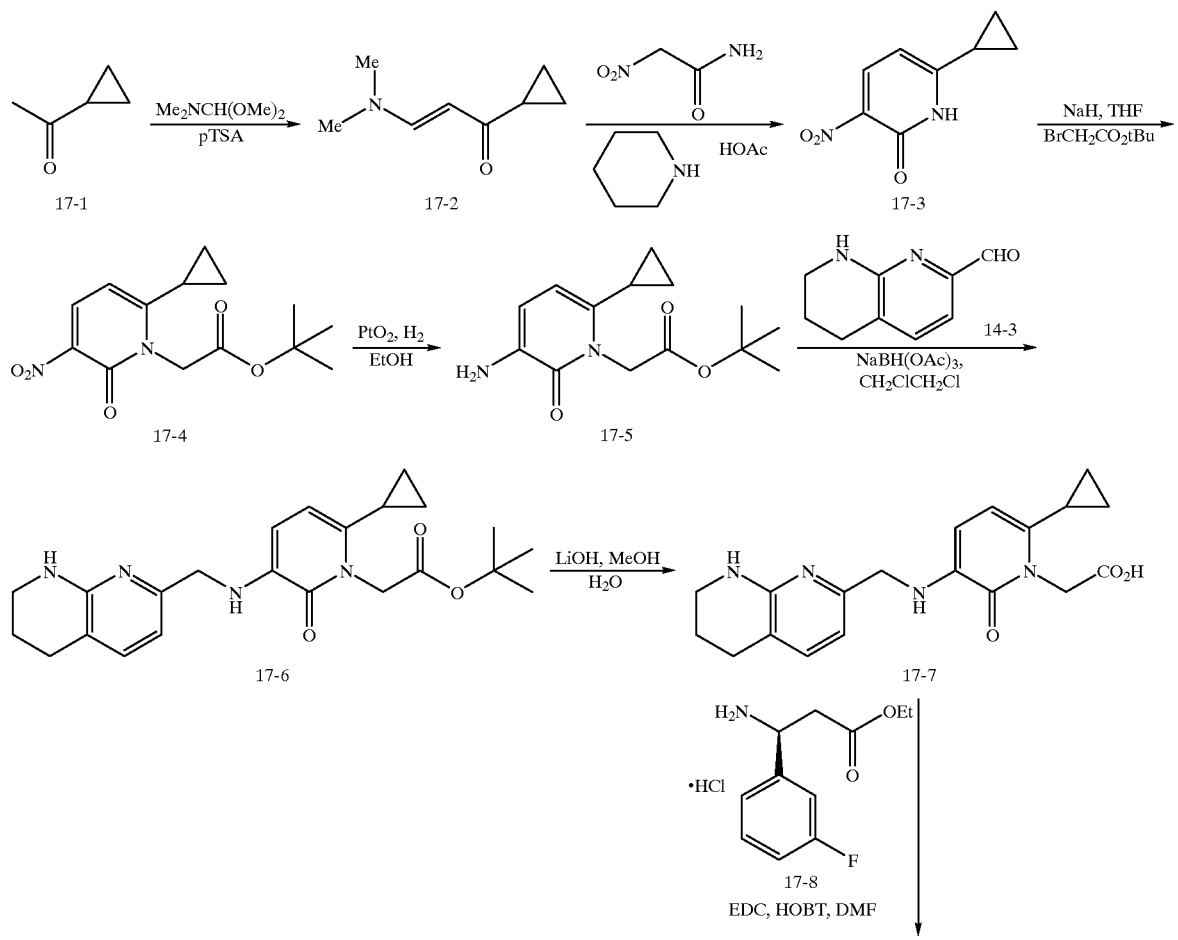

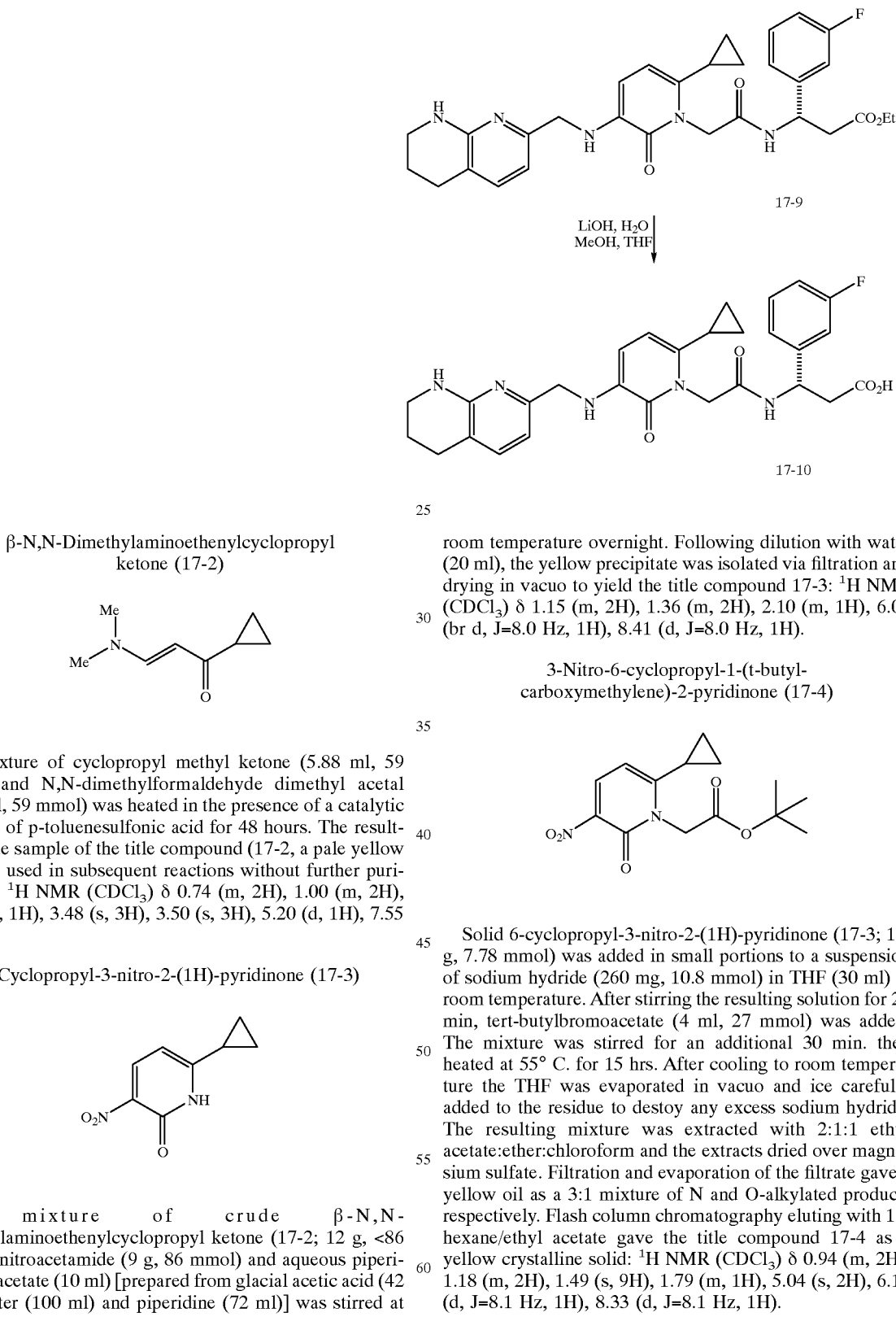

β-N,N-Dimethylaminoethenylcyclopropyl ketone (17-2)

A mixture of cyclopropyl methyl ketone (5.88 ml, 59 mmol) and N,N-dimethylformaldehyde dimethyl acetal (7.83 ml, 59 mmol) was heated in the presence of a catalytic quantity of p-toluenesulfonic acid for 48 hours. The resulting crude sample of the title compound (17-2, a pale yellow oil) was used in subsequent reactions without further purification: $^1$H NMR (CDCl$_3$) δ 0.74 (m, 2H), 1.00 (m, 2H), 1.75 (m, 1H), 3.48 (s, 3H), 3.50 (s, 3H), 5.20 (d, 1H), 7.55 (d, 1H).

6-Cyclopropyl-3-nitro-2-(1H)-pyridinone (17-3)

A mixture of crude β-N,N-dimethylaminoethenylcyclopropyl ketone (17-2; 12 g, <86 mmol), nitroacetamide (9 g, 86 mmol) and aqueous piperidinium acetate (10 ml) [prepared from glacial acetic acid (42 ml), water (100 ml) and piperidine (72 ml)] was stirred at room temperature overnight. Following dilution with water (20 ml), the yellow precipitate was isolated via filtration and drying in vacuo to yield the title compound 17-3: $^1$H NMR (CDCl$_3$) δ 1.15 (m, 2H), 1.36 (m, 2H), 2.10 (m, 1H), 6.02 (br d, J=8.0 Hz, 1H), 8.41 (d, J=8.0 Hz, 1H).

3-Nitro-6-cyclopropyl-1-(t-butyl-carboxymethylene)-2-pyridinone (17-4)

Solid 6-cyclopropyl-3-nitro-2-(1H)-pyridinone (17-3; 1.4 g, 7.78 mmol) was added in small portions to a suspension of sodium hydride (260 mg, 10.8 mmol) in THF (30 ml) at room temperature. After stirring the resulting solution for 20 min, tert-butylbromoacetate (4 ml, 27 mmol) was added. The mixture was stirred for an additional 30 min. then heated at 55° C. for 15 hrs. After cooling to room temperature the THF was evaporated in vacuo and ice carefully added to the residue to destoy any excess sodium hydride. The resulting mixture was extracted with 2:1:1 ethyl acetate:ether:chloroform and the extracts dried over magnesium sulfate. Filtration and evaporation of the filtrate gave a yellow oil as a 3:1 mixture of N and O-alkylated products respectively. Flash column chromatography eluting with 1:1 hexane/ethyl acetate gave the title compound 17-4 as a yellow crystalline solid: $^1$H NMR (CDCl$_3$) δ 0.94 (m, 2H), 1.18 (m, 2H), 1.49 (s, 9H), 1.79 (m, 1H), 5.04 (s, 2H), 6.10 (d, J=8.1 Hz, 1H), 8.33 (d, J=8.1 Hz, 1H).

3-Amino-6-cyclopropyl-1-(t-butyl-carboxymethylene)-2-pyridinone (17-5)

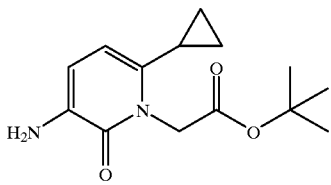

A mixture of 3-nitro-6-cyclopropyl-1-(t-butyl-methylenecarboxy)-2-pyridinone (17-4; 760 mg, 2.58 mmol) and platinum oxide (250 mg) in ethanol (30 ml) was stirred at 0° C. under an atmosphere of hydrogen for 3 hours. Following removal of most of the catalyst by filtration through a bed of Celite, the filtrate was concentrated and the residue purified by flash column chromatography eluting with 2:1 hexane/ethyl acetate. This yielded the title product 17-5 as a viscous orange gum: $^1$H NMR (CDCl$_3$) δ 0.67 (m, 2H), 0.89 (m, 2H), 1.49 (s, 9H), 1.63 (m, 1H), 4.07 (br s, 2H), 4.99 (s, 2H), 5.91 (dd, J=1.2 and 7.4 Hz, 1H), 6.47 (d, J=7.4 Hz, 1H).

{6-Cyclopropyl-2-oxo-3-[(5,6,7,8-tetrahydro-[1,8]naphthyridin-2-ylmethyl)-amino]-2H-pyridin-1-yl}-acetic acid tert-butyl ester (17-6)

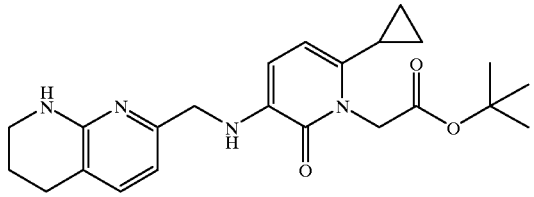

Following the procedure described for the synthesis of 16-7, the amine 17-5 was coupled with 14-3 to yield the title compound 17-6 as an oil.

R$_f$ (silica gel; 5% MeOH in CHCl$_3$)=0.39

{6-Cyclopropyl-2-oxo-3-[(5,6,7,8-tetrahydro-[1,8]naphthyridin-2-ylmethyl)-amino]-2H-pyridin-1-yl}-acetic acid (17-7)

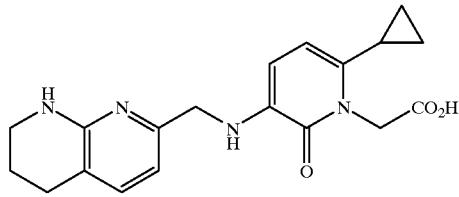

Following the procedure described for the preparation of 16-8, the ester 17-6 was hydrolysed to give the title compound 17-7. $^1$H NMR (CD$_3$OD) δ 0.66 (m, 2H), 0.9 (m, 2H), 1.78 (m, 1H), 1.9 (m, 2H), 2.75 (m, 2H), 3.4 (m, 2H), 4.6 (br s, 2H), 6.02 (d, 1H), 6.19 (d, 1H), 6.58 (m, 1H), 7.27 (m, 1H).

Ethyl 3-amino-3(S)-(3-fluorophenyl)propionate hydrochloride (17-8)

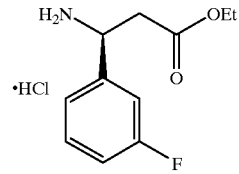

The title compound was prepared starting from 3-fluorobenzaldehyde (Aldrich) by conversion to ethyl 3-fluorocinnamate and employing the asymmetric addition/hydrogenolysis methodology described by Rico et al; *J. Org. Chem.*, 1993, 58, 7948.

$^1$H NMR (CD$_3$OD) δ 1.21 (t, 3H), 3.03 (dd, 1H), 3.13 (dd, 1H), 4.15 (q, 2H), 4.77 (t, 1H), 7.19 (m, 1H), 7.3 (m, 2H), 7.5 (m, 1H).

3-(2-{6-Cyclopropyl-2-oxo-3-[(5,6,7,8-tetrahydro-[1,8]naphthyridin-2-ylmethyl)-amino]-2H-pyridin-1-yl}-acetylamino)-3(S)-(3-fluorophenyl)-propionic acid ethyl ester (17-9)

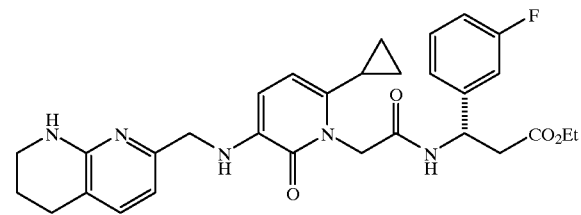

Following the procedure described for the preparation of 16-5, the acid 17-7 was coupled with the amine 17-8 to yield the title compound 17-9.

Analysis calculated for C$_{30}$H$_{34}$N$_5$O$_4$ F$_1$·0.25H$_2$O; C, 65.26; H, 6.30; N, 12.69; found C, 65.20; H, 6.04; N, 13.00. FAB mass spectrum. m/z=548.12 (M+H).

3-(2-{6-Cyclopropyl-2-oxo-3-[(5,6,7,8-tetrahydro-[1,8]naphthyridin-2-ylmethyl)-amino]-2H-pyridin-1-yl}-acetylamino)-3(S)-(3-fluorophenyl)-propionic acid ditrifluoroacetate (17-10)

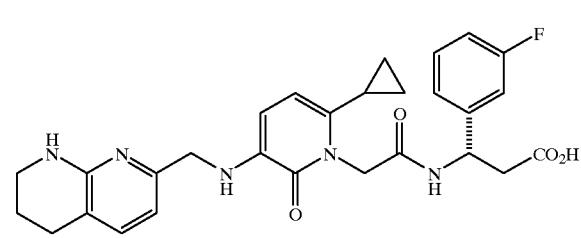

Following the procedure described for the preparation of 16-8, the ester 17-9 was hydrolysed to give the title compound 17-10.

Analysis calculated for C$_{28}$H$_{30}$N$_5$O$_4$ F$_1$·2.15TFA·0.5H$_2$O; C, 55.16; H, 4.91; N, 10.62; found C, 55.19; H, 4.91; N, 10.89. FAB mass spectrum. m/z=520.05 (M+H).

3-(2-{6-Cyclopropyl-2-oxo-3-[(5,6,7,8-tetrahydro-[1,8]naphthyridin-2-ylmethyl)-amino]-2H-pyridin-1-yl}-acetylamino)-3(S)-(3-pyridyl)-propionic acid ditrifluoroacetate (17-1 1)

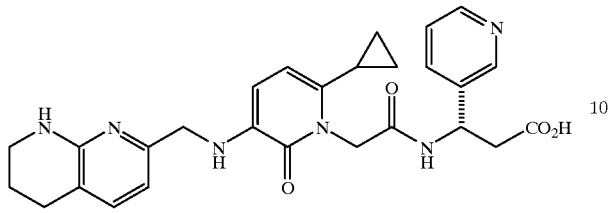

Following the procedures described for Scheme 16, the acid 17-7 was coupled with the amine 1-9 followed by saponification of the ester to afford the title compound 17-11.

Analysis calculated for $C_{27}H_{30}N_6O_4 \cdot 2.5TFA \cdot 0.6H_2O$; C, 48.13; H, 4.25; N, 10.53; found C, 48.11; H, 4.23; N, 10.64. FAB mass spectrum. m/z=503.25 (M+H).

3-(2-{6-Cyclopropyl-2-oxo-3-[(5,6,7,8-tetrahydro-[1,8]naphthyridin-2-ylmethyl)-amino]-2H-pyridin-1-yl}-acetylamino)-3(S)-(ethynyl)-propionic acid ethyl ester (17-12)

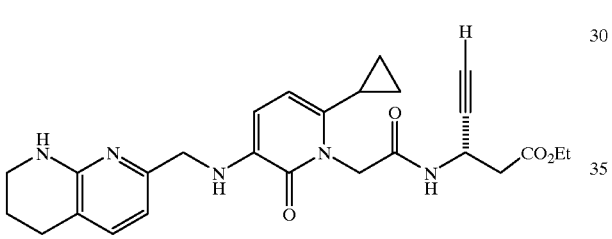

Following the procedures described for Scheme 16, the acid 17-7 was coupled with 3-amino-3(S)-(ethynyl)-propionic acid ethyl ester 2-9 (Zablokie et al, *J. Med. Chem.*, 1995, 38, 2378) to afford the title compound 17-12.

Analysis calculated for $C_{26}H_{31}N_5O_4 \cdot 0.35H_2O$; C, 64.53; H, 6.60; N, 14.47; found C, 64.52; H, 6.71; N, 14.54. FAB mass spectrum. m/z=478.35 (M+H).

3-(2-{6-Cyclopropyl-2-oxo-3-[(5,6,7,8-tetrahydro-[1,8]naphthyridin-2-ylmethyl)-amino-2H-pyridin-1-yl}-acetylamino)-3(S)-(ethynyl)-propionic acid (17-13).

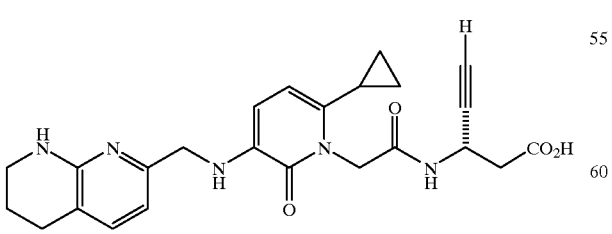

Following the procedure described for the preparation of 16-8, the ester 17-12 was hydrolysed to give the title compound 17-13.

FAB mass spectrum. m/z=450.23 (M+H).

SCHEME 18

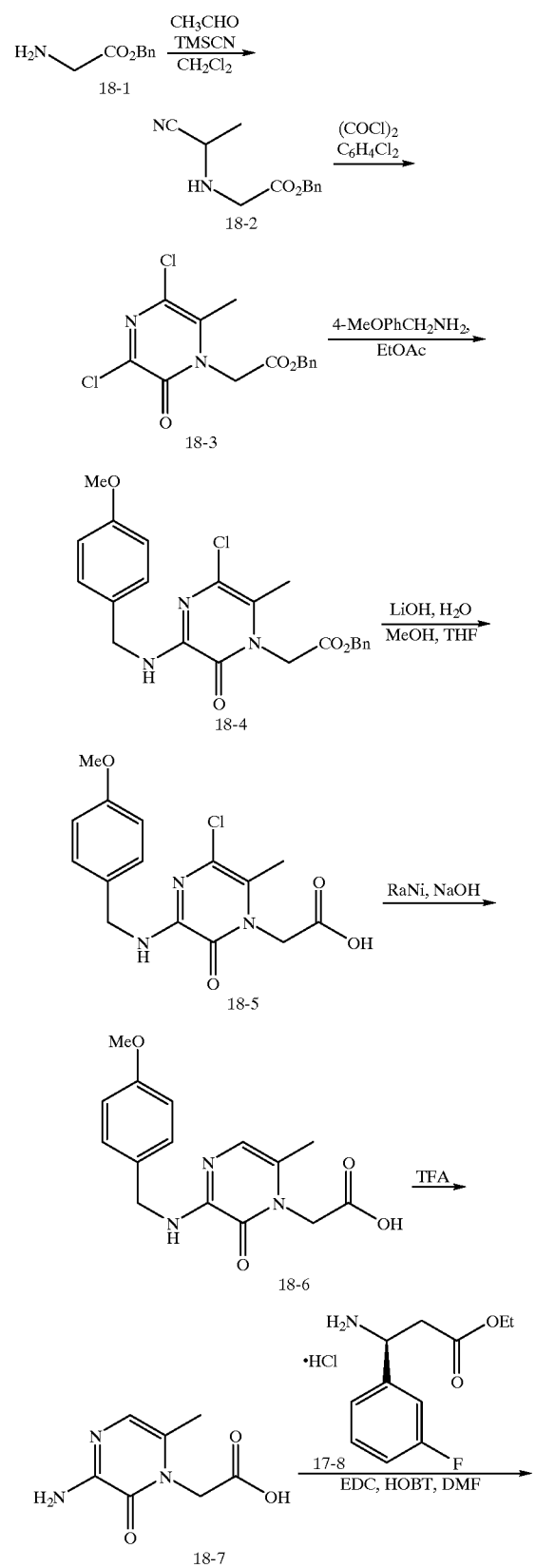

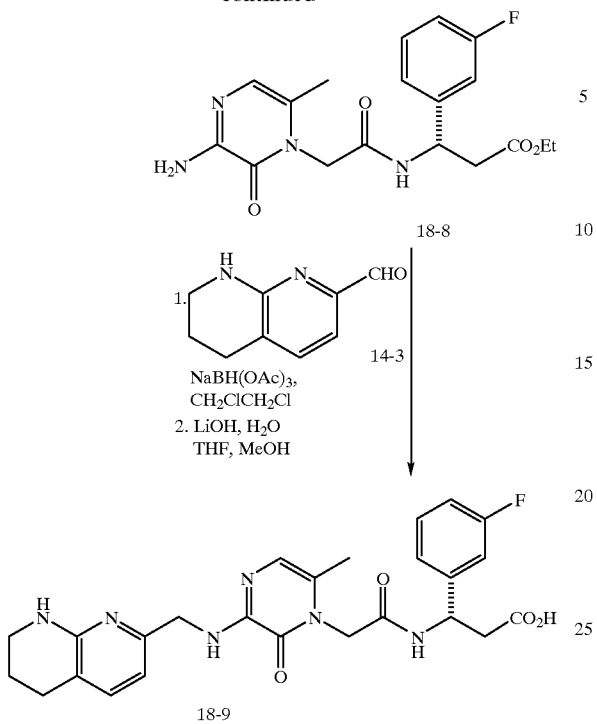

Benzyl-N-(1-cyanoethyl)glycine hydrochloride (18-2)

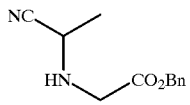

TMSCN (18.8 mL, 141 mmol) was added cautiosly to a stirred solution of benzylglycine free base (23.3 g 141 mmol—from the HCl salt by partition between EtOAc and brine basified with saturated $Na_2CO_3$ solution) and acetaldehyde (7.88 mL, 141 mmol) in $CH_2Cl_2$ (50 mL). After 4 h the volatiles were removed in vacuo and the residue was taken up in EtOAc and washed with brine, dried ($Na_2SO_4$) and evaporated in vacuo to an oil. The oil was redissolved in EtOAc and 9.9 M HCl in EtOH (15.25 mL, 151 mmol) was added to give a crystalline precipitate which was isolated by filtration, washing with EtOAc and $Et_2O$ to give the title compound (18-2):

$^1$H NMR ($CD_3OD$) δ 1.70 (d, 3H), 4.16 (d, 1H), 4.21 (d, 1H), 4.64 (q, 1H), 5.31 (s, 2H), 7.35–7.44 (m, 5H).

1-Benzyloxycarbonylmethyl-3,5-dichloro-6-methylpyrazinone (18-3)

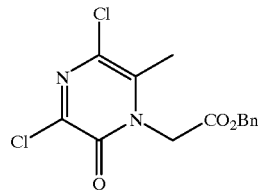

A stirred mixture of oxalyl chloride (40.4 mL, 463 mmol) and 18-2 (29.51 g, 116 mmol) in 1,2-dichlorobenzene (110 mL) was heated to 100° C. for 15 h. The volatiles were removed in vacuo and the residue was purified by chromatography (silica gel; hexanes followed by 30% EtOAc in hexanes) to give a solid which was heated in EtOAC/hexanes 2:5 (140 mL), cooled and collected by filtration to give the title compound 18-3 as a pale green solid:

$^1$H NMR ($CDCl_3$) δ 2.35 (s, 3H), 4.88 (s, 2H), 5.24 (s, 2H), 7.38 (m, 5H).

3-(4-Methoxybenzylamino)-5-chloro-6-methyl-1-benzyloxycarbonylmethyl-pyrazinone (18-4)

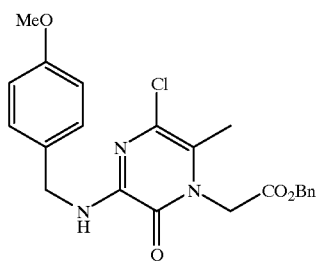

A solution of the pyrazinone 18-3 (5 g, 15.3 mmol) and 4 methoxybenzylamine (6.0 mL, 45.9 mmol) in EtOAc (60 mL) was heated at 80° C. for 2 h. The solution was cooled and filtered. The filtrate was concentrated in vacuo, the residue swished with MeOH and filtered to afford the title compound as a solid:

$^1$H NMR ($CDCl_3$) δ 2.23 (s, 3H), 3.82 (s, 3H), 4.5 (d, 2H), 4.81 (s, 2H), 5.22 (s, 2H), 6.25 (t, 1H), 6.85 (m, 2H), 7.27 (m, 2H), 7.38 (m, 5H).

3-(4-Methoxybenzylamino)-5-chloro-6-methyl-1-carboxymethyl pyrazinone (18-5)

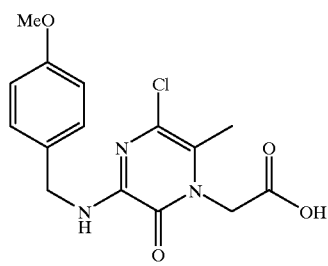

A solution of the benzyl ester 18-4 (1.06 g, 2.48 mmol) in toluene (60 mL) was degassed with argon and then 150 mg 10% palladium on carbon was added. The mixture was stirred under an atmosphere of hydrogen gas for 16 h. The solution was filtered through celite and the solvent evaporated to give the title compound 18-5 as a white solid:

$^1$H NMR ($CD_3OD$) δ 2.25 (s, 3H), 3.78 (s, 3H), 4.45 (s, 2H), 4.81 (s, 2H), 4.90 (s, 2H), 6.85 (d, 2H), 7.28 (d, 2H).

3-(4-Methoxybenzylamino)-6-methyl-1-carboxymethyl pyrazinone (18-6)

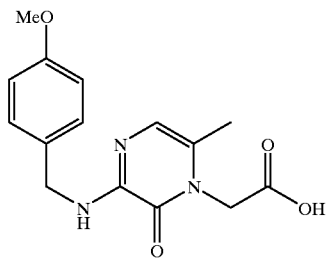

The acid 18-5 (810 mg) was dissolved in 40 mL 1 N NaOH and 40 mL MeOH at room temperature and was treated with Raney nickel suspension (~5 g). A second charge of Raney nickel (~5 g) and 1 N NaOH (20 mL) was added after 3 h. After 6 h, the suspension was filtered through celite washing with water and MeOH. The volatiles were removed in vacuo and the residue then taken up 1 N HCl (~5 mL). Saturated NaHCO$_3$ solution was added until pH~7–8 and the solution was extracted exhaustively with EtOAc/THF. After drying (MgSO$_4$), the solvent was removed to give the title compound 18-6 as a solid which was used as such:

$^1$H NMR (CD$_3$OD) δ 2.16 (s, 3H), 3.76 (s, 3H), 4.46 (s, 2H), 4.64 (s, 2H), 4.86 (s, 2H), 6.65 (s, 1H), 6.85 (d, 2H), 7.25 (d, 2H).

3-Amino-6-methyl-1-carboxymethylpyrazinone (18-7)

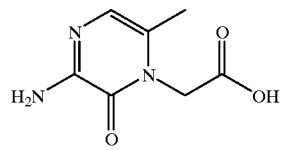

The pyrazinone 18-6 (900 mg) was heated at reflux in trifluoroacetic acid (20 mL) for 7 h. The volatiles were removed in vacuo and the residue was azeotroped with CH$_2$Cl$_2$, then EtOAc then MeOH. MeOH was added to the residue and the solution filtered to remove impurities. Removal of the methanol then afforded the title compound 18-7 which was used as such:

$^1$H NMR (CD$_3$OD) δ 2.22 (s, 3H), 4.82 (s, 2H), 6.58 (s, 1H).

3-(3-Fluorophenyl)-3-(2-{6-methyl-2-oxo-3-amino]-2H-pyrazin-1-yl}-acetylamino)propionic acid ethyl ester (18-8)

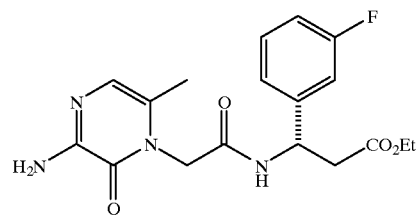

Following the procedure described for the preparation of 16-6, the acid 18-7 was coupled with the amine 17-8 to yield the title compound 18-8. $^1$H NMR (CDCl$_3$) δ 1.15 (t, 3H), 2.23 (s, 3H), 2.78 (dd, 1H), 2.84 (dd, 1H), 4.05 (q, 2H), 4.68 (ABq, 2H), 5.30 (br s, 2H), 5.35 (m, 1H), 6.68 (s, 1H), 6.9–7.1 (m, 3H), 7.27 (m, 1H), 7.57 (d, 2H).

3-(3-Fluorophenyl)-3-(2-{6-methyl-2-oxo-3-[(5,6,7,8-tetrahydro-[1,8]naphthyridin-2-ylmethyl)-amino]-2H-pyrazin-1-yl}-acetylamino)-propionic acid ditrifluoroacetate (18-9)

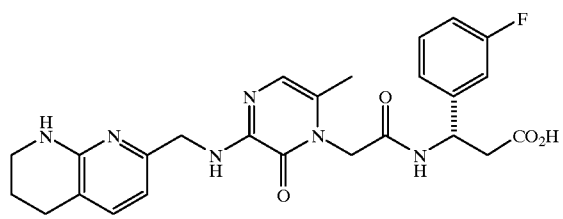

Following the procedure described for the synthesis of 16-9, the amine 18-8 was coupled with 14-3 and the product hydrolyzed to yield the title compound 18-9.

Analysis calculated for C$_{25}$H$_{27}$N$_6$O$_4$F·2.25TFA·0.85H$_2$O; C, 46.23; H, 4.07; N, 10.97; found C, 46.22; H, 4.00; N, 11.12. FAB mass spectrum. m/z=495.26 (M+H).

SCHEME 19

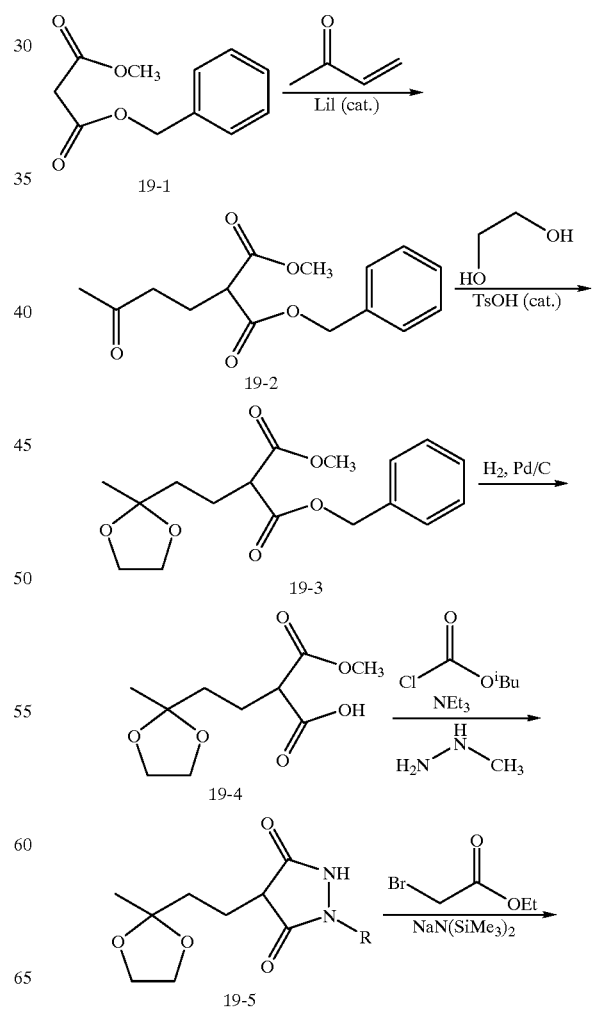

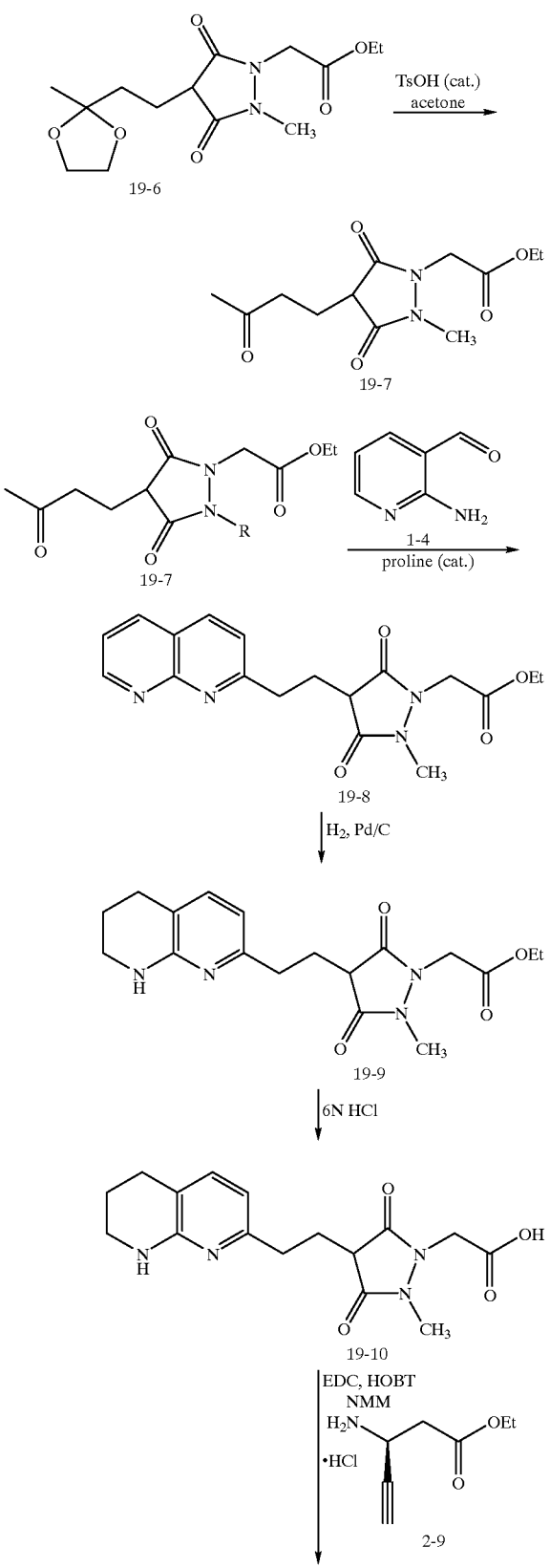

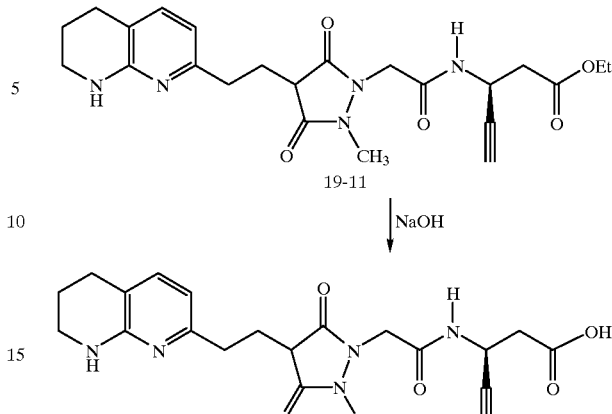

The test procedures employed to measure αvβ3 binding and the bone resorption inhibiting activity of the compounds of the present invention are described below.

BONE RESORPTION-PIT ASSAY

When osteoclasts engage in bone resorption, they will literally cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive 200 micron thick cross sections from a six mm cylinder of bovine femur diaphysis were cut with a low speed diamond saw (Isomet, Beuler, Ltd., Lake Bluff, Ill.). Bone slices were pooled, placed in a 10% ethanol solution and refrigerated until further use.

Prior to experimentation, bone slices were ultrasonicated twice, 20 minutes each in H$_2$O. Cleaned slices were placed in 96 well plates such that two control lanes and one lane for each drug dosage are available. Each lane represents either triplicate or quadruplicate cultures. The bone slices in 96 well plates were sterilized by UV irradiation. Prior to incubation with osteoclasts, the bone slices were hydrated by the addition of 0.1 ml Medium 199, pH 6.9 containing 15% fetal bovine serum and 1% penicillin/streptomycin.

Osteoclasts were isolated from the long bones of 1 to 3 day old rat pups (Sprague-Dawley) by modifications of Chambers et al., (J. Cell. Science, 66:383–399). The resulting suspension (0.75 ml/bone) was gently triturated 90–120 times using a wide bore transfer pipet. The cellular population was separated from bone fragments by a cell strainer with a 100 micron nylon mesh. 100 μl of the cell suspension was placed onto each bone slice. Test compounds were then added at the desired experimental concentrations.

Bone slices exposed to osteoclasts for 20–24 hrs were processed for staining. Tissue culture media was removed from each bone slice. Each well was washed with 200 μl of H$_2$O, and the bone slices were then fixed for 20 minutes in 2.5% glutaraldehyde, 0.1 M cacodylate, pH 7.4. After fixation, any remaining cellular debris was removed by 2 min. ultrasonication in the presence of 0.25 M NH$_4$OH followed by 2×15 min ultrasonication in H$_2$O. The bone slices were immediately stained for 6–8 min with filtered 1% toluidine blue and 1% borax.

After the bone slices have dried, resorption pits were counted in test and control slices. Resorption pits were viewed in a Microphot Fx (Nikon) fluorescence microscope using a polarizing Nikon IGS filter cube. Test dosage results were compared with controls and resulting $IC_{50}$ values were determined for each compound tested.

The appropriateness of extrapolating data from this assay to utility and use in mammalian (including human) disease states is supported by the teaching found in Sato, M., et al. *Journal of Bone and Mineral Research*, Vol. 5, No. 1, 1990. That article teaches that certain bisphosphonates have been used clinically and appear to be effective in the treatment of Paget's disease, hypercalcemia of malignancy, osteolytic lesions produced by bone metastases, and bone loss due to immobilization or sex hormone deficiency. These same bisphosphonates are then tested in the resorption pit assay described above to confirm a correlation between their known utility and positive performance in the assay.

EIB ASSAY

Duong et al., *J. Bone Miner. Res.*, 8:S 378, describe a system for expressing the human integrin $\alpha v \beta 3$. It has been suggested that the integrin stimulates attachment of osteoclasts to bone matrix, since antibodies against the integrin, or RGD-containing molecules, such as echistatin (European Publication 382 451), can effectively block bone resorption.

Reaction Mixture:
1. 175 µl TBS buffer (50 mM Tris·HCl pH 7.2, 150 mM NaCl, 1% BSA, 1 mM $CaCl_2$, 1 mM $MgCl_2$).
2. 25 µl cell extract (dilute with 100 mM octylglucoside buffer to give 2000 cpm/25 µl).
3. $^{125}$I-echistatin (25 µl/50,000 cpm) (see EP 382 451).
4. 25 µl buffer (total binding) or unlabeled echistatin (non-specific binding).

The reaction mixture was then incubated for 1 h at room temp. The unbound and the bound $\alpha v \beta 3$ were separated by filtration using a Skatron Cell Harvester. The filters (prewet in 1.5% polyethyleneimine for 10 mins) were then washed with the wash buffer (50 mM TRis HCl, 1 mM $CaCl_2$/ $MgCl_2$, pH 7.2). The filter was then counted in a gamma counter.

SPA ASSAY

MATERIALS:
1. Wheatgerm agglutinin Scintillation Proximity Beads (SPA): Amersham
2. Octylglucopyranoside: Calbiochem
3. HEPES: Calbiochem
4. NaCl: Fisher
5. $CaCl_2$: Fisher
6. $MgCl_2$: SIGMA
7. Phenylmethylsulfonylfluoride (PMSF): SIGMA
8. Optiplate: PACKARD
9. Compound 8-10 (specific activity 500–1000 Ci/mmole)
10. test compound
11. Purified integrin receptor: $\alpha V \beta 3$ was purified from 293 cells overexpressing $\alpha v \beta 3$ (Duong et al., *J. Bone Min. Res.*, 8:S378, 1993) according to Pytela (*Methods in Enzymology*, 144:475, 1987)
12. Binding buffer: 50 mM HEPES, pH 7.8, 100 mM NaCl, 1 mM $Ca^{2+}/Mg^{2+}$, 0.5 mM PMSF
13. 50 mM octylglucoside in binding buffer: 50-OG buffer.

PROCEDURE:
1. Pretreatment of SPA beads:
500 mg of lyophilized SPA beads were first washed four times with 200 ml of 50-OG buffer and once with 100 ml of binding buffer, and then resuspended in 12.5 ml of binding buffer.

2. Preparation of SPA beads and receptor mixture
In each assay tube, 2.5 µl (40 mg/ml) of pretreated beads were suspended in 97.5 µl of binding buffer and 20 µl of 50-OG buffer. 5 µl (~30 ng/µl) of purified receptor was added to the beads in suspension with stirring at room temperature for 30 minutes. The mixture was then centrifuged at 2,500 rpm in a Beckman GPR Benchtop centrifuge for 10 minutes at 4° C. The pellets were then resuspended in 50 µl of binding buffer and 25 µl of 50-OG buffer.

3. Reaction
The following were sequentially added into Optiplate in corresponding wells:
(i) Receptor/beads mixture (75 µl)
(ii) 25 µl of each of the following: compound to be tested, binding buffer for total binding or 8-8 for non-specific binding (final concentration 1 µM)
(iii) 8-10 in binding buffer (25 µl, final concentration 40 pM)
(iv) Binding buffer (125 µl)
(v) Each plate was sealed with plate sealer from PACK-ARD and incubated overnight with rocking at 4° C.
4. Plates were counted using PACKARD TOPCOUNT
5. % inhibition was calculated as follows:
A=total counts
B=nonspecific counts
C=sample counts
% inhibition=[{(A-B)-(C-B)}/(A-B)]/(A-B)×100.

OCFORM ASSAY

Osteoblast-like cells (1.8 cells), originally derived from mouse calvaria, were plated in CORNING 24 well tissue culture plates in α MEM medium containing ribo- and deoxyribonucleosides, 10% fetal bovine serum and penicillin-streptomycin. Cells were seeded at 40,000/well in the morning. In the afternoon, bone marrow cells were prepared from six week old male Balb/C mice as follows:

Mice were sacrificed, tibiae removed and placed in the above medium. The ends were cut off and the marrow was flushed out of the cavity into a tube with a 1 mL syringe with a 27.5 gauge needle. The marrow was suspended by pipetting up and down. The suspension was passed through >100 µm nylon cell strainer. The resulting suspension was centrifuged at 350×g for seven minutes. The pellet was resuspended, and a sample was diluted in 2% acetic acid to lyse the red cells. The remaining cells were counted in a hemacytometer. The cells were pelleted and resuspended at $1 \times 10^6$ cells/mL. 50 µL was added to each well of 1.8 cells to yield 50,000 cells/well and 1,25-dihydroxy-vitamin $D_3(D_3)$ was added to each well to a final concentration of 10 nM. The cultures were incubated at 37° C. in a humidified, 5% $CO_2$ atmosphere. After 48 h, the medium was changed. 72 h after the addition of bone marrow, test compounds were added with fresh medium containing $D_3$ to quadruplicate wells. Compounds were added again after 48 h with fresh medium containing $D_3$. After an additional 48 h the medium was removed, cells were fixed with 10% formaldehyde in phosphate buffered saline for 10 minutes at room temperature, followed by a 1–2 minute treatment with ethanol:acetone (1:1) and air dried. The cells were then stained for tartrate resistant acid phosphatase as follows:

The cells were stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS -MX phosphate. After staining, the plates were washed extensively with deionized water and air dried. The number of multinucleated, positive staining cells were counted in each well.

αvβ5 ATTACHMENT ASSAY

Duong et al., *J. Bone Miner. Res.*, 11:S 290, describe a system for expressing the human αvβ5.

Materials:
1. Media and solutions used in this assay are purchased from BRL/Gibco, except BSA and the chemicals are from Sigma.
2. Attachment medium: HBSS with 1 mg/ml heat-inactivated fatty acid free BSA and 2 mM $CaCl_2$.
3. Glucosaminidase substrate solution: 3.75 mM p-nitrophenyl-N-acetyl-beta-D-glucosaminide, 0.1 M sodium citrate, 0.25% Triton, pH 5.0.
4. Glycine-EDTA developing solution: 50 mM glycine, 5 mM EDTA, pH 10.5.

Methods:
1. Plates (96 well, Nunc Maxi Sorp) were coated overnight at 4° C. with human vitronectin (3 ug/ml) in 50 mM carbonate buffer (pH 9/0.6), using 100 μl/well. Plates were then washed 2×with DPBS and blocked with 2% BSA in DPBS for 2 h at room temperature. After additional washes (2×) with DPBS, plates were used for cell attachment assay.
2. 293 (alpha v beta 5) cells were grown in MEM media in presence of 10% fetal calf serum to 90% confluence. Cells were then lifted from dishes with 1×Trypsin/EDTA and washed 3×with serum free MEM. Cells were resuspended in attachment medium ($3×10^5$ cells/ml).
3. Test compounds were prepared as a series of dilutions at 2×concentrations and added as 50 μl/well. Cell suspension was then added as 50 ml/well. Plates were incubated at 37° C. with 55 $CO_2$ for 1 hour to allow attachment.
4. Non-adherent cells were removed by gently washing the plates (3×) with DPBS and then incubated with glucosaminidase substrate solution (100 μl/well), overnight at room temperature in the dark. To quantitate cell numbers, standard curve of glucosaminidase activity was determined for each experiment by adding samples of cell suspension directly to wells containing the enzyme substrate solution.
5. The next day, the reaction was developed by addition of 185 μl/well of gylcine/EDTA solution and reading absorbance at 405 nm using a Molecular Devices V-Max plate reader. Average test absorbance values (4 wells per test samples) were calculated. Then, the number of attached cells at each drug concentration was quantitated versus the standard curve of cells using the Softmax program.

EXAMPLE OF A PHARMACEUTICAL FORMULATION

As a specific embodiment of an oral composition, 100 mg of compound 3-13 is formulated with sufficient finely divided lactose to provide a total amount of 580 to 590 mg to fill a size O hard gel capsule.

Representative compounds of the present invention were tested and found to bind to human αvβ3 integrin. These compounds were found to have $IC_{50}$ values in the range of 0.1 to 100 nM in the SPA assay.

Representative compounds of the present invention were tested and found to inhibit ≧50% the attachment of αvβ5 expressing cells to plates coated with vitronectin at concentrations of 1 μM.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A method of eliciting a vitronectin receptor antagonizing effect in a mammal in need thereof, comprising administering to the mammal a therapeutically effective amount of a compound of the formula

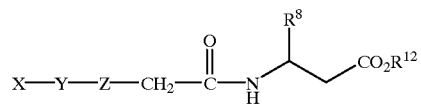

wherein X is selected from a 9- to 10-membered polycyclic ring system, wherein one or more of the rings is aromatic, and wherein the polycyclic ring system contains 0, 1, 2, 3 or 4 heteroatoms selected from N, O or S, and wherein the polycyclic ring system is either unsubstituted or substituted with $R^1$ and $R^2$;

Y is selected from —$(CH_2)_r$— or —$(CH_2)_m$—$NR^3$—$(CH_2)_t$—;

Z is

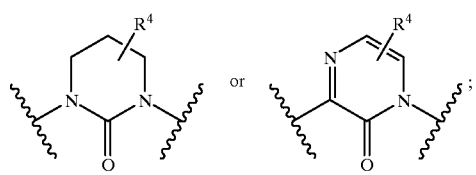

$R^1$, $R^2$ and $R^4$ are each independently selected from hydrogen, halogen, $C_{1-10}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $(C_{1-6}$ alkyl$)_q$amino, $(C_{1-6}$ alkyl$)_q$ amino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl-S(O)$_q$, $(C_{1-8}$ alkyl$)_q$aminocarbonyl, $C_{1-8}$ alkyloxycarbonylamino, $(C_{1-8}$ alkyl$)_q$ aminocarbonyloxy, oxo, (aryl $C_{1-8}$ alkyl$)_q$amino, (aryl$)_q$ amino, aryl $C_{1-8}$ alkylsulfonylamino, or $C_{1-8}$ alkylsulfonylamino;

$R^3$ is selected from
  hydrogen,
  aryl-$(CH_2)_p$—

$C_{1-5}$ alkoxycarbonyl,
$C_{3-8}$ cycloalkyl,
$(aryl)_q$aminocarbonyl,
$(aryl\ C_{1-5}\ alkyl)_q$aminocarbonyl,
$C_{1-8}$ alkyl,
aryl $C_{1-6}$ alkyl,
$C_{1-8}$ alkylsulfonyl,
arylsulfonyl,
aryl $C_{1-6}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl, or
$(C_{1-8}\ alkyl)_q$aminocarbonyl,
wherein any of the alkyl groups may be unsubstituted or substituted with $R^1$ and $R^2$;
$R^8$ is selected from
hydrogen,
aryl,
aryl-$(CH_2)_p$—,
HC≡C—$(CH_2)_s$—,
$C_{1-6}$ alkyl-C≡C—$(CH_2)_s$—,
$C_{3-7}$ cycloalkyl-C≡C—$(CH_2)_s$—,
aryl-C≡C—$(CH_2)_s$—,
$C_{1-6}$ alkylaryl-C≡C—$(CH_2)_s$—,
$CH_2$=CH—$(CH_2)_s$—,
$C_{1-6}$ alkyl-CH=CH—$(CH_2)_s$—,
$C_{3-7}$ cycloalkyl-CH=CH—$(CH_2)_s$—,
aryl-CH=CH—$(CH_2)_s$—,
$C_{1-6}$ alkylaryl-CH=CH—$(CH_2)_s$—,
$C_{1-6}$ alkyl-$SO_2$—$(CH_2)_s$—, or
$C_{1-6}$ alkylaryl-$SO_2$-$(CH_2)_s$—; and
$R^{12}$ is selected from
hydrogen,
$C_{1-8}$ alkyl,
aryl,
aryl $C_{1-8}$ alkyl,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, or
$C_{1-8}$ dialkylaminocarbonylmethylene;
m, s and t are each independently an integer from 0 to 3;
p is an integer from 0 to 4;
q is an integer from 0 to 2;
r is an integer from 0 to 6;
and the pharmaceutically acceptable salts thereof.

2. The method of claim 1 wherein X is selected from

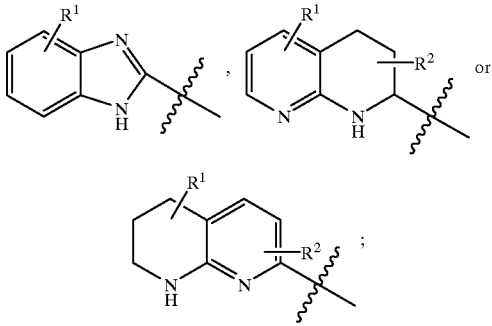

$R^4$ is selected from
hydrogen, $C_{1-6}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, or aryl $C_{1-8}$ alkyl; and $R^8$ is selected from
hydrogen,

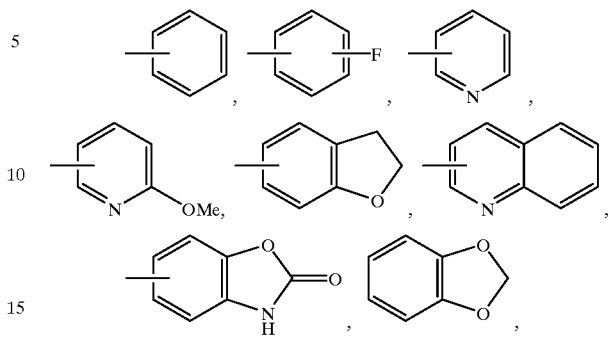

indolyl-$(CH_2)_p$—,
HC≡C—$(CH_2)_s$—,
$C_{1-6}$ alkyl-C≡C—$(CH_2)_s$—,
$C_{3-7}$ cycloalkyl-C≡C—$(CH_2)_s$—,
aryl-C≡C—$(CH_2)_s$—,
$C_{1-6}$ alkylaryl-C≡C—$(CH_2)_s$—,
$CH_2$=CH—$(CH_2)_s$—,
$C_{1-6}$ alkyl-CH=CH—$(CH_2)_s$—,
$C_{3-7}$ cycloalkyl-CH=CH—$(CH_2)_s$—,
aryl-CH=CH—$(CH_2)_s$—,
$C_{1-6}$ alkylaryl-CH=CH—$(CH_2)_s$—,
$C_{1-6}$ alkyl-$SO_2$—$(CH_2)_s$—, or
$C_{1-6}$ alkylaryl-$SO_2$—$(CH_2)_s$—;

s and r are each independently an integer from 0 to 3;
p is an integer from 1 to 2;
and the pharmaceutically acceptable salts thereof.

3. The method of claim 2 wherein the compound has the formula

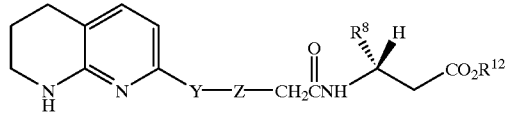

wherein $R^8$ is selected from

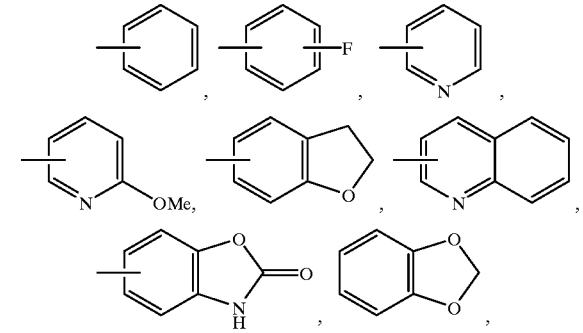

and indolyl-$(CH_2)_p$—;
and $R^{12}$ is selected from hydrogen or $C_{1-8}$ alkyl;
and the pharmaceutically acceptable salts thereof.

4. The method of claim 3 wherein the compound is selected from
Ethyl 2-oxo-3-[2-(5,6,7,8-tetrahydro[1,8]naphthyridin-2-yl)ethyl]-tetrahydropyrimidin-1-yl-acetyl-3(S)-(pyridin-3-yl)-β-alanine;

2-Oxo-3-[2-(5,6,7,8-tetrahydro[1,8]naphthyridin-2-yl) ethyl]-tetrahydropyrimidin-1-yl-acetyl-3(S)-(pyridin-3-yl)-β-alanine;

Ethyl 3-(3-fluorophenyl)-3-(2-{6-methyl-2-oxo-3-[(5,6,7,8-tetrahydro-[1,8]naphthyridin-2-ylmethyl)-amino]-2H-pyrazin-1-yl}-acetylamino)-propionate ditrifluoroacetate; and 3-(3-Fluorophenyl)-3-(2-{6-methyl-2-oxo-3-[(5,6,7,8-tetrahydro-[1,8]naphthyridin-2-ylmethyl)-amino]-2H-pyrazin-1-yl}-acetylamino)-propionic acid ditrifluoroacetate;

and the pharmaceutically acceptable salts thereof.

5. The method of claim 4 wherein the compound is selected from

2-Oxo-3-[2-(5,6,7,8-tetrahydro[1,8]naphthyridin-2-yl) ethyl]-tetrahydropyrimidin-1-yl-acetyl-3-(S)-(pyridin-3-yl)-β-alanine; and 3-(3-Fluorophenyl)-3-(2-{6-methyl-2-oxo-3-[(5,6,7,8-tetrahydro-[1,8]naphthyridin-2-ylmethyl)-amino ]-2H-pyrazin-1-yl}-acetylamino)-propionic acid ditrifluoroacetate;

and the pharmaceutically acceptable salts thereof.

6. The method of claim 1, wherein the vitronectin receptor antagonizing effect is an αvβ3 antagonizing effect.

7. The method of claim 6 wherein the αvβ3 antagonizing effect is selected from inhibition of: bone resorption, restenosis, angiogenesis, diabetic retinopathy, macular degeneration, inflammation or tumor growth.

8. The method of claim 7, wherein the αvβ3 antagonizing effect is the inhibition of bone resorption.

9. A compound of the formula $$X-Y-Z-CH_2-\overset{O}{\underset{}{C}}-\underset{H}{N}-\overset{R^8}{\underset{}{CH}}-CO_2R^{12}$$

wherein X is selected from a 9- to 10-membered polycyclic ring system, wherein one or more of the rings is aromatic, and wherein the polycyclic ring system contains 0, 1, 2, 3 or 4 heteroatoms selected from N, O or S, and wherein the polycyclic ring system is either unsubstituted or substituted with $R^1$ and $R^2$;

Y is selected from $-(CH_2)_r-$ or $-(CH_2)_m-NR^3-(CH_2)_t-$;

Z is $R^1$, $R^2$ and $R^4$ are each independently selected from hydrogen, halogen, $C_{1-10}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $(C_{1-6}$ alkyl$)_q$amino, $(C_{1-6}$ alkyl$)_q$ amino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl-S(O)$_q$, $(C_{1-8}$ alkyl$)_q$ aminocarbonyl, $C_{1-8}$ alkyloxycarbonylamino, $(C_{1-8}$ alkyl$)_q$aminocarbonyloxy, oxo, (aryl $C_{1-8}$ alkyl$)_q$ amino, (aryl$)_q$amino, aryl $C_{1-8}$ alkylsulfonylamino, or $C_{1-8}$ alkylsulfonylamino;

R3 is selected from hydrogen, aryl-$(CH_2)_p-$ $C_{1-5}$ alkoxycarbonyl, $C_{3-8}$ cycloalkyl, (aryl)$_q$aminocarbonyl, (aryl $C_{1-5}$ alkyl)$_q$aminocarbonyl, $C_{1-8}$ alkyl, aryl $C_{1-6}$ alkyl, $C_{1-8}$ alkylsulfonyl, arylsulfonyl, aryl $C_{1-6}$ alkylsulfonyl, $C_{1-8}$ alkoxycarbonyl, aryloxycarbonyl, aryl $C_{1-8}$ alkoxycarbonyl, $C_{1-8}$ alkylcarbonyl, arylcarbonyl, aryl $C_{1-6}$ alkylcarbonyl, or $(C_{1-8}$ alkyl$)_q$aminocarbonyl, wherein any of the alkyl groups may be unsubstituted or substituted with $R^1$ and $R^2$;

$R^8$ is selected from hydrogen, aryl, aryl-$(CH_2)_p-$, $HC\equiv C-(CH_2)_s-$, $C_{1-6}$ alkyl-$C\equiv C-(CH_2)_s-$, $C_{3-7}$ cycloalkyl-$C\equiv C-(CH_2)_s-$, aryl-$C\equiv C-(CH_2)_s-$, $C_{1-6}$ alkylaryl-$C\equiv C-(CH_2)_s-$, $CH_2=CH-(CH_2)_s-$, $C_{1-6}$ alkyl-$CH=CH-(CH_2)_s-$, $C_{3-7}$ cycloalkyl-$CH=CH-(CH_2)_s-$, aryl-$CH=CH-(CH_2)_s-$, $C_{1-6}$ alkylaryl-$CH=CH-(CH_2)_s-$, $C_{1-6}$ alkyl-$SO_2-(CH_2)_s-$, or $C_{1-6}$ alkylaryl-$SO_2-(CH_2)_s-$; and $R^{12}$ is selected from hydrogen, $C_{1-8}$ alkyl, aryl, aryl $C_{1-8}$ alkyl, $C_{1-8}$ alkylcarbonyloxy $C_{1-4}$ alkyl, aryl $C_{1-8}$ alkylcarbonyloxy $C_{1-4}$ alkyl, $C_{1-8}$ alkylaminocarbonylmethylene, or $C_{1-8}$ dialkylaminocarbonylmethylene;

m, s and t are each independently an integer from 0 to 3;

p is an integer from 0 to 4;

q is an integer from 0 to 2;

r is an integer from 0 to 6;

and the pharmaceutically acceptable salts thereof.

10. A pharmaceutical composition comprising the compound of claim 9 and a pharmaceutically acceptable carrier.

11. A pharmaceutical composition made by combining a compound of claim 9 and a pharmaceutically acceptable carrier.

12. A method of eliciting a vitronectin receptor antagonizing effect in a mammal in need thereof, comprising administering to the mammal a therapeutically effective amount of the composition of claim 10.

13. The compound of claim 9 wherein X is selected from

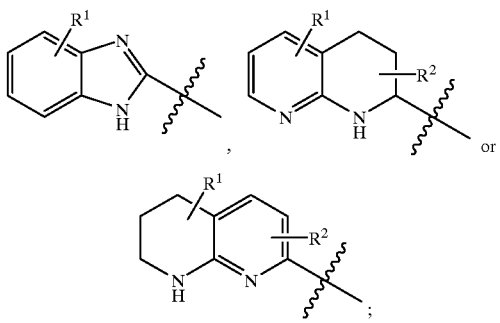

$R^4$ is selected from
hydrogen, $C_{1-6}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, or aryl $C_{1-8}$ alkyl; and
$R^8$ is selected from
hydrogen,

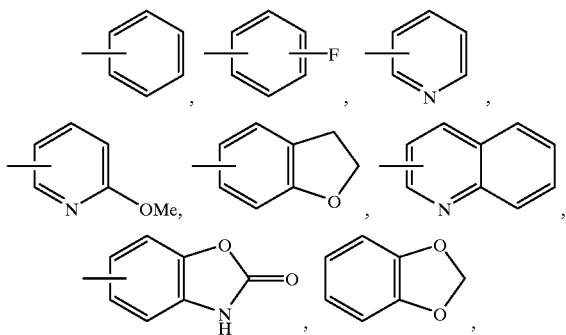

indolyl-$(CH_2)_p$—,
HC≡C—$(CH_2)_s$—,
$C_{1-6}$ alkyl-C≡C—$(CH_2)_s$—,
$C_{3-7}$ cycloalkyl-C≡C—$(CH_2)_s$—,
aryl-C≡C—$(CH_2)_s$—,
$C_{1-6}$ alkylaryl-C≡C—$(CH_2)_s$—,
$CH_2$=CH—$(CH_2)_s$—,
$C_{1-6}$ alkyl-CH=CH—$(CH_2)_s$—,
$C_{3-7}$ cycloalkyl-CH=CH—$(CH_2)_s$—,
aryl-CH=CH—$(CH_2)_s$—,
$C_{1-6}$ alkylaryl-CH=CH—$(CH_2)_s$—,
$C_{1-6}$ alkyl-$SO_2$—$(CH_2)_s$—, or
$C_{1-6}$ alkylaryl-$SO_2$—$(CH_2)_s$—;
s and r are each independently an integer from 0 to 3;
p is an integer from 1 to 2;
and the pharmaceutically acceptable salts thereof.

14. The compound of claim 13 of the formula

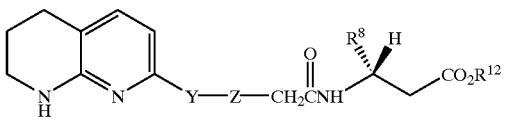

wherein $R^8$ is selected from

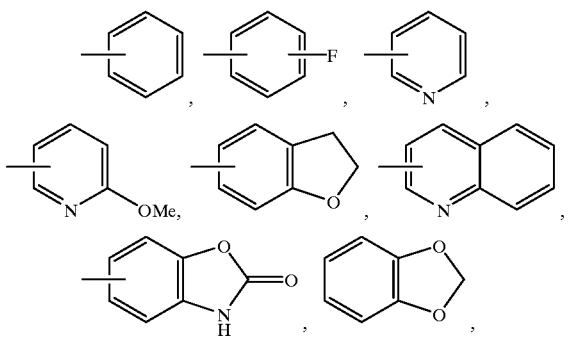

and indolyl-$(CH_2)_p$—;
and $R^{12}$ is selected from hydrogen or $C_{1-8}$ alkyl;
and the pharmaceutically acceptable salts thereof.

15. The compound of claim 14 selected from
Ethyl 2-oxo-3-[2-(5,6,7,8-tetrahydro[1,8]naphthyridin-2-yl)ethyl]-tetrahydropyrimidin-1-yl-acetyl-3(S)-(pyridin-3-yl)-β-alanine;

2-Oxo-3-[2-(5,6,7,8-tetrahydro[1,8]naphthyridin-2-yl)ethyl]-tetrahydropyrimidin-1-yl-acetyl-3(S)-(pyridin-3-yl)-β-alanine;

Ethyl 3-(3-fluorophenyl)-3-(2-{6-methyl-2-oxo-3-[(5,6,7,8-tetrahydro-[1,8]naphthyridin-2-ylmethyl)-amino]-2H-pyrazin-1-yl}-acetylamino)-propionate ditrifluoroacetate; and 3-(3-Fluorophenyl)-3-(2-{6-methyl-2-oxo-3-[(5,6,7,8-tetrahydro-[1,8]naphthyridin-2-ylmethyl)-amino]-2H-pyrazin-1-yl}-acetylamino)-propionic acid ditrifluoroacetate;
and the pharmaceutically acceptable salts thereof.

16. The compound of claim 15 selected from
2-Oxo-3-[2-(5,6,7,8-tetrahydro[1,8]naphthyridin-2-yl)ethyl]-tetrahydropyrimidin-1-yl-acetyl-3-(S)-(pyridin-3-yl)-β-alanine; and 3-(3-Fluorophenyl)-3-(2-{6-methyl-2-oxo-3-[(5,6,7,8-tetrahydro-[1,8]naphthyridin-2-ylmethyl)-amino]-2H-pyrazin-1-yl}-acetylamino)-propionic acid ditrifluoroacetate;
and the pharmaceutically acceptable salts thereof.

* * * * *